United States Patent
Johnson et al.

(10) Patent No.: US 11,427,632 B2
(45) Date of Patent: Aug. 30, 2022

(54) ANTIBODIES WITH LOW IMMUNOGENICITY AND USES THEREOF

(71) Applicant: CELGENE CORPORATION, Summit, NJ (US)

(72) Inventors: Jeffrey C. Johnson, Carlsbad, CA (US); Lawrence Dearth, Encinitas, CA (US); Haralambos Hadjivassiliou, San Diego, CA (US); Jeonghoon Sun, San Francisco, CA (US); Kandasamy Hariharan, San Diego, CA (US)

(73) Assignee: CELGENE CORPORATION, Summit, NJ (US)

( * ) Notice: Subject to any disclaimer, the term of this patent is extended or adjusted under 35 U.S.C. 154(b) by 376 days.

(21) Appl. No.: 16/315,141

(22) PCT Filed: Jul. 5, 2017

(86) PCT No.: PCT/US2017/040653
§ 371 (c)(1),
(2) Date: Jan. 3, 2019

(87) PCT Pub. No.: WO2018/009499
PCT Pub. Date: Jan. 11, 2018

(65) Prior Publication Data
US 2019/0241654 A1 Aug. 8, 2019

Related U.S. Application Data

(60) Provisional application No. 62/359,150, filed on Jul. 6, 2016.

(51) Int. Cl.
*C07K 16/28* (2006.01)
*A61K 39/00* (2006.01)
*C07K 16/46* (2006.01)
*C07K 16/00* (2006.01)

(52) U.S. Cl.
CPC .......... *C07K 16/2803* (2013.01); *C07K 16/00* (2013.01); *C07K 16/461* (2013.01); *C07K 16/464* (2013.01); *C07K 16/465* (2013.01); *C07K 2317/24* (2013.01); *C07K 2317/52* (2013.01); *C07K 2317/565* (2013.01); *C07K 2317/567* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,693,780 A | 12/1997 | Newman et al. | |
| 6,300,064 B1 | 10/2001 | Knappik et al. | |
| 7,354,854 B2 | 4/2008 | Reed et al. | |
| 7,491,514 B2 | 2/2009 | Leung | |
| 7,709,226 B2 | 5/2010 | Foote | |
| 7,964,707 B2 | 6/2011 | Bauerle et al. | |
| 9,045,541 B2 * | 6/2015 | Eckelman | C07K 16/2803 |
| 9,650,441 B2 * | 5/2017 | Grosveld | A61P 35/02 |
| 9,663,575 B2 * | 5/2017 | Eckelman | C07K 16/2803 |
| 9,803,016 B2 * | 10/2017 | Grosveld | C07K 16/2896 |
| 10,870,699 B2 * | 12/2020 | Sato | C07K 16/2803 |
| 2006/0003334 A1 | 1/2006 | Achim et al. | |
| 2008/0182975 A1 | 7/2008 | Leung | |
| 2009/0022738 A1 | 1/2009 | Hofmeister et al. | |
| 2009/0285813 A1 | 11/2009 | Frey et al. | |
| 2010/0216975 A1 | 8/2010 | Wu et al. | |
| 2014/0046030 A1 | 2/2014 | Thanos et al. | |
| 2014/0066598 A1 | 3/2014 | Stafford et al. | |

FOREIGN PATENT DOCUMENTS

| | | |
|---|---|---|
| CL | 201201696 A1 | 3/2013 |
| JP | 2013519389 A | 2/2011 |
| WO | 90002809 A | 3/1990 |
| WO | 91010737 A | 7/1991 |
| WO | 9210737 A | 1/1992 |
| WO | 92018619 A | 10/1992 |
| WO | 92022324 A | 12/1992 |
| WO | 93011236 A | 6/1993 |
| WO | 2007126799 A2 | 11/2007 |
| WO | WO 2009/007427 * | 1/2009 |
| WO | 2011/075861 A1 | 6/2011 |
| WO | WO 2013/119714 * | 8/2013 |
| WO | 2014123580 A1 | 8/2014 |
| WO | 2016073906 A2 | 5/2016 |
| WO | 2016081423 A1 | 5/2016 |

OTHER PUBLICATIONS

NCBI GenBank MN287888.1 (printed May 2021).*
Shields et al., High resolution mapping of the binding site on human IgG 1 for Fc gamma RI, Fc gamma RII, Fc gamma RIII, and FcRn and design of IgG1 variants with improved binding to the Fc gamma R, 2001 JBC, 276( 9): 6591-6604 Mar. 2, 2001.
Stavenhagen et al., Fc optimization of therapeutic antibodies enhances their ability to kill tumor cells in vitro and controls tumor expansion in vivo via low-affinity activating Fcgamma receptors, 2007 Cancer Res, 67(18): 8882-8890 Sep. 15, 2007.
Alegre et al, Effect of a single amino acid mutation on the activating and immunosuppressive properties of a "humanized" OKT3 monoclonal antibody, 1992 J Immunol, 148: 3461-3468 Jun. 1, 1992.

(Continued)

*Primary Examiner* — Laura B Goddard

(74) *Attorney, Agent, or Firm* — Eckert Seamans Cherin & Mellott, LLC

(57) ABSTRACT

Provided herein are antibodies and antigen-binding fragments thereof with low or no immunogenicity in humans and optionally with desirable manufacturing properties. Also provided are compositions comprising such antibodies or antigen-binding fragments, methods of using such antibodies, and methods for making such antibodies.

15 Claims, 7 Drawing Sheets

Figure 1:
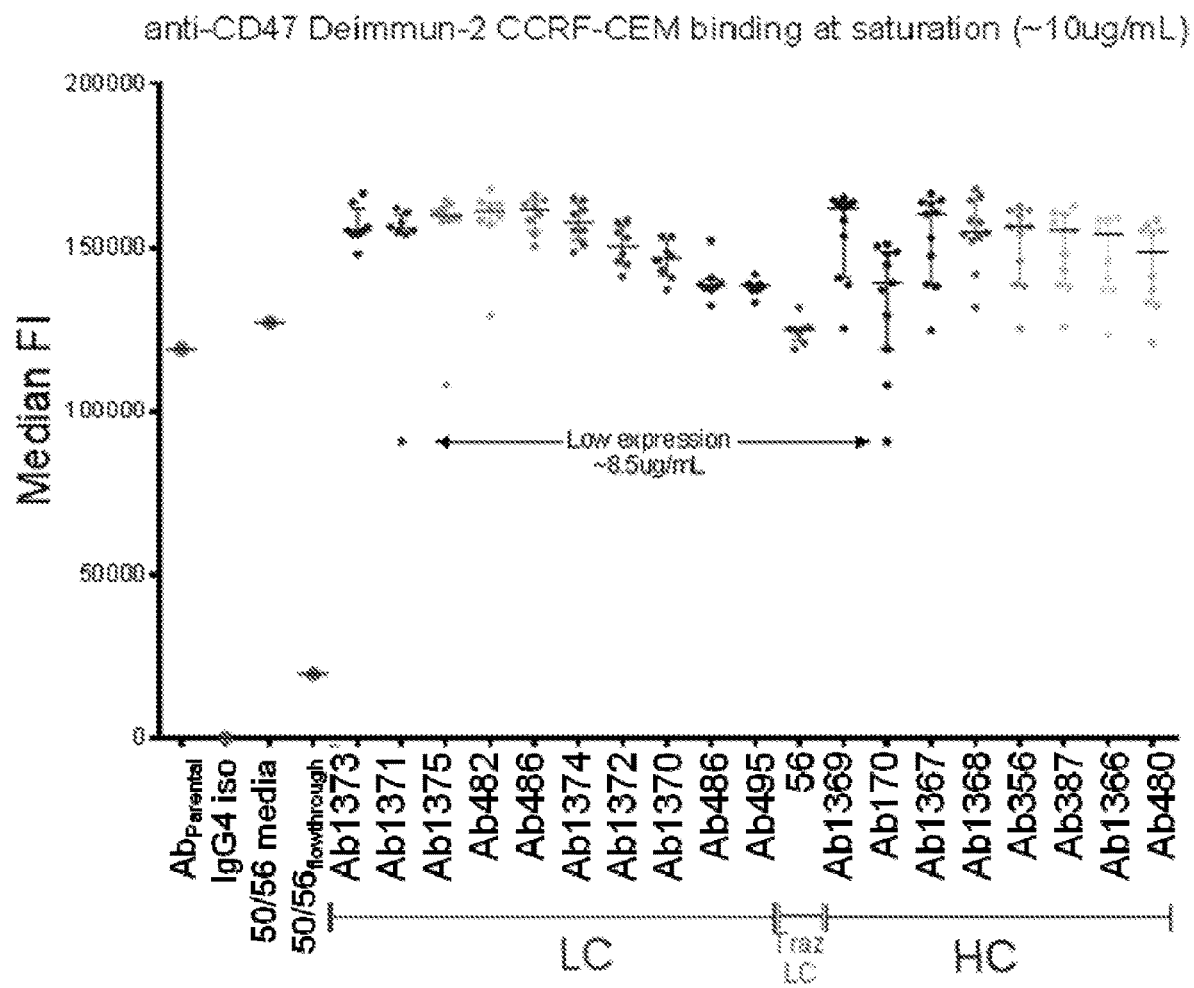

Specification includes a Sequence Listing.

(56) References Cited

OTHER PUBLICATIONS

Koren, E., et al., Clinical validation of the "in silico" prediction of immunogenicity of a human recombinant therapeutic protein, 2007, Clin Immunol 124(1):26-32 Jul. 2007.
Karlin S. and Altschul, S. F., Methods for assessing the statistical significance of molecular sequence features by using general scoring schemes, 1990, Proc. Natl. Acad. Sci. U.S.A. 87:2264 2268 Mar. 1990.
Karlin, S. and Altschul, S. F., Applications and statistics for multiple high-scoring segments in molecular sequences, 1993, Proc. Natl. Acad. Sci. U.S.A. 90:5873 5877 Jun. 15, 1993.
Altschul S.F., Gapped BLAST and PSI-BLAST: a new generation of protein database search programs, 1997, Nucl Acids Res 25, 3389-3402 1997.
Lefranc, M. P., The IMGT Unique Numbering for Imunoglobulins, T-Cell Receptors, and Ig-Like Domains, 1999, The Immunologist, 7:132-136 1999.
Lefranc, M. P., et al., IMGT, the international ImMunoGeneTics database, Nucleic Acids Research, 1999, vol. 27, No. 1 1999.
Martin et al., Modeling antibody hypervariable loops: A combined algorithm, Dec. 1989, Proc.Natl Acad. Sci. USA, 86, 9268-9272 Dec. 1989.
Pedersen, J., et al., Antibody modeling: Beyond homology, Oct. 1992, Immunomethods, 1:126-136 Oct. 1992.
Yin, G. et al., Aglycosylated antibodies and antibody fragments produced in a scalable in vitro transcription-translation system, , Mar-Apr. 2012, 4(2):217-225 Mar. 2012.
Studnicka, G. M., et al., Human-engineered Monoclonal Antibodies Retain Full Specific Binding Activity by Preserving non-CDR Complementarity-Modulating Residues, Jun. 7, 1994, Protein Engineering 7(6):805-814 Jun. 7, 1994.
Roguska, M. A., et al., Humanization of Murine Monoclonal Antibodies Through Variable Domain Resurfacing, Feb. 1, 1994, PNAS 91(3):969-973 Feb. 1, 1994.
Tan, P., et al., "Superhumanized" Antibodies: Reduction of Immunogenic Potential by Complementarity-Determining Region Grafting With Human Germline Sequences: Application to an anti-CD28, J Immunol. Jul. 15, 2002; 169(2):1119-25 Jul. 15, 2002.
Saidas, C., et al., Design and Synthesis of Germline-Based Hemi-Humanized Single-Chain Fv Against the CD18 Surface Antigen, Protein Eng . May 2000;13(5):353-60 May 2000.
Baca, M. et al., Antibody Humanization Using Monovalent Phage Display, J Biol Chem . Apr. 18, 1997;272(16):10678-84 Apr. 18, 1997.
Couto, J. R., et al., Designing Human Consensus Antibodies With Minimal Positional Templates, Cancer Res . Dec. 1, 1995;55(23 Suppl):5973s-5977s. Dec. 1, 1995.
Couto, J. R., et al., Anti-BA46 Monoclonal Antibody Mc3: Humanization Using a Novel Positional Consensus and in Vivo and in Vitro Characterization, Cancer Res . Apr. 15, 1995;55(8):1717-22. Apr. 15, 1995.
Riechmann, L., et al., Single Domain Antibodies: Comparison of Camel VH and Camelised Human VH Domains, J Immunol Methods . Dec. 10, 1999;231(1-2):25-38 Dec. 10, 1999.
Shinmoto, H., et al., Generation of Mouse-Human Hybridomas Secreting Antibodies Against Peanut Allergen Ara h1, Cytotechnology . Sep. 2004;46(1):19-23 Sep. 2004.
Foecking, M. K., et al., Powerful and Versatile Enhancer-Promoter Unit for Mammalian Expression Vectors, Gene . 1986;45(1):101-5 1986.

Inouye, S. and Inouye, M., Up-promoter Mutations in the Lpp Gene of *Escherichia coli*, Nucleic Acids Res . May 10, 1985;13(9):3101-10 May 10, 1985.
Van Heeke, G. and Schuster, S. M., Expression of Human Asparagine Synthetase in *Escherichia coli*, J Biol Chem . Apr. 5, 1989;264(10):5503-9 Apr. 5, 1989.
De Groot, A.S. and Martin, W., Reducing risk, improving outcomes: bioengineering less immunogenic protein therapeutics, 2009, Clin Immunol 131(2):189-201 May 2009.
Natsume et al., Engineered antibodies of IgG1/IgG3 mixed isotype with enhanced cytotoxic activities, 2008 Cancer Res, 68(10): 3863-72 May 15, 2008.
Idusogie et al., Engineered antibodies with increased activity to recruit complement, 2001 J Immunol, 166(4): 2571-5 2001.
Moore et al., Engineered Fc variant antibodies with enhanced ability to recruit complement and mediate effector functions, 2010 mAbs, 2(2): 181-189 Mar. 2010.
Lazar et al., Engineered antibody Fc variants with enhanced effector function, 2006 PNAS, 103(11): 4005-4010 Mar. 14, 2006.
O'Hare, K. et al., Transformation of mouse fibroblasts to methotrexate resistance by a recombinant plasmid expressing a prokaryotic dihydrofolate reductase, Proc Natl Acad Sci U S A. Mar. 1981;78(3):1527-31 Mar. 1981.
Mulligan, R. C. and Berg, P., Selection for animal cells that express the *Escherichia coli* gene coding for xanthine-guanine phosphoribosyltransferase, Proc Natl Acad Sci U S A. Apr. 1981;78(4):2072-6. Apr. 1981.
Tolstoshev, P., Gene therapy, concepts, current trials and future directions, Rev Pharmacol Toxicol. 1993;33:573-96. 1993.
Morgan, R. A. and Anderson, W. F., Human gene therapy, Annu Rev Biochem. 1993;62:191-217. 1993.
Crouse, G. F., et al., Expression and amplification of engineered mouse dihydrofolate reductase minigenes, Cell Biol. Feb. 1983;3(2):257-66. Feb. 1983.
Kohler, G., Immunoglobulin chain loss in hybridoma linesProc Natl. Acad Sci. USA Apr. 1980, 77(4):2197-9 Apr. 1980.
Jalkanen, M. et al., Heparan sulfate proteoglycans from mouse mammary epithelial cells: localization on the cell surface with a monoclonal antibody, J Cell Biol. Sep. 1985;101(3):976-84 Sep. 1985.
Jalkanen, M., et al., Cell surface proteoglycan of mouse mammary epithelial cells is shed by cleavage of its matrix-binding ectodomain from its membrane-associated domain, J Cell Biol. Dec. 1987;105(6 Pt 2):3087-96. Dec. 1987.
Anonymous, "Antitope—Antibody huminization", (Mar. 9, 2016), URL: http://www.antitope.com/antibody-humanization, (Mar. 9, 2016), XP055256546 [A] 1.
Anonymous, "Antibody Humanization | Antibody Engineering", (Mar. 9, 2016), URL: https://lakepharma.com/productlist.php?category=2&secondary=3, (Mar. 9, 2016), XP055256758 [A].
ESSR issued in EP3481862 dated Jul. 15, 2020.
Harding, F. A., et al., The immunogenicity of humanized and fully human antibodies: residual immunogenicity resides in the CDR regions, MAbs, May-Jun. 2010;2(3):256-65.
Knappik, A., et al., Fully Synthetic Human Combinatorial Antibody Libraries (HuCAL) Based on Modular Consensus Frameworks and CDRs Randomized with Trinucleotides, J Mol Biol. Feb. 11, 2000;296(1):57-86.
Luo, G. X., et al , Humanization of an anti-ICAM-1 antibody with over 50-fold affinity and functional improvement, J Immunol Methods. Apr. 1, 2003;275(1-2):31-40.

\* cited by examiner

Figure 2

ANTIBODIES WITH LOW IMMUNOGENICITY AND USES THEREOF

CROSS-REFERENCE TO RELATED APPLICATIONS

This application is a U.S. National Stage Application of International Patent Application No. PCT/US2017/040653, filed Jul. 5, 2017, which claims the benefit of U.S. Provisional Patent Application No. 62/359,150, filed Jul. 6, 2016, which is incorporated by reference herein in its entirety.

REFERENCE TO SEQUENCE LISTING SUBMITTED ELECTRONICALLY

This application incorporates by reference a Sequence Listing submitted with this application as a text file entitled "12827-862-228_SL.txt" created on Jun. 26, 2017 and having a size of 60.9 kilobytes.

1. FIELD

Provided herein are antibodies and antigen-binding fragments thereof with low or no immunogenicity in humans and additional desirable characteristics, e.g., desirable manufacturing, storage and formulation properties. Also provided are compositions comprising such antibodies or antigen-binding fragments, methods of using such antibodies, and methods for making such antibodies.

2. BACKGROUND

As amply demonstrated over the past twenty-plus years, antibodies hold great potential as therapeutics for treatment and management of a wide range of disorders. An antibody's therapeutic efficacy, however, can be substantially impaired or even negaed if the antibody exhibits substantial immunogenicity when administered to a subject, e.g., a human subject. For example, the manufacturing, storage and/or formulation potentials of therapeutic antibodies can be limited by their properties such as solubility, stability, and expression levels.

Accordingly, there exists a need for antibodies exhibiting advantageously low immunogenicity and, ideally, additional characteristics desirable for antibody manufacturing, storage, and formulation.

3. SUMMARY

In one aspect, provided herein is an antibody or an antigen-binding fragment thereof, comprising a heavy chain variable region (VH) that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1, VH FR2, VH FR3 and VH FR4 comprise the amino acid sequence of
$X_{H1}X_{H2}X_{H3}$QLVQSG$X_{H4}$EVKK$X_{H5}$G$X_{H6}X_{H7}$VK$X_{H8}$SCK$X_{H9}$S (SEQ ID NO: 1);
WV$X_{H10}$QA$X_{H11}$G$X_{H12}X_{H13}$LEW$X_{H14}$G (SEQ ID NO: 2);
YA$X_{H15}$K$X_{H16}$Q$X_{H17}$RVT$X_{H18}$T$X_{H19}X_{H20}X_{H21}$S$X_{H22}$ $X_{H23}$T$X_{H24}$YMEL$X_{H25}X_{H26}$LRA$X_{H27}$DTA $X_{H28}$YYC (SEQ ID NO: 3); and
WG$X_{H29}$GT$X_{H30}$VTVSS (SEQ ID NO: 4), respectively, wherein $X_{H1}$ is M or no amino acid, $X_{H2}$ is Q or E, $X_{H3}$ is V or M, $X_{H4}$ is A or P, $X_{H5}$ is P or T, $X_{H6}$ is A, S, or T, $X_{H7}$ is S or T, $X_{H8}$ is V or I, $X_{H9}$ is A or V, $X_{H10}$ is R or Q, $X_{H11}$ is P, R, or T, $X_{H12}$ is Q or K, $X_{H13}$ is G, R, or A, $X_{H14}$ is M or I, $X_{H15}$ is Q or E, $X_{H16}$ is F or L, $X_{H17}$ is G, D, or E, $X_{H18}$ is M or I, $X_{H19}$ is R, T, E or A, $X_{H20}$ is D or N, $X_{H21}$ is T, R, M, E, or K, $X_{H22}$ is I, A T, or M, $X_{H23}$ is S or D, $X_{H24}$ is A or V, $X_{H25}$ is S or R, $X_{H26}$ is S or R, $X_{H27}$ is D or E, $X_{H28}$ is V or M, $X_{H29}$ is Q or R, and $X_{H30}$ is L, M or T.

In certain embodiments of the preceding aspect, at least one of the following is satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

In certain embodiments of the preceding aspect, at least one of the following is satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L.

In certain embodiments of the preceding aspect, at least one of the following is satisfied: $X_{H12}$ is K, $X_{H13}$ is G, and $X_{H30}$ is L. In a specific embodiment of the certain embodiments, at least one of the following is further satisfied: $X_{H5}$ is P, $X_{H17}$ is G, $X_{H22}$ is T, $X_{H25}$ is R, and $X_{H28}$ is V. In a further specific embodiment, at least one of the following is further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another specific embodiment of the certain embodiments, at least one of the following is further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

In specific embodiments of the preceding aspect, $X_{H3}$ is M, $X_{H6}$ is S, $X_{H16}$ is F, $X_{H18}$ is I, $X_{H19}$ is R, $X_{H21}$ is R, and $X_{H27}$ is E.

In another aspect, provided herein is an antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1, VH FR2, VH FR3 and VH FR4 comprise the amino acid sequence of
$X_{H1}$Q$X_{H3}$QLVQSGAEVKK$X_{H5}$G$X_{H6}$SVKVSCKAS (SEQ ID NO: 5),
WVRQAPG$X_{H12}X_{H13}$LEWMG (SEQ ID NO: 6),
YAQK$X_{H16}$Q$X_{H17}$RVT$X_{H18}$T$X_{H19}$D$X_{H21}$S$X_{H22}$ STAYMEL$X_{H25}$SLR$X_{H31}X_{H27}$DTA$X_{H28}$YYC (SEQ ID NO: 7), and
WG$X_{H29}$GT$X_{H30}$VTVSS (SEQ ID NO: 4) respectively, wherein $X_{H1}$ is M or no amino acid, $X_{H3}$ is V or M, $X_{H5}$ is P or T, $X_{H6}$ is A, S, or T, $X_{H12}$ is Q or K, $X_{H13}$ is G, R, or A, $X_{H16}$ is F or L, $X_{H17}$ is G, D, or E, $X_{H18}$ is M or I, $X_{H19}$ is R, T, E or A, $X_{H21}$ is T, R, M, E, or K, $X_{H22}$ is I, A T, or M, $X_{H25}$ is S or R, Xmi$_{31}$ is S or A, $X_{H27}$ is D or E, and $X_{H28}$ is V or M, $X_{H29}$ is Q or R, and $X_{H30}$ is L, M or T, and wherein at least one of the following is satisfied: $X_{H12}$ is K, $X_{H13}$ is G, $X_{H31}$ is A, and $X_{H30}$ is L.

In a specific embodiment of the preceding aspect, at least one of the following is further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

In another specific embodiment of the preceding aspect, at least one of the following is further satisfied: $X_{H5}$ is P, $X_{H17}$ is G, $X_{H22}$ is T, $X_{H25}$ is R, and $X_{H28}$ is V. In a further specific embodiment, at least one of the following is further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

In another specific embodiment of the preceding aspect, at least one of the following is further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

In specific embodiments of the preceding aspect, $X_{H3}$ is M, $X_{H6}$ is S, $X_{H16}$ is F, $X_{H18}$ is I, $X_{H19}$ is R, $X_{H21}$ is R, and $X_{H27}$ is E.

In another aspect, provided herein is an antibody or antigen-binding fragment thereof comprising a light chain variable region (VL) that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1, VL FR2, VL FR3 and VL FR4 comprise the amino acid sequence of NIQMTQSPSX$_{L1}$X$_{L2}$SASVGDRVTITC (SEQ ID NO: 8); WX$_{L3}$QQKPGKX$_{L4}$PKHLIY (SEQ ID NO: 9); GVPSRFSGSGSGTEFTLTISSLQPEDFATYYC (SEQ ID NO: 10); and FGGGTKVEIK (SEQ ID NO: 11), respectively, wherein $X_{L1}$ is A or S, $X_{L2}$ is M or L, $X_{L3}$ is F or Y, and $X_{L4}$ is V or A.

In certain embodiments, any of the preceding antibodies or antigen-binding fragments thereof comprise such a VL.

In certain embodiments of the preceding aspect, at least one of the following is satisfied: $X_{L1}$ is S, $X_{L2}$ is L, $X_{L3}$ is Y, and $X_{L4}$ is A. In certain embodiments, any of the preceding antibodies or antigen-binding fragments thereof comprise such a VL.

In another aspect, provided herein is an antibody or an antigen-binding fragment thereof, which specifically binds to CD47 and comprises a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein at least one of the following is satisfied: (1) VH CDR1 comprises the amino acid sequence of GFNIKDYYLH (SEQ ID NO: 59); (2) VH CDR2 comprises the amino acid sequence of WIDPDQGDTE (SEQ ID NO: 60); and (3) VH CDR3 comprises the amino acid sequence of NAAYGSSSYPMDY (SEQ ID NO: 61).

In another aspect, provided herein is an antibody or an antigen-binding fragment thereof, which specifically binds to CD47 and comprises a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein (1) VH CDR1 comprises the amino acid sequence of GFNIKDYYLH (SEQ ID NO: 59); (2) VH CDR2 comprises the amino acid sequence of WIDPDQGDTE (SEQ ID NO: 60); and (3) VH CDR3 comprises the amino acid sequence of NAAYGSSSYPMDY (SEQ ID NO: 61).

In some embodiments, the antibody or antigen-binding fragment further comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein at least one of the following is satisfied: (1) VL CDR1 comprises the amino acid sequence of X$_{C1}$ASQDIHRYLS (SEQ ID NO: 62), wherein $X_{C1}$ is K or R; (2) VL CDR2 comprises the amino acid sequence of RANRLVS (SEQ ID NO: 63); and (3) VL CDR3 comprises the amino acid sequence of LQYDEFPYT (SEQ ID NO: 64).

In other embodiments, the antibody or antigen-binding fragment further comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of X$_{C1}$ASQDIHRYLS(SEQ ID NO: 62), wherein $X_{C1}$ is K or R; (2) VL CDR2 comprises the amino acid sequence of RANRLVS(SEQ ID NO: 63); and (3) VL CDR3 comprises the amino acid sequence of LQYDEFPYT (SEQ ID NO: 64).

In other embodiments, the antibody or antigen-binding fragment further comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein at least one of the following is satisfied: (1) VL CDR1 comprises the amino acid sequence of X$_{C1}$ASQDIHRYLS (SEQ ID NO: 62), wherein $X_{C1}$ is K or R; (2) VL CDR2 comprises the amino acid sequence of RX$_{C2}$X$_{C3}$RFVD (SEQ ID NO: 65), wherein $X_{C2}$ is any amino acid with a polar or charged side chain, and $X_{C3}$ is V, I, E, or S; and (3) VL CDR3 comprises the amino acid sequence of LQYDEFPYT (SEQ ID NO: 64). In a specific embodiment, $X_{C2}$ is Y, E, or H. In a specific embodiment, $X_{C1}$ is R.

In other embodiments, the antibody or antigen-binding fragment further comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of X$_{C1}$ASQDIHRYLS (SEQ ID NO: 62), wherein $X_{C1}$ is K or R; (2) VL CDR2 comprises the amino acid sequence of RX$_{C2}$X$_{C3}$RFVD (SEQ ID NO: 65), wherein $X_{C2}$ is any amino acid with a polar or charged side chain, and $X_{C3}$ is V, I, E, or S; and (3) VL CDR3 comprises the amino acid sequence of LQYDEFPYT (SEQ ID NO: 64). In a specific embodiment, $X_{C2}$ is Y, E, or H. In a specific embodiment, $X_{C1}$ is R.

In other embodiments, the antibody or antigen-binding fragment further comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL CDR2 comprises the amino acid sequence of RX$_{C2}$X$_{C3}$RFVD (SEQ ID NO: 65), wherein $X_{C2}$ is any amino acid with a polar or charged side chain, and $X_{C3}$ is V, I, E, or S. In specific embodiments, $X_{C2}$ is Y, E, or H. In certain embodiments, VL CDR1 comprises the amino acid sequence of X$_{C1}$ASQDIHRYLS (SEQ ID NO: 62), wherein $X_{C1}$ is K or R. In certain embodiments, VL CDR3 comprises the amino acid sequence of LQYDEFPYT (SEQ ID NO: 64).

In another aspect, provided herein is an antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein at least one of the following is satisfied: (1) VL CDR1 comprises the amino acid sequence of X$_{C1}$ASQDIHRYLS (SEQ ID NO: 62), wherein $X_{C1}$ is K or R; (2) VL CDR2 comprises the amino acid sequence of RANRLVS (SEQ ID NO: 63); and (3) VL CDR3 comprises the amino acid sequence of LQYDEFPYT (SEQ ID NO: 64).

In another aspect, provided herein is an antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of $X_{C1}$ASQDIHRYLS(SEQ ID NO: 62), wherein $X_{C1}$ is K or R; (2) VL CDR2 comprises the amino acid sequence of RANRLVS(SEQ ID NO: 63); and (3) VL CDR3 comprises the amino acid sequence of LQYDEFPYT (SEQ ID NO: 64).

In another aspect, provided herein is an antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein at least one of the following is satisfied: (1) VL CDR1 comprises the amino acid sequence of $X_{C1}$ASQDIHRYLS (SEQ ID NO: 62), wherein $X_{C1}$ is K or R; (2) VL CDR2 comprises the amino acid sequence of $RX_{C2}X_{C3}$RFVD (SEQ ID NO: 65), wherein $X_{C2}$ is any amino acid with a polar or charged side chain, and $X_{C3}$ is V, I, E, or S; and (3) VL CDR3 comprises the amino acid sequence of LQYDEFPYT (SEQ ID NO: 64). In a specific embodiment, $X_{C2}$ is Y, E, or H. In a specific embodiment, $X_{C1}$ is R.

In another aspect, provided herein is an antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of $X_{C1}$ASQDIHRYLS (SEQ ID NO: 62), wherein $X_{C1}$ is K or R; (2) VL CDR2 comprises the amino acid sequence of $RX_{C2}X_{C3}$RFVD (SEQ ID NO: 65), wherein $X_{C2}$ is any amino acid with a polar or charged side chain, and $X_{C3}$ is V, I, E, or S; and (3) VL CDR3 comprises the amino acid sequence of LQYDEFPYT (SEQ ID NO: 64). In a specific embodiment, $X_{C2}$ is Y, E, or H. In a specific embodiment, $X_{C1}$ is R.

In another aspect, provided herein is an antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL CDR2 comprises the amino acid sequence of $RX_{C2}X_{C3}$RFVD (SEQ ID NO: 65), wherein $X_{C2}$ is any amino acid with a polar or charged side chain, and $X_{C3}$ is V, I, E, or S. In specific embodiments, $X_{C2}$ is Y, E, or H. In certain embodiments, VL CDR1 comprises the amino acid sequence of $X_{C1}$ASQDIHRYLS (SEQ ID NO: 62), wherein $X_{C1}$ is K or R. In certain embodiments, VL CDR3 comprises the amino acid sequence of LQYDEFPYT (SEQ ID NO: 64).

In another aspect, provided herein is an antibody or antigen-binding fragment thereof comprising a VH described above, and further comprising a VL described above.

In another aspect, provided herein is an antibody or antigen-binding fragment thereof which specifically binds to CD47 and comprises a VH described above, wherein the VH CDRs are as described above.

In another aspect, provided herein is an antibody or antigen-binding fragment thereof which specifically binds to CD47 and comprises a VL described above, wherein the VL CDRs are as described above.

In another aspect, provided herein is an antibody or antigen-binding fragment thereof which specifically binds to CD47 and comprises a VH described above and a VL described above, wherein the VH CDRs are as described above.

In another aspect, provided herein is an antibody or antigen-binding fragment thereof which specifically binds to CD47 and comprises a VH described above and a VL described above, wherein the VL CDRs are as described above.

In another aspect, provided herein is an antibody or antigen-binding fragment thereof which specifically binds to CD47 and comprises a VH described above and a VL described above, wherein the VH CDRs are as described above, and the VL CDRs are as described above.

In another aspect, provided herein is an antibody or antigen-binding fragment thereof which specifically binds to CD47 and comprises VH CDRs described above and VL CDRs described above.

In another aspect, provided herein is an antibody or antigen-binding fragment thereof which specifically binds to CD47 and comprises a VH described above, VH CDRs described above, and VL CDRs described above.

In another aspect, provided herein is an antibody or antigen-binding fragment thereof which specifically binds to CD47 and comprises a VL described above, VH CDRs described above, and VL CDRs described above.

In various aspects, the antibody or antigen-binding fragment described herein comprises a heavy chain constant region (e.g., a human constant region). In certain embodiments, the heavy chain constant region is a human IgG constant region. In a specific embodiment, the heavy chain constant region is a human IgG1 constant region. In another specific embodiment, the heavy chain constant region is a human IgG4 constant region. In a further specific embodiment, the heavy chain constant region is a human IgG4 constant region comprising a S228P amino acid substitution according to the EU numbering index. In another further specific embodiment, the heavy chain constant region is a human IgG4 constant region comprising a S228P and L235E amino acid substitutions according to the EU numbering index.

In various aspects, the antibody or antigen-binding fragment described herein comprises a light chain constant region selected from the group consisting of a human kappa constant region and a human lambda constant region.

In various aspects, the antigen-binding fragment is an Fv, Fab, F(ab')$_2$, Fab', dsFv, scFv, or sc(Fv)$_2$.

In various aspects, the antibody is a human antibody, a humanized antibody, a chimeric antibody, a recombinant antibody, a multispecific antibody, or an antigen-binding fragment thereof.

In various aspects, the antibody is a monoclonal antibody or antigen-binding fragment thereof.

In various aspects, the antibody or antigen-binding fragment described herein is an antibody.

In various aspects, the antibody or antigen-binding fragment described herein is conjugated to an agent. In specific embodiments, the agent is a label or a toxin.

In another aspect, provided herein is a pharmaceutical composition comprising a therapeutically effective amount of the antibody or antigen-binding fragment described herein, and a pharmaceutically acceptable carrier.

In another aspect, provided herein is a polynucleotide comprising a nucleotide sequence encoding the antibody or antigen-binding fragment described herein.

In another aspect, provided herein is a vector comprising the polynucleotide described herein.

In another aspect, provided herein is a method of treating cancer in a subject in need thereof, the method comprising administering to the subject the antibody or antigen-binding fragment described herein or the pharmaceutical composition described herein. In another aspect, provided herein is a method of alleviating a symptom of a cancer in a subject in need thereof, the method comprising administering to the subject the antibody or antigen-binding fragment described herein or the pharmaceutical composition described herein. In some embodiments, the method further comprises administering to the subject radiotherapy or chemotherapy. In other embodiments, the method further comprises administering to the subject another anti-cancer agent. In a specific embodiment, the cancer is a hematological cancer. In another specific embodiment, the cancer is a solid cancer. In another specific embodiment, the cancer is multiple myeloma, non-Hodgkin's lymphoma, acute myeloid leukemia (AML), breast cancer, bladder cancer, non-small cell lung cancer/carcinoma, hepatocellular carcinoma (HCC), sarcoma, or head and neck cancer. In particular embodiments, such methods of treating cancer in a subject in need thereof, comprise administering to the subject an antibody or antigen-binding fragment described herein which specifically binds CD47, or a pharmaceutical composition thereof.

In another aspect, provided herein is an isolated cell comprising the polynucleotide described herein.

In another aspect, provided herein is an isolated cell comprising the vector described herein.

In another aspect, provided herein is an isolated cell producing the antibody or antigen-binding fragment described herein.

In another aspect, provided herein is a method of making an antibody or antigen-binding fragment thereof, comprising (a) culturing an isolated cell comprising the polynucleotide described herein; and (b) isolating the antibody or antigen-binding fragment thereof.

In another aspect, provided herein is a method of making an antibody or antigen-binding fragment thereof, comprising (a) culturing an isolated cell described herein; and (b) isolating the antibody or antigen-binding fragment thereof.

Presented, below, are non-limiting exemplary embodiments of the invention described herein:

1. An antibody or an antigen-binding fragment thereof, comprising a heavy chain variable region (VH) that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1, VH FR2, VH FR3 and VH FR4 comprise the amino acid sequence of
$X_{H1}X_{H2}X_{H3}$QLVQSGX$_{H4}$EVKKX$_{H5}$GX$_{H6}$X$_{H7}$VKX$_{H8}$SCKX$_{H9}$S (SEQ ID NO: 1);
WVX$_{H10}$QAX$_{H11}$GX$_{H12}$X$_{H13}$LEWX$_{H14}$G (SEQ ID NO: 2);
YAX$_{H15}$KX$_{H16}$QX$_{H17}$RVTX$_{H18}$TX$_{H19}$X$_{H20}$X$_{H21}$SX$_{H22}$X$_{H23}$TX$_{H24}$YMELX$_{H25}$X$_{H26}$LRAX$_{H27}$DTA X$_{H28}$YYC (SEQ ID NO: 3); and
WGX$_{H29}$GTX$_{H30}$VTVSS (SEQ ID NO: 4), respectively, wherein $X_{H1}$ is M or no amino acid, $X_{H2}$ is Q or E, $X_{H3}$ is V or M, $X_{H4}$ is A or P, $X_{H5}$ is P or T, $X_{H6}$ is A, S, or T, $X_{H7}$ is S or T, $X_{H8}$ is V or I, $X_{H9}$ is A or V, $X_{H10}$ is R or Q, $X_{H11}$ is P, R, or T, $X_{H12}$ is Q or K, $X_{H13}$ is G, R, or A, $X_{H14}$ is M or I, $X_{H15}$ is Q or E, $X_{H16}$ is F or L, $X_{H17}$ is G, D, or E, $X_{H18}$ is M or I, $X_{H19}$ is R, T, E or A, $X_{H20}$ is D or N, $X_{H21}$ is T, R, M, E, or K, $X_{H22}$ is I, A T, or M, $X_{H23}$ is S or D, $X_{H24}$ is A or V, $X_{H25}$ is S or R, $X_{H26}$ is S or R, $X_{H27}$ is D or E, $X_{H28}$ is V or M, $X_{H29}$ is Q or R, and $X_{H30}$ is L, M or T.

2. The antibody or antigen-binding fragment of embodiment 1, wherein at least one of the following is satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

3. The antibody or antigen-binding fragment of embodiment 2, wherein at least two of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

4. The antibody or antigen-binding fragment of embodiment 2, wherein at least three of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

5. The antibody or antigen-binding fragment of embodiment 2, wherein at least four of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

6. The antibody or antigen-binding fragment of embodiment 2, wherein at least five of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

7. The antibody or antigen-binding fragment of embodiment 2, wherein at least six of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

8. The antibody or antigen-binding fragment of embodiment 2, wherein at least seven of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

9. The antibody or antigen-binding fragment of embodiment 2, wherein at least eight of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

10. The antibody or antigen-binding fragment of embodiment 2, wherein at least nine of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

11. The antibody or antigen-binding fragment of embodiment 2, wherein at least ten of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

12. The antibody or antigen-binding fragment of embodiment 2, wherein at least eleven of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

13. The antibody or antigen-binding fragment of embodiment 2, wherein at least twelve of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

14. The antibody or antigen-binding fragment of embodiment 2, wherein at least thirteen of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

15. The antibody or antigen-binding fragment of embodiment 2, wherein at least fourteen of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

16. The antibody or antigen-binding fragment of embodiment 2, wherein $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

17. The antibody or antigen-binding fragment of embodiment 1, wherein at least one of the following is satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L.

18. The antibody or antigen-binding fragment of embodiment 17, wherein at least two of the following are satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L.

19. The antibody or antigen-binding fragment of embodiment 17, wherein at least three of the following are satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L.

20. The antibody or antigen-binding fragment of embodiment 17, wherein at least four of the following are satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L.

21. The antibody or antigen-binding fragment of embodiment 17, wherein at least five of the following are satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L.

22. The antibody or antigen-binding fragment of embodiment 17, wherein at least six of the following are satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L.

23. The antibody or antigen-binding fragment of embodiment 17, wherein at least seven of the following are satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L.

24. The antibody or antigen-binding fragment of embodiment 17, wherein $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L.

25. The antibody or antigen-binding fragment of embodiment 1, wherein at least one of the following is satisfied: $X_{H12}$ is K, $X_{H13}$ is G, and $X_{H30}$ is L.

26. The antibody or antigen-binding fragment of embodiment 25, wherein at least two of the following are satisfied: $X_{H12}$ is K, $X_{H13}$ is G, and $X_{H30}$ is L.

27. The antibody or antigen-binding fragment of embodiment 25, wherein $X_{H12}$ is K, $X_{H13}$ is G, and $X_{H30}$ is L.

28. The antibody or antigen-binding fragment of any of embodiments 25-27, wherein at least one of the following is satisfied: $X_{H5}$ is P, $X_{H17}$ is G, $X_{H22}$ is T, $X_{H25}$ is R, and $X_{H28}$ is V.

29. The antibody or antigen-binding fragment of embodiment 28, wherein at least two of the following are satisfied: $X_{H5}$ is P, $X_{H17}$ is G, $X_{H22}$ is T, $X_{H25}$ is R, and $X_{H28}$ is V.

30. The antibody or antigen-binding fragment of embodiment 28, wherein at least three of the following are satisfied: $X_{H5}$ is P, $X_{H17}$ is G, $X_{H22}$ is T, $X_{H25}$ is R, and $X_{H28}$ is V.

31. The antibody or antigen-binding fragment of embodiment 28, wherein at least four of the following are satisfied: $X_{H5}$ is P, $X_{H17}$ is G, $X_{H22}$ is T, $X_{H25}$ is R, and $X_{H28}$ is V.

32. The antibody or antigen-binding fragment of embodiment 28, wherein $X_{H5}$ is P, $X_{H17}$ is G, $X_{H22}$ is T, $X_{H25}$ is R, and $X_{H28}$ is V.

33. The antibody or antigen-binding fragment of any of embodiments 1-32, wherein $X_{H3}$ is M, $X_{H6}$ is S, $X_{H16}$ is F, $X_{H18}$ is I, $X_{H19}$ is R, $X_{H21}$ is R, and $X_{H27}$ is E.

34. The antibody or antigen-binding fragment of any of embodiments 25-27, wherein at least one of the following is satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

35. The antibody or antigen-binding fragment of embodiment 34, wherein at least two of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

36. The antibody or antigen-binding fragment of embodiment 34, wherein at least three of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

37. The antibody or antigen-binding fragment of embodiment 34, wherein at least four of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

38. The antibody or antigen-binding fragment of embodiment 34, wherein at least five of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

39. The antibody or antigen-binding fragment of embodiment 34, wherein at least six of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

40. The antibody or antigen-binding fragment of embodiment 34, wherein at least seven of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

41. The antibody or antigen-binding fragment of embodiment 34, wherein at least eight of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

42. The antibody or antigen-binding fragment of embodiment 34, wherein at least nine of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

43. The antibody or antigen-binding fragment of embodiment 34, wherein at least ten of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

44. The antibody or antigen-binding fragment of embodiment 34, wherein at least eleven of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

45. The antibody or antigen-binding fragment of embodiment 34, wherein $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

46. The antibody or antigen-binding fragment of any of embodiments 28-32, wherein at least one of the following is satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

47. The antibody or antigen-binding fragment of embodiment 46, wherein at least two of the following are satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

48. The antibody or antigen-binding fragment of embodiment 46, wherein at least three of the following are satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

49. The antibody or antigen-binding fragment of embodiment 46, wherein at least four of the following are satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

50. The antibody or antigen-binding fragment of embodiment 46, wherein at least five of the following are satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

51. The antibody or antigen-binding fragment of embodiment 46, wherein at least six of the following are satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

52. The antibody or antigen-binding fragment of embodiment 46, wherein $X_{H3}$ is V, $X_{H6}$ is A, $X_{H16}$ is L, $X_{H18}$ is M, $X_{H19}$ is T, $X_{H21}$ is T, and $X_{H27}$ is D.

53. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1, VH FR2, VH FR3 and VH FR4 comprise the amino acid sequence of $X_{H1}QX_{H3}QLVQSGAEVKKX_{H5}GX_{H6}SVKVSCKAS$ (SEQ ID NO: 5),
WVRQAPGX$_{H12}$X$_{H13}$LEWMG (SEQ ID NO: 6),
YAQKX$_{H16}$QX$_{H17}$RVTX$_{H18}$TX$_{H19}$DX$_{H21}$SX$_{H22}$STAYME LX$_{H25}$SLRX$_{H31}$X$_{H27}$DTAX$_{H28}$YYC (SEQ ID NO: 7), and WGX$_{H29}$GTX$_{H30}$VTVSS (SEQ ID NO: 4) respectively, wherein $X_{H1}$ is M or no amino acid, $X_{H3}$ is V or M, $X_{H5}$ is P or T, $X_{H6}$ is A, S, or T, $X_{H12}$ is Q or K, $X_{H13}$ is G, R, or A, $X_{H16}$ is F or L, $X_{H17}$ is G, D, or E, $X_{H18}$ is M or I, $X_{H19}$ is R, T, E or A, $X_{H21}$ is T, R, M, E, or K, $X_{H22}$ is I, A T, or M, $X_{H25}$ is S or R, $X_{H31}$ is S or A, $X_{H27}$ is D or E, and $X_{H28}$ is V or M, $X_{H29}$ is Q or R, and $X_{H30}$ is L, M or T, and wherein at least one of the following is satisfied: $X_{H12}$ is K, $X_{H13}$ is G, $X_{H31}$ is A, and $X_{H30}$ is L.

54. The antibody or antigen-binding fragment of embodiment 53, wherein at least two of the following are satisfied: $X_{H12}$ is K, $X_{H13}$ is G, $X_{H31}$ is A, and $X_{H30}$ is L.

55. The antibody or antigen-binding fragment of embodiment 53, wherein at least three of the following are satisfied: $X_{H12}$ is K, $X_{H13}$ is G, $X_{H31}$ is A, and $X_{H30}$ is L.

56. The antibody or antigen-binding fragment of embodiment 53, wherein $X_{H12}$ is K, $X_{H13}$ is G, $X_{H31}$ is A, and $X_{H30}$ is L.

57. The antibody or antigen-binding fragment of any of embodiments 53-56, wherein at least one of the following is satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

58. The antibody or antigen-binding fragment of embodiment 57, wherein at least two of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

59. The antibody or antigen-binding fragment of embodiment 57, wherein at least three of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

60. The antibody or antigen-binding fragment of embodiment 57, wherein at least four of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

61. The antibody or antigen-binding fragment of embodiment 57, wherein at least five of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

62. The antibody or antigen-binding fragment of embodiment 57, wherein at least six of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

63. The antibody or antigen-binding fragment of embodiment 57, wherein at least seven of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

64. The antibody or antigen-binding fragment of embodiment 57, wherein at least eight of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

65. The antibody or antigen-binding fragment of embodiment 57, wherein at least nine of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

66. The antibody or antigen-binding fragment of embodiment 57, wherein at least ten of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

67. The antibody or antigen-binding fragment of embodiment 57, wherein at least eleven of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

68. The antibody or antigen-binding fragment of embodiment 57, wherein $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

69. The antibody or antigen-binding fragment of any of embodiments 53-56, wherein at least one of the following is satisfied: $X_{H5}$ is P, $X_{H17}$ is G, $X_{H22}$ is T, $X_{H25}$ is R, and $X_{H28}$ is V.

70. The antibody or antigen-binding fragment of embodiment 69, wherein at least two of the following are satisfied: $X_{H5}$ is P, $X_{H17}$ is G, $X_{H22}$ is T, $X_{H25}$ is R, and $X_{H28}$ is V.

71. The antibody or antigen-binding fragment of embodiment 69, wherein at least three of the following are satisfied: $X_{H5}$ is P, $X_{H17}$ is G, $X_{H22}$ is T, $X_{H25}$ is R, and $X_{H28}$ is V.

72. The antibody or antigen-binding fragment of embodiment 69, wherein at least four of the following are satisfied: $X_{H5}$ is P, $X_{H17}$ is G, $X_{H22}$ is T, $X_{H25}$ is R, and $X_{H28}$ is V.

73. The antibody or antigen-binding fragment of embodiment 69, wherein $X_{H5}$ is P, $X_{H17}$ is G, $X_{H22}$ is T, $X_{H25}$ is R, and $X_{H28}$ is V.

74. The antibody or antigen-binding fragment of any of embodiments 53-73, wherein $X_{H3}$ is M, $X_{H6}$ is S, $X_{H16}$ is F, $X_{H18}$ is I, $X_{H19}$ is R, $X_{H21}$ is R, and $X_{H27}$ is E.

75. The antibody or antigen-binding fragment of any of embodiments 53-56, wherein at least one of the following is satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

76. The antibody or antigen-binding fragment of embodiment 75, wherein at least two of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

77. The antibody or antigen-binding fragment of embodiment 75, wherein at least three of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

78. The antibody or antigen-binding fragment of embodiment 75, wherein at least four of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

79. The antibody or antigen-binding fragment of embodiment 75, wherein at least five of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

80. The antibody or antigen-binding fragment of embodiment 75, wherein at least six of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

81. The antibody or antigen-binding fragment of embodiment 75, wherein at least seven of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

82. The antibody or antigen-binding fragment of embodiment 75, wherein at least eight of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

83. The antibody or antigen-binding fragment of embodiment 75, wherein at least nine of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

84. The antibody or antigen-binding fragment of embodiment 75, wherein at least ten of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

85. The antibody or antigen-binding fragment of embodiment 75, wherein at least eleven of the following are satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

86. The antibody or antigen-binding fragment of embodiment 75, wherein $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

87. The antibody or antigen-binding fragment of any of embodiments 69-73, wherein at least one of the following is satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

88. The antibody or antigen-binding fragment of embodiment 87, wherein at least two of the following are satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

89. The antibody or antigen-binding fragment of embodiment 87, wherein at least three of the following are satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

90. The antibody or antigen-binding fragment of embodiment 87, wherein at least four of the following are satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

91. The antibody or antigen-binding fragment of embodiment 87, wherein at least five of the following are satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

92. The antibody or antigen-binding fragment of embodiment 87, wherein at least six of the following are satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

93. The antibody or antigen-binding fragment of embodiment 87, wherein $X_{H3}$ is V, $X_{H6}$ is A, $X_{H16}$ is L, $X_{H18}$ is M, $X_{H19}$ is T, $X_{H21}$ is T, and $X_{H27}$ is D.

94. The antibody or antigen-binding fragment of any of embodiments 1-93, further comprising a light chain variable region (VL) that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1, VL FR2, VL FR3 and VL FR4 comprise the amino acid sequence of NIQMTQSPSX$_{L1}$X$_{L2}$SASVGDRVTITC (SEQ ID NO: 8); WX$_{L3}$QQKPGKX$_{L4}$PKHLIY (SEQ ID NO: 9); GVPSRFSGSGSGTEFTLTISSLQPEDFATYYC (SEQ ID NO: 10); and FGGGTKVEIK (SEQ ID NO: 11), respectively, wherein $X_{L1}$ is A or S, $X_{L2}$ is M or L, $X_{L3}$ is F or Y, and $X_{L4}$ is V or A.

95. The antibody or antigen-binding fragment of embodiment 94, wherein at least one of the following is satisfied: $X_{L1}$ is S, $X_{L2}$ is L, $X_{L3}$ is Y, and $X_{L4}$ is A.

96. The antibody or antigen-binding fragment of embodiment 95, wherein at least two of the following are satisfied: $X_{L1}$ is S, $X_{L2}$ is L, $X_{L3}$ is Y, and $X_{L4}$ is A.

97. The antibody or antigen-binding fragment of embodiment 95, wherein at least three of the following are satisfied: $X_{L1}$ is S, $X_{L2}$ is L, $X_{L3}$ is Y, and $X_{L4}$ is A.

98. The antibody or antigen-binding fragment of embodiment 95, wherein $X_{L1}$ is S, $X_{L2}$ is L, $X_{L3}$ is Y, and $X_{L4}$ is A.

99. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1, VL FR2, VL FR3 and VL FR4 comprise the amino acid sequence of NIQMTQSPSX$_{L1}$X$_{L2}$SASVGDRVTITC (SEQ ID NO: 8); WX$_{L3}$QQKPGKX$_{L4}$PKHLIY (SEQ ID NO: 9); GVPSRF SGSGSGTEFTLTIS SLQPEDFATYYC (SEQ ID NO: 10); and FGGGTKVEIK (SEQ ID NO: 11), respectively, wherein $X_{L1}$ is A or S, $X_{L2}$ is M or L, $X_{L3}$ is F or Y, and $X_{L4}$ is V or A, and at least one of the following is satisfied: $X_{L1}$ is S, $X_{L2}$ is L, $X_{L3}$ is Y, and $X_{L4}$ is A.

100. The antibody or antigen-binding fragment of embodiment 99, wherein at least two of the following are satisfied: $X_{L1}$ is S, $X_{L2}$ is L, $X_{L3}$ is Y, and $X_{L4}$ is A.

101. The antibody or antigen-binding fragment of embodiment 99, wherein at least three of the following are satisfied: $X_{L1}$ is S, $X_{L2}$ is L, $X_{L3}$ is Y, and $X_{L4}$ is A.

102. The antibody or antigen-binding fragment of embodiment 99, wherein $X_{L1}$ is S, $X_{L2}$ is L, $X_{L3}$ is Y, and $X_{L4}$ is A.

103. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTTVTVSS (SEQ ID NO: 15).

104. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTTVTVSS (SEQ ID NO: 15).

105. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAEDTAMYYC (SEQ ID NO: 18); and VH FR4 comprises the amino acid sequence of WGQGTTVTVSS (SEQ ID NO: 15).

106. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTLVTVSS (SEQ ID NO: 19).

107. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTTVTVSS (SEQ ID NO: 15).

108. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRAEDTAMYYC (SEQ ID NO: 18); and VH FR4 comprises the amino acid sequence of WGQGTTVTVSS (SEQ ID NO: 15).

109. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTLVTVSS (SEQ ID NO: 19).

110. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRAEDTAMYYC (SEQ ID NO: 18); and VH FR4 comprises the amino acid sequence of WGQGTTVTVSS (SEQ ID NO: 15).

111. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRSEDTAMYYC (SEQ ID NO: 14); and VH FR4 comprises the amino acid sequence of WGQGTLVTVSS (SEQ ID NO: 19).

112. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAED-TAMYYC (SEQ ID NO: 18); and VH FR4 comprises the amino acid sequence of WGQGTLVTVSS (SEQ ID NO: 19).

113. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTTVTVSS (SEQ ID NO: 15).

114. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRSEDTAMYYC (SEQ ID NO: 14); and VH FR4 comprises the amino acid sequence of WGQGTLVTVSS (SEQ ID NO: 19).

115. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTLVTVSS (SEQ ID NO: 19).

116. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTLVTVSS (SEQ ID NO: 19).

117. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTLVTVSS (SEQ ID NO: 19).

118. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELSSLRSEDTAMYYC (SEQ ID NO: 14); and VH FR4 comprises the amino acid sequence of WGQGTTVTVSS (SEQ ID NO: 15).

119. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELSSLRSEDTAMYYC (SEQ ID NO: 22); and VH FR4 comprises the amino acid sequence of WGQGTTVTVSS (SEQ ID NO: 15).

120. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTTVTVSS (SEQ ID NO: 15).

121. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTTVTVSS (SEQ ID NO: 15).

122. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTTVTVSS (SEQ ID NO: 15).

123. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTTVTVSS (SEQ ID NO: 15).

124. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTTVTVSS (SEQ ID NO: 15).

125. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTTVTVSS (SEQ ID NO: 15).

126. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTTVTVSS (SEQ ID NO: 15).

127. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRSEDTAMYYC (SEQ ID NO: 26); and VH FR4 comprises the amino acid sequence of WGQGTTVTVSS (SEQ ID NO: 15).

128. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTTVTVSS (SEQ ID NO: 15).

129. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTTVTVSS (SEQ ID NO: 15).

130. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTTVTVSS (SEQ ID NO: 15).

131. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTTVTVSS (SEQ ID NO: 15).

132. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTTVTVSS (SEQ ID NO: 15).

133. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRSEDTAMYYC (SEQ ID NO: 26); and VH FR4 comprises the amino acid sequence of WGQGTTVTVSS (SEQ ID NO: 15).

134. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTTVTVSS (SEQ ID NO: 15).

135. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTTVTVSS (SEQ ID NO: 15).

136. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTTVTVSS (SEQ ID NO: 15).

137. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTTVTVSS (SEQ ID NO: 15).

138. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTTVTVSS (SEQ ID NO: 15).

139. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRSEDTAMYYC (SEQ ID NO: 32); and VH FR4 comprises the amino acid sequence of WGQGTTVTVSS (SEQ ID NO: 15).

140. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRSEDTAVYYC (SEQ ID NO: 33); and VH FR4 comprises the amino acid sequence of WGQGTTVTVSS (SEQ ID NO: 15).

141. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRSEDTAVYYC (SEQ ID NO: 34); and VH FR4 comprises the amino acid sequence of WGQGTTVTVSS (SEQ ID NO: 15).

142. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRSEDTAVYYC (SEQ ID NO: 35); and VH FR4 comprises the amino acid sequence of WGQGTTVTVSS (SEQ ID NO: 15).

143. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRSEDTAMYYC (SEQ ID NO: 32); and VH FR4 comprises the amino acid sequence of WGQGTTVTVSS (SEQ ID NO: 15).

144. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRSEDTAVYYC (SEQ ID NO: 33); and VH FR4 comprises the amino acid sequence of WGQGTTVTVSS (SEQ ID NO: 15).

145. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRSEDTAVYYC (SEQ ID NO: 34); and VH FR4 comprises the amino acid sequence of WGQGTTVTVSS (SEQ ID NO: 15).

146. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRSEDTAVYYC (SEQ ID NO: 35); and VH FR4 comprises the amino acid sequence of WGQGTTVTVSS (SEQ ID NO: 15).

147. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTTVTVSS (SEQ ID NO: 15).

148. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTTVTVSS (SEQ ID NO: 15).

149. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRSEDTAMYYC (SEQ ID NO: 14); and VH FR4 comprises the amino acid sequence of WGQGTTVTVSS (SEQ ID NO: 15).

150. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELSSLRSEDTAMYYC (SEQ ID NO: 22); and VH FR4 comprises the amino acid sequence of WGQGTTVTVSS (SEQ ID NO: 15).

151. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELSSLRSEDTAMYYC (SEQ ID NO: 23); and VH FR4 comprises the amino acid sequence of WGQGTTVTVSS (SEQ ID NO: 15).

152. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRSEDTAMYYC (SEQ ID NO: 24); and VH FR4 comprises the amino acid sequence of WGQGTTVTVSS (SEQ ID NO: 15).

153. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRSEDTAVYYC (SEQ ID NO: 25); and VH FR4 comprises the amino acid sequence of WGQGTTVTVSS (SEQ ID NO: 15).

154. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELSSLRSEDTAMYYC (SEQ ID NO: 22); and VH FR4 comprises the amino acid sequence of WGQGTTVTVSS (SEQ ID NO: 15).

155. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELSSLRSEDTAMYYC (SEQ ID NO: 23); and VH FR4 comprises the amino acid sequence of WGQGTTVTVSS (SEQ ID NO: 15).

156. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTTVTVSS (SEQ ID NO: 15).

157. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTTVTVSS (SEQ ID NO: 15).

158. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRSEDTAMYYC (SEQ ID NO: 26); and VH FR4 comprises the amino acid sequence of WGQGTTVTVSS (SEQ ID NO: 15).

159. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTTVTVSS (SEQ ID NO: 15).

160. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTTVTVSS (SEQ ID NO: 15).

161. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTTVTVSS (SEQ ID NO: 15).

162. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTTVTVSS (SEQ ID NO: 15).

163. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTTVTVSS (SEQ ID NO: 15).

164. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRSEDTAMYYC (SEQ ID NO: 26); and VH FR4 comprises the amino acid sequence of WGQGTTVTVSS (SEQ ID NO: 15).

165. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTTVTVSS (SEQ ID NO: 15).

166. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTTVTVSS (SEQ ID NO: 15).

167. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTTVTVSS (SEQ ID NO: 15).

168. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTTVTVSS (SEQ ID NO: 15).

169. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTTVTVSS (SEQ ID NO: 15).

170. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRSEDTAMYYC (SEQ ID NO: 32); and VH FR4 comprises the amino acid sequence of WGQGTTVTVSS (SEQ ID NO: 15).

171. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTTVTVSS (SEQ ID NO: 15).

172. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRSEDTAVYYC (SEQ ID NO: 34); and VH FR4 comprises the amino acid sequence of WGQGTTVTVSS (SEQ ID NO: 15).

173. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTTVTVSS (SEQ ID NO: 15).

174. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRSEDTAMYYC (SEQ ID NO: 32); and VH FR4 comprises the amino acid sequence of WGQGTTVTVSS (SEQ ID NO: 15).

175. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTTVTVSS (SEQ ID NO: 15).

176. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRSEDTAVYYC (SEQ ID NO: 34); and VH FR4 comprises the amino acid sequence of WGQGTTVTVSS (SEQ ID NO: 15).

177. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTTVTVSS (SEQ ID NO: 15).

178. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTTVTVSS (SEQ ID NO: 15).

179. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTTVTVSS (SEQ ID NO: 15).

180. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAEDTAMYYC (SEQ ID NO: 18); and VH FR4 comprises the amino acid sequence of WGQGTTVTVSS (SEQ ID NO: 15).

181. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTTVTVSS (SEQ ID NO: 15).

182. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of 183. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAMYYC (SEQ ID NO: 39); and VH FR4 comprises the amino acid sequence of WGQGTTVTVSS (SEQ ID NO: 15).

184. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAED-TAVYYC (SEQ ID NO: 40); and VH FR4 comprises the amino acid sequence of WGQGTTVTVSS (SEQ ID NO: 15).

185. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAMYYC (SEQ ID NO: 37); and VH FR4 comprises the amino acid sequence of WGQGTTVTVSS (SEQ ID NO: 15).

186. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAED-TAMYYC (SEQ ID NO: 38); and VH FR4 comprises the amino acid sequence of WGQGTTVTVSS (SEQ ID NO: 15).

187. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAMYYC (SEQ ID NO: 39); and VH FR4 comprises the amino acid sequence of WGQGTTVTVSS (SEQ ID NO: 15).

188. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAED-TAVYYC (SEQ ID NO: 40); and VH FR4 comprises the amino acid sequence of WGQGTTVTVSS (SEQ ID NO: 15).

189. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAED-TAMYYC (SEQ ID NO: 41); and VH FR4 comprises the amino acid sequence of WGQGTTVTVSS (SEQ ID NO: 15).

190. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAED-TAMYYC (SEQ ID NO: 42); and VH FR4 comprises the amino acid sequence of WGQGTTVTVSS (SEQ ID NO: 15).

191. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAVYYC (SEQ ID NO: 43); and VH FR4 comprises the amino acid sequence of WGQGTTVTVSS (SEQ ID NO: 15).

192. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAED-TAMYYC (SEQ ID NO: 44); and VH FR4 comprises the amino acid sequence of WGQGTTVTVSS (SEQ ID NO: 15).

193. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTTVTVSS (SEQ ID NO: 15).

194. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAVYYC (SEQ ID NO: 46); and VH FR4 comprises the amino acid sequence of WGQGTTVTVSS (SEQ ID NO: 15).

195. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAED-TAMYYC (SEQ ID NO: 41); and VH FR4 comprises the amino acid sequence of WGQGTTVTVSS (SEQ ID NO: 15).

196. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAED-TAMYYC (SEQ ID NO: 42); and VH FR4 comprises the amino acid sequence of WGQGTTVTVSS (SEQ ID NO: 15).

197. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAVYYC (SEQ ID NO: 43); and VH FR4 comprises the amino acid sequence of WGQGTTVTVSS (SEQ ID NO: 15).

198. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAED-TAMYYC (SEQ ID NO: 44); and VH FR4 comprises the amino acid sequence of WGQGTTVTVSS (SEQ ID NO: 15).

199. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTTVTVSS (SEQ ID NO: 15).

200. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTTVTVSS (SEQ ID NO: 15).

201. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAEDTAMYYC (SEQ ID NO: 47); and VH FR4 comprises the amino acid sequence of WGQGTTVTVSS (SEQ ID NO: 15).

202. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTTVTVSS (SEQ ID NO: 15).

203. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAEDTAVYYC (SEQ ID NO: 49); and VH FR4 comprises the amino acid sequence of WGQGTTVTVSS (SEQ ID NO: 15).

204. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTTVTVSS (SEQ ID NO: 15).

205. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAEDTAMYYC (SEQ ID NO: 47); and VH FR4 comprises the amino acid sequence of WGQGTTVTVSS (SEQ ID NO: 15).

206. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTTVTVSS (SEQ ID NO: 15).

207. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAEDTAVYYC (SEQ ID NO: 49); and VH FR4 comprises the amino acid sequence of WGQGTTVTVSS (SEQ ID NO: 15).

208. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTTVTVSS (SEQ ID NO: 15).

209. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTTVTVSS (SEQ ID NO: 15).

210. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTTVTVSS (SEQ ID NO: 15).

211. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTLVTVSS (SEQ ID NO: 19).

212. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19).

213. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19).

214. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTLVTVSS (SEQ ID NO: 19).

215. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTLVTVSS (SEQ ID NO: 19).

216. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19).

217. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19).

218. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTLVTVSS (SEQ ID NO: 19).

219. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTLVTVSS (SEQ ID NO: 19).

220. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRSEDTAMYYC (SEQ ID NO: 26); and VH FR4 comprises the amino acid sequence of WGQGTLVTVSS (SEQ ID NO: 19).

221. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTLVTVSS (SEQ ID NO: 19).

222. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTLVTVSS (SEQ ID NO: 19).

223. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRSEDTAMYYC (SEQ ID NO: 29); and VH FR4 comprises the amino acid sequence of WGQGTLVTVSS (SEQ ID NO: 19).

224. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTLVTVSS (SEQ ID NO: 19).

225. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTLVTVSS (SEQ ID NO: 19).

226. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRSEDTAMYYC (SEQ ID NO: 26); and VH FR4 comprises the amino acid sequence of WGQGTLVTVSS (SEQ ID NO: 19).

227. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTLVTVSS (SEQ ID NO: 19).

228. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTLVTVSS (SEQ ID NO: 19).

229. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTLVTVSS (SEQ ID NO: 19).

230. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTLVTVSS (SEQ ID NO: 19).

231. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTLVTVSS (SEQ ID NO: 19).

232. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRSEDTAMYYC (SEQ ID NO: 32); and VH FR4 comprises the amino acid sequence of WGQGTLVTVSS (SEQ ID NO: 19).

233. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTLVTVSS (SEQ ID NO: 19).

234. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRSED-TAVYYC (SEQ ID NO: 34); and VH FR4 comprises the amino acid sequence of WGQGTLVTVSS (SEQ ID NO: 19).

235. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTLVTVSS (SEQ ID NO: 19).

236. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRSED-TAMYYC (SEQ ID NO: 32); and VH FR4 comprises the amino acid sequence of WGQGTLVTVSS (SEQ ID NO: 19).

237. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTLVTVSS (SEQ ID NO: 19).

238. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRSED-TAVYYC (SEQ ID NO: 34); and VH FR4 comprises the amino acid sequence of WGQGTLVTVSS (SEQ ID NO: 19).

239. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTLVTVSS (SEQ ID NO: 19).

240. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTLVTVSS (SEQ ID NO: 19).

241. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTLVTVSS (SEQ ID NO: 19).

242. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFDRVTITRDRSM-STAYMELSSLRSEDTAMYYC (SEQ ID NO: 14); and VH FR4 comprises the amino acid sequence of WGQGTTVTVSS (SEQ ID NO: 15).

243. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELSSLRSEDTAMYYC (SEQ ID NO: 22); and VH FR4 comprises the amino acid sequence of WGQGTTVTVSS (SEQ ID NO: 15).

244. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELSSLRSEDTAMYYC (SEQ ID NO: 23); and VH FR4 comprises the amino acid sequence of WGQGTTVTVSS (SEQ ID NO: 15).

245. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELRSLRSEDTAMYYC (SEQ ID NO: 24); and VH FR4 comprises the amino acid sequence of WGQGTTVTVSS (SEQ ID NO: 15).

246. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRSEDTAVYYC (SEQ ID NO: 25); and VH FR4 comprises the amino acid sequence of WGQGTTVTVSS (SEQ ID NO: 15).

247. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELSSLRSEDTAMYYC (SEQ ID NO: 22); and VH FR4 comprises the amino acid sequence of WGQGTTVTVSS (SEQ ID NO: 15).

248. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELSSLRSEDTAMYYC (SEQ ID NO: 23); and VH FR4 comprises the amino acid sequence of WGQGTTVTVSS (SEQ ID NO: 15).

249. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELRSLRSEDTAMYYC (SEQ ID NO: 24); and VH FR4 comprises the amino acid sequence of WGQGTTVTVSS (SEQ ID NO: 15).

250. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRSEDTAVYYC (SEQ ID NO: 25); and VH FR4 comprises the amino acid sequence of WGQGTTVTVSS (SEQ ID NO: 15).

251. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRST-STAYMELSSLRSEDTAMYYC (SEQ ID NO: 26); and VH FR4 comprises the amino acid sequence of WGQGTTVTVSS (SEQ ID NO: 15).

252. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSM-STAYMELRSLRSEDTAMYYC (SEQ ID NO: 27); and VH FR4 comprises the amino acid sequence of WGQGTTVTVSS (SEQ ID NO: 15).

253. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSM-STAYMELSSLRSEDTAVYYC (SEQ ID NO: 28); and VH FR4 comprises the amino acid sequence of WGQGTTVTVSS (SEQ ID NO: 15).

254. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRST-STAYMELRSLRSEDTAMYYC (SEQ ID NO: 29); and VH FR4 comprises the amino acid sequence of WGQGTTVTVSS (SEQ ID NO: 15).

255. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTTVTVSS (SEQ ID NO: 15).

256. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTTVTVSS (SEQ ID NO: 15).

257. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRST-STAYMELSSLRSEDTAMYYC (SEQ ID NO: 26); and VH FR4 comprises the amino acid sequence of WGQGTTVTVSS (SEQ ID NO: 15).

258. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSM-STAYMELRSLRSEDTAMYYC (SEQ ID NO: 27); and VH FR4 comprises the amino acid sequence of WGQGTTVTVSS (SEQ ID NO: 15).

259. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSM-STAYMELSSLRSEDTAVYYC (SEQ ID NO: 28); and VH FR4 comprises the amino acid sequence of WGQGTTVTVSS (SEQ ID NO: 15).

260. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTTVTVSS (SEQ ID NO: 15).

261. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTTVTVSS (SEQ ID NO: 15).

262. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTTVTVSS (SEQ ID NO: 15).

263. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRSEDTAMYYC (SEQ ID NO: 32); and VH FR4 comprises the amino acid sequence of WGQGTTVTVSS (SEQ ID NO: 15).

264. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTTVTVSS (SEQ ID NO: 15).

265. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRSEDTAVYYC (SEQ ID NO: 34); and VH FR4 comprises the amino acid sequence of WGQGTTVTVSS (SEQ ID NO: 15).

266. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTTVTVSS (SEQ ID NO: 15).

267. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRSEDTAMYYC (SEQ ID NO: 32); and VH FR4 comprises the amino acid sequence of WGQGTTVTVSS (SEQ ID NO: 15).

268. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTTVTVSS (SEQ ID NO: 15).

269. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELRSLRSEDTAVYYC (SEQ ID NO: 34); and VH FR4 comprises the amino acid sequence of WGQGTTVTVSS (SEQ ID NO: 15).

270. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELRSLRSEDTAVYYC (SEQ ID NO: 35); and VH FR4 comprises the amino acid sequence of WGQGTTVTVSS (SEQ ID NO: 15).

271. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTTVTVSS (SEQ ID NO: 15).

272. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTTVTVSS (SEQ ID NO: 15).

273. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTTVTVSS (SEQ ID NO: 15).

274. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELSSLRAEDTAMYYC (SEQ ID NO: 37); and VH FR4 comprises the amino acid sequence of WGQGTTVTVSS (SEQ ID NO: 15).

275. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELSSLRAEDTAMYYC (SEQ ID NO: 38); and VH FR4 comprises the amino acid sequence of WGQGTTVTVSS (SEQ ID NO: 15).

276. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTTVTVSS (SEQ ID NO: 15).

277. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELSSLRAEDTAVYYC (SEQ ID NO: 40); and VH FR4 comprises the amino acid sequence of WGQGTTVTVSS (SEQ ID NO: 15).

278. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTTVTVSS (SEQ ID NO: 15).

279. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTTVTVSS (SEQ ID NO: 15).

280. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRAEDTAMYYC (SEQ ID NO: 39); and VH FR4 comprises the amino acid sequence of WGQGTTVTVSS (SEQ ID NO: 15).

281. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTTVTVSS (SEQ ID NO: 15).

282. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTTVTVSS (SEQ ID NO: 15).

283. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTTVTVSS (SEQ ID NO: 15).

284. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTTVTVSS (SEQ ID NO: 15).

285. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTTVTVSS (SEQ ID NO: 15).

286. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTTVTVSS (SEQ ID NO: 15).

287. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTTVTVSS (SEQ ID NO: 15).

288. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTTVTVSS (SEQ ID NO: 15).

289. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTTVTVSS (SEQ ID NO: 15).

290. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTTVTVSS (SEQ ID NO: 15).

291. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTTVTVSS (SEQ ID NO: 15).

292. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTTVTVSS (SEQ ID NO: 15).

293. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTTVTVSS (SEQ ID NO: 15).

294. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRAEDTAMYYC (SEQ ID NO: 47); and VH FR4 comprises the amino acid sequence of WGQGTTVTVSS (SEQ ID NO: 15).

295. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTTVTVSS (SEQ ID NO: 15).

296. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRAEDTAVYYC (SEQ ID NO: 49); and VH FR4 comprises the amino acid sequence of WGQGTTVTVSS (SEQ ID NO: 15).

297. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTTVTVSS (SEQ ID NO: 15).

298. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRAEDTAMYYC (SEQ ID NO: 47); and VH FR4 comprises the amino acid sequence of WGQGTTVTVSS (SEQ ID NO: 15).

299. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTTVTVSS (SEQ ID NO: 15).

300. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRAEDTAVYYC (SEQ ID NO: 49); and VH FR4 comprises the amino acid sequence of WGQGTTVTVSS (SEQ ID NO: 15).

301. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTTVTVSS (SEQ ID NO: 15).

302. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTTVTVSS (SEQ ID NO: 15).

303. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTTVTVSS (SEQ ID NO: 15).

304. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTLVTVSS (SEQ ID NO: 19).

305. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19).

306. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19).

307. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTLVTVSS (SEQ ID NO: 19).

308. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTLVTVSS (SEQ ID NO: 19).

309. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19).

310. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19).

311. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTLVTVSS (SEQ ID NO: 19).

312. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTLVTVSS (SEQ ID NO: 19).

313. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRST- STAYMELSSLRSEDTAMYYC (SEQ ID NO: 26); and VH FR4 comprises the amino acid sequence of WGQGTLVTVSS (SEQ ID NO: 19).

314. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTLVTVSS (SEQ ID NO: 19).

315. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTLVTVSS (SEQ ID NO: 19).

316. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTLVTVSS (SEQ ID NO: 19).

317. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTLVTVSS (SEQ ID NO: 19).

318. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTLVTVSS (SEQ ID NO: 19).

319. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRSEDTAMYYC (SEQ ID NO: 26); and VH FR4 comprises the amino acid sequence of WGQGTLVTVSS (SEQ ID NO: 19).

320. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTLVTVSS (SEQ ID NO: 19).

321. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTLVTVSS (SEQ ID NO: 19).

322. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino 323. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTLVTVSS (SEQ ID NO: 19).

324. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTLVTVSS (SEQ ID NO: 19).

325. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRSEDTAMYYC (SEQ ID NO: 32); and VH FR4 comprises the amino acid sequence of WGQGTLVTVSS (SEQ ID NO: 19).

326. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTLVTVSS (SEQ ID NO: 19).

327. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRSEDTAVYYC (SEQ ID NO: 34); and VH FR4 comprises the amino acid sequence of WGQGTLVTVSS (SEQ ID NO: 19).

328. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTLVTVSS (SEQ ID NO: 19).

329. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRSEDTAMYYC (SEQ ID NO: 32); and VH FR4 comprises the amino acid sequence of WGQGTLVTVSS (SEQ ID NO: 19).

330. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTLVTVSS (SEQ ID NO: 19).

331. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA- LEWMG (SEQ ID NO: 13); VH FR3 comprises the amino acid sequence of YAQKFQGRVTITRDRSM-STAYMELRSLRSEDTAVYYC (SEQ ID NO: 34); and VH FR4 comprises the amino acid sequence of WGQGTLVTVSS (SEQ ID NO: 19).

332. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRSEDTAVYYC (SEQ ID NO: 35); and VH FR4 comprises the amino acid sequence of WGQGTLVTVSS (SEQ ID NO: 19).

333. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTLVTVSS (SEQ ID NO: 19).

334. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTLVTVSS (SEQ ID NO: 19).

335. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTTVTVSS (SEQ ID NO: 15).

336. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELSSLRAEDTAMYYC (SEQ ID NO: 37); and VH FR4 comprises the amino acid sequence of WGQGTTVTVSS (SEQ ID NO: 15).

337. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELSSLRAEDTAMYYC (SEQ ID NO: 38); and VH FR4 comprises the amino acid sequence of WGQGTTVTVSS (SEQ ID NO: 15).

338. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTTVTVSS (SEQ ID NO: 15).

339. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRAEDTAVYYC (SEQ ID NO: 40); and VH FR4 comprises the amino acid sequence of WGQGTTVTVSS (SEQ ID NO: 15).

340. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELSSLRAEDTAMYYC (SEQ ID NO: 37); and VH FR4 comprises the amino acid sequence of WGQGTTVTVSS (SEQ ID NO: 15).

341. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELSSLRAEDTAMYYC (SEQ ID NO: 38); and VH FR4 comprises the amino acid sequence of WGQGTTVTVSS (SEQ ID NO: 15).

342. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTTVTVSS (SEQ ID NO: 15).

343. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRAEDTAVYYC (SEQ ID NO: 40); and VH FR4 comprises the amino acid sequence of WGQGTTVTVSS (SEQ ID NO: 15).

344. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELSSLRAEDTAMYYC (SEQ ID NO: 41); and VH FR4 comprises the amino acid sequence of WGQGTTVTVSS (SEQ ID NO: 15).

345. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRAEDTAMYYC (SEQ ID NO: 42); and VH FR4 comprises the amino acid sequence of WGQGTTVTVSS (SEQ ID NO: 15).

346. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELSSLRAEDTAVYYC (SEQ ID NO: 43); and VH FR4 comprises the amino acid sequence of WGQGTTVTVSS (SEQ ID NO: 15).

347. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRAEDTAMYYC (SEQ ID NO: 44); and VH FR4 comprises the amino acid sequence of WGQGTTVTVSS (SEQ ID NO: 15).

348. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELSSLRAEDTAVYYC (SEQ ID NO: 45); and VH FR4 comprises the amino acid sequence of WGQGTTVTVSS (SEQ ID NO: 15).

349. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSM-STAYMELRSLRAEDTAVYYC (SEQ ID NO: 46); and VH FR4 comprises the amino acid sequence of WGQGTTVTVSS (SEQ ID NO: 15).

350. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRST-STAYMELSSLRAEDTAMYYC (SEQ ID NO: 41); and VH FR4 comprises the amino acid sequence of WGQGTTVTVSS (SEQ ID NO: 15).

351. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSM-STAYMELRSLRAEDTAMYYC (SEQ ID NO: 42); and VH FR4 comprises the amino acid sequence of WGQGTTVTVSS (SEQ ID NO: 15).

352. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSM-STAYMELSSLRAEDTAVYYC (SEQ ID NO: 43); and VH FR4 comprises the amino acid sequence of WGQGTTVTVSS (SEQ ID NO: 15).

353. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRST-STAYMELRSLRAEDTAMYYC (SEQ ID NO: 44); and VH FR4 comprises the amino acid sequence of WGQGTTVTVSS (SEQ ID NO: 15).

354. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRST-STAYMELSSLRAEDTAVYYC (SEQ ID NO: 45); and VH FR4 comprises the amino acid sequence of WGQGTTVTVSS (SEQ ID NO: 15).

355. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSM-STAYMELRSLRAEDTAVYYC (SEQ ID NO: 46); and VH FR4 comprises the amino acid sequence of WGQGTTVTVSS (SEQ ID NO: 15).

356. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTTVTVSS (SEQ ID NO: 15).

357. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTTVTVSS (SEQ ID NO: 15).

358. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTTVTVSS (SEQ ID NO: 15).

359. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTTVTVSS (SEQ ID NO: 15).

360. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTTVTVSS (SEQ ID NO: 15).

361. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTTVTVSS (SEQ ID NO: 15).

362. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTTVTVSS (SEQ ID NO: 15).

363. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTTVTVSS (SEQ ID NO: 15).

364. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRAEDTAVYYC (SEQ ID NO: 139); and VH FR4 comprises the amino acid sequence of WGQGTTVTVSS (SEQ ID NO: 15).

365. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRAEDTAVYYC (SEQ ID NO: 139); and VH FR4 comprises the amino acid sequence of WGQGTTVTVSS (SEQ ID NO: 15).

366. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRSEDTAMYYC (SEQ ID NO: 14); and VH FR4 comprises the amino acid sequence of WGQGTLVTVSS (SEQ ID NO: 19).

367. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19).

368. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19).

369. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTLVTVSS (SEQ ID NO: 19).

370. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTLVTVSS (SEQ ID NO: 19).

371. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19).

372. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19).

373. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTLVTVSS (SEQ ID NO: 19).

374. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTLVTVSS (SEQ ID NO: 19).

375. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRSEDTAMYYC (SEQ ID NO: 26); and VH FR4 comprises the amino acid sequence of WGQGTLVTVSS (SEQ ID NO: 19).

376. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTLVTVSS (SEQ ID NO: 19).

377. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTLVTVSS (SEQ ID NO: 19).

378. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTLVTVSS (SEQ ID NO: 19).

379. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTLVTVSS (SEQ ID NO: 19).

380. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTLVTVSS (SEQ ID NO: 19).

381. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRSEDTAMYYC (SEQ ID NO: 26); and VH FR4 comprises the amino acid sequence of WGQGTLVTVSS (SEQ ID NO: 19).

382. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTLVTVSS (SEQ ID NO: 19).

383. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTLVTVSS (SEQ ID NO: 19).

384. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTLVTVSS (SEQ ID NO: 19).

385. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTLVTVSS (SEQ ID NO: 19).

386. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTLVTVSS (SEQ ID NO: 19).

387. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRST-STAYMELRSLRSEDTAMYYC (SEQ ID NO: 32); and VH FR4 comprises the amino acid sequence of WGQGTLVTVSS (SEQ ID NO: 19).

388. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRST-STAYMELSSLRSEDTAVYYC (SEQ ID NO: 33); and VH FR4 comprises the amino acid sequence of WGQGTLVTVSS (SEQ ID NO: 19).

389. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSM-STAYMELRSLRSEDTAVYYC (SEQ ID NO: 34); and VH FR4 comprises the amino acid sequence of WGQGTLVTVSS (SEQ ID NO: 19).

390. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRST-STAYMELRSLRSEDTAVYYC (SEQ ID NO: 35); and VH FR4 comprises the amino acid sequence of WGQGTLVTVSS (SEQ ID NO: 19).

391. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRST-STAYMELRSLRSEDTAMYYC (SEQ ID NO: 32); and VH FR4 comprises the amino acid sequence of WGQGTLVTVSS (SEQ ID NO: 19).

392. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRST-STAYMELSSLRSEDTAVYYC (SEQ ID NO: 33); and VH FR4 comprises the amino acid sequence of WGQGTLVTVSS (SEQ ID NO: 19).

393. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSM-STAYMELRSLRSEDTAVYYC (SEQ ID NO: 34); and VH FR4 comprises the amino acid sequence of WGQGTLVTVSS (SEQ ID NO: 19).

394. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTLVTVSS (SEQ ID NO: 19).

395. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTLVTVSS (SEQ ID NO: 19).

396. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTLVTVSS (SEQ ID NO: 19).

397. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAEDTAMYYC (SEQ ID NO: 18); and VH FR4 comprises the amino acid sequence of WGQGTLVTVSS (SEQ ID NO: 19).

398. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTLVTVSS (SEQ ID NO: 19).

399. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTLVTVSS (SEQ ID NO: 19).

400. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAEDTAMYYC (SEQ ID NO: 39); and VH FR4 comprises the amino acid sequence of WGQGTLVTVSS (SEQ ID NO: 19).

401. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTLVTVSS (SEQ ID NO: 19).

402. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAMYYC (SEQ ID NO: 37); and VH FR4 comprises the amino acid sequence of WGQGTLVTVSS (SEQ ID NO: 19).

403. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAED-TAMYYC (SEQ ID NO: 38); and VH FR4 comprises the amino acid sequence of WGQGTLVTVSS (SEQ ID NO: 19).

404. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAMYYC (SEQ ID NO: 39); and VH FR4 comprises the amino acid sequence of WGQGTLVTVSS (SEQ ID NO: 19).

405. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAED-TAVYYC (SEQ ID NO: 40); and VH FR4 comprises the amino acid sequence of WGQGTLVTVSS (SEQ ID NO: 19).

406. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAED-TAMYYC (SEQ ID NO: 41); and VH FR4 comprises the amino acid sequence of WGQGTLVTVSS (SEQ ID NO: 19).

407. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAED-TAMYYC (SEQ ID NO: 42); and VH FR4 comprises the amino acid sequence of WGQGTLVTVSS (SEQ ID NO: 19).

408. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAVYYC (SEQ ID NO: 43); and VH FR4 comprises the amino acid sequence of WGQGTLVTVSS (SEQ ID NO: 19).

409. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAED-TAMYYC (SEQ ID NO: 44); and VH FR4 comprises the amino acid sequence of WGQGTLVTVSS (SEQ ID NO: 19).

410. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTLVTVSS (SEQ ID NO: 19).

411. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAVYYC (SEQ ID NO: 46); and VH FR4 comprises the amino acid sequence of WGQGTLVTVSS (SEQ ID NO: 19).

412. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAED-TAMYYC (SEQ ID NO: 41); and VH FR4 comprises the amino acid sequence of WGQGTLVTVSS (SEQ ID NO: 19).

413. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAED-TAMYYC (SEQ ID NO: 42); and VH FR4 comprises the amino acid sequence of WGQGTLVTVSS (SEQ ID NO: 19).

414. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAVYYC (SEQ ID NO: 43); and VH FR4 comprises the amino acid sequence of WGQGTLVTVSS (SEQ ID NO: 19).

415. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAED-TAMYYC (SEQ ID NO: 44); and VH FR4 comprises the amino acid sequence of WGQGTLVTVSS (SEQ ID NO: 19).

416. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTLVTVSS (SEQ ID NO: 19).

417. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAVYYC (SEQ ID NO: 46); and VH FR4 comprises the amino acid sequence of WGQGTLVTVSS (SEQ ID NO: 19).

418. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAED-TAMYYC (SEQ ID NO: 47); and VH FR4 comprises the amino acid sequence of WGQGTLVTVSS (SEQ ID NO: 19).

419. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTLVTVSS (SEQ ID NO: 19).

420. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAED-TAVYYC (SEQ ID NO: 49); and VH FR4 comprises the amino acid sequence of WGQGTLVTVSS (SEQ ID NO: 19).

421. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTLVTVSS (SEQ ID NO: 19).

422. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAED-TAMYYC (SEQ ID NO: 47); and VH FR4 comprises the amino acid sequence of WGQGTLVTVSS (SEQ ID NO: 19).

423. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTLVTVSS (SEQ ID NO: 19).

424. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAED-TAVYYC (SEQ ID NO: 49); and VH FR4 comprises the amino acid sequence of WGQGTLVTVSS (SEQ ID NO: 19).

425. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTLVTVSS (SEQ ID NO: 19).

426. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTLVTVSS (SEQ ID NO: 19).

427. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTLVTVSS (SEQ ID NO: 19).

428. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRAEDTAMYYC (SEQ ID NO: 18); and VH FR4 comprises the amino acid sequence of WGQGTTVTVSS (SEQ ID NO: 15).

429. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTTVTVSS (SEQ ID NO: 15).

430. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTTVTVSS (SEQ ID NO: 15).

431. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRAEDTAMYYC (SEQ ID NO: 39); and VH FR4 comprises the amino acid sequence of WGQGTTVTVSS (SEQ ID NO: 15).

432. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTTVTVSS (SEQ ID NO: 15).

433. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTTVTVSS (SEQ ID NO: 15).

434. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTTVTVSS (SEQ ID NO: 15).

435. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRAEDTAMYYC (SEQ ID NO: 39); and VH FR4 comprises the amino acid sequence of WGQGTTVTVSS (SEQ ID NO: 15).

436. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTTVTVSS (SEQ ID NO: 15).

437. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTTVTVSS (SEQ ID NO: 15).

438. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTTVTVSS (SEQ ID NO: 15).

439. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTTVTVSS (SEQ ID NO: 15).

440. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTTVTVSS (SEQ ID NO: 15).

441. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTTVTVSS (SEQ ID NO: 15).

442. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTTVTVSS (SEQ ID NO: 15).

443. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTTVTVSS (SEQ ID NO: 15).

444. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTTVTVSS (SEQ ID NO: 15).

445. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTTVTVSS (SEQ ID NO: 15).

446. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTTVTVSS (SEQ ID NO: 15).

447. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTTVTVSS (SEQ ID NO: 15).

448. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTTVTVSS (SEQ ID NO: 15).

449. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRAEDTAMYYC (SEQ ID NO: 47); and VH FR4 comprises the amino acid sequence of WGQGTTVTVSS (SEQ ID NO: 15).

450. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTTVTVSS (SEQ ID NO: 15).

451. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRAEDTAVYYC (SEQ ID NO: 49); and VH FR4 comprises the amino acid sequence of WGQGTTVTVSS (SEQ ID NO: 15).

452. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTTVTVSS (SEQ ID NO: 15).

453. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRAEDTAMYYC (SEQ ID NO: 47); and VH FR4 comprises the amino acid sequence of WGQGTTVTVSS (SEQ ID NO: 15).

454. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTTVTVSS (SEQ ID NO: 15).

455. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRAEDTAVYYC (SEQ ID NO: 49); and VH FR4 comprises the amino acid sequence of WGQGTTVTVSS (SEQ ID NO: 15).

456. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTTVTVSS (SEQ ID NO: 15).

457. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTTVTVSS (SEQ ID NO: 15).

458. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTTVTVSS (SEQ ID NO: 15).

459. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTLVTVSS (SEQ ID NO: 19).

460. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19).

461. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19).

462. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTLVTVSS (SEQ ID NO: 19).

463. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSM- STAYMELSSLRSEDTAVYYC (SEQ ID NO: 25); and VH FR4 comprises the amino acid sequence of WGQGTLVTVSS (SEQ ID NO: 19).

464. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19).

465. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19).

466. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTLVTVSS (SEQ ID NO: 19).

467. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTLVTVSS (SEQ ID NO: 19).

468. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRSEDTAMYYC (SEQ ID NO: 26); and VH FR4 comprises the amino acid sequence of WGQGTLVTVSS (SEQ ID NO: 19).

469. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTLVTVSS (SEQ ID NO: 19).

470. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTLVTVSS (SEQ ID NO: 19).

471. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTLVTVSS (SEQ ID NO: 19).

472. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTLVTVSS (SEQ ID NO: 19).

473. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTLVTVSS (SEQ ID NO: 19).

474. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRST-STAYMELSSLRSEDTAMYYC (SEQ ID NO: 26); and VH FR4 comprises the amino acid sequence of WGQGTLVTVSS (SEQ ID NO: 19).

475. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSM-STAYMELRSLRSEDTAMYYC (SEQ ID NO: 27); and VH FR4 comprises the amino acid sequence of WGQGTLVTVSS (SEQ ID NO: 19).

476. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSM-STAYMELSSLRSEDTAVYYC (SEQ ID NO: 28); and VH FR4 comprises the amino acid sequence of WGQGTLVTVSS (SEQ ID NO: 19).

477. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRST-STAYMELRSLRSEDTAMYYC (SEQ ID NO: 29); and VH FR4 comprises the amino acid sequence of WGQGTLVTVSS (SEQ ID NO: 19).

478. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTLVTVSS (SEQ ID NO: 19).

479. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTLVTVSS (SEQ ID NO: 19).

480. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRST-STAYMELRSLRSEDTAMYYC (SEQ ID NO: 32); and VH FR4 comprises the amino acid sequence of WGQGTLVTVSS (SEQ ID NO: 19).

481. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK- GLEWMG (SEQ ID NO: 20); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTLVTVSS (SEQ ID NO: 19).

482. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRSEDTAVYYC (SEQ ID NO: 34); and VH FR4 comprises the amino acid sequence of WGQGTLVTVSS (SEQ ID NO: 19).

483. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTLVTVSS (SEQ ID NO: 19).

484. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRSEDTAMYYC (SEQ ID NO: 32); and VH FR4 comprises the amino acid sequence of WGQGTLVTVSS (SEQ ID NO: 19).

485. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTLVTVSS (SEQ ID NO: 19).

486. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRSEDTAVYYC (SEQ ID NO: 34); and VH FR4 comprises the amino acid sequence of WGQGTLVTVSS (SEQ ID NO: 19).

487. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTLVTVSS (SEQ ID NO: 19).

488. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTLVTVSS (SEQ ID NO: 19).

489. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTLVTVSS (SEQ ID NO: 19).

490. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTLVTVSS (SEQ ID NO: 19).

491. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELSSLRAEDTAMYYC (SEQ ID NO: 37); and VH FR4 comprises the amino acid sequence of WGQGTLVTVSS (SEQ ID NO: 19).

492. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELSSLRAEDTAMYYC (SEQ ID NO: 38); and VH FR4 comprises the amino acid sequence of WGQGTLVTVSS (SEQ ID NO: 19).

493. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTLVTVSS (SEQ ID NO: 19).

494. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELSSLRAEDTAVYYC (SEQ ID NO: 40); and VH FR4 comprises the amino acid sequence of WGQGTLVTVSS (SEQ ID NO: 19).

495. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELSSLRAEDTAMYYC (SEQ ID NO: 37); and VH FR4 comprises the amino acid sequence of WGQGTLVTVSS (SEQ ID NO: 19).

496. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELSSLRAEDTAMYYC (SEQ ID NO: 38); and VH FR4 comprises the amino acid sequence of WGQGTLVTVSS (SEQ ID NO: 19).

497. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTLVTVSS (SEQ ID NO: 19).

498. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELSSLRAEDTAVYYC (SEQ ID NO: 40); and VH FR4 comprises the amino acid sequence of WGQGTLVTVSS (SEQ ID NO: 19).

499. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRAEDTAMYYC (SEQ ID NO: 41); and VH FR4 comprises the amino acid sequence of WGQGTLVTVSS (SEQ ID NO: 19).

500. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRAEDTAMYYC (SEQ ID NO: 42); and VH FR4 comprises the amino acid sequence of WGQGTLVTVSS (SEQ ID NO: 19).

501. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELSSLRAEDTAVYYC (SEQ ID NO: 43); and VH FR4 comprises the amino acid sequence of WGQGTLVTVSS (SEQ ID NO: 19).

502. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRAEDTAMYYC (SEQ ID NO: 44); and VH FR4 comprises the amino acid sequence of WGQGTLVTVSS (SEQ ID NO: 19).

503. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELSSLRAEDTAVYYC (SEQ ID NO: 45); and VH FR4 comprises the amino acid sequence of WGQGTLVTVSS (SEQ ID NO: 19).

504. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELRSLRAEDTAVYYC (SEQ ID NO: 46); and VH FR4 comprises the amino acid sequence of WGQGTLVTVSS (SEQ ID NO: 19).

505. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRAEDTAMYYC (SEQ ID NO: 41); and VH FR4 comprises the amino acid sequence of WGQGTLVTVSS (SEQ ID NO: 19).

506. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRAEDTAMYYC (SEQ ID NO: 42); and VH FR4 comprises the amino acid sequence of WGQGTLVTVSS (SEQ ID NO: 19).

507. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELSSLRAEDTAVYYC (SEQ ID NO: 43); and VH FR4 comprises the amino acid sequence of WGQGTLVTVSS (SEQ ID NO: 19).

508. An antibody or an antigen-binding fragment thereof, comprising a VH that comprises four VH framework regions (VH FR1-4) and three VH complementarity determining regions (VH CDR1-3) in the following N-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRAEDTAMYYC (SEQ ID NO: 44); and VH FR4 comprises the amino acid sequence of WGQGTLVTVSS (SEQ ID NO: 19).

509. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELSSLRAEDTAVYYC (SEQ ID NO: 45); and VH FR4 comprises the amino acid sequence of WGQGTLVTVSS (SEQ ID NO: 19).

510. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELRSLRAEDTAVYYC (SEQ ID NO: 46); and VH FR4 comprises the amino acid sequence of WGQGTLVTVSS (SEQ ID NO: 19).

511. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTLVTVSS (SEQ ID NO: 19).

512. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTLVTVSS (SEQ ID NO: 19).

513. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTLVTVSS (SEQ ID NO: 19).

514. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTLVTVSS (SEQ ID NO: 19).

515. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTLVTVSS (SEQ ID NO: 19).

516. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTLVTVSS (SEQ ID NO: 19).

517. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTLVTVSS (SEQ ID NO: 19).

518. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTLVTVSS (SEQ ID NO: 19).

519. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRAEDTAVYYC (SEQ ID NO: 139); and VH FR4 comprises the amino acid sequence of WGQGTLVTVSS (SEQ ID NO: 19).

520. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRAEDTAVYYC (SEQ ID NO: 139); and VH FR4 comprises the amino acid sequence of WGQGTLVTVSS (SEQ ID NO: 19).

521. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTLVTVSS (SEQ ID NO: 19).

522. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELSSLRAEDTAMYYC (SEQ ID NO: 37); and VH FR4 comprises the amino acid sequence of WGQGTLVTVSS (SEQ ID NO: 19).

523. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELSSLRAEDTAMYYC (SEQ ID NO: 38); and VH FR4 comprises the amino acid sequence of WGQGTLVTVSS (SEQ ID NO: 19).

524. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTLVTVSS (SEQ ID NO: 19).

525. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRAEDTAVYYC (SEQ ID NO: 40); and VH FR4 comprises the amino acid sequence of WGQGTLVTVSS (SEQ ID NO: 19).

526. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTLVTVSS (SEQ ID NO: 19).

527. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTLVTVSS (SEQ ID NO: 19).

528. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRAEDTAMYYC (SEQ ID NO: 39); and VH FR4 comprises the amino acid sequence of WGQGTLVTVSS (SEQ ID NO: 19).

529. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTLVTVSS (SEQ ID NO: 19).

530. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTLVTVSS (SEQ ID NO: 19).

531. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTLVTVSS (SEQ ID NO: 19).

532. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTLVTVSS (SEQ ID NO: 19).

533. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTLVTVSS (SEQ ID NO: 19).

534. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTLVTVSS (SEQ ID NO: 19).

535. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTLVTVSS (SEQ ID NO: 19).

536. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTLVTVSS (SEQ ID NO: 19).

537. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTLVTVSS (SEQ ID NO: 19).

538. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTLVTVSS (SEQ ID NO: 19).

539. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTLVTVSS (SEQ ID NO: 19).

540. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTLVTVSS (SEQ ID NO: 19).

541. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTLVTVSS (SEQ ID NO: 19).

542. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRAEDTAMYYC (SEQ ID NO: 47); and VH FR4 comprises the amino acid sequence of WGQGTLVTVSS (SEQ ID NO: 19).

543. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTLVTVSS (SEQ ID NO: 19).

544. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTLVTVSS (SEQ ID NO: 19).

545. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTLVTVSS (SEQ ID NO: 19).

546. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTLVTVSS (SEQ ID NO: 19).

547. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTLVTVSS (SEQ ID NO: 19).

548. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTLVTVSS (SEQ ID NO: 19).

549. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTLVTVSS (SEQ ID NO: 19).

550. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRAEDTAVYYC (SEQ ID NO: 139); and VH FR4 comprises the amino acid sequence of WGQGTLVTVSS (SEQ ID NO: 19).

551. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRAEDTAVYYC (SEQ ID NO: 139); and VH FR4 comprises the amino acid sequence of WGQGTLVTVSS (SEQ ID NO: 19).

552. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTLVTVSS (SEQ ID NO: 19).

553. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTLVTVSS (SEQ ID NO: 19).

554. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTLVTVSS (SEQ ID NO: 19).

555. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRAEDTAMYYC (SEQ ID NO: 39); and VH FR4 comprises the amino acid sequence of WGQGTLVTVSS (SEQ ID NO: 19).

556. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTLVTVSS (SEQ ID NO: 19).

557. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTLVTVSS (SEQ ID NO: 19).

558. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTLVTVSS (SEQ ID NO: 19).

559. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRAEDTAMYYC (SEQ ID NO: 39); and VH FR4 comprises the amino acid sequence of WGQGTLVTVSS (SEQ ID NO: 19).

560. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTLVTVSS (SEQ ID NO: 19).

561. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRST- STAYMELSSLRAEDTAMYYC (SEQ ID NO: 41); and VH FR4 comprises the amino acid sequence of WGQGTLVTVSS (SEQ ID NO: 19).

562. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTLVTVSS (SEQ ID NO: 19).

563. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTLVTVSS (SEQ ID NO: 19).

564. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTLVTVSS (SEQ ID NO: 19).

565. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTLVTVSS (SEQ ID NO: 19).

566. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTLVTVSS (SEQ ID NO: 19).

567. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTLVTVSS (SEQ ID NO: 19).

568. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTLVTVSS (SEQ ID NO: 19).

569. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTLVTVSS (SEQ ID NO: 19).

570. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRST-STAYMELRSLRAEDTAMYYC (SEQ ID NO: 44); and VH FR4 comprises the amino acid sequence of WGQGTLVTVSS (SEQ ID NO: 19).

571. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELSSLRAEDTAVYYC (SEQ ID NO: 45); and VH FR4 comprises the amino acid sequence of WGQGTLVTVSS (SEQ ID NO: 19).

572. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELRSLRAEDTAVYYC (SEQ ID NO: 46); and VH FR4 comprises the amino acid sequence of WGQGTLVTVSS (SEQ ID NO: 19).

573. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTLVTVSS (SEQ ID NO: 19).

574. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTLVTVSS (SEQ ID NO: 19).

575. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTLVTVSS (SEQ ID NO: 19).

576. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTLVTVSS (SEQ ID NO: 19).

577. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTLVTVSS (SEQ ID NO: 19).

578. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTLVTVSS (SEQ ID NO: 19).

579. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK- GLEWMG (SEQ ID NO: 20); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTLVTVSS (SEQ ID NO: 19).

580. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTLVTVSS (SEQ ID NO: 19).

581. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRAEDTAVYYC (SEQ ID NO: 139); and VH FR4 comprises the amino acid sequence of WGQGTLVTVSS (SEQ ID NO: 19).

582. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRAEDTAVYYC (SEQ ID NO: 139); and VH FR4 comprises the amino acid sequence of WGQGTLVTVSS (SEQ ID NO: 19).

583. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

584. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

585. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

586. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

587. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

588. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

589. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

590. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

591. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

592. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

593. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

594. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

595. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

596. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

597. The antibody or antigen-binding fragment of any of embodiments 103-582, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

598. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

599. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSM-SASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

600. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

601. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAM-SASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

602. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAM-SASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

603. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

604. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSM-SASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

605. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSM-SASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

606. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

607. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

608. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAM-SASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

609. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

610. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

611. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

612. An antibody or an antigen-binding fragment thereof, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11).

613. The antibody or antigen-binding fragment of any of embodiments 1-612, which specifically binds to CD47 and comprises a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein at least one of the following is satisfied: (1) VH CDR1 comprises the amino acid sequence of GFNIKDYYLH (SEQ ID NO: 59); (2) VH CDR2 comprises the amino acid sequence of WIDPDQGDTE (SEQ ID NO: 60); and (3) VH CDR3 comprises the amino acid sequence of NAAYGSSSYPMDY (SEQ ID NO: 61).

614. The antibody or antigen-binding fragment of any of embodiments 1-612, which specifically binds to CD47 and comprises a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein (1) VH CDR1 comprises the amino acid sequence of GFNIKDYYLH (SEQ ID NO: 59); (2) VH CDR2 comprises the amino acid sequence of WIDPDQGDTE(SEQ ID NO: 60); and (3) VH CDR3 comprises the amino acid sequence of NAAYGSSSYPMDY(SEQ ID NO: 61).

615. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein at least one of the following is satisfied: (1) VL CDR1 comprises the amino acid sequence of $X_{C1}$ASQDIHRYLS (SEQ ID NO: 62), wherein $X_{C1}$ is K or R; (2) VL CDR2 comprises the amino acid sequence of RANRLVS (SEQ ID NO: 63); and (3) VL CDR3 comprises the amino acid sequence of LQYDEFPYT (SEQ ID NO: 64).

616. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of $X_{C1}$ASQDIHRYLS(SEQ ID NO: 62), wherein $X_{C1}$ is K or R; (2) VL CDR2 comprises the amino acid sequence of RANRLVS(SEQ ID NO: 63); and (3) VL CDR3 comprises the amino acid sequence of LQYDEFPYT(SEQ ID NO: 64).

617. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein at least one of the following is satisfied: (1) VL CDR1 comprises the amino acid sequence of $X_{C1}$ASQDIHRYLS (SEQ ID NO: 62), wherein $X_{C1}$ is K or R; (2) VL CDR2 comprises the amino acid sequence of R$X_{C2}X_{C3}$RFVD (SEQ ID NO: 65), wherein $X_{C2}$ is any amino acid with a polar or charged side chain, and $X_{C3}$ is V, I, E, or S; and (3) VL CDR3 comprises the amino acid sequence of LQYDEFPYT (SEQ ID NO: 64).

618. The antibody or antigen-binding fragment of embodiment 617, wherein $X_{C2}$ is Y, E, or H.

619. The antibody or antigen-binding fragment of any of embodiments 615-618, wherein $X_{C1}$ is R.

620. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RANRLVS (SEQ ID NO: 63); and (3) VL CDR3 comprises the amino acid sequence of LQYDEFPYT (SEQ ID NO: 64).

621. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RYVRFVD (SEQ ID NO: 67); and (3) VL CDR3 comprises the amino acid sequence of LQYDEFPYT (SEQ ID NO: 64).

622. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RYIRFVD (SEQ ID NO: 68); and (3) VL CDR3 comprises the amino acid sequence of LQYDEFPYT (SEQ ID NO: 64).

623. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RYERFVD (SEQ ID NO: 69); and (3) VL CDR3 comprises the amino acid sequence of LQYDEFPYT (SEQ ID NO: 64).

624. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RYSRFVD (SEQ ID NO: 70); and (3) VL CDR3 comprises the amino acid sequence of LQYDEFPYT (SEQ ID NO: 64).

625. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of REVRFVD (SEQ ID NO: 71); and (3) VL CDR3 comprises the amino acid sequence of LQYDEFPYT (SEQ ID NO: 64).

626. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of REIRFVD (SEQ ID NO: 72); and (3) VL CDR3 comprises the amino acid sequence of LQYDEFPYT (SEQ ID NO: 64).

627. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of REERFVD (SEQ ID NO: 73); and (3) VL CDR3 comprises the amino acid sequence of LQYDEFPYT (SEQ ID NO: 64).

628. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RESRFVD (SEQ ID NO: 74); and (3) VL CDR3 comprises the amino acid sequence of LQYDEFPYT (SEQ ID NO: 64).

629. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RHVRFVD (SEQ ID NO: 75); and (3) VL CDR3 comprises the amino acid sequence of LQYDEFPYT (SEQ ID NO: 64).

630. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RHIRFVD (SEQ ID NO: 76); and (3) VL CDR3 comprises the amino acid sequence of LQYDEFPYT (SEQ ID NO: 64).

631. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RHERFVD (SEQ ID NO: 77); and (3) VL CDR3 comprises the amino acid sequence of LQYDEFPYT (SEQ ID NO: 64).

632. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RHSRFVD (SEQ ID NO: 78); and (3) VL CDR3 comprises the amino acid sequence of LQYDEFPYT (SEQ ID NO: 64).

633. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RANRLVS (SEQ ID NO: 63); and (3) VL CDR3 comprises the amino acid sequence of LQYDEFPYT (SEQ ID NO: 64).

634. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RYVRFVD (SEQ ID NO: 67); and (3) VL CDR3 comprises the amino acid sequence of LQYDEFPYT (SEQ ID NO: 64).

635. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RYIRFVD (SEQ ID NO: 68); and (3) VL CDR3 comprises the amino acid sequence of LQYDEFPYT (SEQ ID NO: 64).

636. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RYERFVD (SEQ ID NO: 69); and (3) VL CDR3 comprises the amino acid sequence of LQYDEFPYT (SEQ ID NO: 64).

637. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RYSRFVD (SEQ ID NO: 70); and (3) VL CDR3 comprises the amino acid sequence of LQYDEFPYT (SEQ ID NO: 64).

638. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of REVRFVD (SEQ ID NO: 71); and (3) VL CDR3 comprises the amino acid sequence of LQYDEFPYT (SEQ ID NO: 64).

639. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of REIRFVD (SEQ ID NO: 72); and (3) VL CDR3 comprises the amino acid sequence of LQYDEFPYT (SEQ ID NO: 64).

640. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of REERFVD (SEQ ID NO: 73); and (3) VL CDR3 comprises the amino acid sequence of LQYDEFPYT (SEQ ID NO: 64).

641. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RESRFVD (SEQ ID NO: 74); and (3) VL CDR3 comprises the amino acid sequence of LQYDEFPYT (SEQ ID NO: 64).

642. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RHVRFVD (SEQ ID NO: 75); and (3) VL CDR3 comprises the amino acid sequence of LQYDEFPYT (SEQ ID NO: 64).

643. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RHIRFVD (SEQ ID NO: 76); and (3) VL CDR3 comprises the amino acid sequence of LQYDEFPYT (SEQ ID NO: 64).

644. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RHERFVD (SEQ ID NO: 77); and (3) VL CDR3 comprises the amino acid sequence of LQYDEFPYT (SEQ ID NO: 64).

645. The antibody or antigen-binding fragment of any of embodiments 1-614, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RHSRFVD (SEQ ID NO: 78); and (3) VL CDR3 comprises the amino acid sequence of LQYDEFPYT (SEQ ID NO: 64).

646. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL CDR2 comprises the amino acid sequence of $RX_{C2}X_{C3}RFVD$ (SEQ ID NO: 65), wherein $X_{C2}$ is any amino acid with a polar or charged side chain, and $X_{C3}$ is V, I, E, or S.

647. The antibody or antigen-binding fragment of embodiment 646, wherein $X_{C2}$ is Y, E, or H.

648. The antibody or antigen-binding fragment of embodiment 646, wherein $X_{C2}$ is Y and $X_{C3}$ is V.

649. The antibody or antigen-binding fragment of embodiment 646, wherein $X_{C2}$ is Y and $X_{C3}$ is I.

650. The antibody or antigen-binding fragment of embodiment 646, wherein $X_{C2}$ is Y and $X_{C3}$ is E.

651. The antibody or antigen-binding fragment of embodiment 646, wherein $X_{C2}$ is Y and $X_{C3}$ is S.

652. The antibody or antigen-binding fragment of embodiment 646, wherein $X_{C2}$ is E and $X_{C3}$ is V.

653. The antibody or antigen-binding fragment of embodiment 646, wherein $X_{C2}$ is E and $X_{C3}$ is I.

654. The antibody or antigen-binding fragment of embodiment 646, wherein $X_{C2}$ is E and $X_{C3}$ is E.

655. The antibody or antigen-binding fragment of embodiment 646, wherein $X_{C2}$ is E and $X_{C3}$ is S.

656. The antibody or antigen-binding fragment of embodiment 646, wherein $X_{C2}$ is H and $X_{C3}$ is V.

657. The antibody or antigen-binding fragment of embodiment 646, wherein $X_{C2}$ is H and $X_{C3}$ is I.

658. The antibody or antigen-binding fragment of embodiment 646, wherein $X_{C2}$ is H and $X_{C3}$ is E.

659. The antibody or antigen-binding fragment of embodiment 646, wherein $X_{C2}$ is H and $X_{C3}$ is S.

660. The antibody or antigen-binding fragment of any of embodiments 646-659, wherein VL CDR1 comprises the amino acid sequence of $X_{C1}$ASQDIHRYLS (SEQ ID NO: 62), wherein $X_{C1}$ is K or R.

661. The antibody or antigen-binding fragment of embodiment 660, wherein $X_{C1}$ is R.

662. The antibody or antigen-binding fragment of any of embodiments 646-661, wherein VL CDR3 comprises the amino acid sequence of LQYDEFPYT (SEQ ID NO: 64).

663. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RYVRFVD (SEQ ID NO: 67); and (3) VL CDR3 comprises the amino acid sequence of LQYDEFPYT (SEQ ID NO: 64).

664. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RYIRFVD (SEQ ID NO: 68); and (3) VL CDR3 comprises the amino acid sequence of LQYDEFPYT (SEQ ID NO: 64).

665. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RYERFVD (SEQ ID NO: 69); and (3) VL CDR3 comprises the amino acid sequence of LQYDEFPYT (SEQ ID NO: 64).

666. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RYSRFVD (SEQ ID NO: 70); and (3) VL CDR3 comprises the amino acid sequence of LQYDEFPYT (SEQ ID NO: 64).

667. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of REVRFVD (SEQ ID NO: 71); and (3) VL CDR3 comprises the amino acid sequence of LQYDEFPYT (SEQ ID NO: 64).

668. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of REIRFVD (SEQ ID NO: 72); and (3) VL CDR3 comprises the amino acid sequence of LQYDEFPYT (SEQ ID NO: 64).

669. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of REERFVD (SEQ ID NO: 73); and (3) VL CDR3 comprises the amino acid sequence of LQYDEFPYT (SEQ ID NO: 64).

670. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RESRFVD (SEQ ID NO: 74); and (3) VL CDR3 comprises the amino acid sequence of LQYDEFPYT (SEQ ID NO: 64).

671. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RHVRFVD (SEQ ID NO: 75); and (3) VL CDR3 comprises the amino acid sequence of LQYDEFPYT (SEQ ID NO: 64).

672. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RHIRFVD (SEQ ID NO: 76); and (3) VL CDR3 comprises the amino acid sequence of LQYDEFPYT (SEQ ID NO: 64).

673. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RHERFVD (SEQ ID NO: 77); and (3) VL CDR3 comprises the amino acid sequence of LQYDEFPYT (SEQ ID NO: 64).

674. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 66); (2) VL CDR2 comprises the amino acid sequence of RHSRFVD (SEQ ID NO: 78); and (3) VL CDR3 comprises the amino acid sequence of LQYDEFPYT (SEQ ID NO: 64).

675. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RYVRFVD (SEQ ID NO: 67); and (3) VL CDR3 comprises the amino acid sequence of LQYDEFPYT (SEQ ID NO: 64).

676. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RYIRFVD (SEQ ID NO: 68); and (3) VL CDR3 comprises the amino acid sequence of LQYDEFPYT (SEQ ID NO: 64).

677. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RYERFVD (SEQ ID NO: 69); and (3) VL CDR3 comprises the amino acid sequence of LQYDEFPYT (SEQ ID NO: 64).

678. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RYSRFVD (SEQ ID NO: 70); and (3) VL CDR3 comprises the amino acid sequence of LQYDEFPYT (SEQ ID NO: 64).

679. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of REVRFVD (SEQ ID NO: 71); and (3) VL CDR3 comprises the amino acid sequence of LQYDEFPYT (SEQ ID NO: 64).

680. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of REIRFVD (SEQ ID NO: 72); and (3) VL CDR3 comprises the amino acid sequence of LQYDEFPYT (SEQ ID NO: 64).

681. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of REERFVD (SEQ ID NO: 73); and (3) VL CDR3 comprises the amino acid sequence of LQYDEFPYT (SEQ ID NO: 64).

682. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RESRFVD (SEQ ID NO: 74); and (3) VL CDR3 comprises the amino acid sequence of LQYDEFPYT (SEQ ID NO: 64).

683. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RHVRFVD (SEQ ID NO: 75); and (3) VL CDR3 comprises the amino acid sequence of LQYDEFPYT (SEQ ID NO: 64).

684. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RHIRFVD (SEQ ID NO: 76); and (3) VL CDR3 comprises the amino acid sequence of LQYDEFPYT (SEQ ID NO: 64).

685. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RHERFVD (SEQ ID NO: 77); and (3) VL CDR3 comprises the amino acid sequence of LQYDEFPYT (SEQ ID NO: 64).

686. An antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of RASQDIHRYLS (SEQ ID NO: 79); (2) VL CDR2 comprises the amino acid sequence of RHSRFVD (SEQ ID NO: 78); and (3) VL CDR3 comprises the amino acid sequence of LQYDEFPYT (SEQ ID NO: 64).

687. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

688. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

689. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAEDTAMYYC (SEQ ID NO: 18); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

690. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

691. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

692. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRAEDTAMYYC (SEQ ID NO: 18); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

693. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

694. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRAEDTAMYYC (SEQ ID NO: 18); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

695. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

696. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAED-TAMYYC (SEQ ID NO: 18); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

697. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

698. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRSEDTAMYYC (SEQ ID NO: 14); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

699. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

700. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

701. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

702. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELSSLRSEDTAMYYC (SEQ ID NO: 14); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

703. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

704. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

705. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

706. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

707. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

708. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

709. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

710. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

711. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELSSLRSEDTAMYYC (SEQ ID NO: 26); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

712. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELRSLRSEDTAMYYC (SEQ ID NO: 27); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

713. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSM-STAYMELSSLRSEDTAVYYC (SEQ ID NO: 28); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

714. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELRSLRSEDTAMYYC (SEQ ID NO: 29); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

715. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

716. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

717. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRST-STAYMELSSLRSEDTAMYYC (SEQ ID NO: 26); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

718. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSM-STAYMELRSLRSEDTAMYYC (SEQ ID NO: 27); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

719. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSM-STAYMELSSLRSEDTAVYYC (SEQ ID NO: 28); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

720. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELRSLRSEDTAMYYC (SEQ ID NO: 29); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

721. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

722. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

723. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRSEDTAMYYC (SEQ ID NO: 32); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

724. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRSEDTAVYYC (SEQ ID NO: 33); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

725. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRSEDTAVYYC (SEQ ID NO: 34); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

726. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRSEDTAVYYC (SEQ ID NO: 35); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

727. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRSEDTAMYYC (SEQ ID NO: 32); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

728. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRSEDTAVYYC (SEQ ID NO: 33); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

729. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRSEDTAVYYC (SEQ ID NO: 34); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

730. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

731. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

732. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

733. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

734. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

735. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

736. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSM-STAYMELRSLRSEDTAMYYC (SEQ ID NO: 24); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

737. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRSEDTAVYYC (SEQ ID NO: 25); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

738. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSEDTAMYYC (SEQ ID NO: 22); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

739. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSEDTAMYYC (SEQ ID NO: 23); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

740. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRSEDTAMYYC (SEQ ID NO: 24); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

741. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRSEDTAVYYC (SEQ ID NO: 25); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

742. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELSSLRSEDTAMYYC (SEQ ID NO: 26); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

743. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRSEDTAMYYC (SEQ ID NO: 27); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

744. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELSSLRSEDTAVYYC (SEQ ID NO: 28); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

745. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSEDTAMYYC (SEQ ID NO: 29); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

746. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

747. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

748. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELSSLRSEDTAMYYC (SEQ ID NO: 26); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

749. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRSEDTAMYYC (SEQ ID NO: 27); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

750. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

751. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

752. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

753. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

754. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRSEDTAMYYC (SEQ ID NO: 32); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

755. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

756. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSM-STAYMELRSLRSEDTAVYYC (SEQ ID NO: 34); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

757. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRSEDTAVYYC (SEQ ID NO: 35); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

758. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRSEDTAMYYC (SEQ ID NO: 32); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

759. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELSSLRSEDTAVYYC (SEQ ID NO: 33); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

760. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRSEDTAVYYC (SEQ ID NO: 34); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

761. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRSEDTAVYYC (SEQ ID NO: 35); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

762. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

763. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

764. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAED-TAMYYC (SEQ ID NO: 18); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

765. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAMYYC (SEQ ID NO: 37); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

766. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAED-TAMYYC (SEQ ID NO: 38); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

767. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAMYYC (SEQ ID NO: 39); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

768. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAED-TAVYYC (SEQ ID NO: 40); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

769. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAMYYC (SEQ ID NO: 37); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO:

60); and VH CDR3 comprises the amino acid sequence of NAAYGSSSYPMDY (SEQ ID NO: 61).

770. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAED-TAMYYC (SEQ ID NO: 38); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

771. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAMYYC (SEQ ID NO: 39); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

772. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAED-TAVYYC (SEQ ID NO: 40); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

773. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAED-TAMYYC (SEQ ID NO: 41); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

774. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAED-TAMYYC (SEQ ID NO: 42); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

775. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAVYYC (SEQ ID NO: 43); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

776. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAED-TAMYYC (SEQ ID NO: 44); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

777. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

778. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAVYYC (SEQ ID NO: 46); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

779. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAED-TAMYYC (SEQ ID NO: 41); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

780. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAED-TAMYYC (SEQ ID NO: 42); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

781. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAVYYC (SEQ ID NO: 43); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

782. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAED-TAMYYC (SEQ ID NO: 44); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

783. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

784. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAVYYC (SEQ ID NO: 46); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

785. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAED-TAMYYC (SEQ ID NO: 47); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

786. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

787. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAED-TAVYYC (SEQ ID NO: 49); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

788. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

789. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAED-TAMYYC (SEQ ID NO: 47); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO:

60); and VH CDR3 comprises the amino acid sequence of NAAYGSSSYPMDY (SEQ ID NO: 61).

790. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

791. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAED-TAVYYC (SEQ ID NO: 49); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

792. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

793. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

794. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

795. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRSED-TAMYYC (SEQ ID NO: 14); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

796. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRSED-TAMYYC (SEQ ID NO: 22); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

797. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

798. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRSED-TAMYYC (SEQ ID NO: 24); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

799. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

800. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRSED-TAMYYC (SEQ ID NO: 22); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

801. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

802. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRSED-TAMYYC (SEQ ID NO: 24); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

803. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

804. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRSEDTAMYYC (SEQ ID NO: 26); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

805. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

806. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

807. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

808. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

809. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO:

60); and VH CDR3 comprises the amino acid sequence of NAAYGSSSYPMDY (SEQ ID NO: 61).

810. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRSEDTAMYYC (SEQ ID NO: 26); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

811. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

812. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

813. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

814. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

815. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

816. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRSED-TAMYYC (SEQ ID NO: 32); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

817. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

818. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRSED-TAVYYC (SEQ ID NO: 34); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

819. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

820. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRSED-TAMYYC (SEQ ID NO: 32); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

821. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

822. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRSED-TAVYYC (SEQ ID NO: 34); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

823. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

824. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

825. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

826. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRSEDTAMYYC (SEQ ID NO: 14); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

827. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELSSLRSEDTAMYYC (SEQ ID NO: 22); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

828. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELSSLRSEDTAMYYC (SEQ ID NO: 23); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

829. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELRSLRSEDTAMYYC (SEQ ID NO: 24); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

830. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

831. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

832. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRST-STAYMELSSLRSEDTAMYYC (SEQ ID NO: 23); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

833. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

834. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

835. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRST-STAYMELSSLRSEDTAMYYC (SEQ ID NO: 26); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

836. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

837. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRSEDTAVYYC (SEQ ID NO: 28); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

838. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

839. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRSEDTAVYYC (SEQ ID NO: 30); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

840. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

841. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRSEDTAMYYC (SEQ ID NO: 26); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

842. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

843. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELSSLRSEDTAVYYC (SEQ ID NO: 28); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

844. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELRSLRSEDTAMYYC (SEQ ID NO: 29); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

845. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

846. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

847. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRSEDTAMYYC (SEQ ID NO: 32); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

848. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELSSLRSEDTAVYYC (SEQ ID NO: 33); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

849. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELRSLRSEDTAVYYC (SEQ ID NO: 34); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

850. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

851. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRSEDTAMYYC (SEQ ID NO: 32); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

852. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRSEDTAVYYC (SEQ ID NO: 33); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

853. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRSEDTAVYYC (SEQ ID NO: 34); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

854. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

855. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

856. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

857. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

858. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELSSLRAEDTAMYYC (SEQ ID NO: 37); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

859. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELSSLRAEDTAMYYC (SEQ ID NO: 38); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

860. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

861. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELSSLRAEDTAVYYC (SEQ ID NO: 40); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

862. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELSSLRAEDTAMYYC (SEQ ID NO: 37); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

863. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

864. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRAEDTAMYYC (SEQ ID NO: 39); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

865. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

866. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

867. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

868. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

869. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

870. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELSSLRAEDTAVYYC (SEQ ID NO: 45); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

871. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELRSLRAEDTAVYYC (SEQ ID NO: 46); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

872. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRST-STAYMELSSLRAEDTAMYYC (SEQ ID NO: 41); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

873. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSM-STAYMELRSLRAEDTAMYYC (SEQ ID NO: 42); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

874. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSM-STAYMELSSLRAEDTAVYYC (SEQ ID NO: 43); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

875. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELRSLRAEDTAMYYC (SEQ ID NO: 44); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

876. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELSSLRAEDTAVYYC (SEQ ID NO: 45); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

877. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELRSLRAEDTAVYYC (SEQ ID NO: 46); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

878. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

879. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

880. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

881. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

882. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

883. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

884. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRAEDTAVYYC (SEQ ID NO: 49); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

885. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

886. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

887. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

888. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

889. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

890. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELSSLRSEDTAMYYC (SEQ ID NO: 23); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

891. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELRSLRSEDTAMYYC (SEQ ID NO: 24); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

892. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELSSLRSEDTAVYYC (SEQ ID NO: 25); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

893. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSM-STAYMELSSLRSEDTAMYYC (SEQ ID NO: 22); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

894. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELSSLRSEDTAMYYC (SEQ ID NO: 23); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

895. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELRSLRSEDTAMYYC (SEQ ID NO: 24); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

896. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELSSLRSEDTAVYYC (SEQ ID NO: 25); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

897. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRSEDTAMYYC (SEQ ID NO: 26); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

898. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRSEDTAMYYC (SEQ ID NO: 27); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

899. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELSSLRSEDTAVYYC (SEQ ID NO: 28); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

900. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRSEDTAMYYC (SEQ ID NO: 29); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

901. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

902. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

903. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRST-STAYMELSSLRSEDTAMYYC (SEQ ID NO: 26); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

904. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSM-STAYMELRSLRSEDTAMYYC (SEQ ID NO: 27); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

905. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSM-STAYMELSSLRSEDTAVYYC (SEQ ID NO: 28); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

906. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELRSLRSEDTAMYYC (SEQ ID NO: 29); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

907. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

908. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

909. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRST-STAYMELRSLRSEDTAMYYC (SEQ ID NO: 32); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

910. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

911. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRSEDTAVYYC (SEQ ID NO: 34); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

912. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

913. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSEDTAMYYC (SEQ ID NO: 32); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

914. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

915. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRSEDTAVYYC (SEQ ID NO: 34); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

916. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELRSLRSEDTAVYYC (SEQ ID NO: 35); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

917. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

918. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

919. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

920. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELSSLRAEDTAMYYC (SEQ ID NO: 37); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

921. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELSSLRAEDTAMYYC (SEQ ID NO: 38); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

922. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

923. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

924. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

925. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

926. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRAEDTAMYYC (SEQ ID NO: 39); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

927. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

928. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

929. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

930. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

931. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

932. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

933. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

934. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

935. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

936. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSM-STAYMELSSLRAEDTAVYYC (SEQ ID NO: 43); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

937. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRAEDTAMYYC (SEQ ID NO: 44); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

938. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELSSLRAEDTAVYYC (SEQ ID NO: 45); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

939. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRAEDTAVYYC (SEQ ID NO: 46); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

940. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

941. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

942. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

943. An antibody or an antigen-binding fragment thereof, comprising a VH that comprises four VH framework regions (VH FR1-4) and three VH complementarity determining regions (VH CDR1-3) in the following N-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

944. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRAEDTAMYYC (SEQ ID NO: 47); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

945. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

946. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRAEDTAVYYC (SEQ ID NO: 49); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

947. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

948. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

949. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

950. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

951. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

952. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

953. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

954. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

955. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

956. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRST-STAYMELSSLRSEDTAMYYC (SEQ ID NO: 23); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

957. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRSEDTAMYYC (SEQ ID NO: 24); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

958. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRSEDTAVYYC (SEQ ID NO: 25); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

959. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRSEDTAMYYC (SEQ ID NO: 26); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

960. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRSEDTAMYYC (SEQ ID NO: 27); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

961. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELSSLRSEDTAVYYC (SEQ ID NO: 28); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

962. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRSEDTAMYYC (SEQ ID NO: 29); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

963. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

964. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

965. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELSSLRSEDTAMYYC (SEQ ID NO: 26); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

966. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRSEDTAMYYC (SEQ ID NO: 27); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

967. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELSSLRSEDTAVYYC (SEQ ID NO: 28); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

968. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRSEDTAMYYC (SEQ ID NO: 29); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

969. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

970. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

971. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRSEDTAMYYC (SEQ ID NO: 32); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

972. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRSEDTAVYYC (SEQ ID NO: 33); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

973. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRSEDTAVYYC (SEQ ID NO: 34); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

974. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

975. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRSEDTAMYYC (SEQ ID NO: 32); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

976. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRST-STAYMELSSLRSEDTAVYYC (SEQ ID NO: 33); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

977. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRSEDTAVYYC (SEQ ID NO: 34); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

978. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRSEDTAVYYC (SEQ ID NO: 35); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

979. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

980. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRSEDTAVYYC (SEQ ID NO: 36); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

981. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAED-TAMYYC (SEQ ID NO: 18); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

982. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAMYYC (SEQ ID NO: 37); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

983. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAED-TAMYYC (SEQ ID NO: 38); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

984. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAMYYC (SEQ ID NO: 39); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

985. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAED-TAVYYC (SEQ ID NO: 40); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

986. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAMYYC (SEQ ID NO: 37); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

987. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAED-TAMYYC (SEQ ID NO: 38); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

988. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAMYYC (SEQ ID NO: 39); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

989. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELSSLRAED-TAVYYC (SEQ ID NO: 40); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO:

60); and VH CDR3 comprises the amino acid sequence of NAAYGSSSYPMDY (SEQ ID NO: 61).

990. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAED-TAMYYC (SEQ ID NO: 41); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

991. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAED-TAMYYC (SEQ ID NO: 42); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

992. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAVYYC (SEQ ID NO: 43); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

993. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAED-TAMYYC (SEQ ID NO: 44); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

994. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

995. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAVYYC (SEQ ID NO: 46); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

996. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAED-TAMYYC (SEQ ID NO: 41); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

997. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAED-TAMYYC (SEQ ID NO: 42); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

998. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELSSLRAED-TAVYYC (SEQ ID NO: 43); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

999. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAED-TAMYYC (SEQ ID NO: 44); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1000. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1001. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSMSTAYMELRSLRAED-TAVYYC (SEQ ID NO: 46); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1002. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAED-TAMYYC (SEQ ID NO: 47); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1003. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1004. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAEDTAVYYC (SEQ ID NO: 49); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1005. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1006. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAEDTAMYYC (SEQ ID NO: 47); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1007. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1008. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSMSTAYMELRSLRAEDTAVYYC (SEQ ID NO: 49); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1009. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO:

60); and VH CDR3 comprises the amino acid sequence of NAAYGSSSYPMDY (SEQ ID NO: 61).

1010. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1011. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQALEWMG (SEQ ID NO: 17); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1012. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSM-STAYMELSSLRAEDTAMYYC (SEQ ID NO: 18); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1013. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSM-STAYMELSSLRAEDTAMYYC (SEQ ID NO: 37); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1014. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRST-STAYMELSSLRAEDTAMYYC (SEQ ID NO: 38); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1015. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1016. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSM- STAYMELSSLRAEDTAVYYC (SEQ ID NO: 40); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1017. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELSSLRAEDTAMYYC (SEQ ID NO: 37); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1018. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELSSLRAEDTAMYYC (SEQ ID NO: 38); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1019. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1020. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRAEDTAVYYC (SEQ ID NO: 40); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1021. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELSSLRAEDTAMYYC (SEQ ID NO: 41); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1022. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELRSLRAEDTAMYYC (SEQ ID NO: 42); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1023. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1024. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1025. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1026. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1027. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1028. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1029. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1030. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1031. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1032. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1033. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRAEDTAMYYC (SEQ ID NO: 47); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1034. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1035. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRAEDTAVYYC (SEQ ID NO: 49); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1036. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1037. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1038. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1039. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1040. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1041. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRAEDTAVYYC (SEQ ID NO: 139); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1042. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRAEDTAVYYC (SEQ ID NO: 139); and VH FR4 comprises the amino acid sequence of WGQGTTVTVSS (SEQ ID NO: 15); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1043. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRSEDTAMYYC (SEQ ID NO: 14); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1044. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1045. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1046. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1047. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1048. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRSEDTAMYYC (SEQ ID NO: 22); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1049. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRSEDTAMYYC (SEQ ID NO: 23); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1050. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRSEDTAMYYC (SEQ ID NO: 24); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1051. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRSEDTAVYYC (SEQ ID NO: 25); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1052. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRSEDTAMYYC (SEQ ID NO: 26); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1053. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRSEDTAMYYC (SEQ ID NO: 27); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1054. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRSEDTAVYYC (SEQ ID NO: 28); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1055. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRSEDTAMYYC (SEQ ID NO: 29); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1056. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1057. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELRSLRSEDTAVYYC (SEQ ID NO: 31); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1058. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELSSLRSEDTAMYYC (SEQ ID NO: 26); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1059. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELRSLRSEDTAMYYC (SEQ ID NO: 27); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1060. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELSSLRSEDTAVYYC (SEQ ID NO: 28); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1061. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELRSLRSEDTAMYYC (SEQ ID NO: 29); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1062. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELSSLRSEDTAVYYC (SEQ ID NO: 30); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1063. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRSEDTAVYYC (SEQ ID NO: 31); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1064. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRSEDTAMYYC (SEQ ID NO: 32); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1065. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1066. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRSEDTAVYYC (SEQ ID NO: 34); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1067. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1068. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRSEDTAMYYC (SEQ ID NO: 32); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1069. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRSEDTAVYYC (SEQ ID NO: 33); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1070. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRSEDTAVYYC (SEQ ID NO: 34); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1071. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRSEDTAVYYC (SEQ ID NO: 35); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1072. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1073. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELRSLRSEDTAVYYC (SEQ ID NO: 36); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1074. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELSSLRAEDTAMYYC (SEQ ID NO: 18); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1075. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1076. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELSSLRAEDTAMYYC (SEQ ID NO: 38); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1077. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1078. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELSSLRAEDTAVYYC (SEQ ID NO: 40); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1079. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSM-STAYMELSSLRAEDTAMYYC (SEQ ID NO: 37); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1080. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRST-STAYMELSSLRAEDTAMYYC (SEQ ID NO: 38); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1081. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1082. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSM-STAYMELSSLRAEDTAVYYC (SEQ ID NO: 40); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1083. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRAEDTAMYYC (SEQ ID NO: 41); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1084. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRAEDTAMYYC (SEQ ID NO: 42); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1085. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELSSLRAEDTAVYYC (SEQ ID NO: 43); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1086. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRAEDTAMYYC (SEQ ID NO: 44); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1087. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELSSLRAEDTAVYYC (SEQ ID NO: 45); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1088. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRSM-STAYMELRSLRAEDTAVYYC (SEQ ID NO: 46); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1089. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRAEDTAMYYC (SEQ ID NO: 41); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1090. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1091. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1092. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1093. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1094. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1095. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRAEDTAMYYC (SEQ ID NO: 47); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1096. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1097. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1098. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1099. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1100. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1101. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1102. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKA-LEWMG (SEQ ID NO: 13); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1103. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1104. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKALEWMG (SEQ ID NO: 13); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1105. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRAEDTAMYYC (SEQ ID NO: 18); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1106. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1107. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1108. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRAEDTAMYYC (SEQ ID NO: 39); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1109. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1110. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1111. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1112. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELRSLRAEDTAMYYC (SEQ ID NO: 39); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1113. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1114. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1115. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1116. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSM-STAYMELSSLRAEDTAVYYC (SEQ ID NO: 43); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1117. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRAEDTAMYYC (SEQ ID NO: 44); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1118. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRAEDTAVYYC (SEQ ID NO: 45); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1119. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRAEDTAVYYC (SEQ ID NO: 46); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1120. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELSSLRAEDTAMYYC (SEQ ID NO: 41); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1121. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRAEDTAMYYC (SEQ ID NO: 42); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1122. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELSSLRAEDTAVYYC (SEQ ID NO: 43); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1123. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRAEDTAMYYC (SEQ ID NO: 44); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1124. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELSSLRAEDTAVYYC (SEQ ID NO: 45); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1125. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRSM-STAYMELRSLRAEDTAVYYC (SEQ ID NO: 46); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1126. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1127. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1128. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1129. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQ-GLEWMG (SEQ ID NO: 16); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1130. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRAEDTAMYYC (SEQ ID NO: 47); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1131. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELSSLRAEDTAVYYC (SEQ ID NO: 48); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1132. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSMSTAYMELRSLRAEDTAVYYC (SEQ ID NO: 49); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1133. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQDRVTITRDRSTSTAYMELRSLRAEDTAVYYC (SEQ ID NO: 50); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1134. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1135. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGQGLEWMG (SEQ ID NO: 16); VH FR3 comprises the amino acid sequence of YAQKFQGRVTITRDRSTSTAYMELRSLRAEDTAVYYC (SEQ ID NO: 139); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1136. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRAEDTAMYYC (SEQ ID NO: 18); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1137. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1138. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1139. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRAEDTAMYYC (SEQ ID NO: 39); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1140. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELSSLRAEDTAVYYC (SEQ ID NO: 40); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1141. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAMYYC (SEQ ID NO: 37); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1142. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRAEDTAMYYC (SEQ ID NO: 38); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1143. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELRSLRAEDTAMYYC (SEQ ID NO: 39); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1144. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRAEDTAVYYC (SEQ ID NO: 40); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1145. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELSSLRAEDTAMYYC (SEQ ID NO: 41); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1146. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELRSLRAEDTAMYYC (SEQ ID NO: 42); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1147. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRSM-STAYMELSSLRAEDTAVYYC (SEQ ID NO: 43); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1148. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELRSLRAEDTAMYYC (SEQ ID NO: 44); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1149. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELSSLRAEDTAVYYC (SEQ ID NO: 45); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1150. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSMSTAYMELRSLRAEDTAVYYC (SEQ ID NO: 46); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1151. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSTSTAYMELSSLRAEDTAMYYC (SEQ ID NO: 41); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1152. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELRSLRAEDTAMYYC (SEQ ID NO: 42); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1153. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQGRVTITRDRSMSTAYMELSSLRAEDTAVYYC (SEQ ID NO: 43); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1154. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELRSLRAEDTAMYYC (SEQ ID NO: 44); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1155. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSTSTAYMELSSLRAEDTAVYYC (SEQ ID NO: 45); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1156. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGKGLEWMG (SEQ ID NO: 20); VH FR3 comprises the amino acid sequence of YAQKFQDRVTITRDRSM-STAYMELRSLRAEDTAVYYC (SEQ ID NO: 46); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1157. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1158. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1159. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1160. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKTGSSVKVSCKAS (SEQ ID NO: 12), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1161. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRAEDTAMYYC (SEQ ID NO: 47); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1162. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of $X_{H1}$QMQLVQSGAEVKKPGSSVKVSCKAS (SEQ ID NO: 21), wherein $X_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELSSLRAEDTAVYYC (SEQ ID NO: 48); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1163. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRSM-STAYMELRSLRAEDTAVYYC (SEQ ID NO: 49); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1164. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQDRVTITRDRST-STAYMELRSLRAEDTAVYYC (SEQ ID NO: 50); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1165. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKTGSSVKVSCKAS (SEQ ID NO: 12), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRAEDTAVYYC (SEQ ID NO: 139); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1166. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence of X$_{H1}$QMQLVQSGAEVKKPGSSVKVSCKAS (SEQ ID NO: 21), wherein X$_{H1}$ is M or no amino acid; VH FR2 comprises the amino acid sequence of WVRQAPGK-GLEWMG (SEQ ID NO: 20); VH FR3 comprises the amino acid sequence of YAQKFQGRVTITRDRST-STAYMELRSLRAEDTAVYYC (SEQ ID NO: 139); and VH FR4 comprises the amino acid sequence of WGQGTLVTVSS (SEQ ID NO: 19); VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61).

1167. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1168. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1169. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1170. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1171. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1172. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1173. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1174. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1175. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1176. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1177. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1178. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1179. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1180. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1181. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1182. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1183. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1184. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1185. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1186. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1187. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1188. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1189. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1190. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1191. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1192. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1193. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1194. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1195. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1196. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1197. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1198. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1199. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1200. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1201. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1202. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1203. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1204. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1205. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1206. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1207. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1208. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1209. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1210. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1211. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1212. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1213. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1214. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1215. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1216. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1217. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1218. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1219. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1220. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1221. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1222. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1223. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1224. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1225. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1226. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1227. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1228. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1229. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1230. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1231. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1232. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1233. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1234. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1235. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1236. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1237. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1238. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1239. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1240. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1241. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1242. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1243. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1244. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1245. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1246. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1247. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1248. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1249. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1250. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1251. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1252. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1253. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1254. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1255. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1256. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1257. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1258. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1259. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1260. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1261. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1262. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1263. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1264. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1265. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1266. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1267. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1268. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1269. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1270. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1271. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1272. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1273. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1274. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1275. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1276. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1277. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1278. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1279. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1280. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1281. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1282. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1283. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1284. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1285. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1286. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1287. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1288. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1289. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1290. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1291. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1292. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1293. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1294. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1295. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1296. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1297. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1298. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1299. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1300. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1301. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1302. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1303. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1304. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1305. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1306. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1307. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1308. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1309. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1310. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1311. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1312. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1313. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1314. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1315. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1316. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1317. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1318. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1319. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1320. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1321. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1322. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1323. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1324. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1325. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1326. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1327. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1328. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1329. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1330. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1331. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1332. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1333. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1334. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1335. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1336. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1337. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1338. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1339. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1340. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1341. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1342. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1343. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1344. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1345. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1346. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1347. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1348. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1349. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1350. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1351. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1352. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1353. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1354. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1355. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1356. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1357. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1358. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1359. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1360. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1361. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1362. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1363. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1364. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1365. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1366. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1367. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1368. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1369. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1370. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1371. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1372. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1373. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1374. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1375. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1376. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1377. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1378. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1379. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1380. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1381. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1382. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1383. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1384. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1385. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1386. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1387. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1388. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1389. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1390. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1391. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1392. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1393. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1394. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1395. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1396. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1397. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1398. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1399. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1400. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1401. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1402. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66);

VL CDR2 comprises the amino acid sequence of RYVRFVD (SEQ ID NO: 67); and VL CDR3 comprises the amino acid sequence of LQYDEFPYT (SEQ ID NO: 64).

1403. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1404. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1405. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1406. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1407. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1408. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1409. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1410. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1411. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1412. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1413. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1414. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1415. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1416. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1417. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79);

VL CDR2 comprises the amino acid sequence of RYERFVD (SEQ ID NO: 69); and VL CDR3 comprises the amino acid sequence of LQYDEFPYT (SEQ ID NO: 64).

1418. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1419. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1420. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1421. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1422. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1423. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1424. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1425. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1426. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1427. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1428. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1429. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1430. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1431. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1432. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66);

1433. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1434. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1435. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1436. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1437. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1438. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1439. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1440. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1441. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1442. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1443. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1444. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1445. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1446. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1447. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79);

VL CDR2 comprises the amino acid sequence of REERFVD (SEQ ID NO: 73); and VL CDR3 comprises the amino acid sequence of LQYDEFPYT (SEQ ID NO: 64).

1448. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1449. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1450. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1451. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1452. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1453. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1454. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1455. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1456. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1457. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1458. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1459. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1460. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1461. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1462. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66);

VL CDR2 comprises the amino acid sequence of RHVRFVD (SEQ ID NO: 75); and VL CDR3 comprises the amino acid sequence of LQYDEFPYT (SEQ ID NO: 64).

1463. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1464. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1465. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1466. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1467. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1468. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1469. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1470. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1471. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1472. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1473. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1474. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1475. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1476. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1477. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79);

VL CDR2 comprises the amino acid sequence of RHER-FVD (SEQ ID NO: 77); and VL CDR3 comprises the amino acid sequence of LQYDEFPYT (SEQ ID NO: 64).

1478. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1479. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1480. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1481. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1482. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1483. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1484. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1485. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1486. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1487. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1488. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1489. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1490. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1491. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1492. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79);

VL CDR2 comprises the amino acid sequence of RANRLVS (SEQ ID NO: 63); and VL CDR3 comprises the amino acid sequence of LQYDEFPYT (SEQ ID NO: 64).

1493. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1494. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1495. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1496. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1497. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1498. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1499. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1500. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1501. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1502. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1503. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1504. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1505. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1506. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1507. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66);

VL CDR2 comprises the amino acid sequence of RYIRFVD (SEQ ID NO: 68); and VL CDR3 comprises the amino acid sequence of LQYDEFPYT (SEQ ID NO: 64).

1508. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1509. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1510. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1511. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1512. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1513. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1514. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1515. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1516. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1517. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1518. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1519. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1520. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1521. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1522. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79);

VL CDR2 comprises the amino acid sequence of RYSRFVD (SEQ ID NO: 70); and VL CDR3 comprises the amino acid sequence of LQYDEFPYT (SEQ ID NO: 64).

1523. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1524. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1525. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1526. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1527. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1528. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1529. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1530. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1531. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1532. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1533. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1534. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1535. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1536. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1537. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66);

VL CDR2 comprises the amino acid sequence of REIRFVD (SEQ ID NO: 72); and VL CDR3 comprises the amino acid sequence of LQYDEFPYT (SEQ ID NO: 64).

1538. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1539. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1540. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1541. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1542. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1543. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1544. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1545. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1546. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1547. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1548. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1549. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1550. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1551. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1552. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79);

VL CDR2 comprises the amino acid sequence of RESRFVD (SEQ ID NO: 74); and VL CDR3 comprises the amino acid sequence of LQYDEFPYT (SEQ ID NO: 64).

1553. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1554. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1555. The antibody or antigen-binding fragment of any of embodiments 687-1166, further comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1556. The antibody or antigen-binding fragment of any of embodiments 687-1166, further comprising a VL that comprises four VL framework regions (VL FR1-4) and three VL order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1557. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1558. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1559. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1560. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1561. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1562. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1563. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1564. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1565. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1566. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1567. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66);

VL CDR2 comprises the amino acid sequence of RHIRFVD (SEQ ID NO: 76); and VL CDR3 comprises the amino acid sequence of LQYDEFPYT (SEQ ID NO: 64).

1568. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1569. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1570. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1571. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1572. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1573. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1574. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1575. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1576. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1577. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1578. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1579. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1580. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1581. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1582. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1583. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1584. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1585. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1586. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1587. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1588. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1589. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1590. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1591. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1592. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1593. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1594. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1595. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1596. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1597. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1598. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1599. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1600. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1601. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1602. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1603. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1604. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1605. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1606. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1607. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1608. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1609. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1610. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1611. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1612. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1613. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1614. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1615. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1616. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1617. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1618. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1619. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1620. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1621. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1622. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1623. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1624. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1625. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1626. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1627. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1628. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1629. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1630. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1631. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1632. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1633. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1634. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1635. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1636. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1637. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1638. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1639. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1640. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1641. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1642. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1643. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1644. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1645. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1646. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1647. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1648. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1649. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1650. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1651. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1652. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1653. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1654. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1655. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1656. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1657. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1658. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1659. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1660. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1661. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1662. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1663. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1664. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1665. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1666. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1667. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1668. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1669. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1670. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1671. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1672. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1673. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1674. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1675. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1676. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1677. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1678. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1679. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1680. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1681. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1682. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1683. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1684. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1685. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1686. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1687. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1688. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1689. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1690. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1691. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1692. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1693. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1694. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1695. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1696. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1697. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1698. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1699. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1700. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1701. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1702. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1703. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1704. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1705. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1706. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1707. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1708. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1709. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1710. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1711. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1712. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKVPKHLIY (SEQ ID NO: 52); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1713. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1714. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1715. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1716. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1717. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1718. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1719. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1720. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1721. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1722. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1723. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1724. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1725. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1726. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1727. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1728. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1729. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1730. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1731. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1732. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1733. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1734. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1735. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1736. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1737. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1738. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1739. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1740. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1741. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1742. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1743. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1744. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1745. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1746. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1747. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1748. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1749. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1750. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1751. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1752. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1753. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1754. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1755. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1756. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1757. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1758. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1759. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1760. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1761. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1762. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1763. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1764. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSMSASVGDRVTITC (SEQ ID NO: 53); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1765. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1766. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1767. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1768. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1769. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1770. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1771. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1772. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1773. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1774. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1775. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1776. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1777. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1778. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1779. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1780. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1781. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1782. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1783. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1784. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1785. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1786. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1787. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1788. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1789. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1790. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1791. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1792. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1793. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1794. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1795. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1796. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1797. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1798. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1799. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1800. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1801. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1802. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1803. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1804. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1805. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1806. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1807. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1808. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1809. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1810. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1811. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1812. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1813. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1814. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1815. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1816. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1817. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1818. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1819. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1820. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1821. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1822. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1823. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1824. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1825. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1826. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1827. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1828. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1829. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1830. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1831. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1832. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1833. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1834. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1835. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1836. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1837. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1838. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1839. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1840. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1841. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1842. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSAMSASVGDRVTITC (SEQ ID NO: 51); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1843. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1844. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1845. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1846. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1847. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1848. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1849. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1850. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1851. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1852. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1853. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1854. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1855. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1856. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1857. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1858. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1859. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1860. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1861. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1862. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1863. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1864. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1865. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1866. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1867. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1868. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKVPKHLIY (SEQ ID NO: 55); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1869. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1870. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1871. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1872. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1873. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1874. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1875. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1876. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1877. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1878. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1879. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1880. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1881. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1882. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1883. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1884. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1885. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1886. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1887. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1888. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1889. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1890. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1891. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1892. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1893. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1894. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WFQQKPGKAPKHLIY (SEQ ID NO: 56); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1895. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1896. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1897. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1898. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1899. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1900. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1901. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1902. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1903. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1904. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1905. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1906. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1907. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1908. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1909. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1910. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1911. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1912. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1913. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1914. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1915. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1916. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1917. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1918. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1919. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1920. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSALSASVGDRVTITC (SEQ ID NO: 54); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1921. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RANRLVS (SEQ ID NO: 63); and VL CDR3 comprises the amino acid sequence of LQYDEFPYT (SEQ ID NO: 64).

1922. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYVRFVD (SEQ ID NO: 67); and VL CDR3 comprises the amino acid sequence of LQYDEFPYT (SEQ ID NO: 64).

1923. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYIRFVD (SEQ ID NO: 68); and VL CDR3 comprises the amino acid sequence of LQYDEFPYT (SEQ ID NO: 64).

1924. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYERFVD (SEQ ID NO: 69); and VL CDR3 comprises the amino acid sequence of LQYDEFPYT (SEQ ID NO: 64).

1925. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RYSRFVD (SEQ ID NO: 70); and VL CDR3 comprises the amino acid sequence of LQYDEFPYT (SEQ ID NO: 64).

1926. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REVRFVD (SEQ ID NO: 71); and VL CDR3 comprises the amino acid sequence of LQYDEFPYT (SEQ ID NO: 64).

1927. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REIRFVD (SEQ ID NO: 72); and VL CDR3 comprises the amino acid sequence of LQYDEFPYT (SEQ ID NO: 64).

1928. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of REERFVD (SEQ ID NO: 73); and VL CDR3 comprises the amino acid sequence of LQYDEFPYT (SEQ ID NO: 64).

1929. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RESRFVD (SEQ ID NO: 74); and VL CDR3 comprises the amino acid sequence of LQYDEFPYT (SEQ ID NO: 64).

1930. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHVRFVD (SEQ ID NO: 75); and VL CDR3 comprises the amino acid sequence of LQYDEFPYT (SEQ ID NO: 64).

1931. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHIRFVD (SEQ ID NO: 76); and VL CDR3 comprises the amino acid sequence of LQYDEFPYT (SEQ ID NO: 64).

1932. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHERFVD (SEQ ID NO: 77); and VL CDR3 comprises the amino acid sequence of LQYDEFPYT (SEQ ID NO: 64).

1933. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of KASQDIHRYLS (SEQ ID NO: 66); VL CDR2 comprises the amino acid sequence of RHSRFVD (SEQ ID NO: 78); and VL CDR3 comprises the amino acid sequence of LQYDEFPYT (SEQ ID NO: 64).

1934. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RANRLVS (SEQ ID NO: 63); and VL CDR3 comprises the amino acid sequence of LQYDEFPYT (SEQ ID NO: 64).

1935. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYVRFVD (SEQ ID NO: 67); and VL CDR3 comprises the amino acid sequence of LQYDEFPYT (SEQ ID NO: 64).

1936. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYIRFVD (SEQ ID NO: 68); and VL CDR3 comprises the amino acid sequence of LQYDEFPYT (SEQ ID NO: 64).

1937. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYERFVD (SEQ ID NO: 69); and VL CDR3 comprises the amino acid sequence of LQYDEFPYT (SEQ ID NO: 64).

1938. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RYSRFVD (SEQ ID NO: 70); and VL CDR3 comprises the amino acid sequence of LQYDEFPYT (SEQ ID NO: 64).

1939. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REVRFVD (SEQ ID NO: 71); and VL CDR3 comprises the amino acid sequence of LQYDEFPYT (SEQ ID NO: 64).

1940. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REIRFVD (SEQ ID NO: 72); and VL CDR3 comprises the amino acid sequence of LQYDEFPYT (SEQ ID NO: 64).

1941. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of REERFVD (SEQ ID NO: 73); and VL CDR3 comprises the amino acid sequence of LQYDEFPYT (SEQ ID NO: 64).

1942. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RESRFVD (SEQ ID NO: 74); and VL CDR3 comprises the amino acid sequence of LQYDEFPYT (SEQ ID NO: 64).

1943. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHVRFVD (SEQ ID NO: 75); and VL CDR3 comprises the amino acid sequence of LQYDEFPYT (SEQ ID NO: 64).

1944. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHIRFVD (SEQ ID NO: 76); and VL CDR3 comprises the amino acid sequence of LQYDEFPYT (SEQ ID NO: 64).

1945. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHERFVD (SEQ ID NO: 77); and VL CDR3 comprises the amino acid sequence of LQYDEFPYT (SEQ ID NO: 64).

1946. An antibody or an antigen-binding fragment thereof, which specifically binds to CD47, comprising a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence of NIQMTQSPSSLSASVGDRVTITC (SEQ ID NO: 57); VL FR2 comprises the amino acid sequence of WYQQKPGKAPKHLIY (SEQ ID NO: 58); VL FR3 comprises the amino acid sequence of GVPSRFSGSGSGTEFTLTISSLQPEDFATYYC (SEQ ID NO: 10); and VL FR4 comprises the amino acid sequence of FGGGTKVEIK (SEQ ID NO: 11); VL CDR1 comprises the amino acid sequence of RASQDIHRYLS (SEQ ID NO: 79); VL CDR2 comprises the amino acid sequence of RHSRFVD (SEQ ID NO: 78); and VL CDR3 comprises the amino acid sequence of LQYDEFPYT (SEQ ID NO: 64).

1947. The antibody or antigen-binding fragment of any of embodiments 1-1946, which comprises a heavy chain constant region.

1948. The antibody or antigen-binding fragment of embodiment 1947, wherein the heavy chain constant region is a human constant region.

1949. The antibody or antigen-binding fragment of embodiment 1947, wherein the heavy chain constant region is a human IgG constant region.

1950. The antibody or antigen-binding fragment of embodiment 1947, wherein the heavy chain constant region is a human IgG1 constant region.

1951. The antibody or antigen-binding fragment of embodiment 1947, wherein the heavy chain constant region is a human IgG4 constant region.

1952. The antibody or antigen-binding fragment of embodiment 1947, wherein the heavy chain constant region is a human IgG4 constant region comprising a S228P amino acid substitution according to the EU numbering index.

1953. The antibody or antigen-binding fragment of embodiment 1947, wherein the heavy chain constant region is a human IgG4 constant region comprising a S228P and L235E amino acid substitutions according to the EU numbering index.

1954. The antibody or antigen-binding fragment of any of embodiments 1-1953, which comprises a light chain constant region selected from the group consisting of a human kappa constant region and a human lambda constant region.

1955. The antibody or antigen-binding fragment of any of embodiments 1-1946, wherein the antigen-binding fragment is an Fv, Fab, F(ab')$_2$, Fab', dsFv, scFv, or sc(Fv)$_2$. 1956. The antibody or antigen-binding fragment of any of embodiments 1-1955, wherein the antibody is a human antibody, a humanized antibody, a chimeric antibody, a recombinant antibody, a multispecific antibody, or an antigen-binding fragment thereof.

1957. The antibody or antigen-binding fragment of any of embodiments 1-1956, wherein the antibody is a monoclonal antibody or antigen-binding fragment thereof.

1958. The antibody or antigen-binding fragment of any of embodiments 1-1957, wherein the antibody or antigen-binding fragment thereof is an antibody.

1959. The antibody or antigen-binding fragment of any of embodiments 1-1958, which is conjugated to an agent.

1960. The antibody or antigen-binding fragment of embodiment 1959, wherein the agent is a label or a toxin.

1961. A pharmaceutical composition comprising a therapeutically effective amount of the antibody or antigen-binding fragment of any of embodiments 1-1960, and a pharmaceutically acceptable carrier.

1962. A polynucleotide comprising a nucleotide sequence encoding the antibody or antigen-binding fragment of any of embodiments 1-1960.

1963. A vector comprising the polynucleotide of embodiment 1962.

1964. A method of treating cancer in a subject in need thereof, the method comprising administering to the subject the antibody or antigen-binding fragment of any of embodiments 1-1960 or the pharmaceutical composition of embodiment 1961.

1965. A method of alleviating a symptom of a cancer in a subject in need thereof, the method comprising administering to the subject the antibody or antigen-binding fragment of any of embodiments 1-1960 or the pharmaceutical composition of embodiment 1961.

1966. The method of embodiment 1964 or 1965, further comprising administering to the subject radiotherapy or chemotherapy.

1967. The method of any of embodiments 1964-1966, further comprising administering to the subject another anti-cancer agent.

1968. The method of any of embodiments 1964-1967, wherein the cancer is a hematological cancer.

1969. The method of any of embodiments 1964-1967, wherein the cancer is a solid cancer.

1970. The method of any of embodiments 1964-1967, wherein the cancer is multiple myeloma, non-Hodgkin's lymphoma, acute myeloid leukemia (AML), breast cancer, bladder cancer, non-small cell lung cancer/carcinoma, hepatocellular carcinoma (HCC), sarcoma, or head and neck cancer.

1971. An isolated cell comprising the polynucleotide of embodiment 1962.

1972. An isolated cell comprising the vector of embodiment 1963.

1973. An isolated cell producing the antibody or antigen-binding fragment of any of embodiments 1-1960.

1974. A method of making an antibody or antigen-binding fragment thereof, comprising (a) culturing an isolated cell comprising the polynucleotide of embodiment 1962; and (b) isolating the antibody or antigen-binding fragment thereof.

1975. A method of making an antibody or antigen-binding fragment thereof, comprising (a) culturing an isolated cell of any of embodiments 1971-1973; and (b) isolating the antibody or antigen-binding fragment thereof.

4. BRIEF DESCRIPTION OF THE FIGURES

FIG. 1. Median staining of the matrixed variant transient transfection. At saturating conditions, all samples demonstrate binding to CD47 on CCRF CEM cells at equivalent or greater levels than the Ab$_{Parental}$ antibody. Samples with titers below 10 µg/mL, or the parental antibody CDR's grafted into the Herceptin LC frameworks (denoted by "Traz" or "50" (HC) and "56" (LC)-previously shown to be functionally compromised); and the LC's designated as Ab486, Ab495 and HC Ab170 appear to indicate some compromise in functionality. However, LC Ab486 was tested twice; thus demonstrating the unreliability of cell binding data at saturation. Therefore, only those molecules with the greatest in silico improvement in immunogenicity were purified (see FIG. 2).

Figure 2:
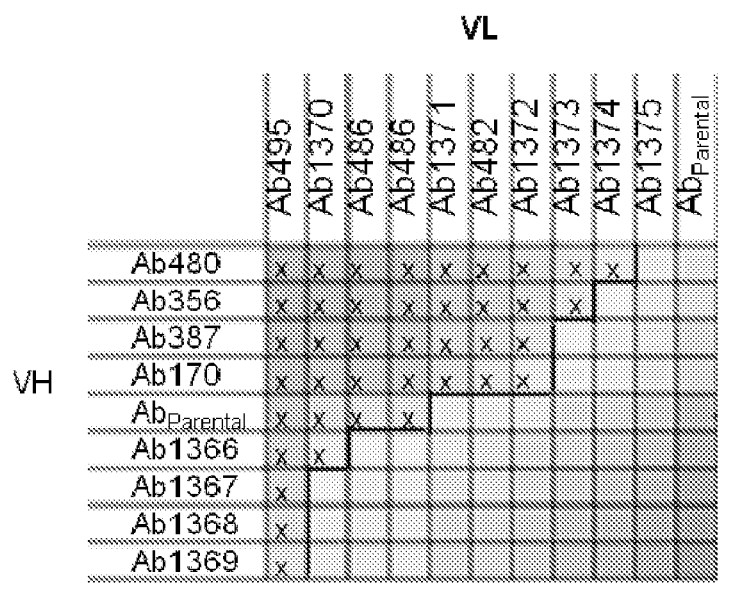

FIG. 2. In silico immunogenicity heat map: VH and VL combinations are shaded (predicted lower immunogenicity) and pairs marked with an "x" were prioritized for purification.

Figure 3:
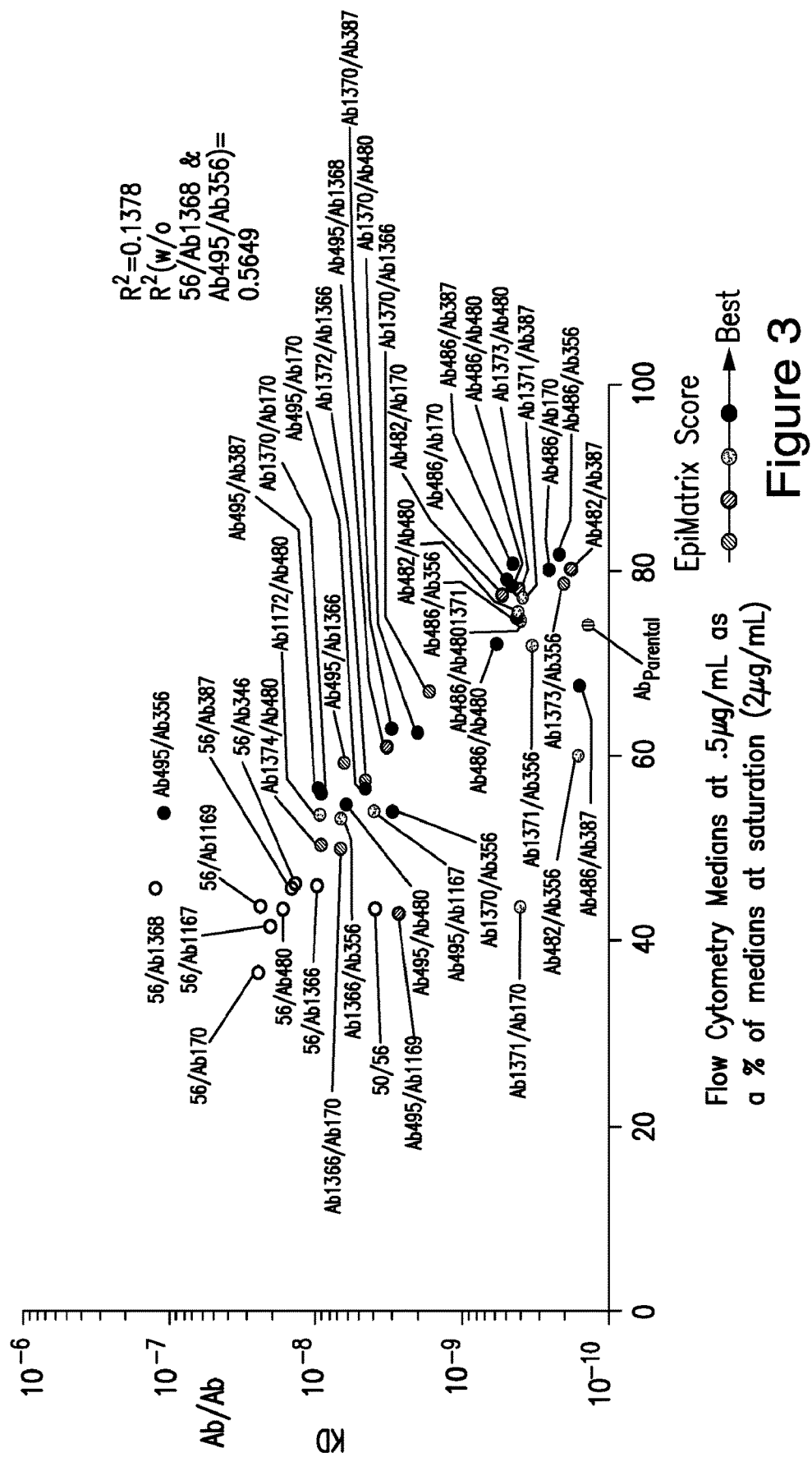

FIG. 3. Antibodies in FIG. 2 were compared using cell binding and K$_D$'s and EpiMatrix scores.

Figure 4:
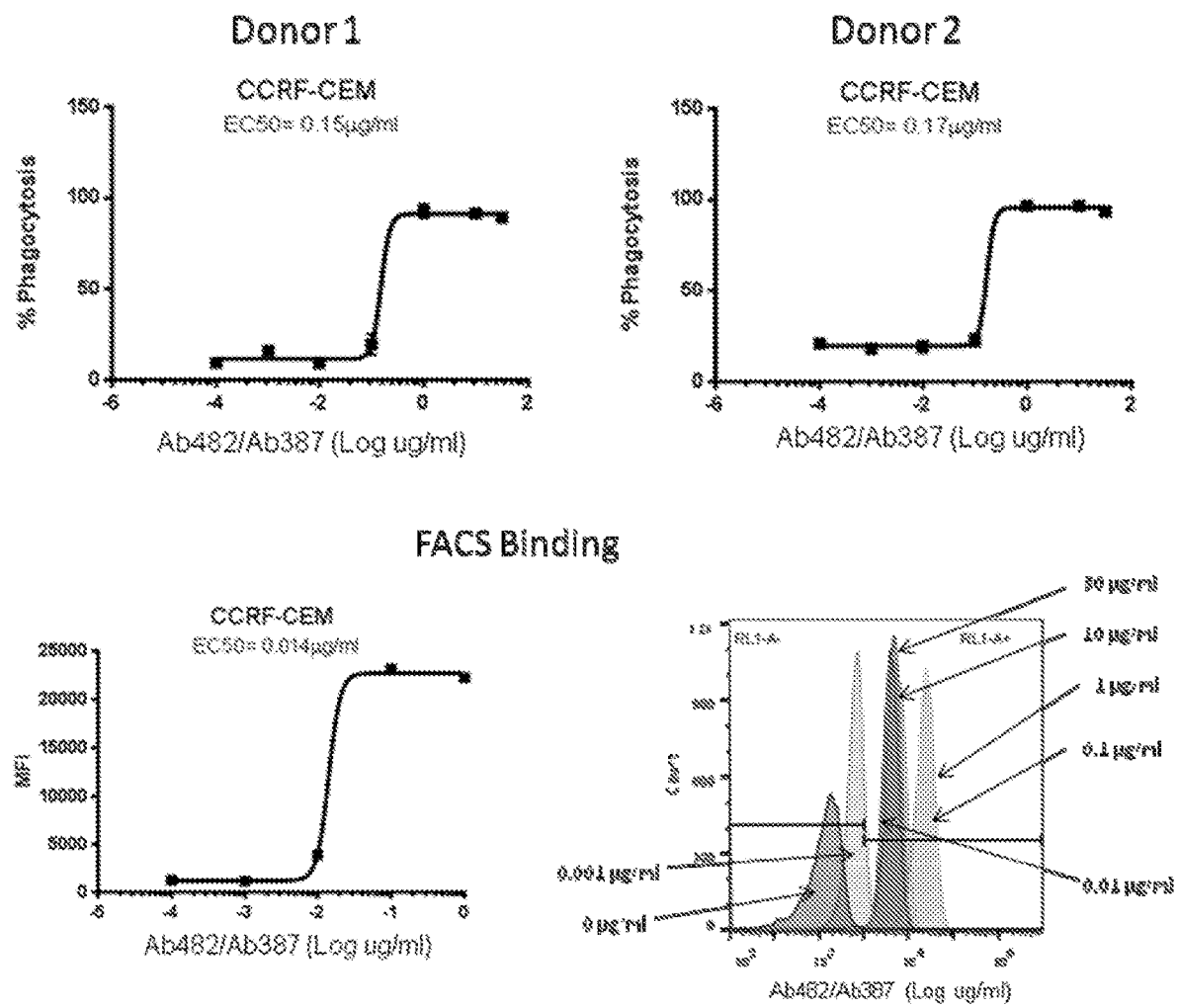

FIG. 4. Cell binding data of a representative antibody.

Figure 5:
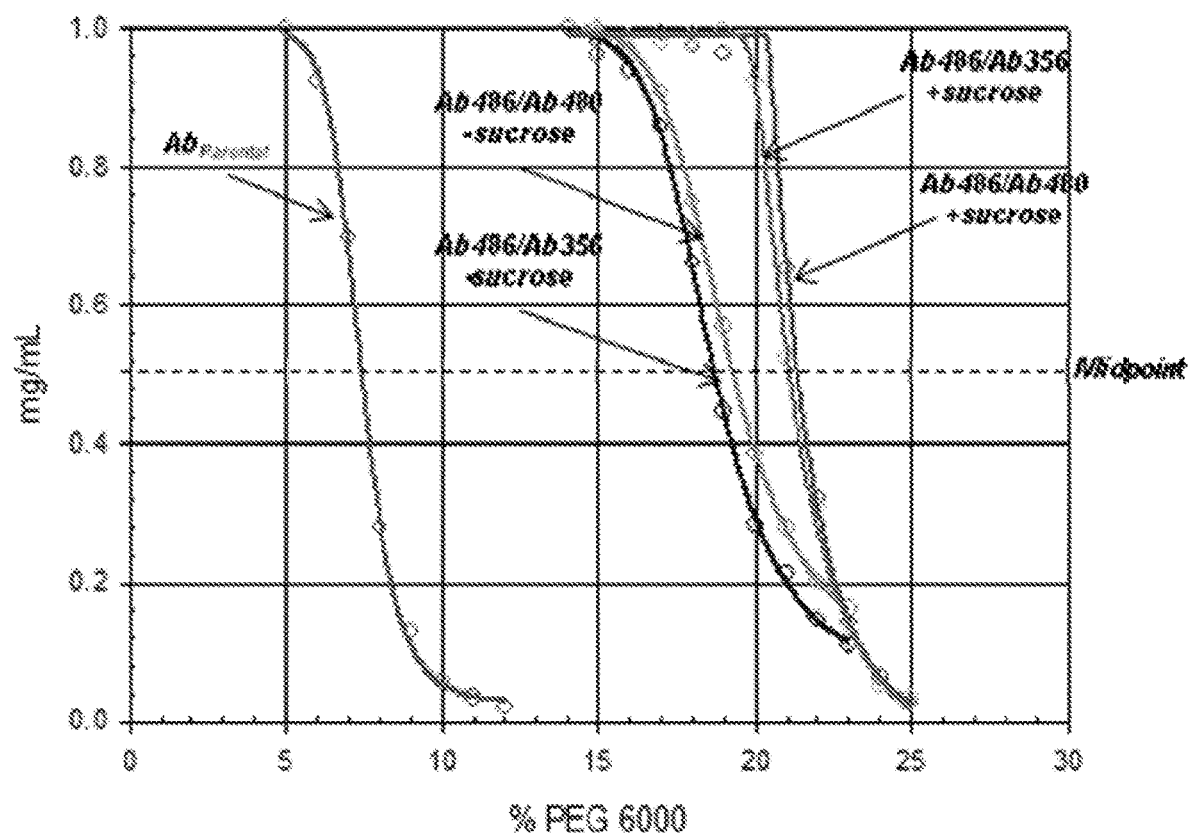

FIG. 5. Solubility assessment of representative antibodies in the absence and presence of sucrose.

Figure 6:
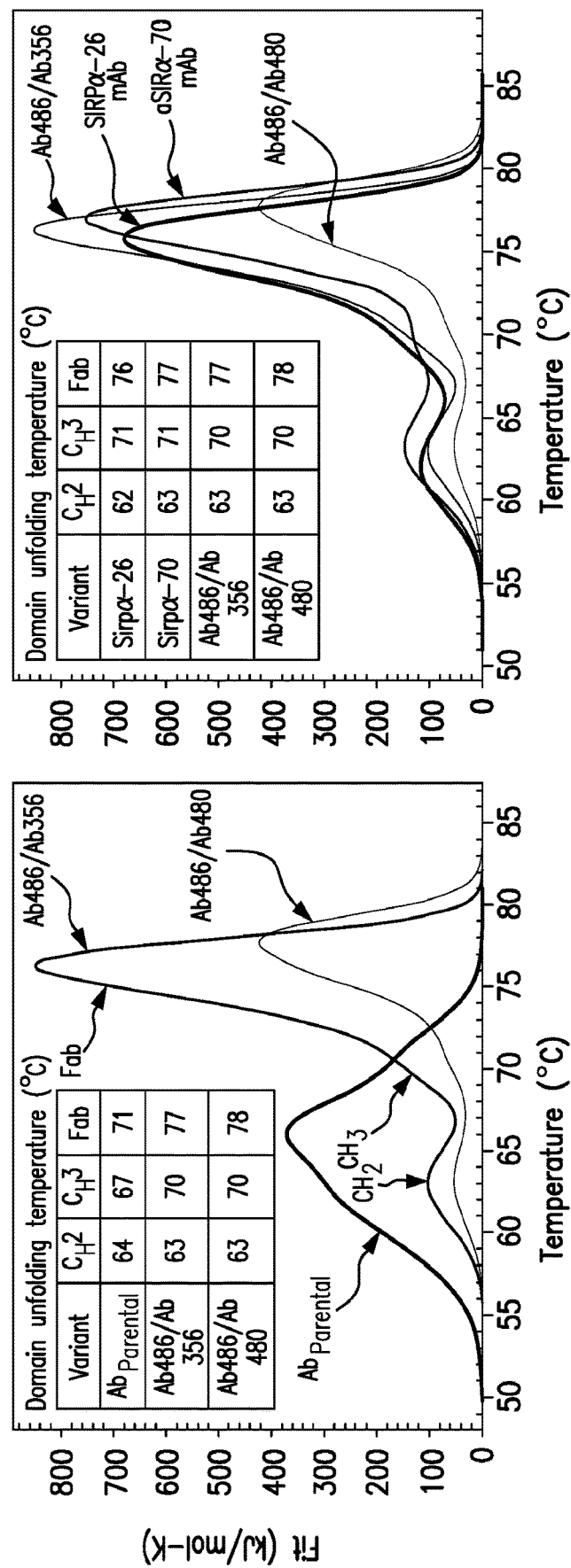

FIG. 6. Stability assessment of representative antibodies. Curves show melting peaks of the CH$_2$, CH$_3$ and Fab regions as indicated.

Figure 7:
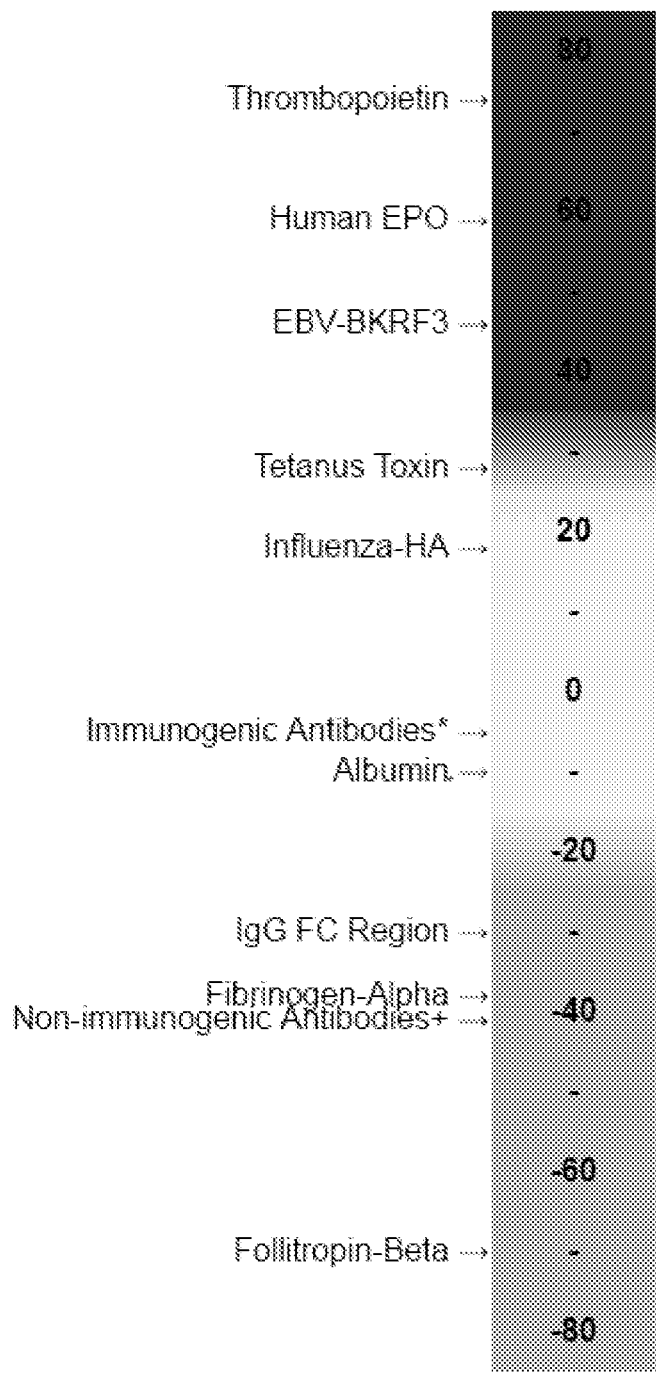

FIG. 7. EpiMatrix Epx score scale.

5. DETAILED DESCRIPTION

Provided herein are antibodies and antigen-binding fragments thereof with low or no immunogenicity in humans additional desirable characteristics, e.g., manufacturing, storage and formulation properties (e.g., high solubility, high stability, and/or high expression levels). In various aspects, the antibodies and antigen-binding fragments provided herein also have desirable antigen-binding affinities. Also provided are compositions comprising such antibodies, methods of using such antibodies, and methods for making such antibodies.

Immunogenicity

In various aspects, the antibodies or antigen-binding fragments thereof provided herein have low or no immunogenicity in humans, or have low or no immunogenicity potential in humans. An antibody or antigen-binding fragment thereof has "no" immunogenicity or "no" immunogenicity potential in humans if its EpiMatrix Epx score is equal to or lower than −40, based on EpiVax analysis (Koren, E., et al., 2007, Clin Immunol 124(1):26-32; De Groot, A. S. and Martin, W., 2009, Clin Immunol 131(2):189-201; epivax.com/epimatrix; see FIG. 7 for the EpiMatrix Epx score scale). Thus, the antibodies or antigen-binding fragments thereof do not or are less likely to provoke host immune responses in the human body directed against them, or produce or likely to produce low risk host immune responses in the human body directed against them (e.g., having an immunogenic potential that is less than 7.5%, less than 5.0%, less than 2.0%, less than 1.5%, less than 1.0%, or preferably less than 0.5%) Immunogenicity or potential immunogenicity can be measured by any method known in the art for assessing immunogenicity of antibodies in humans, such as EpiVax analysis, Epibase™ analysis, or anti-drug-antibody (ADA) assay In some embodiments, the antibodies or antigen-binding fragments thereof provided herein are tier II antibodies or antigen-binding fragments based on EpiVax analysis (i.e., antibodies that contain low ratios of effector T cell epitopes and low ratios of regulatory T cell epitopes (see www.epivax.com/immunogenicity-screening/ispri-web-based-immunogenicity-screening/). In other and embodiments, the antibodies or antigen-binding fragments thereof provided herein are tier I antibodies or antigen-binding fragments based on EpiVax analysis (i.e., antibodies that contain low ratios of effector T cell epitopes and high ratios of regulatory T cell epitopes.

In specific embodiments, the antibodies or antigen-binding fragments thereof provided herein have an EpMatrix Epx score that is equal to or lower than −20. In a specific embodiment, the antibodies or antigen-binding fragments thereof provided herein have an EpMatrix Epx score that is equal to or lower than −25. In another specific embodiment, the antibodies or antigen-binding fragments thereof provided herein have an EpMatrix Epx score that is equal to or lower than −30. In another specific embodiment, the antibodies or antigen-binding fragments thereof provided herein have an EpMatrix Epx score that is equal to or lower than −35. In another specific embodiment, the antibodies or antigen-binding fragments thereof provided herein have an EpMatrix Epx score that is equal to or lower than −40. In another specific embodiment, the antibodies or antigen-binding fragments thereof provided herein have an EpMatrix Epx score that is equal to or lower than −45. In another specific embodiment, the antibodies or antigen-binding fragments thereof provided herein have an EpMatrix Epx score that is equal to or lower than −50. EpiMatrix is an in silico immunogenicity analysis platform developed by EpiVax (Koren, E., et al., 2007, Clin Immunol 124(1):26-32; De Groot, A. S. and Martin, W., 2009, Clin Immunol 131(2): 189-201; epivax.com/epimatrix).

In specific embodiments, the antibodies or antigen-binding fragments thereof provided herein are variants of a parental antibody or parental antigen-binding fragment (as the case may be) and have lower (e.g., about 1.5-fold, 2-fold, 5-fold, 10-fold, 20-fold, 50-fold, 100-fold, 200-fold, 500-fold, or 1000-fold lower, or less) immunogenicity relative to the parental antibody or parental antigen-binding fragment (as the case may be). A variant of a parental antibody or parental antigen-binding fragment comprises the amino acid sequence of the parental antibody or parental antigen-binding fragment (as the case may be) with mutations (for example, 1, 2, 3, 4, 5, 6, 7, 8, 9, 10, 11, 12, 13, 14, 15, 16, 17, 18, 19, or 20 mutations) introduced into one or more framework regions (FRs) and/or one or more complementarity determining regions (CDRs) while retaining the binding specificity of the parental antibody or parental antigen-binding fragment (as the case may be) to the antigen epitope. In one embodiment, a variant of a parental antibody or parental antigen-binding fragment comprises the amino acid sequence of the parental antibody or parental antigen-binding fragment (as the case may be) with mutations (for example, 1, 2, 3, 4, 5, 6, 7, 8, 9, 10, 11, 12, 13, 14, 15, 16, 17, 18, 19, or 20 mutations) introduced into one or more framework regions (FRs) while retaining the binding specificity of the parental antibody or parental antigen-binding fragment (as the case may be) to the antigen epitope.

In a specific embodiment, the parental antibody or the parental antigen-binding fragment is an antibody that comprises a heavy chain variable region (VH) comprising the amino acid sequence of QMQLVQSGAEVKKTGSSVKVSCKASGFNIKDYYLHWVRQAPGQALEWMGWIDPDQGDTEYAQKFQDRVTITRDRSMSTAYMELSSLRSEDTAMYYCNAAYGSSSYPMDYWGQG TTVTVSS (SEQ ID NO: 80), and a light chain variable region (VL) comprising the amino acid sequence of NIQMTQSPSAMSASVGDRVTITCKASQDIHRYLSWFQQKPGKVPKHLIYRANRLVSGVPSRFSGSGSGTEFTLTISSLQPEDFATYYCLQYDEFPYTFGGGTKVEIK (SEQ ID NO: 81), or an antigen-binding fragment thereof (as the case may be). In another specific embodiment, the parental antibody or the parental antigen-binding fragment is an antibody that comprises a heavy chain comprising the amino acid sequence of QMQLVQSGAEVKKTGSSVKVSCKASGFNIKDYYLHWVRQAPGQALEWMGWIDPDQGDTEYAQKFQDRVTITRDRSMSTAYMELSSLRSEDTAMYYCNAAYGSSSYPMDYWGQG TTVTVSSASTKGPSVFPLAPCSRSTSESTAALGCLVKDYFPEPVTVSWNSGALTSGVHTF PAVLQSSGLYSLSSVVTVPSSSLGTKTYTCNVDHKPSNTKVDKRVESKYGPPCPPCPAPE FEGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 82) and a light chain comprising the amino acid sequence of NIQMTQSPSAMSASVGDRVTITCKASQDIHRYLSWFQQKPGKVPKHLIYRANRLVSGVPSRFSGSGSGTEFTLTISSLQPEDFATYYCLQYDEFPYTFGGGTKVEIKRTVAAPSVFIFPPS DEQLKSGTASVVCLLNNFYPREAKVQWKVDNALQSGNSQESVTEQDSKDSTYSLSSTL TLSKADYEKHKVYACEVTHQGLSSPVTKSFNRGEC (SEQ ID NO: 83) (i.e. Ab$_{Parental}$).

Solubility

In various aspects, the antibodies or antigen-binding fragments thereof provided herein have high solubility, a desirable antibody characteristic. Solubility can be measured by any method known in the art for assessing solubility of antibodies, such as any experimental or sequence-based method, for example, polyethylene glycol (PEG) (e.g., PEG6000) precipitation. In some embodiments, solubility is measured with sucrose. In other embodiments, solubility is measured without sucrose.

In specific embodiments, the antibodies or antigen-binding fragments thereof provided herein are variants of a parental antibody or parental antigen-binding fragment (as the case may be) and have higher (e.g., about 1.5-fold, 2-fold, 5-fold, 10-fold, 20-fold, 50-fold, 100-fold, 200-fold, 500-fold, or 1000-fold lower, or more) solubility relative to the parental antibody or parental antigen-binding fragment (as the case may be).

A variant of a parental antibody or parental antigen-binding fragment comprises the amino acid sequence of the parental antibody or parental antigen-binding fragment (as the case may be) with mutations (for example, 1, 2, 3, 4, 5, 6, 7, 8, 9, 10, 11, 12, 13, 14, 15, 16, 17, 18, 19, or 20 mutations) introduced into one or more framework regions (FRs) and/or one or more complementarity determining regions (CDRs) while retaining the binding specificity of the parental antibody or parental antigen-binding fragment (as the case may be) to the antigen epitope. In one embodiment, a variant of a parental antibody or parental antigen-binding fragment comprises the amino acid sequence of the parental antibody or parental antigen-binding fragment (as the case may be) with mutations (for example, 1, 2, 3, 4, 5, 6, 7, 8, 9, 10, 11, 12, 13, 14, 15, 16, 17, 18, 19, or 20 mutations) introduced into one or more framework regions (FRs) while retaining the binding specificity of the parental antibody or parental antigen-binding fragment (as the case may be) to the antigen epitope. In particular embodiments, the antigen-binding affinity of a variant of a parental antibody or parental antigen-binding fragment (as the case may be) is no less than 50%, 40%, 30%, 20%, or 10% that of the antigen-binding affinities of the antibodies or antigen-binding fragments thereof. In particular embodiments, the antigen-binding affinity of a variant of a parental antibody or parental antigen-binding fragment (as the case may be) is the same as, or is 110% more than, 120% more than, 130% more than, 140% more than, or 150% more than that of the antigen-binding affinities of the antibodies or antigen-binding fragments thereof. Antigen-binding affinity can be measured by any method known in the art for assessing antibody-antigen binding affinities, such as Biacore™ analysis or a cell binding assay (i.e., a binding assay using cells expressing the antigen on the surface, usually performed using flow cytometry such as fluorescence-activated cell sorting).

In a specific embodiment, the parental antibody or the parental antigen-binding fragment is an antibody that comprises a heavy chain variable region (VH) comprising the amino acid sequence of QMQLVQS-GAEVKKTGSSVKVSCK-ASGFNIKDYYLHWVRQAPGQALEWMGWIDPDQG DTEYAQKFQDRVTITRDRSMSTAYMELSSLRSED-TAMYYCNAAYGSSSYPMDYWGQG TTVTVSS (SEQ ID NO: 80) and a light chain variable region (VL) comprising the amino acid sequence of NIQMTQSPSAM-SASVGDRVTITCKASQDIHR-YLSWFQQKPGKVPKHLIYRANRLVSGVP SRFSGSGSGTEFTLTISSLQPEDFATYYCLQYDEFPY-TFGGGTKVEIK (SEQ ID NO: 81), or an antigen-binding fragment thereof (as the case may be). In another specific embodiment, the parental antibody or the parental antigen-binding fragment is an antibody that comprises a heavy chain comprising the amino acid sequence of QMQLVQS-GAEVKKTGSSVKVSCK-ASGFNIKDYYLHWVRQAPGQALEWMGWIDPDQG DTEYAQKFQDRVTITRDRSMSTAYMELSSLRSED-TAMYYCNAAYGSSSYPMDYWGQG TTVTVSSAS-TKGPSVFPLAPCSRSTSESTAALGCLVKDYF-PEPVTVSWNSGALTSGVHTF PAVLQSSGLYSLSSVVTVPSSSLGTKTY TCNVDHKPSNTKVDKRVESKYGPPCPPCPAPE FEGGPSVFLFPPKPKDTLMISRTPE-VTCVVVDVSQEDPEVQFNWYVDGVEVHNAKTKPR EEQFNSTYRVVSVLTVLHQDWLNGKEYKC KVSNKGLPSSIEKTISKAKGQPREPQVYTL PPSQEEMTKNQVSLTCLVKGFYPSDIAVEWESNGQ-PENNYKTTPPVLDSDGSFFLYSRLT VDKSRWQEGNVFSCSVMHEALHN-HYTQKSLSLSLGK (SEQ ID NO: 82) and a light chain comprising the amino acid sequence of NIQMTQSPSAM-SASVGDRVTITCKASQDIHR-YLSWFQQKPGKVPKHLIYRANRLVSGVP SRFSGSGSGTEFTLTISSLQPEDFATYYCLQYDEFPY-TFGGGTKVEIKRTVAAPSVFIFPPS DEQLKSG-TASVVCLLNNFYPREAKVQWKVD-NALQSGNSQESVTEQDSKDSTYSLSSTL TLSKADYEKHKVYACEVTHQGLSSPVTKSFNRGEC (SEQ ID NO: 83) (i.e. Ab$_{Parental}$).

Stability

In various aspects, the antibodies or antigen-binding fragments provided herein have high stability, a desirable characteristic. Stability can be measured by any method known in the art for assessing stability of antibodies, such as thermostability assay (e.g., differential scanning calorimetry) or thermal shift assay.

In specific embodiments, the antibodies or antigen-binding fragments thereof provided herein are variants of a parental antibody or parental antigen-binding fragment (as the case may be) and have higher (e.g., about 1.5-fold, 2-fold, 5-fold, 10-fold, 20-fold, 50-fold, 100-fold, 200-fold, 500-fold, or 1000-fold lower, or more) stability relative to the parental antibody or parental antigen-binding fragment (as the case may be). In a specific embodiment when stability is measured by a thermostability assay (e.g., differential scanning calorimetry), the Fab fragment melting temperature ($T_m$) of the antibodies or antigen-binding fragments thereof provided herein are higher (e.g., about 2, 3, 4, 5, 5, 7, 8, 9, or 10° C. higher, or more) than the Fab fragment Tm of the parental antibody or parental antigen-binding fragment (as the case may be).

A variant of a parental antibody or parental antigen-binding fragment comprises the amino acid sequence of the parental antibody or parental antigen-binding fragment (as the case may be) with mutations (for example, 1, 2, 3, 4, 5, 6, 7, 8, 9, 10, 11, 12, 13, 14, 15, 16, 17, 18, 19, or 20 mutations) introduced into one or more framework regions (FRs) and/or one or more complementarity determining regions (CDRs) while retaining the binding specificity of the parental antibody or parental antigen-binding fragment (as the case may be) to the antigen epitope. In one embodiment, a variant of a parental antibody or parental antigen-binding fragment comprises the amino acid sequence of the parental antibody or parental antigen-binding fragment (as the case may be) with mutations (for example, 1, 2, 3, 4, 5, 6, 7, 8, 9, 10, 11, 12, 13, 14, 15, 16, 17, 18, 19, or 20 mutations) introduced into one or more framework regions (FRs) while retaining the binding specificity of the parental antibody or parental antigen-binding fragment (as the case may be) to the antigen epitope. In particular embodiments, the antigen-binding affinity of a variant of a parental antibody or parental antigen-binding fragment (as the case may be) is no less than 50%, 40%, 30%, 20%, or 10% that of the antigen-binding affinities of the antibodies or antigen-binding fragments thereof. In particular embodiments, the antigen-binding affinity of a variant of a parental antibody or parental antigen-binding fragment (as the case may be) is the same as, or is 110% more than, 120% more than, 130% more than, 140% more than, or 150% more than that of the antigen-binding affinities of the antibodies or antigen-binding fragments thereof. Antigen-binding affinity can be measured by any method known in the art for assessing antibody-antigen binding affinities, such as Biacore™ analysis or a cell binding assay (i.e., a binding assay using cells expressing the antigen on the surface, usually performed using flow cytometry such as fluorescence-activated cell sorting).

In a specific embodiment, the parental antibody or the parental antigen-binding fragment is an antibody that comprises a heavy chain variable region (VH) comprising the amino acid sequence of QMQLVQS-GAEVKKTGSSVKVSCK-ASGFNIKDYYLHWVRQAPGQALEWMGWIDPDQG DTEYAQKFQDRVTITRDRSMSTAYMELSSLRSED-TAMYYCNAAYGSSSYPMDYWGQG TTVTVSS (SEQ ID NO: 80) and a light chain variable region (VL) comprising the amino acid sequence of NIQMTQSPSAM-SASVGDRVTITCKASQDIHR-YLSWFQQKPGKVPKHLIYRANRLVSGVP SRFSGSGSGTEFTLTISSLQPEDFATYYCLQYDEFPY-TFGGGTKVEIK (SEQ ID NO: 81), or an antigen-binding fragment thereof (as the case may be). In another specific embodiment, the parental antibody or the parental antigen-binding fragment is an antibody that comprises a heavy chain comprising the amino acid sequence of QMQLVQS-GAEVKKTGSSVKVSCK-ASGFNIKDYYLHWVRQAPGQALEWMGWIDPDQG DTEYAQKFQDRVTITRDRSMSTAYMELSSLRSED-TAMYYCNAAYGSSSYPMDYWGQG TTVTVSSAS-TKGPSVFPLAPCSRSTSESTAALGCLVKDYF-PEPVTVSWNSGALTSGVHTF PAVLQSSGLYS-LSSVVTVPSSSLGTKTYTCNVDHKPSNTKVDKRVESK YGPPCPPCPAPE FEGGPSVFLFPPKPKDTLMISRTPE-VTCVVVDVSQEDPEVQFNWYVDGVEVHNAKTKPR EEQFN-STYRVVSVLTVLHQDWLNGKEYKCKVSNKGLPSSIE KTISKAKGQPREPQVYTL PPSQEEMTKNQVSLT-CLVKGFYPSDIAVEWESNGQPEN-NYKTTPPVLDSDGSFFLYSRLT VDKSRWQEGNVFSCSVMHEALHN-HYTQKSLSLSLGK (SEQ ID NO: 82) and a light chain comprising the amino acid sequence of NIQMTQSPSAM-SASVGDRVTITCKASQDIHR-YLSWFQQKPGKVPKHLIYRANRLVSGVP SRFSGSGSGTEFTLTISSLQPEDFATYYCLQYDEFPY-TFGGGTKVEIKRTVAAPSVFIFPPS DEQLKSG-TASVVCLLNNFYPREAKVQWKVD-NALQSGNSQESVTEQDSKDSTYSLSSTL TLSKADYEKHKVYACEVTHQGLSSPVTKSFNRGEC (SEQ ID NO: 83) (i.e. Ab$_{Parental}$).

Expression

In various aspects, the antibodies or antigen-binding fragments thereof provided herein have high expression levels, a desirable antibody charateristic. Expression levels can be measured by any method known in the art for assessing expression of antibodies, such as polyacrylamide gel electrophoresis, surface plasmon resonance (SPR), biolayer interferometry, or colorimetric protein assay such as Bradford assay or bicinchoninic acid (BCA) assay, or size-exclusion chromatography (SEC).

In specific embodiments, the antibodies or antigen-binding fragments thereof provided herein are variants of a parental antibody or parental antigen-binding fragment (as the case may be) and have higher (e.g., about 1.5-fold, 2-fold, 5-fold, 10-fold, 20-fold, 50-fold, 100-fold, 200-fold, 500-fold, or 1000-fold lower, or more) expression levels relative to the parental antibody or parental antigen-binding fragment (as the case may be).

A variant of a parental antibody or parental antigen-binding fragment comprises the amino acid sequence of the parental antibody or parental antigen-binding fragment (as the case may be) with mutations (for example, 1, 2, 3, 4, 5, 6, 7, 8, 9, 10, 11, 12, 13, 14, 15, 16, 17, 18, 19, or 20 mutations) introduced into one or more framework regions (FRs) and/or one or more complementarity determining regions (CDRs) while retaining the binding specificity of the parental antibody or parental antigen-binding fragment (as the case may be) to the antigen epitope. In one embodiment, a variant of a parental antibody or parental antigen-binding fragment comprises the amino acid sequence of the parental antibody or parental antigen-binding fragment (as the case may be) with mutations (for example, 1, 2, 3, 4, 5, 6, 7, 8, 9, 10, 11, 12, 13, 14, 15, 16, 17, 18, 19, or 20 mutations) introduced into one or more framework regions (FRs) while retaining the binding specificity of the parental antibody or parental antigen-binding fragment (as the case may be) to the antigen epitope. In particular embodiments, the antigen-binding affinity of a variant of a parental antibody or parental antigen-binding fragment (as the case may be) is no less than 50%, 40%, 30%, 20%, or 10% that of the antigen-binding affinities of the antibodies or antigen-binding fragments thereof. In particular embodiments, the antigen-binding affinity of a variant of a parental antibody or parental antigen-binding fragment (as the case may be) is the same as, or is 110% more than, 120% more than, 130% more than, 140% more than, or 150% more than that of the antigen-binding affinities of the antibodies or antigen-binding fragments thereof. Antigen-binding affinity can be measured by any method known in the art for assessing antibody-antigen binding affinities, such as Biacore™ analysis or a cell binding assay (i.e., a binding assay using cells expressing the antigen on the surface, usually performed using flow cytometry such as fluorescence-activated cell sorting).

In a specific embodiment, the parental antibody or the parental antigen-binding fragment is an antibody that comprises a heavy chain variable region (VH) comprising the amino acid sequence of QMQLVQS-GAEVKKTGSSVKVSCK-ASGFNIKDYYLHWVRQAPGQALEWMGWIDPDQG DTEYAQKFQDRVTITRDRSMSTAYMELSSLRSED-TAMYYCNAAYGSSSYPMDYWGQG TTVTVSS (SEQ ID NO: 80) and a light chain variable region (VL) comprising the amino acid sequence of NIQMTQSPSAM-SASVGDRVTITCKASQDIHR-YLSWFQQKPGKVPKHLIYRANRLVSGVP SRFSGSGSGTEFTLTISSLQPEDFATYYCLQYDEFPY-TFGGGTKVEIK (SEQ ID NO: 81), or an antigen-binding fragment thereof (as the case may be). In another specific embodiment, the parental antibody or the parental antigen-binding fragment is an antibody that comprises a heavy chain comprising the amino acid sequence of QMQLVQS-GAEVKKTGSSVKVSCK-ASGFNIKDYYLHWVRQAPGQALEWMGWIDPDQGDTEYAQKFQDRVTITRDRSMSTAYMELSSLRSED-TAMYYCNAAYGSSSYPMDYWGQG TTVTVSSAS-TKGPSVFPLAPCSRSTSESTAALGCLVKDYF-PEPVTVSWNSGALTSGVHTFPAVLQSSGGLYS-LSSVVTVPSSSLGTKTYTCNVDHKPSNTKVDKRVESK YGPPCPPCPAPE FEGGPSVFLFPPKPKDTLMISRTPE-VTCVVVDVSQEDPEVQFNWYVDGVEVHNAKTKPR EEQFNSTYRVVSVLTVLHQDWLNGKEYKCKVS NKGLPSSIEKTISKAKGQPREPQVYTL PPSQEEMT-KNQVSLTCLVKGFYPSDIAVEWESNGQPEN-NYKTTPPVLDSDGSFFLYSRLT VDKSRWQEGNVFSCSVMHEALHN-HYTQKSLSLSLGK (SEQ ID NO: 82) and a light chain comprising the amino acid sequence of NIQMTQSPSAM-SASVGDRVTITCKASQDIHR-YLSWFQQKPGKVPKHLIYRANRLVSGVP SRFSGSGSGTEFTLTISSLQPEDFATYYCLQYDEFPY-TFGGGTKVEIKRTVAAPSVFIFPPS DEQLKSG-TASVVCLLNNFYPREAKVQWKVD-NALQSGNSQESVTEQDSKDSTYSLSSTL TLSKADYEKHKVYACEVTHQGLSSPVTKSFNRGEC (SEQ ID NO: 83) (i.e. Ab$_{parental}$).

In certain embodiments, the antibodies or antigen-binding fragments thereof, described herein exhibit low or no immunogenicity, and additionally exhibit any two or three of: high solubility, high stability and high expression levels.

5.1 Antibodies

As used herein and unless otherwise specified, the terms "about" or "approximately" mean within plus or minus 10% of a given value or range. In instances where an integer is required, the terms mean within plus or minus 10% of a given value or range, rounded either up or down to the nearest integer.

As used herein, the terms "antibody" and "immunoglobulin" and "Ig" are terms of art and can be used interchangeably herein and refer to a molecule with an antigen binding site that specifically binds an antigen.

Antibodies can include, for example, monoclonal antibodies, recombinantly produced antibodies, monospecific antibodies, multispecific antibodies (including bispecific antibodies), human antibodies, humanized antibodies, such as composite human antibodies or deimmunized antibodies, murine antibodies (e.g., mouse or rat antibodies), chimeric antibodies, synthetic antibodies, and tetrameric antibodies comprising two heavy chain and two light chain molecules. In specific embodiments, antibodies can include, but are not limited to an antibody light chain monomer, an antibody heavy chain monomer, an antibody light chain dimer, an antibody heavy chain dimer, an antibody light chain/antibody heavy chain pair, an antibody with two light chain/heavy chain pairs (e.g., identical pairs), intrabodies, heteroconjugate antibodies, single domain antibodies, monovalent antibodies, bivalent antibodies, single chain antibodies or single-chain Fvs (scFv) (e.g., including monospecific, bispecific, etc.), camelized antibodies, and affybodies. In specific embodiments, the antibody is a human antibody, a humanized antibody, a chimeric antibody, a recombinant antibody, a multispecific antibody, or an antigen-binding fragment thereof. In a specific embodiment, the antibody is a monoclonal antibody or antigen-binding fragment thereof. Antigen-binding fragments can include antigen-binding fragments or epitope binding fragments such as, but not limited to, Fv, Fab fragments, F(ab') fragments, F(ab')$_2$ fragments, scFv, sc(Fv)$_2$ and disulfide-linked Fvs (dsFv). In certain embodiments, antibodies described herein refer to polyclonal antibody populations. In a specific embodiment, the antibody or antigen-binding fragment thereof as described herein is an antibody.

Antibodies can be of any type (e.g., IgG, IgE, IgM, IgD, IgA or IgY), any class, (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies (e.g., human IgG), or a class (e.g., human IgG$_1$, IgG$_2$, IgG$_3$, or IgG$_4$) or subclass thereof. In specific embodiments, the antibody described herein is an IgG4, such as an IgG4P or IgG4PE, isotype antibody.

In various aspects, the antibody or antigen-binding fragment thereof provided herein comprises a heavy chain constant region.

In certain embodiments, the heavy chain constant region is a human constant region (e.g., a human IgG constant region). In some embodiments, the heavy chain constant region is a human IgG1 constant region. In some embodiments, the human IgG1 constant region is modified at amino acid Asn297 (Kabat Numbering) to prevent to glycosylation of the antibody, for example Asn297Ala (N297A). In some embodiments, the human IgG1 constant region of the antibody is modified at amino acid Leu235 (Kabat Numbering) to alter Fc receptor interactions, for example Leu235Glu (L235E) or Leu235Ala (L235A). In some embodiments, the human IgG1 constant region of the antibody is modified at amino acid Leu234 (Kabat Numbering) to alter Fc receptor interactions, e.g., Leu234Ala (L234A). In some embodiments, the human IgG1 constant region of the antibody is altered at both amino acid 234 and 235, for example Leu234Ala and Leu235Ala (L234A/L235A) (EU index of Kabat et al 1991 *Sequences of Proteins of Immunological Interest*).

In certain embodiments, the heavy chain constant region is a human IgG2 constant region. In some embodiments, the human IgG2 constant region is modified at amino acid Asn297 (Kabat Numbering) to prevent glycosylation of the antibody, e.g., Asn297Ala (N297A).

In some embodiments, the heavy chain constant region is a human IgG3 constant region. In some embodiments, the human IgG3 constant region is modified at amino acid Asn297 (Kabat Numbering) to prevent glycosylation of the antibody, e.g., Asn297Ala (N297A). In some embodiments, the human IgG3 constant region is modified at amino acid 435 to extend the half-life, e.g., Arg435His (R435H) (EU index of Kabat et al 1991 *Sequences of Proteins of Immunological Interest*).

In some embodiments, the heavy chain constant region is a human IgG4 constant region. In some embodiments, the human IgG4 constant region is modified within the hinge region to prevent or reduce strand exchange, e.g., Ser228Pro (S228P). In other embodiments, the human IgG4 constant region is modified at amino acid 235 to alter Fc receptor interactions, e.g., Leu235Glu (L235E). In some embodiments, the human IgG4 constant region is modified within the hinge and at amino acid 235, e.g., Ser228Pro and Leu235Glu (S228P/L235E). In some embodiments, the human IgG4 constant region is modified at amino acid Asn297 (Kabat Numbering) to prevent to glycosylation of the antibody, e.g., Asn297Ala (N297A). In some embodiments of the invention, the human IgG4 constant region is modified at amino acid positions Ser228, Leu235, and Asn297 (e.g., S228P/L235E/N297A). (EU index of Kabat et al 1991 *Sequences of Proteins of Immunological Interest*). In other embodiments of the invention, the antibody is of human IgG4 subclass and lacks glycosylation. In these embodiments the glycosylation can be eliminated by mutation at position 297 (Kabat numbering), for example N297A. In other embodiments, the glycosylation can be eliminated by production of the antibody in a host cell that lacks the ability for post-translational glycosylation, for example a bacterial or yeast derived system or a modified mammalian cell expression system. In a specific embodiment, the heavy chain constant region is a human IgG4 constant region comprising a S228P amino acid substitution according to the EU numbering index. In another specific embodiment, the heavy chain constant region is a human IgG4 constant region comprising a S228P and L235E amino acid substitutions according to the EU numbering index.

In some embodiments, the human IgG constant region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11.

In some embodiments, the human IgG constant region is modified to induce heterodimerization. For example, having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Y349 to Cys (Y349C) on opposite CH3 domains (Reviewed in Carter, 2001 Journal of Immunological Methods, 248: 7-15).

In various aspects, the antibody or antigen-binding fragment thereof provided herein comprises a light chain constant region selected from the group consisting of a human kappa constant region and a human lambda constant region. In a specific embodiment, the variable portion of the light chain comprises kappa light chain sequences and the constant region of the light chain comprises kappa light chain sequences. In another specific embodiment, the variable portion of the light chain comprises lambda light chain sequences and the constant region of the light chain comprises lambda light chain sequences. In another specific embodiment, the light chain is a mixed sequence, e.g., the variable portion of the light chain comprises kappa light chain sequences and the constant region of the light chain comprises lambda light chain sequences, or vice versa. In certain embodiments, the light chain of an antibody described herein is a human kappa light chain or a human lambda light chain.

Non-limiting examples of human constant region sequences have been described in the art and are contemplated in this disclosure, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242

In a particular embodiment, the antibody is a 4-chain antibody unit comprising two heavy (H) chain/light (L) chain pairs, wherein the amino acid sequences of the H chains are identical and the amino acid sequences of the L chains are identical. In a specific embodiment, the H and L chain comprise constant regions, for example, human constant regions. In a yet more specific embodiment, the L chain constant region of such antibodies is a kappa or lambda light chain constant region, for example, a human kappa or lambda light chain constant region. In another specific embodiment, the H chain constant region of such antibodies comprise a gamma heavy chain constant region, for example, a human gamma heavy chain constant region. In a particular embodiment, such antibodies comprise IgG constant regions, for eample, human IgG constant regions.

In certain aspects, the antibody lacks glycosylation, but is not modified at amino acid Asn297 (Kabat numbering). In these embodiments the glycosylation can, for example, be eliminated by production of the antibody in a host cell that lacks a post-translational glycosylation capacity, for example a bacterial or yeast derived system or a modified mammalian cell expression system. In certain aspects, such a system can be a cell-free (CF) expression system.

In certain embodiments, an antibody or antigen-binding fragment thereof described herein comprises amino acid sequences with certain percent identity relative to the parental antibody or parental antigen-binding fragement (as the case may be).

The determination of percent identity between two sequences (e.g., amino acid sequences or nucleic acid sequences) can be accomplished using a mathematical algorithm. A non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In certain embodiments, an antibody described herein or an antigen-binding fragment thereof comprises a VH domain having at least 80%, at least 85%, at least 90%, at least 95%, at least 98%, or at least 99% sequence identity to the amino acid sequence of the VH of the parental antibody or parental antigen-binding fragment (as the case may be). In certain embodiments, an antibody described herein or an antigen-binding fragment thereof comprises a VL domain having at least 80%, at least 85%, at least 90%, at least 95%, at least 98%, or at least 99% sequence identity to the amino acid sequence of the VL of the parental antibody or parental antigen-binding fragment (as the case may be).

In particular aspects, an antibody or antigen-binding fragment provided herein comprise one or more non-natural amino acid residues at site-specific positions. See, e.g., U.S. Application Publication No. US 2014/0046030 A1, which is incorporated herein by reference in its entirety. In specific aspects, non-natural amino acid residues at site specific positions has advantages for antibody production yield, solubility, binding affinity, and/or activity. Non-limiting examples of non-natural amino acids have been described, see, e.g., U.S. Application Publication No. US 2014/0066598 A1.

As used herein, the term "non-natural amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

In a particular aspect, an antibody or antigen-binding fragment provided herein is conjugated to a conjugation moiety or an agent such as a label or toxin. A conjugation moiety can be any conjugation moiety deemed useful to one of skill in the art. For instance, a conjugation moiety can be a polymer, such as polyethylene glycol, that can improve the stability of the antibody in vitro or in vivo. A conjugation moiety can have therapeutic activity, thereby yielding an antibody-drug conjugate. A conjugation moiety can be a molecular payload that is harmful to target cells. A conjugation moiety can be a label useful for detection or diagnosis. In certain aspects, a conjugation moiety is linked to the antibody via a direct covalent bond. In certain aspects, a conjugation moiety is linked to the antibody via a linker. In particular aspects, a conjugation moiety or a linker is attached via one of the non-natural amino acids of an antibody or antigen-binding fragment thereof descried herein. Exemplary conjugation moieties and linkers have been described, e.g., see U.S. Application Publication No. US2014/0046030 A1, which is incorporated herein by reference in its entirety.

The term "antigen-binding agent" or "binding agent" or "binding protein" refers to an agent (e.g., a protein) comprising a portion (e.g., one or more binding regions such as CDRs) that binds to the antigen, and, optionally, a scaffold or framework portion (e.g., one or more scaffold or framework regions) that allows the binding portion to adopt a conformation that promotes binding of the antigen-binding agent to an antigen polypeptide, fragment, or epitope. Examples of such antigen-binding agents include antibodies, such as a human antibody, a humanized antibody, a chimeric antibody, a recombinant antibody, a single chain antibody, a diabody, a triabody, a tetrabody, a Fab fragment, a F(ab')$_2$ fragment, an IgD antibody, an IgE antibody, an IgM antibody, an IgG1 antibody, an IgG2 antibody, an IgG3 antibody, or an IgG4 antibody, and fragments thereof. The antigen-binding agent can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the binding protein as well as wholly synthetic scaffolds comprising, for example, a biocompatible polymer. See, e.g., Korndorfer et al., 2003, Proteins: Structure, Function, and Bioinformatics 53(1):121-29; and Roque et al., 2004, Biotechnol. Prog. 20:639-54. In addition, peptide antibody mimetics ("PAMs") can be used, as well as scaffolds based on antibody mimetics utilizing fibronectin components as a scaffold.

As used herein, an "antigen" is a moiety or molecule that contains an epitope to which an antibody can specifically bind. As such, an antigen is also specifically bound by an antibody. In a particular embodiment, the antigen to which an antibody described herein binds, is CD47 (e.g., human CD47), or a fragment thereof.

As used herein, an "epitope" is a term in the art and refers to a localized region of an antigen to which an antibody can specifically bind. An epitope can be a linear epitope or a conformational, non-linear, or discontinuous, epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure. For example, in some embodiments, an antibody binds to a group of amino acids regardless of whether they are folded in a natural three dimensional protein structure. In other embodiments, an antibody requires amino acid residues making up the epitope to exhibit a particular conformation (e.g., bend, twist, turn or fold) in order to recognize and bind the epitope.

As used herein, the terms "immunospecifically binds," "immunospecifically recognizes," "specifically binds," and "specifically recognizes" are analogous terms in the context of antibodies and refer to molecules that bind to an antigen/epitope as such binding is understood by one skilled in the art. For example, a molecule that specifically binds to an antigen may bind to other peptides or polypeptides, generally with lower affinity as determined by, e.g., immunoassays, surface plasmon resonance assays, for example, Biacore™, KinExA platform (Sapidyne Instruments, Boise, Id.), or other assays known in the art. In a specific embodiment, molecules that specifically bind to an antigen bind to the antigen with a $K_a$ that is at least 2 logs, 2.5 logs, 3 logs, 4 logs or greater than the $K_a$ when the molecules bind to another antigen. In another specific embodiment, molecules that specifically bind to an antigen do not cross react with other proteins.

As used herein, the term "monoclonal antibody" is a well known term of art that refers to an antibody obtained from a population of homogenous or substantially homogeneous antibodies. The term "monoclonal" is not limited to any particular method for making the antibody. Generally, a population of monoclonal antibodies can be generated by cells, a population of cells, or a cell line. In specific embodiments, a "monoclonal antibody," as used herein, is an antibody produced by a single cell or cell line wherein the antibody immunospecifically binds to an antigen epitope (e.g., an epitope of human CD47) as determined, e.g., by ELISA or other antigen-binding or competitive binding assay known in the art or in the Examples provided herein.

In particular embodiments, a monoclonal antibody can be a chimeric antibody or a humanized antibody. In particular embodiments, a monoclonal antibody can be a composite human antibody. In particular embodiments, a monoclonal antibody can be a deimmunized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody).

As used herein, the term "polyclonal antibodies" refers to an antibody population that includes a variety of different antibodies that immunospecifically bind to the same and/or to different epitopes within an antigen or antigens.

As used herein, the terms "variable region" or "variable domain" refer to a portion of an antibody, generally, a portion of an antibody light or heavy chain, typically corresponding to about the amino-terminal 110 to 120 amino acids in a mature heavy chain and about the amino-terminal 90 to 100 amino acids in a mature light chain. Variable regions comprise complementarity determining regions (CDRs) flanked by framework regions (FRs). Generally, the spatial orientation of CDRs and FRs are as follows, in an N-terminal to C-terminal direction: FR1-CDR1-FR2-CDR2-FR3-CDR3-FR4. Without wishing to be bound by any particular mechanism or theory, it is believed that the CDRs of the light and heavy chains are primarily responsible for the interaction of the antibody with antigen and for the specificity of the antibody for an epitope. In a specific embodiment, numbering of amino acid positions of antibodies described herein is according to the EU Index, as in Kabat et al. (1991) *Sequences of Proteins of Immunological Interest*, Fifth Edition, U.S. Department of Health and Human Services, NIH Publication No. 91-3242. In certain embodiments, the variable region is a human variable region. In certain embodiments, the variable region comprises murine (e.g., mouse or rat) CDRs and human framework regions (FRs). In particular embodiments, the variable region is a primate (e.g., human or non-human primate) variable region. In certain embodiments, the variable region comprises murine (e.g., mouse or rat) CDRs and primate (e.g., human or non-human primate) framework regions (FRs). As a non-limiting example, a variable region described herein is obtained from assembling two or more fragments of human sequences into a composite human sequence.

In certain aspects, the CDRs of an antibody can be determined according to (i) the Kabat numbering system (Kabat et al. (1971) *Ann. NY Acad. Sci.* 190:382-391 and, Kabat et al. (1991) *Sequences of Proteins of Immunological Interest*, Fifth Edition, U.S. Department of Health and Human Services, NIH Publication No. 91-3242); or (ii) the Chothia numbering scheme, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; Chothia et al., 1992, J. Mol. Biol., 227:799-817; Tramontano A et al., 1990, J. Mol. Biol. 215(1):175-82; and U.S. Pat. No. 7,709,226); or (iii) the ImMunoGeneTics (IMGT) numbering system, for example, as described in Lefranc, M.-P., 1999, The Immunologist, 7:132-136 and Lefranc, M.-P. et al., 1999, Nucleic Acids Res., 27:209-212 ("IMGT CDRs"); or (iv) MacCallum et al., 1996, J. Mol. Biol., 262:732-745; or (v) the AbM numbering system (see, e.g., Martin et al., 1989, Proc. Natl Acad. Sci. USA, 86, 9268-9272; Martin et al., 1991, Methods Enzymol., 203, 121-153; Pedersen et al., 1992, Immunomethods, 1-126.; and Rees et al., 1996, In Sternberg M. J. E. (ed.), Protein Structure Prediction. Oxford University Press, Oxford, 141-172). See also, e.g., Martin, A., "Protein Sequence and Structure Analysis of Antibody Variable Domains," in *Antibody Engineering*, Kontermann and Duibel, eds., Chapter 31, pp. 422-439, Springer-Verlag, Berlin (2001).

With respect to the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

In certain aspects, the CDRs of an antibody described herein are Chothia CDRs (see, e.g., Chothia and Lesk, 1987, J. Mol. Biol., 196:901-917; and U.S. Pat. No. 7,709,226). The term "Chothia CDRs," and like terms are recognized in the art and refer to antibody CDR sequences as determined according to the method of Chothia and Lesk, 1987, J. Mol. Biol., 196:901-917, which will be referred to herein as the "Chothia CDRs" (see also, e.g., U.S. Pat. No. 7,709,226 and Martin, A., "Protein Sequence and Structure Analysis of Antibody Variable Domains," in *Antibody Engineering*, Kontermann and Dibel, eds., Chapter 31, pp. 422-439, Springer-Verlag, Berlin (2001)). Using the Kabat numbering system of numbering amino acid residues in the VH region and VL region, Chothia CDRs within an antibody heavy chain molecule are typically present at amino acid positions 26 to 32 (CDR1), amino acid positions 53 to 55 (CDR2), and amino acid positions 96 to 101 (CDR3). Using the Kabat numbering system of numbering amino acid residues in the VH region and VL region, Chothia CDRs within an antibody light chain molecule are typically present at amino acid positions 26 to 33 (CDR1), amino acid positions 50 to 52 (CDR2), and amino acid positions 91 to 96 (CDR3). In a specific embodiment, using the Kabat numbering system of numbering amino acid residues in the VH chain region and VL chain region, the Chothia CDRs within an antibody heavy chain molecule are at amino acid positions 26 to 32 or 34 (CDR1), amino acid positions 52 to 56 (CDR2; in one embodiment, CDR2 is at positions 52A-56, wherein 52A follows position 52), and amino acid positions 95 to 102 (CDR3; in one embodiment, there is no amino acid at one or more positions numbered 96-100); and the Chothia CDRs within an antibody light chain molecule are at amino acid positions 24 to 34 (CDR1), amino acid positions 50 to 56 (CDR2), and amino acid positions 89 to 97 (CDR3). These Chothia CDR positions may vary depending on the antibody, and may be determined according to methods known in the art.

In certain embodiments, an antibody or antigen-binding fragment thereof described herein comprises CDRs as determined by the IMGT (Immunogenetics) numbering system; see, e.g., Lefranc, M.-P., 1999, The Immunologist, 7:132-136 and Lefranc, M.-P. et al., 1999, Nucleic Acids Res., 27:209-212), both of which are incorporated herein by reference in their entirety. Using the IMGT numbering system, CDRs within an antibody heavy chain molecule are typically present at amino acid positions 27 to 38 (CDR1; 5-12 amino acids in length), amino acid positions 56 to 65 (CDR2; 0-10 amino acid positions in length), and amino acid positions 105 to 117 (CDR3; 2-12 amino acids in length). Using Kabat numbering, these heavy chain amino acid positions correspond to amino acid positions 26-35 for CDR1, 51-57 for CDR2 and 93-102 for CDR3. Using the IMGT numbering system, CDRs within an antibody light chain molecule are typically present at amino acid positions 27 to 38 (CDR1; 5-12 amino acids in length), amino acid positions 56 to 65 (CDR2; 0-10 amino acids in length), and amino acid positions 105 to 117 (CDR3; 2-12 amino acids in length). Using Kabat numbering, these light chain amino acid positions correspond to amino acid positions 27-32 for CDR1, 50-52 for CDR2, and 89-97 for CDR3.

In certain aspects, an antibody or antigen-binding fragment thereof described herein comprises CDRs as determined by the AbM (Oxford Molecular) numbering system (see e.g., Martin et al., 1989, Proc. Natl Acad. Sci. USA, 86, 9268-9272; Martin et al., 1991, Methods Enzymol., 203, 121-153; Pedersen et al., 1992, Immunomethods, 1-126; and Rees et al. 1996, In Sternberg M. J. E. (ed.), Protein Structure Prediction. Oxford University Press, Oxford, 141-172). AbM is a hybrid between the Kabat and Chothia definitions and is based on an algorithm designed by the Oxford Molecular Group (ABM™, a computer program for modeling variable regions of antibodies, Oxford, UK; Oxford Molecular, Ltd.). Using the AbM numbering system, CDRs within an antibody heavy chain molecule are typically present at amino acid positions 26 to 35 (CDR1; 10-12 amino acids in length), amino acid positions 50 to 58 (CDR2; 9-12 amino acid positions in length), and amino acid positions 95 to 102 (CDR3; 3-25 amino acids in length). Using Kabat numbering, these heavy chain amino acid positions correspond to amino acid positions 26-35 for CDR1, 50-58 for CDR2 and 95-102 for CDR3. The AbM CDRs within an antibody light chain molecule are typically present at amino acid positions 24 to 34 (CDR1), amino acid positions 50 to 56 (CDR2), and amino acid positions 89 to 97 (CDR3). Using Kabat numbering, these light chain amino acid positions correspond to amino acid positions 24-34 for CDR1, 50-56 for CDR2, and 89-97 for CDR3. These AbM CDR positions may vary depending on the antibody, and may be determined according to methods known in the art.

Framework regions described herein are determined based upon the boundaries of the CDR numbering system. In other words, if the CDRs are determined by, e.g., Kabat, IMGT, Chothia, or ABM, then the framework regions are the amino acid residues surrounding the CDRs in the variable region in the format, from the N-terminus to C-terminus: FR1-CDR1-FR2-CDR2-FR3-CDR3-FR4. For example, FR1 is defined as the amino acid residues N-terminal to the CDR1 amino acid residues as defined by, e.g., the Kabat numbering system, the IMGT numbering system, the Chothia numbering system, or the ABM numbering system, FR2 is defined as the amino acid residues between CDR1 and CDR2 amino acid residues as defined by, e.g., the Kabat numbering system, the IMGT numbering system, the Chothia numbering system, or the ABM numbering system, FR3 is defined as the amino acid residues between CDR2 and CDR3 amino acid residues as defined by, e.g., the Kabat numbering system, the IMGT numbering system, the Chothia numbering system, or the ABM numbering system, and FR4 is defined as the amino acid residues C-terminal to the CDR3 amino acid residues as defined by, e.g., the Kabat numbering system, the IMGT numbering system, the Chothia numbering system, or the ABM numbering system.

In specific embodiments, an antibody or antigen-binding fragment described herein specifically binds to Cluster of Differentiation 47 (CD47) (e.g., human CD47). As used herein, the terms "Cluster of Differentiation 47" or "CD47" or "integrin-associated protein" or "IAP" or "ovarian cancer antigen" or "OA3" or "Rh-related antigen" or "MER6" can be used interchangeably and refer to a multi-spanning transmembrane receptor belonging to the immunoglobulin superfamily. The amino acid sequence of an exemplary human CD47 is provided below (GenBank Accession No. Q08722.1 (GI: 1171879), incorporated herein by reference). The signal sequence (amino acids 1-18) is underlined.

```
                                                              (SEQ ID NO: 84)
  1  MWPLVAALLL GSACCGSAQL LFNKTKSVEF TFCNDTVVIP CFVTNMEAQN TTEVYVKWKF

61  KGRDIYTFDG ALNKSTVPTD FSSAKIEVSQ LLKGDASLKM DKSDAVSHTG NYTCEVTELT

121  REGETIIELK YRVVSWFSPN ENILIVIFPI FAILLFWGQF GIKTLKYRSG GMDEKTIALL

181  VAGLVITVIV IVGAILFVPG EYSLKNATGL GLIVISTGIL ILLHYYVFST AIGLTSFVIA

241  ILVIQVIAYI LAVVGLSLCI AACIPMHGPL LISGLSILAL AQLLGLVYMK FVASNQKTIQ

301  PPRKAVEEPL NAFKESKGMM NDE
```

For clarity, the amino acid sequence of an exemplary human CD47 excluding the signal sequence is provided below.

```
                                                              (SEQ ID NO: 85)
  1  QLLFNKTKSV EFTFCNDTVV IPCFVTNMEA QNTTEVYVKW KFKGRDIYTF DGALNKSTVP

61  TDFSSAKIEV SQLLKGDASL KMDKSDAVSH TGNYTCEVTE LTREGETIIE LKYRVVSWFS

121  PNENILIVIF PIFAILLFWG QFGIKTLKYR SGGMDEKTIA LLVAGLVITV IVIVGAILFV

181  PGEYSLKNAT GLGLIVISTG ILILLHYYVF STAIGLTSFV IAILVIQVIA YILAVVGLSL

241  CIAACIPMHG PLLISGLSIL ALAQLLGLVY MKFVASNQKT IQPPRKAVEE PLNAFKESKG

301  MMNDE
```

In specific embodiments, anti-CD47 antibodies or antigen-binding fragments thereof described herein promote (e.g., induce or increase) phagocytosis of cells, e.g., CD47-expressing cells (e.g., CCRF-CEM cells), for example, by macrophages. In one aspect, the level of phagocytosis in the presence of anti-CD47 antibodies or antigen-binding fragments thereof described herein is increased by at least 5%, at least 10%, at least 20%, at least 30%, at least 40%, at least 50%, at least 60%, at least 70%, at least 80%, at least 90%, at least 99%, at least 150%, at least 200%, compared to the level of aphagocytosis in the presence of anti-CD47 antibodies described herein.

In specific aspects, anti-CD47 antibodies or antigen-binding fragments thereof described herein do not promote (e.g., induce or increase), or cause a significant level of, agglutination of cells, e.g., anti-CD47 antibodies or antigen-binding fragments thereof described herein do not promote (e.g., induce or increase), or cause a significant level of, hemagglutination of red blood cells. In one aspect, the level of agglutination in the presence of anti-CD47 antibodies or antigen-binding fragments thereof described herein is reduced by at least 5%, at least 10%, at least 20%, at least 30%, at least 40%, at least 50%, at least 60%, at least 70%, at least 80%, at least 90%, or at least 99% compared to the level of agglutination in the presence of anti-CD47 antibodies or antigen-binding fragments thereof known to induce agglutination, such as MCA911 mouse anti-human CD47 antibody (BRIC126). In some aspects, anti-CD47 antibodies or antigen-binding fragments thereof described herein do not promote (e.g., induce or increase), or cause a significant level of, agglutination if the level of agglutination in the presence of anti-CD47 antibodies or antigen-binding fragments thereof described herein is reduced by at least 5%, at least 10%, at least 20%, at least 30%, at least 40%, at least 50%, at least 60%, at least 70%, at least 80%, at least 90%, or at least 99% compared to the level of agglutination in the presence of existing anti-CD47 antibodies or antigen-binding fragments thereof known to induce agglutination, such as MCA911 mouse anti-human CD47 antibody (BRIC126).

Anti-CD47 antibodies or antigen-binding fragments thereof described herien also include monoclonal antibodies that specifically bind CD47, wherein the antibodies or antigen-binding fragments thereof do not promote (e.g., induce or increase), or cause a significant level of, agglutination, e.g., red blood cell hemagglutination ("RBC hemagglutination").

In some aspects, the level of RBC depletion is determined by measuring the RBC count in a subject after administration of a treatment, e.g., an anti-CD47 antibody or an antigen-binding fragment thereof described herein. In some embodiments, anti-CD47 antibodies or antigen-binding fragments thereof described herein do not promote (e.g., induce or increase), or cause a significant level of, RBC depletion if the RBC count in a subject after administration of an anti-CD47 antibody or an antigen-binding fragment thereof described herein is within the range of a normal, healthy subject. For example, the RBC count for a normal, healthy male human is about 4.7 to about 6.1 million cells per microliter of blood sample. For example, the RBC count for a normal, healthy female human is 4.2 to about 5.4 million cells per microliter of blood sample. In some aspects, anti-CD47 antibodies or antigen-binding fragments thereof described herein do not promote (e.g., induce or increase), or cause a significant level of, RBC depletion if the RBC count in a subject after administration (e.g., 5 min, 10 min, 30 min, 1 h, 2 h, 3 h, 4 h, 5 h, 12 h, 24 h, 2 days, 4 days, 6 days, 1 week, 2 weeks, 3 weeks, 1 month, 2 months, or more) of an anti-CD47 antibody or an antigen-binding fragment thereof described herein is at least 50%, 60%, 70%, 80%, 90%, 95%, 97%, 98%, 99%, or 99.5% of the RBC count prior to administration. In specific aspects, anti-CD47 antibodies or antigen-binding fragments thereof described herein do not promote (e.g., induce or increase), or cause a significant level of, RBC depletion if the RBC count in a subject after administration (5 min, 10 min, 30 min, 1 h, 2 h, 3 h, 4 h, 5 h, 12 h, 24 h, 2 days, 4 days, 6 days, 1 week, 2 weeks, 3 weeks, 1 month, 2 months, or more) of an anti47 antibody or an antigen-binding fragment thereof described herein is at least 50%, 60%, 70%, 80%, 90%, 95%, 97%, 98%, 99%, or 99.5% of the RBC count in a subject after administration of a placebo treatment (e.g., vehicle). RBC counts are determined by standard methods in the art.

In specific aspects, anti-CD47 antibodies or antigen-binding fragments thereof described herein do not promote (e.g., induce or increase), or cause a significant level of, platelet depletion. For example, administration of an anti-CD47 antibody or an antigen-binding fragment thereof described herein leads to a percentage of platelets remaining of at least 30%, 40%, 50%, 60%, 70%, 80%, 90%, or 100%.

Also, anti-CD47 antibodies or antigen-binding fragments thereof described herien include but are not limited to antibodies that do not bind to, or have a low binding affinity to, a Fcγ receptor (FcγR). For example, the constant region of an anti-CD47 antibody or an antigen-binding fragment thereof, e.g., when produced using a CF expression system, has a lower binding affinity to a FcγR than the constant region of an anti-CD47 antibody or an antigen-binding fragment thereof, e.g., when produced using a host cell (e.g., CHO cells) expression system.

Those skilled in the art will recognize that it is possible to quantitate, without undue experimentation, the level of agglutination, e.g., the level of hemagglutination of RBCs. For example, those skilled in the art will recognize that the level of hemagglutination is ascertained by measuring the area of an RBC dot after performing a hemagglutination assay in the presence of anti-CD47 antibodies or antigen-binding fragments thereof described. In some cases, the area of the RBC dot in the presence of an anti-CD47 antibody or an antigen-binding fragment thereof described herien is compared to the area of the RBC dot in the absence of the anti-CD47 antibody or antigen-binding fragment thereof, e.g., in the presence of zero hemagglutination. In this manner, hemagglutination is quantified relative to a baseline control. A larger RBC dot area corresponds to a higher level of hemagglutination. Alternatively, densitometry of the RBC dot may also be utilized to quantitate hemagglutination.

Those skilled in the art will recognize that it is possible to quantitate, without undue experimentation, the level of RBC depletion. For example, those skilled in the art will recognize that the level of RBC depletion is ascertained, e.g., by measuring the RBC count (i.e., the total number of RBCs in a sample of blood), e.g., by using a cell counter or a hemacytometer. Those of skill in the art will recognize that the RBCs in a sample of blood can optionally be isolated by fractionating whole blood using, e.g., centrifugation, prior to counting. In some cases, the RBC count in the presence of an anti-CD47 antibody or an antigen-binding fragment thereof described herein is compared to the RBC count in the absence of the CD47 antibody or antigen-binding fragment thereof, e.g., in the presence of zero RBC depletion. In this manner, the level of RBC depletion is normalized relative to a baseline control.

In specific aspects, anti-CD47 antibodies or antigen-binding fragments thereof provided herein exhibit inhibitory activity, for example by inhibiting CD47 expression (e.g., inhibiting cell surface expression of CD47), activity, and/or signaling, or by interfering with the interaction between CD47 and SIRPa. In certain aspects, anti-CD47 antibodies or antigen-binding fragments thereof provided herein completely or partially reduce or otherwise modulate CD47 expression or activity upon binding to, or otherwise interacting with, CD47, e.g., a human CD47. The reduction or modulation of a biological function of CD47 is complete, significant, or partial upon interaction between the antibodies and the human CD47 polypeptide and/or peptide. Anti-CD47 antibodies or antigen-binding fragments thereof described hereinare considered to completely inhibit CD47 expression or activity when the level of CD47 expression or activity in the presence of the antibody is decreased by at least 95%, e.g., by 96%, 97%, 98%, 99% or 100% as compared to the level of CD47 expression or activity in the absence of interaction, e.g., binding, with the antibody described herein. In a particular aspect, anti-CD47 antibodies or antigen-binding fragments thereof are considered to significantly inhibit CD47 expression or activity when the level of CD47 expression or activity in the presence of the CD47 antibody or antigen-binding fragment thereof is decreased by at least 50%, e.g., 55%, 60%, 75%, 80%, 85% or 90% as compared to the level of CD47 expression or activity in the absence of binding with a CD47 antibody or antigen-binding fragment thereof described herein. In certain aspects, anti-CD47 antibodies or antigen-binding fragments thereof are considered to partially inhibit CD47 expression or activity when the level of CD47 expression or activity in the presence of the antibody is decreased by less than 95%, e.g., 10%, 20%, 25%, 30%, 40%, 50%, 60%, 75%, 80%, 85% or 90% as compared to the level of CD47 expression or activity in the absence of interaction, e.g., binding, with an antibody or antigen-binding fragment thereof described herein.

In specific aspects, such anti-CD47 antibody or antigen-binding fragments thereof blocks CD47 binding to SIRPa, promotes phagocytosis, has reduced or no Fc effector function (e.g., binding to FcγR, ADCC, or CDC) and/or has little or no agglutination (e.g., hemagglutination) activity.

In some embodiments, the anti-CD47 antibody or antigen-binding fragment thereof when produced using a cell-free (CF) expression system has a higher antibody expression titer or yield compared to the parental antibody when expressed in the CF system. In a particular aspect, anti-CD47 antibodies or antigen-binding fragments thereof provided herein which are expressed in a CF system, are aglycosylated.

The terms red blood cell(s) and erythrocyte(s) are synonymous and used interchangeably herein.

The term agglutination refers to cellular clumping, while the term hemagglutination refers to clumping of a specific subset of cells, i.e., red blood cells. Thus, hemagglutination is a type of agglutination.

5.1.1 Antibodies with Specific Heavy Chain Variable Region Framework Region Sequences Provided herein are antibodies and antigen-binding fragments thereof comprising specific heavy chain variable region framework region (VH FR) sequences.

In one aspect, provided herein is an antibody or an antigen-binding fragment thereof, comprising a heavy chain variable region (VH) that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1, VH FR2, VH FR3 and VH FR4 comprise the amino acid sequence of $X_{H1}X_{H2}X_{H3}$QLVQSG$X_{H4}$EVKK$X_{H5}$G$X_{H6}X_{H7}$VK$X_{H8}$SCK$X_{H9}$S (SEQ ID NO: 1);
WV$X_{H10}$QA$X_{H11}$G$X_{H12}X_{H13}$LEW$X_{H14}$G (SEQ ID NO: 2);
YA$X_{H15}$K$X_{H16}$Q$X_{H17}$RVT$X_{H18}$T$X_{H19}X_{H20}X_{H21}$S$X_{H22}X_{H23}$T$X_{H24}$YMEL$X_{H25}X_{H26}$LRA$X_{H27}$DTA $X_{H28}$YYC (SEQ ID NO: 3); and
WG$X_{H29}$GT$X_{H30}$VTVSS (SEQ ID NO: 4), respectively, wherein $X_{H1}$ is M or no amino acid, $X_{H2}$ is Q or E, $X_{H3}$ is V or M, $X_{H4}$ is A or P, $X_{H5}$ is P or T, $X_{H6}$ is A, S, or T, $X_{H7}$ is S or T, $X_{H8}$ is V or I, $X_{H9}$ is A or V, $X_{H10}$ is R or Q, $X_{H11}$ is P, R, or T, $X_{H12}$ is Q or K, $X_{H13}$ is G, R, or A, $X_{H14}$ is M or I, $X_{H15}$ is Q or E, $X_{H16}$ is F or L, $X_{H17}$ is G, D, or E, $X_{H18}$ is M or I, $X_{H19}$ is R, T, E or A, $X_{H20}$ is D or N, $X_{H21}$ is T, R, M, E, or K, $X_{H22}$ is I, A T, or M, $X_{H23}$ is S or D, $X_{H24}$ is A or V, $X_{H25}$ is S or R, $X_{H26}$ is S or R, $X_{H27}$ is D or E, $X_{H28}$ is V or M, $X_{H29}$ is Q or R, and $X_{H30}$ is L, M or T.

In certain embodiments of the preceding aspect, at least one of the following is satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least two of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least three of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least four of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least five of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least six of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least seven of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least eight of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least nine of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least ten of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least eleven of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least twelve of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least thirteen of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, at least fourteen of the following are satisfied: $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L. In certain embodiments, $X_{H3}$ is V, $X_{H5}$ is P, $X_{H6}$ is A, $X_{H12}$ is K, $X_{H13}$ is G, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, $X_{H28}$ is V, and $X_{H30}$ is L.

In certain embodiments of the preceding aspect, at least one of the following is satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L. In certain embodiments, at least two of the following are satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L. In certain embodiments, at least three of the following are satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L. In certain embodiments, at least four of the following are satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L. In certain embodiments, at least five of the following are satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L. In certain embodiments, at least six of the following are satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L. In certain embodiments, at least seven of the following are satisfied: $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L. In certain embodiments, $X_{H5}$ is P, $X_{H12}$ is K, $X_{H13}$ is G, $X_{H17}$ is G, $X_{H22}$ is T, $X_{H25}$ is R, $X_{H28}$ is V, and $X_{H30}$ is L.

In certain embodiments of the preceding aspect, at least one of the following is satisfied: $X_{H12}$ is K, $X_{H13}$ is G, and $X_{H30}$ is L. In certain embodiments, at least two of the following are satisfied: $X_{H12}$ is K, $X_{H13}$ is G, and $X_{H30}$ is L. In certain embodiments, $X_{H12}$ is K, $X_{H13}$ is G, and $X_{H30}$ is L.

In a specific embodiment of the certain embodiments wherein at least one, two, or all of the following are satisfied: $X_{H12}$ is K, $X_{H13}$ is G, and $X_{H30}$ is L, at least one of the following is further satisfied: $X_{H5}$ is P, $X_{H17}$ is G, $X_{H22}$ is T, $X_{H25}$ is R, and $X_{H28}$ is V. In another specific embodiment of the certain embodiments wherein at least one, two, or all of the following are satisfied: $X_{H12}$ is K, $X_{H13}$ is G, and $X_{H30}$ is L, at least two of the following are further satisfied: $X_{H5}$ is P, $X_{H17}$ is G, $X_{H22}$ is T, $X_{H25}$ is R, and $X_{H28}$ is V. In another specific embodiment of the certain embodiments wherein at least one, two, or all of the following are satisfied: $X_{H12}$ is K, $X_{H13}$ is G, and $X_{H30}$ is L, at least three of the following are further satisfied: $X_{H5}$ is P, $X_{H17}$ is G, $X_{H22}$ is T, $X_{H25}$ is R, and $X_{H28}$ is V. In another specific embodiment of the certain embodiments wherein at least one, two, or all of the following are satisfied: $X_{H12}$ is K, $X_{H13}$ is G, and $X_{H30}$ is L, at least four of the following are further satisfied: $X_{H5}$ is P, $X_{H17}$ is G, $X_{H22}$ is T, $X_{H25}$ is R, and $X_{H28}$ is V. In another specific embodiment of the certain embodiments wherein at least one, two, or all of the following are satisfied: $X_{H12}$ is K, $X_{H13}$ is G, and $X_{H30}$ is L, the following is further satisfied: $X_{H5}$ is P, $X_{H17}$ is G, $X_{H22}$ is T, $X_{H25}$ is R, and $X_{H28}$ is V.

In a further specific embodiment wherein at least one, two, or all of the following are satisfied: $X_{H12}$ is K, $X_{H13}$ is G, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, at least one of the following is further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another further specific embodiment wherein at least one, two, or all of the following are satisfied: $X_{H12}$ is K, $X_{H13}$ is G, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, at least two of the following are further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another further specific embodiment wherein at least one, two, or all of the following are satisfied: $X_{H12}$ is K, $X_{H13}$ is G, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, at least three of the following are further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another further specific embodiment wherein at least one, two, or all of the following are satisfied: $X_{H12}$ is K, $X_{H13}$ is G, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, at least four of the following are further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another further specific embodiment wherein at least one, two, or all of the following are satisfied: $X_{H12}$ is K, $X_{H13}$ is G, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, at least five of the following are further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another further specific embodiment wherein at least one, two, or all of the following are satisfied: $X_{H12}$ is K, $X_{H13}$ is G, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, at least six of the following are further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another further specific embodiment wherein at least one, two, or all of the following are satisfied: $X_{H12}$ is K, $X_{H13}$ is G, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, the following is further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

In a specific embodiment of the certain embodiments wherein at least one, two, or all of the following are satisfied: $X_{H12}$ is K, $X_{H13}$ is G, and $X_{H30}$ is L, at least one of the following is further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment wherein at least one, two, or all of the following are satisfied: $X_{H12}$ is K, $X_{H13}$ is G, and $X_{H30}$ is L, at least two of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment wherein at least one, two, or all of the following are satisfied: $X_{H12}$ is K, $X_{H13}$ is G, and $X_{H30}$ is L, at least three of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment wherein at least one, two, or all of the following are satisfied: $X_{H12}$ is K, $X_{H13}$ is G, and $X_{H30}$ is L, at least four of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment wherein at least one, two, or all of the following are satisfied: $X_{H12}$ is K, $X_{H13}$ is G, and $X_{H30}$ is L, at least five of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment wherein at least one, two, or all of the following are satisfied: $X_{H12}$ is K, $X_{H13}$ is G, and $X_{H30}$ is L, at least six of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment wherein at least one, two, or all of the following are satisfied: $X_{H12}$ is K, $X_{H13}$ is G, and $X_{H30}$ is L, at least seven of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment wherein at least one, two, or all of the following are satisfied: $X_{H12}$ is K, $X_{H13}$ is G, and $X_{H30}$ is L, at least eight of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment wherein at least one, two, or all of the following are satisfied: $X_{H12}$ is K, $X_{H13}$ is G, and $X_{H30}$ is L, at least nine of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment wherein at least one, two, or all of the following are satisfied: $X_{H12}$ is K, $X_{H13}$ is G, and $X_{H30}$ is L, at least ten of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment wherein at least one, two, or all of the following are satisfied: $X_{H12}$ is K, $X_{H13}$ is G, and $X_{H30}$ is L, at least eleven of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment wherein at least one, two, or all of the following are satisfied: $X_{H12}$ is K, $X_{H13}$ is G, and $X_{H30}$ is L, the following is further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

In specific embodiments of the preceding aspect, $X_{H3}$ is M, $X_{H6}$ is S, $X_{H16}$ is F, $X_{H18}$ is I, $X_{H19}$ is R, $X_{H21}$ is R, and $X_{H27}$ is E.

In another aspect, provided herein is an antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1, VH FR2, VH FR3 and VH FR4 comprise the amino acid sequence of
$X_{H1}QX_{H3}QLVQSGAEVKKX_{H5}GX_{H6}SVKVSCKAS$ (SEQ ID NO: 5),
WVRQAPG$X_{H12}X_{H13}$LEWMG (SEQ ID NO: 6),
YAQK$X_{H16}$Q$X_{H17}$RVTXHls$_8$T$X_{H19}$D$X_{H21}$S$X_{H22}$STAYMEL$X_{H25}$SLR$X_{H31}X_{H27}$DTA$X_{H28}$YYC (SEQ ID NO: 7), and
WG$X_{H29}$GT$X_{H30}$VTVSS (SEQ ID NO: 4) respectively, wherein $X_{H1}$ is M or no amino acid, $X_{H3}$ is V or M, $X_{H5}$ is P or T, $X_{H6}$ is A, S, or T, $X_{H12}$ is Q or K, $X_{H13}$ is G, R, or A, $X_{H16}$ is F or L, $X_{H17}$ is G, D, or E, $X_{H18}$ is M or I, $X_{H19}$ is R, T, E or A, $X_{H21}$ is T, R, M, E, or K, $X_{H22}$ is I, A T, or M, $X_{H25}$ is S or R, XmH31 is S or A, $X_{H27}$ is D or E, and $X_{H28}$ is V or M, $X_{H29}$ is Q or R, and $X_{H30}$ is L, M or T, and wherein at least one of the following is satisfied: $X_{H12}$ is K, $X_{H13}$ is G, $X_{H31}$ is A, and $X_{H30}$ is L. In certain embodiments, at least two of the following are satisfied: $X_{H12}$ is K, $X_{H13}$ is G, $X_{H31}$ is A, and $X_{H30}$ is L. In certain embodiments, at least three of the following are satisfied: $X_{H12}$ is K, $X_{H13}$ is G, $X_{H31}$ is A, and $X_{H30}$ is L. In certain embodiments, $X_{H12}$ is K, $X_{H13}$ is G, $X_{H31}$ is A, and $X_{H30}$ is L.

In a specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least one of the following is further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least two of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least three of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least four of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least five of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least six of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least seven of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least eight of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least nine of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least ten of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least eleven of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, the following is further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

In a specific embodiment of the preceding aspect and certain embodiments wherein at least one, two, three, or all of the following are satisfied: $X_{H12}$ is K, $X_{H13}$ is G, $X_{H31}$ is A, and $X_{H30}$ is L, at least one of the following is further satisfied: $X_{H5}$ is P, $X_{H17}$ is G, $X_{H22}$ is T, $X_{H25}$ is R, and $X_{H28}$ is V. In another specific embodiment of the preceding aspect and certain embodiments wherein at least one, two, three, or all of the following are satisfied: $X_{H12}$ is K, $X_{H13}$ is G, $X_{H31}$ is A, and $X_{H30}$ is L, at least two of the following are further satisfied: $X_{H5}$ is P, $X_{H17}$ is G, $X_{H22}$ is T, $X_{H25}$ is R, and $X_{H28}$ is V. In another specific embodiment of the preceding aspect and certain embodiments wherein at least one, two, three, or all of the following are satisfied: $X_{H12}$ is K, $X_{H13}$ is G, $X_{H31}$ is A, and $X_{H30}$ is L, at least three of the following are further satisfied: $X_{H5}$ is P, $X_{H17}$ is G, $X_{H22}$ is T, $X_{H25}$ is R, and $X_{H28}$ is V. In another specific embodiment of the preceding aspect and certain embodiments wherein at least one, two, three, or all of the following are satisfied: $X_{H12}$ is K, $X_{H13}$ is G, $X_{H31}$ is A, and $X_{H30}$ is L, at least four of the following are further satisfied: $X_{H5}$ is P, $X_{H17}$ is G, $X_{H22}$ is T, $X_{H25}$ is R, and $X_{H28}$ is V. In another specific embodiment of the preceding aspect and certain embodiments wherein at least one, two, three, or all of the following are satisfied: $X_{H12}$ is K, $X_{H13}$ is G, $X_{H31}$ is A, and $X_{H30}$ is L, the following are further satisfied: $X_{H5}$ is P, $X_{H17}$ is G, $X_{H22}$ is T, $X_{H25}$ is R, and $X_{H28}$ is V.

In a further specific embodiment wherein at least one, two, three, or all of the following are satisfied: $X_{H12}$ is K, $X_{H13}$ is G, $X_{H31}$ is A, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, at least one of the following is further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another further specific embodiment wherein at least one, two, three, or all of the following are satisfied: $X_{H12}$ is K, $X_{H13}$ is G, $X_{H31}$ is A, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, at least two of the following are further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another further specific embodiment wherein at least one, two, three, or all of the following are satisfied: $X_{H12}$ is K, $X_{H13}$ is G, $X_{H31}$ is A, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, at least three of the following are further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another further specific embodiment wherein at least one, two, three, or all of the following are satisfied: $X_{H12}$ is K, $X_{H13}$ is G, $X_{H31}$ is A, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, at least four of the following are further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another further specific embodiment wherein at least one, two, three, or all of the following are satisfied: $X_{H12}$ is K, $X_{H13}$ is G, $X_{H31}$ is A, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, at least five of the following are further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another further specific embodiment wherein at least one, two, three, or all of the following are satisfied: $X_{H12}$ is K, $X_{H13}$ is G, $X_{H31}$ is A, and $X_{H30}$ is L, and wherein at least one, two, three, four, or all of the following are satisfied: XH is P, $X_{H17}$ is G, $X_{H22}$ is T, $X_{H25}$ is R, and $X_{H28}$ is V, at least six of the following are further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D. In another further specific embodiment wherein at least one, two, three, or all of the following are satisfied: $X_{H12}$ is K, $X_{H13}$ is G, $X_{H31}$ is A, and $X_{H30}$ is L, and wherein at least one, two, three, four, or all of the following are satisfied: $X_{H5}$ is P, $X_{H17}$ is G, $X_{H22}$ is T, $X_{H25}$ is R, and $X_{H28}$ is V, the following is further satisfied: $X_{H3}$ is V, $X_{H6}$ is A, $X_{H16}$ is L, $X_{H18}$ is M, $X_{H19}$ is T, $X_{H21}$ is T, and $X_{H27}$ is D.

In a specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least one of the following is further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least two of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least three of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least four of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least five of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least six of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least seven of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least eight of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least nine of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least ten of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, at least eleven of the following are further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V. In another specific embodiment of the preceding aspect and certain embodiments wherein at least one, two, three, or all of the following is satisfied: $X_{H12}$ is K, $X_{H13}$ is G, $X_{H31}$ is A, and $X_{H30}$ is L, the following is further satisfied: $X_{H3}$ is V, $X_{H5}$ is P, $X_{H6}$ is A, $X_{H16}$ is L, $X_{H17}$ is G, $X_{H18}$ is M, $X_{H19}$ is T, $X_{H21}$ is T, $X_{H22}$ is T, $X_{H25}$ is R, $X_{H27}$ is D, and $X_{H28}$ is V.

In specific embodiments of the preceding aspect, $X_{H3}$ is M, $X_{H6}$ is S, $X_{H16}$ is F, $X_{H18}$ is I, $X_{H19}$ is R, $X_{H21}$ is R, and $X_{H27}$ is E.

In a specific embodiment, provided herein is an antibody or antigen-binding fragment thereof as listed in Table 1, which comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence listed in the second column of Table 1 for the antibody or antigen-binding fragment, VH FR2 comprises the amino acid sequence listed in the fourth column of Table 1 for the antibody or antigen-binding fragment, VH FR3 comprises the amino acid sequence listed in the sixth column of Table 1 for the antibody or antigen-binding fragment, and VH FR4 comprises the amino acid sequence listed in the eighth column of Table 1 for the antibody or antigen-binding fragment.

TABLE 1

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab1 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELSSLRSEDTAMYYC | (SEQ ID NO: 14) | WGQGTTVTVSS | (SEQ ID NO: 15) |
| Ab2 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELSSLRSEDTAMYYC | (SEQ ID NO: 14) | WGQGTTVTVSS | (SEQ ID NO: 15) |
| Ab3 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELSSLRAEDTAMYYC | (SEQ ID NO: 18) | WGQGTTVTVSS | (SEQ ID NO: 15) |
| Ab4 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELSSLRSEDTAMYYC | (SEQ ID NO: 14) | WGQGTLVTVSS | (SEQ ID NO: 19) |
| Ab5 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRSEDTAMYYC | (SEQ ID NO: 14) | WGQGTTVTVSS | (SEQ ID NO: 15) |
| Ab6 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELSSLRAEDTAMYYC | (SEQ ID NO: 18) | WGQGTTVTVSS | (SEQ ID NO: 15) |
| Ab7 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELSSLRSEDTAMYYC | (SEQ ID NO: 14) | WGQGTLVTVSS | (SEQ ID NO: 19) |
| Ab8 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELSSLRAEDTAMYYC | (SEQ ID NO: 18) | WGQGTTVTVSS | (SEQ ID NO: 15) |
| Ab9 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELSSLRSEDTAMYYC | (SEQ ID NO: 14) | WGQGTLVTVSS | (SEQ ID NO: 19) |
| Ab10 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELSSLRAEDTAMYYC | (SEQ ID NO: 18) | WGQGTLVTVSS | (SEQ ID NO: 19) |
| Ab11 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRAEDTAMYYC | (SEQ ID NO: 18) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab12 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRSEDTAMYYC | (SEQ ID NO: 14) | WGQGTLVTVSS | (SEQ ID NO: 19) |
| Ab13 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELSSLRAEDTAMYYC | (SEQ ID NO: 18) | WGQGTLVTVSS | (SEQ ID NO: 19) |
| Ab14 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELSSLRAEDTAMYYC | (SEQ ID NO: 18) | WGQGTLVTVSS | (SEQ ID NO: 19) |
| Ab15 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRAEDTAMYYC | (SEQ ID NO: 18) | WGQGTLVTVSS | (SEQ ID NO: 19) |
| Ab16 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELSSLRSEDTAMYYC | (SEQ ID NO: 14) | WGQGTTVTVSS | (SEQ ID NO: 15) |
| Ab17 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELSSLRSEDTAMYYC | (SEQ ID NO: 22) | WGQGTTVTVSS | (SEQ ID NO: 15) |
| Ab18 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSTSTAYMELSSLRSEDTAMYYC | (SEQ ID NO: 23) | WGQGTTVTVSS | (SEQ ID NO: 15) |
| Ab19 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRSEDTAMYYC | (SEQ ID NO: 24) | WGQGTTVTVSS | (SEQ ID NO: 15) |
| Ab20 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELSSLRSEDTAVYYC | (SEQ ID NO: 25) | WGQGTTVTVSS | (SEQ ID NO: 15) |
| Ab21 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELSSLRSEDTAMYYC | (SEQ ID NO: 22) | WGQGTTVTVSS | (SEQ ID NO: 15) |
| Ab22 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSTSTAYMELSSLRSEDTAMYYC | (SEQ ID NO: 23) | WGQGTTVTVSS | (SEQ ID NO: 15) |
| Ab23 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELRSLRSEDTAMYYC | (SEQ ID NO: 24) | WGQGTTVTVSS | (SEQ ID NO: 15) |
| Ab24 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELSSLRSEDTAVYYC | (SEQ ID NO: 25) | WGQGTTVTVSS | (SEQ ID NO: 15) |
| Ab25 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSTSTAYMELSSLRSEDTAMYYC | (SEQ ID NO: 26) | WGQGTTVTVSS | (SEQ ID NO: 15) |
| Ab26 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELRSLRSEDTAMYYC | (SEQ ID NO: 27) | WGQGTTVTVSS | (SEQ ID NO: 15) |
| Ab27 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELRSLRSEDTAVYYC | (SEQ ID NO: 28) | WGQGTTVTVSS | (SEQ ID NO: 15) |
| Ab28 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRSEDTAMYYC | (SEQ ID NO: 29) | WGQGTTVTVSS | (SEQ ID NO: 15) |
| Ab29 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRSEDTAVYYC | (SEQ ID NO: 30) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab30 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRSEDTAVYYC | (SEQ ID NO: 31) | WGQGTTVTVSS | (SEQ ID NO: 15) |
| Ab31 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSTSTAYMELSSLRSEDTAMYYC | (SEQ ID NO: 26) | WGQGTTVTVSS | (SEQ ID NO: 15) |
| Ab32 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELRSLRSEDTAMYYC | (SEQ ID NO: 27) | WGQGTTVTVSS | (SEQ ID NO: 15) |
| Ab33 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELRSLRSEDTAVYYC | (SEQ ID NO: 28) | WGQGTTVTVSS | (SEQ ID NO: 15) |
| Ab34 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELRSLRSEDTAMYYC | (SEQ ID NO: 29) | WGQGTTVTVSS | (SEQ ID NO: 15) |
| Ab35 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELRSLRSEDTAVYYC | (SEQ ID NO: 30) | WGQGTTVTVSS | (SEQ ID NO: 15) |
| Ab36 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELRSLRSEDTAVYYC | (SEQ ID NO: 31) | WGQGTTVTVSS | (SEQ ID NO: 15) |
| Ab37 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSTSTAYMELRSLRSEDTAMYYC | (SEQ ID NO: 32) | WGQGTTVTVSS | (SEQ ID NO: 15) |
| Ab38 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSTSTAYMELSSLRSEDTAVYYC | (SEQ ID NO: 33) | WGQGTTVTVSS | (SEQ ID NO: 15) |
| Ab39 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELRSLRSEDTAVYYC | (SEQ ID NO: 34) | WGQGTTVTVSS | (SEQ ID NO: 15) |
| Ab40 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSTSTAYMELRSLRSEDTAVYYC | (SEQ ID NO: 35) | WGQGTTVTVSS | (SEQ ID NO: 15) |
| Ab41 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSTSTAYMELRSLRSEDTAMYYC | (SEQ ID NO: 32) | WGQGTTVTVSS | (SEQ ID NO: 15) |
| Ab42 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSTSTAYMELSSLRSEDTAVYYC | (SEQ ID NO: 33) | WGQGTTVTVSS | (SEQ ID NO: 15) |
| Ab43 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELRSLRSEDTAVYYC | (SEQ ID NO: 34) | WGQGTTVTVSS | (SEQ ID NO: 15) |
| Ab44 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSTSTAYMELRSLRSEDTAVYYC | (SEQ ID NO: 35) | WGQGTTVTVSS | (SEQ ID NO: 15) |
| Ab45 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSTSTAYMELRSLRSEDTAVYYC | (SEQ ID NO: 36) | WGQGTTVTVSS | (SEQ ID NO: 15) |
| Ab46 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSTSTAYMELRSLRSEDTAVYYC | (SEQ ID NO: 36) | WGQGTTVTVSS | (SEQ ID NO: 15) |
| Ab47 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELSSLRSEDTAMYYC | (SEQ ID NO: 14) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab48 | $X_{H1}$QMQLVQSGAEVKKTGSSVKVSCKAS | (SEQ ID NO: 12) | WVRQAPGQGLEWMG | (SEQ ID NO: 16) | YAQKRQGRVTITRDRSMSTAYMELSSLRSEDTAMYYC | (SEQ ID NO: 22) | WGQGTTVTVSS | (SEQ ID NO: 15) |
| Ab49 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSTSTAYMELSSLRSEDTAMYYC | (SEQ ID NO: 23) | WGQGTTVTVSS | (SEQ ID NO: 15) |
| Ab50 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELRSLRSEDTAMYYC | (SEQ ID NO: 24) | WGQGTTVTVSS | (SEQ ID NO: 15) |
| Ab51 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELSSLRSEDTAVYYC | (SEQ ID NO: 25) | WGQGTTVTVSS | (SEQ ID NO: 15) |
| Ab52 | $X_{H1}$QMQLVQSGAEVKKPGSSVKVSCKAS | (SEQ ID NO: 21) | WVRQAPGQGLEWMG | (SEQ ID NO: 16) | YAQKRQGRVTITRDRSMSTAYMELSSLRSEDTAMYYC | (SEQ ID NO: 22) | WGQGTTVTVSS | (SEQ ID NO: 15) |
| Ab53 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSTSTAYMELSSLRSEDTAMYYC | (SEQ ID NO: 23) | WGQGTTVTVSS | (SEQ ID NO: 15) |
| Ab54 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELRSLRSEDTAMYYC | (SEQ ID NO: 24) | WGQGTTVTVSS | (SEQ ID NO: 15) |
| Ab55 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELSSLRSEDTAVYYC | (SEQ ID NO: 25) | WGQGTTVTVSS | (SEQ ID NO: 15) |
| Ab56 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSTSTAYMELSSLRSEDTAMYYC | (SEQ ID NO: 26) | WGQGTTVTVSS | (SEQ ID NO: 15) |
| Ab57 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELRSLRSEDTAMYYC | (SEQ ID NO: 27) | WGQGTTVTVSS | (SEQ ID NO: 15) |
| Ab58 | $X_{H1}$QMQLVQSGAEVKKTGSSVKVSCKAS | (SEQ ID NO: 12) | WVRQAPGQGLEWMG | (SEQ ID NO: 16) | YAQKRQGRVTITRDRSMSTAYMELSSLRSEDTAVYYC | (SEQ ID NO: 28) | WGQGTTVTVSS | (SEQ ID NO: 15) |
| Ab59 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSTSTAYMELRSLRSEDTAMYYC | (SEQ ID NO: 29) | WGQGTTVTVSS | (SEQ ID NO: 15) |
| Ab60 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELRSLRSEDTAVYYC | (SEQ ID NO: 30) | WGQGTTVTVSS | (SEQ ID NO: 15) |
| Ab61 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELRSLRSEDTAVYYC | (SEQ ID NO: 31) | WGQGTTVTVSS | (SEQ ID NO: 15) |
| Ab62 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSTSTAYMELSSLRSEDTAMYYC | (SEQ ID NO: 26) | WGQGTTVTVSS | (SEQ ID NO: 15) |
| Ab63 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELRSLRSEDTAMYYC | (SEQ ID NO: 27) | WGQGTTVTVSS | (SEQ ID NO: 15) |
| Ab64 | $X_{H1}$QMQLVQSGAEVKKPGSSVKVSCKAS | (SEQ ID NO: 21) | WVRQAPGQGLEWMG | (SEQ ID NO: 16) | YAQKRQGRVTITRDRSMSTAYMELSSLRSEDTAVYYC | (SEQ ID NO: 28) | WGQGTTVTVSS | (SEQ ID NO: 15) |
| Ab65 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSTSTAYMELRSLRSEDTAMYYC | (SEQ ID NO: 29) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab66 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELRSLRSEDTAVYYC | (SEQ ID NO: 30) | WGQGTTVTVSS | (SEQ ID NO: 15) |
| Ab67 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELRSLRSEDTAVYYC | (SEQ ID NO: 31) | WGQGTTVTVSS | (SEQ ID NO: 15) |
| Ab68 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSTSTAYMELRSLRSEDTAMYYC | (SEQ ID NO: 32) | WGQGTTVTVSS | (SEQ ID NO: 15) |
| Ab69 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSTSTAYMELSSLRSEDTAVYYC | (SEQ ID NO: 33) | WGQGTTVTVSS | (SEQ ID NO: 15) |
| Ab70 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELRSLRSEDTAVYYC | (SEQ ID NO: 34) | WGQGTTVTVSS | (SEQ ID NO: 15) |
| Ab71 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSTSTAYMELRSLRSEDTAVYYC | (SEQ ID NO: 35) | WGQGTTVTVSS | (SEQ ID NO: 15) |
| Ab72 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSTSTAYMELRSLRSEDTAMYYC | (SEQ ID NO: 32) | WGQGTTVTVSS | (SEQ ID NO: 15) |
| Ab73 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSTSTAYMELSSLRSEDTAVYYC | (SEQ ID NO: 33) | WGQGTTVTVSS | (SEQ ID NO: 15) |
| Ab74 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELRSLRSEDTAVYYC | (SEQ ID NO: 34) | WGQGTTVTVSS | (SEQ ID NO: 15) |
| Ab75 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSTSTAYMELRSLRSEDTAVYYC | (SEQ ID NO: 35) | WGQGTTVTVSS | (SEQ ID NO: 15) |
| Ab76 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSTSTAYMELRSLRSEDTAVYYC | (SEQ ID NO: 36) | WGQGTTVTVSS | (SEQ ID NO: 15) |
| Ab77 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSTSTAYMELRSLRSEDTAVYYC | (SEQ ID NO: 36) | WGQGTTVTVSS | (SEQ ID NO: 15) |
| Ab78 | $X_{H1}$QMQLVQSGAEVKKPGSSVKVSCKAS | (SEQ ID NO: 21) | WVRQAPGQALEWMG | (SEQ ID NO: 17) | YAQKRQDRVTITRDRSMSTAYMELSSLRAEDTAMYYC | (SEQ ID NO: 18) | WGQGTTVTVSS | (SEQ ID NO: 15) |
| Ab79 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELSSLRAEDTAMYYC | (SEQ ID NO: 37) | WGQGTTVTVSS | (SEQ ID NO: 15) |
| Ab80 | $X_{H1}$QMQLVQSGAEVKKTGSSVKVSCKAS | (SEQ ID NO: 12) | WVRQAPGQALEWMG | (SEQ ID NO: 17) | YAQKRQDRVTITRDRSTSTAYMELSSLRAEDTAMYYC | (SEQ ID NO: 38) | WGQGTTVTVSS | (SEQ ID NO: 15) |
| Ab81 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELRSLRAEDTAMYYC | (SEQ ID NO: 39) | WGQGTTVTVSS | (SEQ ID NO: 15) |
| Ab82 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELSSLRAEDTAVYYC | (SEQ ID NO: 40) | WGQGTTVTVSS | (SEQ ID NO: 15) |
| Ab83 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELSSLRAEDTAMYYC | (SEQ ID NO: 37) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab84 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSTSTAYMELSLRAEDTAMYYC | (SEQ ID NO: 38) | WGQGTTVTVSS | (SEQ ID NO: 15) |
| Ab85 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELRSLRAEDTAMYYC | (SEQ ID NO: 39) | WGQGTTVTVSS | (SEQ ID NO: 15) |
| Ab86 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELSSLRAEDTAVYYC | (SEQ ID NO: 40) | WGQGTTVTVSS | (SEQ ID NO: 15) |
| Ab87 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSTSTAYMELSSLRAEDTAMYYC | (SEQ ID NO: 41) | WGQGTTVTVSS | (SEQ ID NO: 15) |
| Ab88 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELRSLRAEDTAMYYC | (SEQ ID NO: 42) | WGQGTTVTVSS | (SEQ ID NO: 15) |
| Ab89 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELSSLRAEDTAVYYC | (SEQ ID NO: 43) | WGQGTTVTVSS | (SEQ ID NO: 15) |
| Ab90 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELSSLRAEDTAMYYC | (SEQ ID NO: 44) | WGQGTTVTVSS | (SEQ ID NO: 15) |
| Ab91 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELSSLRAEDTAVYYC | (SEQ ID NO: 45) | WGQGTTVTVSS | (SEQ ID NO: 15) |
| Ab92 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELRSLRAEDTAVYYC | (SEQ ID NO: 46) | WGQGTTVTVSS | (SEQ ID NO: 15) |
| Ab93 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSTSTAYMELSSLRAEDTAMYYC | (SEQ ID NO: 41) | WGQGTTVTVSS | (SEQ ID NO: 15) |
| Ab94 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELRSLRAEDTAMYYC | (SEQ ID NO: 42) | WGQGTTVTVSS | (SEQ ID NO: 15) |
| Ab95 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELSSLRAEDTAVYYC | (SEQ ID NO: 43) | WGQGTTVTVSS | (SEQ ID NO: 15) |
| Ab96 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELSSLRAEDTAMYYC | (SEQ ID NO: 44) | WGQGTTVTVSS | (SEQ ID NO: 15) |
| Ab97 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELSSLRAEDTAVYYC | (SEQ ID NO: 45) | WGQGTTVTVSS | (SEQ ID NO: 15) |
| Ab98 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELRSLRAEDTAVYYC | (SEQ ID NO: 46) | WGQGTTVTVSS | (SEQ ID NO: 15) |
| Ab99 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELRSLRAEDTAMYYC | (SEQ ID NO: 47) | WGQGTTVTVSS | (SEQ ID NO: 15) |
| Ab100 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELSSLRAEDTAVYYC | (SEQ ID NO: 48) | WGQGTTVTVSS | (SEQ ID NO: 15) |
| Ab101 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELRSLRAEDTAVYYC | (SEQ ID NO: 49) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab102 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELRSLRAEDTAVYYC | (SEQ ID NO: 50) | WGQGTTVTVSS | (SEQ ID NO: 15) |
| Ab103 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELRSLRAEDTAMYYC | (SEQ ID NO: 47) | WGQGTTVTVSS | (SEQ ID NO: 15) |
| Ab104 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELSSLRAEDTAVYYC | (SEQ ID NO: 48) | WGQGTTVTVSS | (SEQ ID NO: 15) |
| Ab105 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELRSLRAEDTAVYYC | (SEQ ID NO: 49) | WGQGTTVTVSS | (SEQ ID NO: 15) |
| Ab106 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELRSLRAEDTAVYYC | (SEQ ID NO: 50) | WGQGTTVTVSS | (SEQ ID NO: 15) |
| Ab107 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSTSTAYMELRSLRAEDTAVYYC | (SEQ ID NO: 139) | WGQGTTVTVSS | (SEQ ID NO: 15) |
| Ab108 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSTSTAYMELRSLRAEDTAVYYC | (SEQ ID NO: 139) | WGQGTTVTVSS | (SEQ ID NO: 15) |
| Ab109 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELSSLRSEDTAMYYC | (SEQ ID NO: 14) | WGQGTLVTVSS | (SEQ ID NO: 19) |
| Ab110 | $X_{H1}$QMQLVQSGAEVKKTGSSVKVSCKAS | (SEQ ID NO: 12) | WVRQAPGQALEWMG | (SEQ ID NO: 17) | YAQKRQGRVTITRDRSMSTAYMELSSLRSEDTAMYYC | (SEQ ID NO: 22) | WGQGTLVTVSS | (SEQ ID NO: 19) |
| Ab111 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSTSTAYMELSSLRSEDTAMYYC | (SEQ ID NO: 23) | WGQGTLVTVSS | (SEQ ID NO: 19) |
| Ab112 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELRSLRSEDTAMYYC | (SEQ ID NO: 24) | WGQGTLVTVSS | (SEQ ID NO: 19) |
| Ab113 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELSSLRSEDTAVYYC | (SEQ ID NO: 25) | WGQGTLVTVSS | (SEQ ID NO: 19) |
| Ab114 | $X_{H1}$QMQLVQSGAEVKKPGSSVKVSCKAS | (SEQ ID NO: 21) | WVRQAPGQALEWMG | (SEQ ID NO: 17) | YAQKRQGRVTITRDRSMSTAYMELSSLRSEDTAMYYC | (SEQ ID NO: 22) | WGQGTLVTVSS | (SEQ ID NO: 19) |
| Ab115 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSTSTAYMELSSLRSEDTAMYYC | (SEQ ID NO: 23) | WGQGTLVTVSS | (SEQ ID NO: 19) |
| Ab116 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELRSLRSEDTAMYYC | (SEQ ID NO: 24) | WGQGTLVTVSS | (SEQ ID NO: 19) |
| Ab117 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELSSLRSEDTAVYYC | (SEQ ID NO: 25) | WGQGTLVTVSS | (SEQ ID NO: 19) |
| Ab118 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSTSTAYMELSSLRSEDTAMYYC | (SEQ ID NO: 26) | WGQGTLVTVSS | (SEQ ID NO: 19) |
| Ab119 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELRSLRSEDTAMYYC | (SEQ ID NO: 27) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab120 | $X_{H1}$QMQLVQSGAEVKKTGSSVKVSCKAS | (SEQ ID NO: 12) | WVRQAPGQALEWMG | (SEQ ID NO: 17) | YAQKRQGRVTITRDRSMSTAYMELSSLRSEDTAVYYC | (SEQ ID NO: 28) | WGQGTLVTVSS | (SEQ ID NO: 19) |
| Ab121 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSTSTAYMELRSLRSEDTAMYYC | (SEQ ID NO: 29) | WGQGTLVTVSS | (SEQ ID NO: 19) |
| Ab122 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELRSLRSEDTAVYYC | (SEQ ID NO: 30) | WGQGTLVTVSS | (SEQ ID NO: 19) |
| Ab123 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELRSLRSEDTAVYYC | (SEQ ID NO: 31) | WGQGTLVTVSS | (SEQ ID NO: 19) |
| Ab124 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSTSTAYMELSSLRSEDTAMYYC | (SEQ ID NO: 26) | WGQGTLVTVSS | (SEQ ID NO: 19) |
| Ab125 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELRSLRSEDTAMYYC | (SEQ ID NO: 27) | WGQGTLVTVSS | (SEQ ID NO: 19) |
| Ab126 | $X_{H1}$QMQLVQSGAEVKKPGSSVKVSCKAS | (SEQ ID NO: 21) | WVRQAPGQALEWMG | (SEQ ID NO: 17) | YAQKRQGRVTITRDRSMSTAYMELSSLRSEDTAVYYC | (SEQ ID NO: 28) | WGQGTLVTVSS | (SEQ ID NO: 19) |
| Ab127 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSTSTAYMELRSLRSEDTAMYYC | (SEQ ID NO: 29) | WGQGTLVTVSS | (SEQ ID NO: 19) |
| Ab128 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELRSLRSEDTAVYYC | (SEQ ID NO: 30) | WGQGTLVTVSS | (SEQ ID NO: 19) |
| Ab129 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELRSLRSEDTAVYYC | (SEQ ID NO: 31) | WGQGTLVTVSS | (SEQ ID NO: 19) |
| Ab130 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSTSTAYMELRSLRSEDTAMYYC | (SEQ ID NO: 32) | WGQGTLVTVSS | (SEQ ID NO: 19) |
| Ab131 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSTSTAYMELSSLRSEDTAVYYC | (SEQ ID NO: 33) | WGQGTLVTVSS | (SEQ ID NO: 19) |
| Ab132 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELRSLRSEDTAVYYC | (SEQ ID NO: 34) | WGQGTLVTVSS | (SEQ ID NO: 19) |
| Ab133 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSTSTAYMELRSLRSEDTAVYYC | (SEQ ID NO: 35) | WGQGTLVTVSS | (SEQ ID NO: 19) |
| Ab134 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSTSTAYMELRSLRSEDTAMYYC | (SEQ ID NO: 32) | WGQGTLVTVSS | (SEQ ID NO: 19) |
| Ab134 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSTSTAYMELSSLRSEDTAVYYC | (SEQ ID NO: 33) | WGQGTLVTVSS | (SEQ ID NO: 19) |
| Ab136 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELRSLRSEDTAVYYC | (SEQ ID NO: 34) | WGQGTLVTVSS | (SEQ ID NO: 19) |
| Ab137 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSTSTAYMELRSLRSEDTAVYYC | (SEQ ID NO: 35) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab138 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSTSTAYMELRSLRSEDTAVYYC | (SEQ ID NO: 36) | WGQGTLVTVSS | (SEQ ID NO: 19) |
| Ab139 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSTSTAYMELRSLRSEDTAVYYC | (SEQ ID NO: 36) | WGQGTLVTVSS | (SEQ ID NO: 19) |
| Ab140 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRSEDTAMYYC | (SEQ ID NO: 14) | WGQGTTVTVSS | (SEQ ID NO: 15) |
| Ab141 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELSSLRSEDTAMYYC | (SEQ ID NO: 22) | WGQGTTVTVSS | (SEQ ID NO: 15) |
| Ab142 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSTSTAYMELSSLRSEDTAMYYC | (SEQ ID NO: 23) | WGQGTTVTVSS | (SEQ ID NO: 15) |
| Ab143 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELRSLRSEDTAMYYC | (SEQ ID NO: 24) | WGQGTTVTVSS | (SEQ ID NO: 15) |
| Ab144 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRSEDTAVYYC | (SEQ ID NO: 25) | WGQGTTVTVSS | (SEQ ID NO: 15) |
| Ab145 | $X_{H1}$QMQLVQSGAEVKKPGSSVKVSCKAS | (SEQ ID NO: 21) | WVRQAPGKGLEWMG | (SEQ ID NO: 20) | YAQKRQGRVTITRDRSMSTAYMELSSLRSEDTAMYYC | (SEQ ID NO: 22) | WGQGTTVTVSS | (SEQ ID NO: 15) |
| Ab146 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSTSTAYMELSSLRSEDTAMYYC | (SEQ ID NO: 23) | WGQGTTVTVSS | (SEQ ID NO: 15) |
| Ab147 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSTSTAYMELRSLRSEDTAMYYC | (SEQ ID NO: 24) | WGQGTTVTVSS | (SEQ ID NO: 15) |
| Ab148 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRSEDTAVYYC | (SEQ ID NO: 25) | WGQGTTVTVSS | (SEQ ID NO: 15) |
| Ab149 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELSSLRSEDTAMYYC | (SEQ ID NO: 26) | WGQGTTVTVSS | (SEQ ID NO: 15) |
| Ab150 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELRSLRSEDTAMYYC | (SEQ ID NO: 27) | WGQGTTVTVSS | (SEQ ID NO: 15) |
| Ab151 | $X_{H1}$QMQLVQSGAEVKKTGSSVKVSCKAS | (SEQ ID NO: 12) | WVRQAPGKGLEWMG | (SEQ ID NO: 20) | YAQKRQGRVTITRDRSMSTAYMELSSLRSEDTAVYYC | (SEQ ID NO: 28) | WGQGTTVTVSS | (SEQ ID NO: 15) |
| Ab152 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELRSLRSEDTAMYYC | (SEQ ID NO: 29) | WGQGTTVTVSS | (SEQ ID NO: 15) |
| Ab153 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELRSLRSEDTAVYYC | (SEQ ID NO: 30) | WGQGTTVTVSS | (SEQ ID NO: 15) |
| Ab154 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELRSLRSEDTAVYYC | (SEQ ID NO: 31) | WGQGTTVTVSS | (SEQ ID NO: 15) |
| Ab155 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSTSTAYMELSSLRSEDTAMYYC | (SEQ ID NO: 26) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab156 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELRSLRSEDTAMYYC | (SEQ ID NO: 27) | WGQGTTVTVSS | (SEQ ID NO: 15) |
| Ab157 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELSSLRSEDTAVYYC | (SEQ ID NO: 28) | WGQGTTVTVSS | (SEQ ID NO: 15) |
| Ab158 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSTSTAYMELRSLRSEDTAMYYC | (SEQ ID NO: 29) | WGQGTTVTVSS | (SEQ ID NO: 15) |
| Ab159 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELRSLRSEDTAVYYC | (SEQ ID NO: 30) | WGQGTTVTVSS | (SEQ ID NO: 15) |
| Ab160 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELRSLRSEDTAVYYC | (SEQ ID NO: 31) | WGQGTTVTVSS | (SEQ ID NO: 15) |
| Ab161 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELRSLRSEDTAMYYC | (SEQ ID NO: 32) | WGQGTTVTVSS | (SEQ ID NO: 15) |
| Ab162 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELSSLRSEDTAVYYC | (SEQ ID NO: 33) | WGQGTTVTVSS | (SEQ ID NO: 15) |
| Ab163 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELRSLRSEDTAVYYC | (SEQ ID NO: 34) | WGQGTTVTVSS | (SEQ ID NO: 15) |
| Ab164 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSTSTAYMELRSLRSEDTAVYYC | (SEQ ID NO: 35) | WGQGTTVTVSS | (SEQ ID NO: 15) |
| Ab165 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSTSTAYMELRSLRSEDTAMYYC | (SEQ ID NO: 32) | WGQGTTVTVSS | (SEQ ID NO: 15) |
| Ab166 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSTSTAYMELSSLRSEDTAVYYC | (SEQ ID NO: 33) | WGQGTTVTVSS | (SEQ ID NO: 15) |
| Ab167 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELRSLRSEDTAVYYC | (SEQ ID NO: 34) | WGQGTTVTVSS | (SEQ ID NO: 15) |
| Ab168 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSTAYMELRSLRSEDTAVYYC | (SEQ ID NO: 35) | WGQGTTVTVSS | (SEQ ID NO: 15) |
| Ab169 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELRSLRSEDTAVYYC | (SEQ ID NO: 36) | WGQGTTVTVSS | (SEQ ID NO: 15) |
| Ab170 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSTSTAYMELRSLRSEDTAVYYC | (SEQ ID NO: 36) | WGQGTTVTVSS | (SEQ ID NO: 15) |
| Ab171 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELSSLRAEDTAMYYC | (SEQ ID NO: 18) | WGQGTTVTVSS | (SEQ ID NO: 15) |
| Ab172 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELSSLRAEDTAMYYC | (SEQ ID NO: 37) | WGQGTTVTVSS | (SEQ ID NO: 15) |
| Ab173 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSTSTAYMELSSLRAEDTAMYYC | (SEQ ID NO: 38) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab174 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRAEDTAMYYC | (SEQ ID NO: 39) | WGQGTTVTVSS | (SEQ ID NO: 15) |
| Ab175 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELSSLRAEDTAVYYC | (SEQ ID NO: 40) | WGQGTTVTVSS | (SEQ ID NO: 15) |
| Ab176 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELSSLRAEDTAMYYC | (SEQ ID NO: 37) | WGQGTTVTVSS | (SEQ ID NO: 15) |
| Ab177 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSTSTAYMELSSLRAEDTAMYYC | (SEQ ID NO: 38) | WGQGTTVTVSS | (SEQ ID NO: 15) |
| Ab178 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELRSLRAEDTAMYYC | (SEQ ID NO: 39) | WGQGTTVTVSS | (SEQ ID NO: 15) |
| Ab179 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELSSLRAEDTAVYYC | (SEQ ID NO: 40) | WGQGTTVTVSS | (SEQ ID NO: 15) |
| Ab180 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSTSTAYMELSSLRAEDTAMYYC | (SEQ ID NO: 41) | WGQGTTVTVSS | (SEQ ID NO: 15) |
| Ab181 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELRSLRAEDTAMYYC | (SEQ ID NO: 42) | WGQGTTVTVSS | (SEQ ID NO: 15) |
| Ab182 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELSSLRAEDTAVYYC | (SEQ ID NO: 43) | WGQGTTVTVSS | (SEQ ID NO: 15) |
| Ab183 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELSSLRAEDTAMYYC | (SEQ ID NO: 44) | WGQGTTVTVSS | (SEQ ID NO: 15) |
| Ab184 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELSSLRAEDTAVYYC | (SEQ ID NO: 45) | WGQGTTVTVSS | (SEQ ID NO: 15) |
| Ab185 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRAEDTAVYYC | (SEQ ID NO: 46) | WGQGTTVTVSS | (SEQ ID NO: 15) |
| Ab186 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSTSTAYMELSSLRAEDTAMYYC | (SEQ ID NO: 41) | WGQGTTVTVSS | (SEQ ID NO: 15) |
| Ab187 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELRSLRAEDTAMYYC | (SEQ ID NO: 42) | WGQGTTVTVSS | (SEQ ID NO: 15) |
| Ab188 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELSSLRAEDTAVYYC | (SEQ ID NO: 43) | WGQGTTVTVSS | (SEQ ID NO: 15) |
| Ab189 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELSSLRAEDTAMYYC | (SEQ ID NO: 44) | WGQGTTVTVSS | (SEQ ID NO: 15) |
| Ab190 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELSSLRAEDTAVYYC | (SEQ ID NO: 45) | WGQGTTVTVSS | (SEQ ID NO: 15) |
| Ab191 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELRSLRAEDTAVYYC | (SEQ ID NO: 46) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab192 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELRSLRAEDTAMYYC | (SEQ ID NO: 47) | WGQGTTVTVSS | (SEQ ID NO: 15) |
| Ab193 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELSSLRAEDTAVYYC | (SEQ ID NO: 48) | WGQGTTVTVSS | (SEQ ID NO: 15) |
| Ab194 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELRSLRAEDTAVYYC | (SEQ ID NO: 49) | WGQGTTVTVSS | (SEQ ID NO: 15) |
| Ab195 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRAEDTAVYYC | (SEQ ID NO: 50) | WGQGTTVTVSS | (SEQ ID NO: 15) |
| Ab196 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELRSLRAEDTAMYYC | (SEQ ID NO: 47) | WGQGTTVTVSS | (SEQ ID NO: 15) |
| Ab197 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELSSLRAEDTAVYYC | (SEQ ID NO: 48) | WGQGTTVTVSS | (SEQ ID NO: 15) |
| Ab198 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELRSLRAEDTAVYYC | (SEQ ID NO: 49) | WGQGTTVTVSS | (SEQ ID NO: 15) |
| Ab199 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELRSLRAEDTAVYYC | (SEQ ID NO: 50) | WGQGTTVTVSS | (SEQ ID NO: 15) |
| Ab200 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSTSTAYMELRSLRAEDTAVYYC | (SEQ ID NO: 139) | WGQGTTVTVSS | (SEQ ID NO: 15) |
| Ab201 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSTSTAYMELRSLRAEDTAVYYC | (SEQ ID NO: 139) | WGQGTTVTVSS | (SEQ ID NO: 15) |
| Ab202 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELSSLRSEDTAMYYC | (SEQ ID NO: 14) | WGQGTLVTVSS | (SEQ ID NO: 19) |
| Ab203 | $X_{H1}$QMQLVQSGAEVKKTGSSVKVSCKAS | (SEQ ID NO: 12) | WVRQAPGKALEWMG | (SEQ ID NO: 13) | YAQKRQGRVTITRDRSMSTAYMELSSLRSEDTAMYYC | (SEQ ID NO: 22) | WGQGTLVTVSS | (SEQ ID NO: 19) |
| Ab204 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSTSTAYMELSSLRSEDTAMYYC | (SEQ ID NO: 23) | WGQGTLVTVSS | (SEQ ID NO: 19) |
| Ab205 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRSEDTAMYYC | (SEQ ID NO: 24) | WGQGTLVTVSS | (SEQ ID NO: 19) |
| Ab206 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELSSLRSEDTAVYYC | (SEQ ID NO: 25) | WGQGTLVTVSS | (SEQ ID NO: 19) |
| Ab207 | $X_{H1}$QMQLVQSGAEVKKPGSSVKVSCKAS | (SEQ ID NO: 21) | WVRQAPGKALEWMG | (SEQ ID NO: 13) | YAQKRQGRVTITRDRSMSTAYMELSSLRSEDTAMYYC | (SEQ ID NO: 22) | WGQGTLVTVSS | (SEQ ID NO: 19) |
| Ab208 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSTSTAYMELSSLRSEDTAMYYC | (SEQ ID NO: 23) | WGQGTLVTVSS | (SEQ ID NO: 19) |
| Ab209 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELRSLRSEDTAMYYC | (SEQ ID NO: 24) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab210 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELSSLRSEDTAVYYC | (SEQ ID NO: 25) | WGQGTLVTVSS | (SEQ ID NO: 19) |
| Ab211 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSTSTAYMELSSLRSEDTAMYYC | (SEQ ID NO: 26) | WGQGTLVTVSS | (SEQ ID NO: 19) |
| Ab212 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELRSLRSEDTAMYYC | (SEQ ID NO: 27) | WGQGTLVTVSS | (SEQ ID NO: 19) |
| Ab213 | $X_{H1}$QMQLVQSGAEVKKTGSSVKVSCKAS | (SEQ ID NO: 12) | WVRQAPGKALEWMG | (SEQ ID NO: 13) | YAQKRQGRVTITRDRSMSTAYMELSSLRSEDTAVYYC | (SEQ ID NO: 28) | WGQGTLVTVSS | (SEQ ID NO: 19) |
| Ab214 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSTSTAYMELRSLRSEDTAMYYC | (SEQ ID NO: 29) | WGQGTLVTVSS | (SEQ ID NO: 19) |
| Ab215 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRSEDTAVYYC | (SEQ ID NO: 30) | WGQGTLVTVSS | (SEQ ID NO: 19) |
| Ab216 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRSEDTAVYYC | (SEQ ID NO: 31) | WGQGTLVTVSS | (SEQ ID NO: 19) |
| Ab217 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSTSTAYMELSSLRSEDTAMYYC | (SEQ ID NO: 26) | WGQGTLVTVSS | (SEQ ID NO: 19) |
| Ab218 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELRSLRSEDTAMYYC | (SEQ ID NO: 27) | WGQGTLVTVSS | (SEQ ID NO: 19) |
| Ab219 | $X_{H1}$QMQLVQSGAEVKKPGSSVKVSCKAS | (SEQ ID NO: 21) | WVRQAPGKALEWMG | (SEQ ID NO: 13) | YAQKRQGRVTITRDRSMSTAYMELSSLRSEDTAVYYC | (SEQ ID NO: 28) | WGQGTLVTVSS | (SEQ ID NO: 19) |
| Ab220 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSTSTAYMELRSLRSEDTAMYYC | (SEQ ID NO: 29) | WGQGTLVTVSS | (SEQ ID NO: 19) |
| Ab221 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELRSLRSEDTAVYYC | (SEQ ID NO: 30) | WGQGTLVTVSS | (SEQ ID NO: 19) |
| Ab222 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELRSLRSEDTAVYYC | (SEQ ID NO: 31) | WGQGTLVTVSS | (SEQ ID NO: 19) |
| Ab223 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSTSTAYMELRSLRSEDTAMYYC | (SEQ ID NO: 32) | WGQGTLVTVSS | (SEQ ID NO: 19) |
| Ab224 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSTSTAYMELSSLRSEDTAVYYC | (SEQ ID NO: 33) | WGQGTLVTVSS | (SEQ ID NO: 19) |
| Ab225 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELRSLRSEDTAVYYC | (SEQ ID NO: 34) | WGQGTLVTVSS | (SEQ ID NO: 19) |
| Ab226 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSTSTAYMELRSLRSEDTAVYYC | (SEQ ID NO: 35) | WGQGTLVTVSS | (SEQ ID NO: 19) |
| Ab227 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSTSTAYMELRSLRSEDTAMYYC | (SEQ ID NO: 32) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab228 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSTSTAYMELRSLRSEDTAVYYC | (SEQ ID NO: 33) | WGQGTLVTVSS | (SEQ ID NO: 19) |
| Ab229 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELRSLRSEDTAVYYC | (SEQ ID NO: 34) | WGQGTLVTVSS | (SEQ ID NO: 19) |
| Ab230 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSTSTAYMELRSLRSEDTAVYYC | (SEQ ID NO: 35) | WGQGTLVTVSS | (SEQ ID NO: 19) |
| Ab231 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSTSTAYMELRSLRSEDTAVYYC | (SEQ ID NO: 36) | WGQGTLVTVSS | (SEQ ID NO: 19) |
| Ab232 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSTSTAYMELRSLRSEDTAVYYC | (SEQ ID NO: 36) | WGQGTLVTVSS | (SEQ ID NO: 19) |
| Ab233 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELSSLRAEDTAMYYC | (SEQ ID NO: 18) | WGQGTTVTVSS | (SEQ ID NO: 15) |
| Ab234 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELSSLRAEDTAMYYC | (SEQ ID NO: 37) | WGQGTTVTVSS | (SEQ ID NO: 15) |
| Ab235 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSTSTAYMELSSLRAEDTAMYYC | (SEQ ID NO: 38) | WGQGTTVTVSS | (SEQ ID NO: 15) |
| Ab236 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELRSLRAEDTAMYYC | (SEQ ID NO: 39) | WGQGTTVTVSS | (SEQ ID NO: 15) |
| Ab237 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELSSLRAEDTAVYYC | (SEQ ID NO: 40) | WGQGTTVTVSS | (SEQ ID NO: 15) |
| Ab238 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELSSLRAEDTAMYYC | (SEQ ID NO: 37) | WGQGTTVTVSS | (SEQ ID NO: 15) |
| Ab239 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSTSTAYMELSSLRAEDTAMYYC | (SEQ ID NO: 38) | WGQGTTVTVSS | (SEQ ID NO: 15) |
| Ab240 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELRSLRAEDTAMYYC | (SEQ ID NO: 39) | WGQGTTVTVSS | (SEQ ID NO: 15) |
| Ab241 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELSSLRAEDTAVYYC | (SEQ ID NO: 40) | WGQGTTVTVSS | (SEQ ID NO: 15) |
| Ab242 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSTSTAYMELSSLRAEDTAMYYC | (SEQ ID NO: 41) | WGQGTTVTVSS | (SEQ ID NO: 15) |
| Ab243 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELRSLRAEDTAMYYC | (SEQ ID NO: 42) | WGQGTTVTVSS | (SEQ ID NO: 15) |
| Ab244 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELSSLRAEDTAVYYC | (SEQ ID NO: 43) | WGQGTTVTVSS | (SEQ ID NO: 15) |
| Ab245 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELSSLRAEDTAMYYC | (SEQ ID NO: 44) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab246 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELSSLRAEDTAVYYC | (SEQ ID NO: 45) | WGQGTTVTVSS | (SEQ ID NO: 15) |
| Ab247 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELRSLRAEDTAVYYC | (SEQ ID NO: 46) | WGQGTTVTVSS | (SEQ ID NO: 15) |
| Ab248 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSTSTAYMELSSLRAEDTAMYYC | (SEQ ID NO: 41) | WGQGTTVTVSS | (SEQ ID NO: 15) |
| Ab249 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELRSLRAEDTAMYYC | (SEQ ID NO: 42) | WGQGTTVTVSS | (SEQ ID NO: 15) |
| Ab250 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELSSLRAEDTAVYYC | (SEQ ID NO: 43) | WGQGTTVTVSS | (SEQ ID NO: 15) |
| Ab251 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELSSLRAEDTAMYYC | (SEQ ID NO: 44) | WGQGTTVTVSS | (SEQ ID NO: 15) |
| Ab252 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELSSLRAEDTAVYYC | (SEQ ID NO: 45) | WGQGTTVTVSS | (SEQ ID NO: 15) |
| Ab253 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELRSLRAEDTAVYYC | (SEQ ID NO: 46) | WGQGTTVTVSS | (SEQ ID NO: 15) |
| Ab254 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELRSLRAEDTAMYYC | (SEQ ID NO: 47) | WGQGTTVTVSS | (SEQ ID NO: 15) |
| Ab255 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELSSLRAEDTAVYYC | (SEQ ID NO: 48) | WGQGTTVTVSS | (SEQ ID NO: 15) |
| Ab256 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELRSLRAEDTAVYYC | (SEQ ID NO: 49) | WGQGTTVTVSS | (SEQ ID NO: 15) |
| Ab257 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELRSLRAEDTAVYYC | (SEQ ID NO: 50) | WGQGTTVTVSS | (SEQ ID NO: 15) |
| Ab258 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELRSLRAEDTAMYYC | (SEQ ID NO: 47) | WGQGTTVTVSS | (SEQ ID NO: 15) |
| Ab259 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELSSLRAEDTAVYYC | (SEQ ID NO: 48) | WGQGTTVTVSS | (SEQ ID NO: 15) |
| Ab260 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELRSLRAEDTAVYYC | (SEQ ID NO: 49) | WGQGTTVTVSS | (SEQ ID NO: 15) |
| Ab261 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELRSLRAEDTAVYYC | (SEQ ID NO: 50) | WGQGTTVTVSS | (SEQ ID NO: 15) |
| Ab262 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSTSTAYMELRSLRAEDTAVYYC | (SEQ ID NO: 139) | WGQGTTVTVSS | (SEQ ID NO: 15) |
| Ab263 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSTSTAYMELRSLRAEDTAVYYC | (SEQ ID NO: 139) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab264 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELSSLRSEDTAMYYC | (SEQ ID NO: 14) | WGQGTLVTVSS | (SEQ ID NO: 19) |
| Ab265 | $X_{H1}$QMQLVQSGAEVKKTGSSVKVSCKAS | (SEQ ID NO: 12) | WVRQAPGQGLEWMG | (SEQ ID NO: 16) | YAQKRQGRVTITRDRSMSTAYMELSSLRSEDTAMYYC | (SEQ ID NO: 22) | WGQGTLVTVSS | (SEQ ID NO: 19) |
| Ab266 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSTSTAYMELSSLRSEDTAMYYC | (SEQ ID NO: 23) | WGQGTLVTVSS | (SEQ ID NO: 19) |
| Ab267 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELRSLRSEDTAMYYC | (SEQ ID NO: 24) | WGQGTLVTVSS | (SEQ ID NO: 19) |
| Ab268 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELSSLRSEDTAVYYC | (SEQ ID NO: 25) | WGQGTLVTVSS | (SEQ ID NO: 19) |
| Ab269 | $X_{H1}$QMQLVQSGAEVKKPGSSVKVSCKAS | (SEQ ID NO: 21) | WVRQAPGQGLEWMG | (SEQ ID NO: 16) | YAQKRQGRVTITRDRSMSTAYMELSSLRSEDTAMYYC | (SEQ ID NO: 22) | WGQGTLVTVSS | (SEQ ID NO: 19) |
| Ab270 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSTSTAYMELSSLRSEDTAMYYC | (SEQ ID NO: 23) | WGQGTLVTVSS | (SEQ ID NO: 19) |
| Ab271 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELRSLRSEDTAMYYC | (SEQ ID NO: 24) | WGQGTLVTVSS | (SEQ ID NO: 19) |
| Ab272 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELSSLRSEDTAVYYC | (SEQ ID NO: 25) | WGQGTLVTVSS | (SEQ ID NO: 19) |
| Ab273 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSTSTAYMELSSLRSEDTAMYYC | (SEQ ID NO: 26) | WGQGTLVTVSS | (SEQ ID NO: 19) |
| Ab274 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELRSLRSEDTAMYYC | (SEQ ID NO: 27) | WGQGTLVTVSS | (SEQ ID NO: 19) |
| Ab275 | $X_{H1}$QMQLVQSGAEVKKTGSSVKVSCKAS | (SEQ ID NO: 12) | WVRQAPGQGLEWMG | (SEQ ID NO: 16) | YAQKRQGRVTITRDRSMSTAYMELSSLRSEDTAVYYC | (SEQ ID NO: 28) | WGQGTLVTVSS | (SEQ ID NO: 19) |
| Ab276 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSTSTAYMELRSLRSEDTAMYYC | (SEQ ID NO: 29) | WGQGTLVTVSS | (SEQ ID NO: 19) |
| Ab277 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELRSLRSEDTAVYYC | (SEQ ID NO: 30) | WGQGTLVTVSS | (SEQ ID NO: 19) |
| Ab278 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELRSLRSEDTAVYYC | (SEQ ID NO: 31) | WGQGTLVTVSS | (SEQ ID NO: 19) |
| Ab279 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSTSTAYMELSSLRSEDTAMYYC | (SEQ ID NO: 26) | WGQGTLVTVSS | (SEQ ID NO: 19) |
| Ab280 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELRSLRSEDTAMYYC | (SEQ ID NO: 27) | WGQGTLVTVSS | (SEQ ID NO: 19) |
| Ab281 | $X_{H1}$QMQLVQSGAEVKKPGSSVKVSCKAS | (SEQ ID NO: 21) | WVRQAPGQGLEWMG | (SEQ ID NO: 16) | YAQKRQGRVTITRDRSMSTAYMELSSLRSEDTAVYYC | (SEQ ID NO: 28) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab282 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSTSTAYMELRSLRSEDTAMYYC | (SEQ ID NO: 29) | WGQGTLVTVSS | (SEQ ID NO: 19) |
| Ab283 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELRSLRSEDTAVYYC | (SEQ ID NO: 30) | WGQGTLVTVSS | (SEQ ID NO: 19) |
| Ab284 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELRSLRSEDTAVYYC | (SEQ ID NO: 31) | WGQGTLVTVSS | (SEQ ID NO: 19) |
| Ab285 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSTSTAYMELRSLRSEDTAMYYC | (SEQ ID NO: 32) | WGQGTLVTVSS | (SEQ ID NO: 19) |
| Ab286 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSTSTAYMELSSLRSEDTAVYYC | (SEQ ID NO: 33) | WGQGTLVTVSS | (SEQ ID NO: 19) |
| Ab287 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELRSLRSEDTAVYYC | (SEQ ID NO: 34) | WGQGTLVTVSS | (SEQ ID NO: 19) |
| Ab288 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSTSTAYMELRSLRSEDTAVYYC | (SEQ ID NO: 35) | WGQGTLVTVSS | (SEQ ID NO: 19) |
| Ab289 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSTSTAYMELRSLRSEDTAMYYC | (SEQ ID NO: 32) | WGQGTLVTVSS | (SEQ ID NO: 19) |
| Ab290 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSTSTAYMELSSLRSEDTAVYYC | (SEQ ID NO: 33) | WGQGTLVTVSS | (SEQ ID NO: 19) |
| Ab291 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELRSLRSEDTAVYYC | (SEQ ID NO: 34) | WGQGTLVTVSS | (SEQ ID NO: 19) |
| Ab292 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSTSTAYMELRSLRSEDTAVYYC | (SEQ ID NO: 35) | WGQGTLVTVSS | (SEQ ID NO: 19) |
| Ab293 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSTSTAYMELRSLRSEDTAVYYC | (SEQ ID NO: 36) | WGQGTLVTVSS | (SEQ ID NO: 19) |
| Ab294 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSTSTAYMELRSLRSEDTAVYYC | (SEQ ID NO: 36) | WGQGTLVTVSS | (SEQ ID NO: 19) |
| Ab295 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELSSLRAEDTAMYYC | (SEQ ID NO: 18) | WGQGTLVTVSS | (SEQ ID NO: 19) |
| Ab296 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELSSLRAEDTAMYYC | (SEQ ID NO: 37) | WGQGTLVTVSS | (SEQ ID NO: 19) |
| Ab297 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSTSTAYMELSSLRAEDTAMYYC | (SEQ ID NO: 38) | WGQGTLVTVSS | (SEQ ID NO: 19) |
| Ab298 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELRSLRAEDTAMYYC | (SEQ ID NO: 39) | WGQGTLVTVSS | (SEQ ID NO: 19) |
| Ab299 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELSSLRAEDTAVYYC | (SEQ ID NO: 40) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab300 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELSSLRAEDTAMYYC | (SEQ ID NO: 37) | WGQGTLVTVSS | (SEQ ID NO: 19) |
| Ab301 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSTSTAYMELSSLRAEDTAMYYC | (SEQ ID NO: 38) | WGQGTLVTVSS | (SEQ ID NO: 19) |
| Ab302 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELRSLRAEDTAMYYC | (SEQ ID NO: 39) | WGQGTLVTVSS | (SEQ ID NO: 19) |
| Ab303 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELSSLRAEDTAVYYC | (SEQ ID NO: 40) | WGQGTLVTVSS | (SEQ ID NO: 19) |
| Ab304 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSTSTAYMELSSLRAEDTAMYYC | (SEQ ID NO: 41) | WGQGTLVTVSS | (SEQ ID NO: 19) |
| Ab305 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELRSLRAEDTAMYYC | (SEQ ID NO: 42) | WGQGTLVTVSS | (SEQ ID NO: 19) |
| Ab306 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELSSLRAEDTAVYYC | (SEQ ID NO: 43) | WGQGTLVTVSS | (SEQ ID NO: 19) |
| Ab307 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELSSLRAEDTAMYYC | (SEQ ID NO: 44) | WGQGTLVTVSS | (SEQ ID NO: 19) |
| Ab308 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELSSLRAEDTAVYYC | (SEQ ID NO: 45) | WGQGTLVTVSS | (SEQ ID NO: 19) |
| Ab309 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELRSLRAEDTAVYYC | (SEQ ID NO: 46) | WGQGTLVTVSS | (SEQ ID NO: 19) |
| Ab310 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSTSTAYMELSSLRAEDTAMYYC | (SEQ ID NO: 41) | WGQGTLVTVSS | (SEQ ID NO: 19) |
| Ab311 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELRSLRAEDTAMYYC | (SEQ ID NO: 42) | WGQGTLVTVSS | (SEQ ID NO: 19) |
| Ab312 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELSSLRAEDTAVYYC | (SEQ ID NO: 43) | WGQGTLVTVSS | (SEQ ID NO: 19) |
| Ab313 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELSSLRAEDTAMYYC | (SEQ ID NO: 44) | WGQGTLVTVSS | (SEQ ID NO: 19) |
| Ab314 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELSSLRAEDTAVYYC | (SEQ ID NO: 45) | WGQGTLVTVSS | (SEQ ID NO: 19) |
| Ab315 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELRSLRAEDTAVYYC | (SEQ ID NO: 46) | WGQGTLVTVSS | (SEQ ID NO: 19) |
| Ab316 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELRSLRAEDTAMYYC | (SEQ ID NO: 47) | WGQGTLVTVSS | (SEQ ID NO: 19) |
| Ab317 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELSSLRAEDTAVYYC | (SEQ ID NO: 48) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab318 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSMSTAYMELRSLRAEDTAVYYC | (SEQ ID NO: 49) | WGQGTLVTVSS | (SEQ ID NO: 19) |
| Ab319 | $X_{H1}$QMQLVQSGAEVKKTGSSVKVSCKAS | (SEQ ID NO: 12) | WVRQAPGQALEWMG | (SEQ ID NO: 17) | YAQKFQDRVTITRDRSMSTAYMELRSLRAEDTAVYYC | (SEQ ID NO: 50) | WGQGTLVTVSS | (SEQ ID NO: 19) |
| Ab320 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELRSLRAEDTAMYYC | (SEQ ID NO: 47) | WGQGTLVTVSS | (SEQ ID NO: 19) |
| Ab321 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELSSLRAEDTAVYYC | (SEQ ID NO: 48) | WGQGTLVTVSS | (SEQ ID NO: 19) |
| Ab322 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSMSTAYMELRSLRAEDTAVYYC | (SEQ ID NO: 49) | WGQGTLVTVSS | (SEQ ID NO: 19) |
| Ab323 | $X_{H1}$QMQLVQSGAEVKKPGSSVKVSCKAS | (SEQ ID NO: 21) | WVRQAPGQALEWMG | (SEQ ID NO: 17) | YAQKFQDRVTITRDRSMSTAYMELRSLRAEDTAVYYC | (SEQ ID NO: 50) | WGQGTLVTVSS | (SEQ ID NO: 19) |
| Ab324 | $X_{H1}$QMQLVQSGAEVKKTGSSVKVSCKAS | (SEQ ID NO: 12) | WVRQAPGQALEWMG | (SEQ ID NO: 17) | YAQKFQGRVTITRDRSTSTAYMELRSLRAEDTAVYYC | (SEQ ID NO: 139) | WGQGTLVTVSS | (SEQ ID NO: 19) |
| Ab325 | $X_{H1}$QMQLVQSGAEVKKPGSSVKVSCKAS | (SEQ ID NO: 21) | WVRQAPGQALEWMG | (SEQ ID NO: 17) | YAQKFQGRVTITRDRSTSTAYMELRSLRAEDTAVYYC | (SEQ ID NO: 139) | WGQGTLVTVSS | (SEQ ID NO: 19) |
| Ab327 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRAEDTAMYYC | (SEQ ID NO: 18) | WGQGTTVTVSS | (SEQ ID NO: 15) |
| Ab327 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRAEDTAMYYC | (SEQ ID NO: 37) | WGQGTTVTVSS | (SEQ ID NO: 15) |
| Ab328 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSTSTAYMELSSLRAEDTAMYYC | (SEQ ID NO: 38) | WGQGTTVTVSS | (SEQ ID NO: 15) |
| Ab329 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELRSLRAEDTAMYYC | (SEQ ID NO: 39) | WGQGTTVTVSS | (SEQ ID NO: 15) |
| Ab330 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRAEDTAVYYC | (SEQ ID NO: 40) | WGQGTTVTVSS | (SEQ ID NO: 15) |
| Ab331 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRAEDTAMYYC | (SEQ ID NO: 37) | WGQGTTVTVSS | (SEQ ID NO: 15) |
| Ab332 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSTSTAYMELSSLRAEDTAMYYC | (SEQ ID NO: 38) | WGQGTTVTVSS | (SEQ ID NO: 15) |
| Ab333 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELRSLRAEDTAMYYC | (SEQ ID NO: 39) | WGQGTTVTVSS | (SEQ ID NO: 15) |
| Ab334 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRAEDTAVYYC | (SEQ ID NO: 40) | WGQGTTVTVSS | (SEQ ID NO: 15) |
| Ab335 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELSSLRAEDTAMYYC | (SEQ ID NO: 41) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab336 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELRSLRAEDTAMYYC | (SEQ ID NO: 42) | WGQGTTVTVSS | (SEQ ID NO: 15) |
| Ab337 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELSSLRAEDTAVYYC | (SEQ ID NO: 43) | WGQGTTVTVSS | (SEQ ID NO: 15) |
| Ab338 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRAEDTAMYYC | (SEQ ID NO: 44) | WGQGTTVTVSS | (SEQ ID NO: 15) |
| Ab339 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRAEDTAVYYC | (SEQ ID NO: 45) | WGQGTTVTVSS | (SEQ ID NO: 15) |
| Ab340 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELRSLRAEDTAVYYC | (SEQ ID NO: 46) | WGQGTTVTVSS | (SEQ ID NO: 15) |
| Ab341 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSTSTAYMELSSLRAEDTAMYYC | (SEQ ID NO: 41) | WGQGTTVTVSS | (SEQ ID NO: 15) |
| Ab342 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELRSLRAEDTAMYYC | (SEQ ID NO: 42) | WGQGTTVTVSS | (SEQ ID NO: 15) |
| Ab343 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELSSLRAEDTAVYYC | (SEQ ID NO: 43) | WGQGTTVTVSS | (SEQ ID NO: 15) |
| Ab344 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRAEDTAMYYC | (SEQ ID NO: 44) | WGQGTTVTVSS | (SEQ ID NO: 15) |
| Ab345 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRAEDTAVYYC | (SEQ ID NO: 45) | WGQGTTVTVSS | (SEQ ID NO: 15) |
| Ab346 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELRSLRAEDTAVYYC | (SEQ ID NO: 46) | WGQGTTVTVSS | (SEQ ID NO: 15) |
| Ab347 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELRSLRAEDTAMYYC | (SEQ ID NO: 47) | WGQGTTVTVSS | (SEQ ID NO: 15) |
| Ab348 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELSSLRAEDTAVYYC | (SEQ ID NO: 48) | WGQGTTVTVSS | (SEQ ID NO: 15) |
| Ab349 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELRSLRAEDTAVYYC | (SEQ ID NO: 49) | WGQGTTVTVSS | (SEQ ID NO: 15) |
| Ab350 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELRSLRAEDTAVYYC | (SEQ ID NO: 50) | WGQGTTVTVSS | (SEQ ID NO: 15) |
| Ab351 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELRSLRAEDTAMYYC | (SEQ ID NO: 47) | WGQGTTVTVSS | (SEQ ID NO: 15) |
| Ab352 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELSSLRAEDTAVYYC | (SEQ ID NO: 48) | WGQGTTVTVSS | (SEQ ID NO: 15) |
| Ab353 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELRSLRAEDTAVYYC | (SEQ ID NO: 49) | WGQGTTVTVSS | (SEQ ID NO: 15) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab354 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELRSLRAEDTAVYYC | (SEQ ID NO: 50) | WGQGTTVTVSS | (SEQ ID NO: 15) |
| Ab355 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELRSLRAEDTAVYYC | (SEQ ID NO: 139) | WGQGTTVTVSS | (SEQ ID NO: 15) |
| Ab356 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSTSTAYMELRSLRAEDTAVYYC | (SEQ ID NO: 139) | WGQGTTVTVSS | (SEQ ID NO: 15) |
| Ab357 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRSEDTAMYYC | (SEQ ID NO: 14) | WGQGTLVTVSS | (SEQ ID NO: 19) |
| Ab358 | $X_{H1}$QMQLVQSGAEVKKTGSSVKVSCKAS | (SEQ ID NO: 12) | WVRQAPGKGLEWMG | (SEQ ID NO: 20) | YAQKRQGRVTITRDRSMSTAYMELSSLRSEDTAMYYC | (SEQ ID NO: 22) | WGQGTLVTVSS | (SEQ ID NO: 19) |
| Ab359 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSTSTAYMELSSLRSEDTAMYYC | (SEQ ID NO: 23) | WGQGTLVTVSS | (SEQ ID NO: 19) |
| Ab360 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELRSLRSEDTAMYYC | (SEQ ID NO: 24) | WGQGTLVTVSS | (SEQ ID NO: 19) |
| Ab361 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRSEDTAVYYC | (SEQ ID NO: 25) | WGQGTLVTVSS | (SEQ ID NO: 19) |
| Ab362 | $X_{H1}$QMQLVQSGAEVKKPGSSVKVSCKAS | (SEQ ID NO: 21) | WVRQAPGKGLEWMG | (SEQ ID NO: 20) | YAQKRQGRVTITRDRSMSTAYMELSSLRSEDTAMYYC | (SEQ ID NO: 22) | WGQGTLVTVSS | (SEQ ID NO: 19) |
| Ab363 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSTSTAYMELSSLRSEDTAMYYC | (SEQ ID NO: 23) | WGQGTLVTVSS | (SEQ ID NO: 19) |
| Ab364 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELRSLRSEDTAMYYC | (SEQ ID NO: 24) | WGQGTLVTVSS | (SEQ ID NO: 19) |
| Ab365 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRSEDTAVYYC | (SEQ ID NO: 25) | WGQGTLVTVSS | (SEQ ID NO: 19) |
| Ab366 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELSSLRSEDTAMYYC | (SEQ ID NO: 26) | WGQGTLVTVSS | (SEQ ID NO: 19) |
| Ab367 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELRSLRSEDTAMYYC | (SEQ ID NO: 27) | WGQGTLVTVSS | (SEQ ID NO: 19) |
| Ab368 | $X_{H1}$QMQLVQSGAEVKKTGSSVKVSCKAS | (SEQ ID NO: 12) | WVRQAPGKGLEWMG | (SEQ ID NO: 20) | YAQKRQGRVTITRDRSMSTAYMELSSLRSEDTAVYYC | (SEQ ID NO: 28) | WGQGTLVTVSS | (SEQ ID NO: 19) |
| Ab369 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSTSTAYMELRSLRSEDTAMYYC | (SEQ ID NO: 29) | WGQGTLVTVSS | (SEQ ID NO: 19) |
| Ab370 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELRSLRSEDTAVYYC | (SEQ ID NO: 30) | WGQGTLVTVSS | (SEQ ID NO: 19) |
| Ab371 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELRSLRSEDTAVYYC | (SEQ ID NO: 31) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab372 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSTSTAYMELRSLRSEDTAMYYC | (SEQ ID NO: 26) | WGQGTLVTVSS | (SEQ ID NO: 19) |
| Ab373 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELRSLRSEDTAMYYC | (SEQ ID NO: 27) | WGQGTLVTVSS | (SEQ ID NO: 19) |
| Ab374 | $X_{H1}$QMQLVQSGAEVKKPGSSVKVSCKAS | (SEQ ID NO: 21) | WVRQAPGKGLEWMG | (SEQ ID NO: 20) | YAQKRQGRVTITRDRSMSTAYMELSSLRSEDTAVYYC | (SEQ ID NO: 28) | WGQGTLVTVSS | (SEQ ID NO: 19) |
| Ab375 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSTSTAYMELRSLRSEDTAMYYC | (SEQ ID NO: 29) | WGQGTLVTVSS | (SEQ ID NO: 19) |
| Ab376 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELRSLRSEDTAVYYC | (SEQ ID NO: 30) | WGQGTLVTVSS | (SEQ ID NO: 19) |
| Ab377 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELRSLRSEDTAVYYC | (SEQ ID NO: 31) | WGQGTLVTVSS | (SEQ ID NO: 19) |
| Ab378 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELRSLRSEDTAMYYC | (SEQ ID NO: 32) | WGQGTLVTVSS | (SEQ ID NO: 19) |
| Ab379 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELSSLRSEDTAVYYC | (SEQ ID NO: 33) | WGQGTLVTVSS | (SEQ ID NO: 19) |
| Ab380 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELRSLRSEDTAVYYC | (SEQ ID NO: 34) | WGQGTLVTVSS | (SEQ ID NO: 19) |
| Ab381 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSTSTAYMELRSLRSEDTAVYYC | (SEQ ID NO: 35) | WGQGTLVTVSS | (SEQ ID NO: 19) |
| Ab382 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSTSTAYMELRSLRSEDTAMYYC | (SEQ ID NO: 32) | WGQGTLVTVSS | (SEQ ID NO: 19) |
| Ab383 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSTSTAYMELSSLRSEDTAVYYC | (SEQ ID NO: 33) | WGQGTLVTVSS | (SEQ ID NO: 19) |
| Ab384 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELRSLRSEDTAVYYC | (SEQ ID NO: 34) | WGQGTLVTVSS | (SEQ ID NO: 19) |
| Ab385 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSTSTAYMELRSLRSEDTAVYYC | (SEQ ID NO: 35) | WGQGTLVTVSS | (SEQ ID NO: 19) |
| Ab386 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELRSLRSEDTAVYYC | (SEQ ID NO: 36) | WGQGTLVTVSS | (SEQ ID NO: 19) |
| Ab387 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSTSTAYMELRSLRSEDTAVYYC | (SEQ ID NO: 36) | WGQGTLVTVSS | (SEQ ID NO: 19) |
| Ab388 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELSSLRAEDTAMYYC | (SEQ ID NO: 18) | WGQGTLVTVSS | (SEQ ID NO: 19) |
| Ab389 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELSSLRAEDTAMYYC | (SEQ ID NO: 37) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab390 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSTSTAYMELSLRAEDTAMYYC | (SEQ ID NO: 38) | WGQGTLVTVSS | (SEQ ID NO: 19) |
| Ab391 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRAEDTAMYYC | (SEQ ID NO: 39) | WGQGTLVTVSS | (SEQ ID NO: 19) |
| Ab392 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELSSLRAEDTAVYYC | (SEQ ID NO: 40) | WGQGTLVTVSS | (SEQ ID NO: 19) |
| Ab393 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELSSLRAEDTAMYYC | (SEQ ID NO: 37) | WGQGTLVTVSS | (SEQ ID NO: 19) |
| Ab394 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSTSTAYMELSSLRAEDTAMYYC | (SEQ ID NO: 38) | WGQGTLVTVSS | (SEQ ID NO: 19) |
| Ab395 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELRSLRAEDTAMYYC | (SEQ ID NO: 39) | WGQGTLVTVSS | (SEQ ID NO: 19) |
| Ab396 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELSSLRAEDTAVYYC | (SEQ ID NO: 40) | WGQGTLVTVSS | (SEQ ID NO: 19) |
| Ab397 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSTSTAYMELSSLRAEDTAMYYC | (SEQ ID NO: 41) | WGQGTLVTVSS | (SEQ ID NO: 19) |
| Ab398 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELRSLRAEDTAMYYC | (SEQ ID NO: 42) | WGQGTLVTVSS | (SEQ ID NO: 19) |
| Ab399 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELSSLRAEDTAVYYC | (SEQ ID NO: 43) | WGQGTLVTVSS | (SEQ ID NO: 19) |
| Ab400 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELSSLRAEDTAMYYC | (SEQ ID NO: 44) | WGQGTLVTVSS | (SEQ ID NO: 19) |
| Ab401 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELSSLRAEDTAVYYC | (SEQ ID NO: 45) | WGQGTLVTVSS | (SEQ ID NO: 19) |
| Ab402 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRAEDTAVYYC | (SEQ ID NO: 46) | WGQGTLVTVSS | (SEQ ID NO: 19) |
| Ab403 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSTSTAYMELSSLRAEDTAMYYC | (SEQ ID NO: 41) | WGQGTLVTVSS | (SEQ ID NO: 19) |
| Ab404 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELRSLRAEDTAMYYC | (SEQ ID NO: 42) | WGQGTLVTVSS | (SEQ ID NO: 19) |
| Ab405 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELSSLRAEDTAVYYC | (SEQ ID NO: 43) | WGQGTLVTVSS | (SEQ ID NO: 19) |
| Ab406 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELSSLRAEDTAMYYC | (SEQ ID NO: 44) | WGQGTLVTVSS | (SEQ ID NO: 19) |
| Ab407 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELSSLRAEDTAVYYC | (SEQ ID NO: 45) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab408 | $X_{H1}$QMQLVQSGAEVKKPGSSVKVSCKAS | (SEQ ID NO: 21) | WVRQAPGKALEWMG | (SEQ ID NO: 13) | YAQKFQDRVTITRDRSMSTAYMELRSLRAEDTAVYYC | (SEQ ID NO: 46) | WGQGTLVTVSS | (SEQ ID NO: 19) |
| Ab409 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELRSLRAEDTAMYYC | (SEQ ID NO: 47) | WGQGTLVTVSS | (SEQ ID NO: 19) |
| Ab410 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELSSLRAEDTAVYYC | (SEQ ID NO: 48) | WGQGTLVTVSS | (SEQ ID NO: 19) |
| Ab411 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSMSTAYMELRSLRAEDTAVYYC | (SEQ ID NO: 49) | WGQGTLVTVSS | (SEQ ID NO: 19) |
| Ab412 | $X_{H1}$QMQLVQSGAEVKKTGSSVKVSCKAS | (SEQ ID NO: 12) | WVRQAPGKALEWMG | (SEQ ID NO: 13) | YAQKFQDRVTITRDRSMSTAYMELRSLRAEDTAVYYC | (SEQ ID NO: 50) | WGQGTLVTVSS | (SEQ ID NO: 19) |
| Ab413 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELRSLRAEDTAMYYC | (SEQ ID NO: 47) | WGQGTLVTVSS | (SEQ ID NO: 19) |
| Ab414 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELSSLRAEDTAVYYC | (SEQ ID NO: 48) | WGQGTLVTVSS | (SEQ ID NO: 19) |
| Ab415 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELRSLRAEDTAVYYC | (SEQ ID NO: 49) | WGQGTLVTVSS | (SEQ ID NO: 19) |
| Ab416 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSMSTAYMELRSLRAEDTAVYYC | (SEQ ID NO: 50) | WGQGTLVTVSS | (SEQ ID NO: 19) |
| Ab417 | $X_{H1}$QMQLVQSGAEVKKTGSSVKVSCKAS | (SEQ ID NO: 12) | WVRQAPGKALEWMG | (SEQ ID NO: 13) | YAQKFQGRVTITRDRSTSTAYMELRSLRAEDTAVYYC | (SEQ ID NO: 139) | WGQGTLVTVSS | (SEQ ID NO: 19) |
| Ab418 | $X_{H1}$QMQLVQSGAEVKKPGSSVKVSCKAS | (SEQ ID NO: 21) | WVRQAPGKALEWMG | (SEQ ID NO: 13) | YAQKFQGRVTITRDRSTSTAYMELRSLRAEDTAVYYC | (SEQ ID NO: 139) | WGQGTLVTVSS | (SEQ ID NO: 19) |
| Ab419 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELSSLRAEDTAMYYC | (SEQ ID NO: 18) | WGQGTLVTVSS | (SEQ ID NO: 19) |
| Ab420 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELSSLRAEDTAMYYC | (SEQ ID NO: 37) | WGQGTLVTVSS | (SEQ ID NO: 19) |
| Ab421 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSTSTAYMELSSLRAEDTAMYYC | (SEQ ID NO: 38) | WGQGTLVTVSS | (SEQ ID NO: 19) |
| Ab422 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELRSLRAEDTAMYYC | (SEQ ID NO: 39) | WGQGTLVTVSS | (SEQ ID NO: 19) |
| Ab423 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELSSLRAEDTAVYYC | (SEQ ID NO: 40) | WGQGTLVTVSS | (SEQ ID NO: 19) |
| Ab424 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELSSLRAEDTAMYYC | (SEQ ID NO: 37) | WGQGTLVTVSS | (SEQ ID NO: 19) |
| Ab425 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSTSTAYMELSSLRAEDTAMYYC | (SEQ ID NO: 38) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab426 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELRSLRAEDTAMYYC | (SEQ ID NO: 39) | WGQGTLVTVSS | (SEQ ID NO: 19) |
| Ab427 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELSSLRAEDTAVYYC | (SEQ ID NO: 40) | WGQGTLVTVSS | (SEQ ID NO: 19) |
| Ab428 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSTSTAYMELSSLRAEDTAMYYC | (SEQ ID NO: 41) | WGQGTLVTVSS | (SEQ ID NO: 19) |
| Ab429 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELRSLRAEDTAMYYC | (SEQ ID NO: 42) | WGQGTLVTVSS | (SEQ ID NO: 19) |
| Ab430 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELSSLRAEDTAVYYC | (SEQ ID NO: 43) | WGQGTLVTVSS | (SEQ ID NO: 19) |
| Ab431 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELSSLRAEDTAMYYC | (SEQ ID NO: 44) | WGQGTLVTVSS | (SEQ ID NO: 19) |
| Ab432 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELSSLRAEDTAVYYC | (SEQ ID NO: 45) | WGQGTLVTVSS | (SEQ ID NO: 19) |
| Ab433 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELRSLRAEDTAVYYC | (SEQ ID NO: 46) | WGQGTLVTVSS | (SEQ ID NO: 19) |
| Ab434 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSTSTAYMELSSLRAEDTAMYYC | (SEQ ID NO: 41) | WGQGTLVTVSS | (SEQ ID NO: 19) |
| Ab435 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELRSLRAEDTAMYYC | (SEQ ID NO: 42) | WGQGTLVTVSS | (SEQ ID NO: 19) |
| Ab436 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELSSLRAEDTAVYYC | (SEQ ID NO: 43) | WGQGTLVTVSS | (SEQ ID NO: 19) |
| Ab437 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELSSLRAEDTAMYYC | (SEQ ID NO: 44) | WGQGTLVTVSS | (SEQ ID NO: 19) |
| Ab438 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELSSLRAEDTAVYYC | (SEQ ID NO: 45) | WGQGTLVTVSS | (SEQ ID NO: 19) |
| Ab439 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELRSLRAEDTAVYYC | (SEQ ID NO: 46) | WGQGTLVTVSS | (SEQ ID NO: 19) |
| Ab440 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELRSLRAEDTAMYYC | (SEQ ID NO: 47) | WGQGTLVTVSS | (SEQ ID NO: 19) |
| Ab441 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELSSLRAEDTAVYYC | (SEQ ID NO: 48) | WGQGTLVTVSS | (SEQ ID NO: 19) |
| Ab442 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSMSTAYMELRSLRAEDTAVYYC | (SEQ ID NO: 49) | WGQGTLVTVSS | (SEQ ID NO: 19) |
| Ab443 | $X_{H1}$QMQLVQSGAEVKKTGSSVKVSCKAS | (SEQ ID NO: 12) | WVRQAPGQGLEWMG | (SEQ ID NO: 16) | YAQKFQDRVTITRDRSMSTAYMELRSLRAEDTAVYYC | (SEQ ID NO: 50) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab444 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELRSLRAEDTAMYYC | (SEQ ID NO: 47) | WGQGTLVTVSS | (SEQ ID NO: 19) |
| Ab445 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELSSLRAEDTAVYYC | (SEQ ID NO: 48) | WGQGTLVTVSS | (SEQ ID NO: 19) |
| Ab446 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSMSTAYMELRSLRAEDTAVYYC | (SEQ ID NO: 49) | WGQGTLVTVSS | (SEQ ID NO: 19) |
| Ab447 | $X_{H1}$QMQLVQSGAEVKKPGSSVKVSCKAS | (SEQ ID NO: 21) | WVRQAPGQGLEWMG | (SEQ ID NO: 16) | YAQKFQDRVTITRDRSMSTAYMELRSLRAEDTAVYYC | (SEQ ID NO: 50) | WGQGTLVTVSS | (SEQ ID NO: 19) |
| Ab448 | $X_{H1}$QMQLVQSGAEVKKTGSSVKVSCKAS | (SEQ ID NO: 12) | WVRQAPGQGLEWMG | (SEQ ID NO: 16) | YAQKFQGRVTITRDRSTSTAYMELRSLRAEDTAVYYC | (SEQ ID NO: 139) | WGQGTLVTVSS | (SEQ ID NO: 19) |
| Ab449 | $X_{H1}$QMQLVQSGAEVKKPGSSVKVSCKAS | (SEQ ID NO: 21) | WVRQAPGQGLEWMG | (SEQ ID NO: 16) | YAQKFQGRVTITRDRSTSTAYMELRSLRAEDTAVYYC | (SEQ ID NO: 139) | WGQGTLVTVSS | (SEQ ID NO: 19) |
| Ab450 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRAEDTAMYYC | (SEQ ID NO: 18) | WGQGTLVTVSS | (SEQ ID NO: 19) |
| Ab451 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELSSLRAEDTAMYYC | (SEQ ID NO: 37) | WGQGTLVTVSS | (SEQ ID NO: 19) |
| Ab452 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSTSTAYMELSSLRAEDTAMYYC | (SEQ ID NO: 38) | WGQGTLVTVSS | (SEQ ID NO: 19) |
| Ab453 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELRSLRAEDTAMYYC | (SEQ ID NO: 39) | WGQGTLVTVSS | (SEQ ID NO: 19) |
| Ab454 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRAEDTAVYYC | (SEQ ID NO: 40) | WGQGTLVTVSS | (SEQ ID NO: 19) |
| Ab455 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELSSLRAEDTAMYYC | (SEQ ID NO: 37) | WGQGTLVTVSS | (SEQ ID NO: 19) |
| Ab456 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSTSTAYMELSSLRAEDTAMYYC | (SEQ ID NO: 38) | WGQGTLVTVSS | (SEQ ID NO: 19) |
| Ab457 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELRSLRAEDTAMYYC | (SEQ ID NO: 39) | WGQGTLVTVSS | (SEQ ID NO: 19) |
| Ab458 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRAEDTAVYYC | (SEQ ID NO: 40) | WGQGTLVTVSS | (SEQ ID NO: 19) |
| Ab459 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELSSLRAEDTAMYYC | (SEQ ID NO: 41) | WGQGTLVTVSS | (SEQ ID NO: 19) |
| Ab460 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELRSLRAEDTAMYYC | (SEQ ID NO: 42) | WGQGTLVTVSS | (SEQ ID NO: 19) |
| Ab461 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELSSLRAEDTAVYYC | (SEQ ID NO: 43) | WGQGTLVTVSS | (SEQ ID NO: 19) |

TABLE 1-continued

Exemplary Antibodies with Specific VH FR sequences ($X_{H1}$ is M or no amino acid).

| Antibody | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab462 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRAEDTAMYYC | (SEQ ID NO: 44) | WGQGTLVTVSS | (SEQ ID NO: 19) |
| Ab463 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELSSLRAEDTAVYYC | (SEQ ID NO: 45) | WGQGTLVTVSS | (SEQ ID NO: 19) |
| Ab464 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELRSLRAEDTAVYYC | (SEQ ID NO: 46) | WGQGTLVTVSS | (SEQ ID NO: 19) |
| Ab465 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSTSTAYMELSSLRAEDTAMYYC | (SEQ ID NO: 41) | WGQGTLVTVSS | (SEQ ID NO: 19) |
| Ab466 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELRSLRAEDTAMYYC | (SEQ ID NO: 42) | WGQGTLVTVSS | (SEQ ID NO: 19) |
| Ab467 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELSSLRAEDTAVYYC | (SEQ ID NO: 43) | WGQGTLVTVSS | (SEQ ID NO: 19) |
| Ab468 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRAEDTAMYYC | (SEQ ID NO: 44) | WGQGTLVTVSS | (SEQ ID NO: 19) |
| Ab469 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELSSLRAEDTAVYYC | (SEQ ID NO: 45) | WGQGTLVTVSS | (SEQ ID NO: 19) |
| Ab470 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELRSLRAEDTAVYYC | (SEQ ID NO: 46) | WGQGTLVTVSS | (SEQ ID NO: 19) |
| Ab471 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELRSLRAEDTAMYYC | (SEQ ID NO: 47) | WGQGTLVTVSS | (SEQ ID NO: 19) |
| Ab472 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELSSLRAEDTAVYYC | (SEQ ID NO: 48) | WGQGTLVTVSS | (SEQ ID NO: 19) |
| Ab473 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSMSTAYMELRSLRAEDTAVYYC | (SEQ ID NO: 49) | WGQGTLVTVSS | (SEQ ID NO: 19) |
| Ab474 | $X_{H1}$QMQLVQSGAEVKKTGSSVKVSCKAS | (SEQ ID NO: 12) | WVRQAPGKGLEWMG | (SEQ ID NO: 20) | YAQKFQDRVTITRDRSMSTAYMELRSLRAEDTAVYYC | (SEQ ID NO: 50) | WGQGTLVTVSS | (SEQ ID NO: 19) |
| Ab475 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELRSLRAEDTAMYYC | (SEQ ID NO: 47) | WGQGTLVTVSS | (SEQ ID NO: 19) |
| Ab476 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELSSLRAEDTAVYYC | (SEQ ID NO: 48) | WGQGTLVTVSS | (SEQ ID NO: 19) |
| Ab477 | $X_{H1}$QMQLVQSGAEVKKPGSSVKVSCKAS | (SEQ ID NO: 21) | WVRQAPGKGLEWMG | (SEQ ID NO: 20) | YAQKFQGRVTITRDRSMSTAYMELRSLRAEDTAVYYC | (SEQ ID NO: 49) | WGQGTLVTVSS | (SEQ ID NO: 19) |
| Ab478 | $X_{H1}$QMQLVQSGAEVKKPGSSVKVSCKAS | (SEQ ID NO: 21) | WVRQAPGKGLEWMG | (SEQ ID NO: 20) | YAQKFQDRVTITRDRSMSTAYMELRSLRAEDTAVYYC | (SEQ ID NO: 50) | WGQGTLVTVSS | (SEQ ID NO: 19) |
| Ab479 | $X_{H1}$QMQLVQSGAEVKKTGSSVKVSCKAS | (SEQ ID NO: 12) | WVRQAPGKGLEWMG | (SEQ ID NO: 20) | YAQKFQGRVTITRDRSTSTAYMELRSLRAEDTAVYYC | (SEQ ID NO: 139) | WGQGTLVTVSS | (SEQ ID NO: 19) |

TABLE 1-continued

Exemplary Antibodies with Specific VH FR sequences ($X_{H1}$ is M or no amino acid).

| Anti-body | VH-FR1 | SEQ ID NO: | VH-FR2 | SEQ ID NO: | VH-FR3 | SEQ ID NO: | VH-FR4 | SEQ ID NO: |
|---|---|---|---|---|---|---|---|---|
| Ab480 | $X_{H1}$QMQLVQSG AEVKKPGSSV KVSCKAS | (SEQ ID NO: 21) | WVRQAPGKGLE WMG | (SEQ ID NO: 20) | YAQKFQGRVTITRD RSTSTAYMELRSLR AEDTAVYYC | (SEQ ID NO: 139) | WGQGTLVTVSS | (SEQ ID NO: 19) |

In another aspect, provided herein is an antibody or an antigen-binding fragment thereof, comprising a heavy chain variable region (VH) that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1, VH FR2, VH FR3 and VH FR4 comprise the amino acid sequence of $X_{H32}$QX$_{H33}$TLX$_{H34}$ESGPX$_{H35}$LVKPTX$_{H36}$TLTLTCTX$_{H37}$S (SEQ ID NO: 86); WIRQPPGKX$_{H73}$LEWLA (SEQ ID NO: 87); YSX$_{H38}$SLKX$_{H39}$RLTX$_{H40}$X$_{H41}$X$_{H42}$DTSX$_{H43}$X$_{H44}$QVVLTMX$_{H45}$NMDX$_{H46}$X$_{H47}$DTAX$_{H48}$YYC (SEQ ID NO: 88); WGX$_{H49}$GTX$_{H50}$VTVSS (SEQ ID NO: 89), respectively, wherein $X_{H32}$ is M or no amino acid, $X_{H33}$ is V or I, $X_{H34}$ is K or R, $X_{H35}$ is V, T or A, $X_{H36}$ is E, Q, or A, $X_{H37}$ is V or F, $X_{H73}$ is A or G, $X_{H38}$ is T or P, $X_{H39}$ is S, T, or G, $X_{H40}$ is I or M, $X_{H41}$ is S or T, $X_{H42}$ is K or T, $X_{H43}$ is K or T, $X_{H44}$ is N or S, $X_{H45}$ is T or R, $X_{H46}$ is P or A, $X_{H47}$ is V or D, $X_{H48}$ is T or V, $X_{H49}$ is Q or R, and $X_{H50}$ is L, M or T, and wherein at least one of the following is satisfied: $X_{H73}$ is G, and $X_{H46}$ is A. In certain embodiments, $X_{H73}$ is G and $X_{H46}$ is A.

In certain embodiments of the preceding aspect, at least one of the following is satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, $X_{H48}$ is V, and $X_{H50}$ is L. In certain embodiments, at least two of the following are satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, $X_{H48}$ is V, and $X_{H50}$ is L. In certain embodiments, at least three of the following are satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, $X_{H48}$ is V, and $X_{H50}$ is L. In certain embodiments, at least four of the following are satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, $X_{H48}$ is V, and $X_{H50}$ is L. In certain embodiments, at least five of the following are satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, $X_{H48}$ is V, and $X_{H50}$ is L. In certain embodiments, at least six of the following are satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, $X_{H48}$ is V, and $X_{H50}$ is L. In certain embodiments, at least seven of the following are satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, $X_{H48}$ is V, and $X_{H50}$ is L. In certain embodiments, at least eight of the following are satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, $X_{H48}$ is V, and $X_{H50}$ is L. In certain embodiments, at least nine of the following are satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, $X_{H48}$ is V, and $X_{H50}$ is L. In certain embodiments, $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, $X_{H48}$ is V, and $X_{H50}$ is L.

In certain embodiments of the preceding aspect, at least one of the following is satisfied: $X_{H39}$ is G, $X_{H43}$ is T, $X_{H45}$ is R, $X_{H48}$ is V, and $X_{H50}$ is L. In certain embodiments, at least two of the following are satisfied: $X_{H39}$ is G, $X_{H43}$ is T, $X_{H45}$ is R, $X_{H48}$ is V, and $X_{H50}$ is L. In certain embodiments, at least three of the following are satisfied: $X_{H39}$ is G, $X_{H43}$ is T, $X_{H45}$ is R, $X_{H48}$ is V, and $X_{H50}$ is L. In certain embodiments, at least four of the following are satisfied: $X_{H39}$ is G, $X_{H43}$ is T, $X_{H45}$ is R, $X_{H48}$ is V, and $X_{H50}$ is L. In certain embodiments, $X_{H39}$ is G, $X_{H43}$ is T, $X_{H45}$ is R, $X_{H48}$ is V, and $X_{H50}$ is L.

In certain embodiments of the preceding aspect, $X_{H50}$ is L.

In a specific embodiment of the certain embodiments wherein $X_{H50}$ is L, at least one of the following is further satisfied: $X_{H39}$ is G, $X_{H43}$ is T, $X_{H45}$ is R, and $X_{H48}$ is V. In another specific embodiment of the certain embodiments wherein $X_{H50}$ is L, at least two of the following are further satisfied: $X_{H39}$ is G, $X_{H43}$ is T, $X_{H45}$ is R, and $X_{H48}$ is V. In another specific embodiment of the certain embodiments wherein $X_{H50}$ is L, at least three of the following are further satisfied: $X_{H39}$ is G, $X_{H43}$ is T, $X_{H45}$ is R, and $X_{H48}$ is V. In another specific embodiment of the certain embodiments wherein $X_{H50}$ is L, the following is further satisfied: $X_{H39}$ is G, $X_{H43}$ is T, $X_{H45}$ is R, and $X_{H48}$ is V.

In a further specific embodiment wherein $X_{H50}$ is L, and wherein at least one, two, three, or all of the following are satisfied: $X_{H39}$ is G, $X_{H43}$ is T, $X_{H45}$ is R, and $X_{H48}$ is V, at least one of the following is further satisfied: $X_{H33}$ is V, $X_{H36}$ is A, $X_{H40}$ is M, $X_{H42}$ is T, $X_{H47}$ is D. In another further specific embodiment wherein $X_{H50}$ is L, and wherein at least one, two, three, or all of the following are satisfied: $X_{H39}$ is G, $X_{H43}$ is T, $X_{H45}$ is R, and $X_{H48}$ is V, at least two of the following are further satisfied: $X_{H33}$ is V, $X_{H36}$ is A, $X_{H40}$ is M, $X_{H42}$ is T, $X_{H47}$ is D. In another further specific embodiment wherein $X_{H50}$ is L, and wherein at least one, two, three, or all of the following are satisfied: $X_{H39}$ is G, $X_{H43}$ is T, $X_{H45}$ is R, and $X_{H48}$ is V, at least three of the following are further satisfied: $X_{H33}$ is V, $X_{H36}$ is A, $X_{H40}$ is M, $X_{H42}$ is T, $X_{H47}$ is D. In another further specific embodiment wherein $X_{H50}$ is L, and wherein at least one, two, three, or all of the following are satisfied: $X_{H39}$ is G, $X_{H43}$ is T, $X_{H45}$ is R, and $X_{H48}$ is V, at least four of the following are further satisfied: $X_{H33}$ is V, $X_{H36}$ is A, $X_{H40}$ is M, $X_{H42}$ is T, $X_{H47}$ is D. In another further specific embodiment wherein $X_{H50}$ is L, and wherein at least one, two, three, or all of the following are satisfied: $X_{H39}$ is G, $X_{H43}$ is T, $X_{H45}$ is R, and $X_{H48}$ is V, the following is further satisfied: $X_{H33}$ is V, $X_{H36}$ is A, $X_{H40}$ is M, $X_{H42}$ is T, $X_{H47}$ is D.

In a specific embodiment of the certain embodiments wherein $X_{H50}$ is L, at least one of the following is further satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, and $X_{H48}$ is V. In another specific embodiment of the certain embodiments wherein $X_{H50}$ is L, at least two of the following are further satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, and $X_{H48}$ is V. In another specific embodiment of the certain embodiments wherein $X_{H50}$ is L, at least three of the following are further satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, and $X_{H48}$ is V. In another specific embodiment of the certain embodiments wherein $X_{H50}$ is L, at least four of the following are further satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, and $X_{H48}$ is V. In another specific embodiment of the certain embodiments wherein $X_{H50}$ is L, at least five of the following are further satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, and $X_{H48}$ is V. In another specific embodiment of the certain embodiments wherein $X_{H50}$ is L, at least six of the following are further satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, and $X_{H48}$ is V. In another specific embodiment of the certain embodiments wherein $X_{H50}$ is L, at least seven of the following are further satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, and $X_{H48}$ is V. In another specific embodiment of the certain embodiments wherein $X_{H50}$ is L, at least eight of the following are further satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, and $X_{H48}$ is V. In another specific embodiment of the certain embodiments wherein $X_{H50}$ is L, the following are further satisfied: $X_{H33}$ is V, $X_{H36}$ is A, $X_{H39}$ is G, $X_{H40}$ is M, $X_{H42}$ is T, $X_{H43}$ is T, $X_{H45}$ is R, $X_{H47}$ is D, and $X_{H48}$ is V.

In specific embodiments of the preceding aspect, $X_{H33}$ is V or I, $X_{H36}$ is E or Q, $X_{H40}$ is I, $X_{H42}$ is K, and $X_{H47}$ is V.

In another aspect, provided herein is an antibody or an antigen-binding fragment thereof, comprising a heavy chain variable region (VH) that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1, VH FR2, VH FR3 and VH FR4 comprise the amino acid sequence of $X_{H71}$QVQLQQSGPGLVKPSX$_{H51}$TLSLTCAIS (SEQ ID NO: 90); WIRQSPSX$_{H52}$GLEWLG (SEQ ID NO: 91); YAVSX$_{H53}$KX$_{H54}$RITX$_{H55}$NX$_{H56}$DTSX$_{H57}$NQFSLQLX$_{H58}$SVT X$_{H74}$X$_{H59}$DTAVYYC (SEQ ID NO: 92); WGX$_{H60}$GTX$_{H61}$VTVSS (SEQ ID NO: 93), respectively, wherein, $X_{H71}$ is M or no amino acid, $X_{H51}$ is Q or A, $X_{H52}$ is R or K, $X_{H53}$ is V or L, $X_{H54}$ is S or G, $X_{H55}$ is I or M, $X_{H56}$ is P or T, $X_{H57}$ is K or T, $X_{H58}$ is N or R, $X_{H74}$ is P or A, $X_{H59}$ is E or D, $X_{H60}$ is Q or R, and $X_{H61}$ is L, M or T, and at least one of the following is satisfied: $X_{H52}$ is K, and $X_{H74}$ is A. In certain embodiments, $X_{H52}$ is K and $X_{H74}$ is A.

In certain embodiments of the preceding aspect, at least one of the following is satisfied: $X_{H51}$ is A, $X_{H53}$ is L, $X_{H54}$ is G, $X_{H55}$ is M, $X_{H56}$ is T, $X_{H57}$ is T, $X_{H58}$ is R, $X_{H59}$ is D, and $X_{H61}$ is L. In certain embodiments, at least two of the following are satisfied: $X_{H51}$ is A, $X_{H53}$ is L, $X_{H54}$ is G, $X_{H55}$ is M, $X_{H56}$ is T, $X_{H57}$ is T, $X_{H58}$ is R, $X_{H59}$ is D, and $X_{H61}$ is L. In certain embodiments, at least three of the following are satisfied: $X_{H51}$ is A, $X_{H53}$ is L, $X_{H54}$ is G, $X_{H55}$ is M, $X_{H56}$ is T, $X_{H57}$ is T, $X_{H58}$ is R, $X_{H59}$ is D, and $X_{H61}$ is L. In certain embodiments, at least four of the following are satisfied: $X_{H51}$ is A, $X_{H53}$ is L, $X_{H54}$ is G, $X_{H55}$ is M, $X_{H56}$ is T, $X_{H57}$ is T, $X_{H58}$ is R, $X_{H59}$ is D, and $X_{H61}$ is L. In certain embodiments, at least five of the following are satisfied: $X_{H51}$ is A, $X_{H53}$ is L, $X_{H54}$ is G, $X_{H55}$ is M, $X_{H56}$ is T, $X_{H57}$ is T, $X_{H58}$ is R, $X_{H59}$ is D, and $X_{H61}$ is L. In certain embodiments, at least six of the following are satisfied: $X_{H51}$ is A, $X_{H53}$ is L, $X_{H54}$ is G, $X_{H55}$ is M, $X_{H56}$ is T, $X_{H57}$ is T, $X_{H58}$ is R, $X_{H59}$ is D, and $X_{H61}$ is L. In certain embodiments, at least seven of the following are satisfied: $X_{H51}$ is A, $X_{H53}$ is L, $X_{H54}$ is G, $X_{H55}$ is M, $X_{H56}$ is T, $X_{H57}$ is T, $X_{H58}$ is R, $X_{H59}$ is D, and $X_{H61}$ is L. In certain embodiments, at least eight of the following are satisfied: $X_{H51}$ is A, $X_{H53}$ is L, $X_{H54}$ is G, $X_{H55}$ is M, $X_{H56}$ is T, $X_{H57}$ is T, $X_{H58}$ is R, $X_{H59}$ is D, and $X_{H61}$ is L. In certain embodiments, $X_{H51}$ is A, $X_{H53}$ is L, $X_{H54}$ is G, $X_{H55}$ is M, $X_{H56}$ is T, $X_{H57}$ is T, $X_{H58}$ is R, $X_{H59}$ is D, and $X_{H61}$ is L.

In certain embodiments of the preceding aspect, at least one of the following is satisfied: $X_{H54}$ is G, $X_{H57}$ is T, $X_{H58}$ is R, and $X_{H61}$ is L. In certain embodiments, at least two of the following are satisfied: $X_{H54}$ is G, $X_{H57}$ is T, $X_{H58}$ is R, and $X_{H61}$ is L. In certain embodiments, at least three of the following are satisfied: $X_{H54}$ is G, $X_{H57}$ is T, $X_{H58}$ is R, and $X_{H61}$ is L. In certain embodiments, $X_{H54}$ is G, $X_{H57}$ is T, $X_{H58}$ is R, and $X_{H61}$ is L.

In certain embodiments of the preceding aspect, $X_{H61}$ is L.

In a specific embodiment of the certain embodiments wherein $X_{H61}$ is L, at least one of the following is further satisfied: $X_{H54}$ is G, $X_{H57}$ is T, and $X_{H58}$ is R. In another specific embodiment of the certain embodiments wherein $X_{H61}$ is L, at least two of the following are further satisfied: $X_{H54}$ is G, $X_{H57}$ is T, and $X_{H58}$ is R. In another specific embodiment of the certain embodiments wherein $X_{H61}$ is L, the following is further satisfied: $X_{H54}$ is G, $X_{H57}$ is T, and $X_{H58}$ is R.

In a further specific embodiment wherein $X_{H61}$ is L, and wherein at least one, two, or all of the following are further satisfied: $X_{H54}$ is G, $X_{H57}$ is T, and $X_{H58}$ is R, at least one of the following is further satisfied: $X_{H51}$ is A, $X_{H53}$ is L, $X_{H55}$ is M, $X_{H56}$ is T, and $X_{H59}$ is D. In another further specific embodiment wherein $X_{H61}$ is L, and wherein at least one, two, or all of the following are further satisfied: $X_{H54}$ is G, $X_{H57}$ is T, and $X_{H58}$ is R, at least two of the following are further satisfied: $X_{H51}$ is A, $X_{H53}$ is L, $X_{H55}$ is M, $X_{H56}$ is T, and $X_{H59}$ is D. In another further specific embodiment wherein $X_{H61}$ is L, and wherein at least one, two, or all of the following are further satisfied: $X_{H54}$ is G, $X_{H57}$ is T, and $X_{H58}$ is R, at least three of the following are further satisfied: $X_{H51}$ is A, $X_{H53}$ is L, $X_{H55}$ is M, $X_{H56}$ is T, and $X_{H59}$ is D. In another further specific embodiment wherein $X_{H61}$ is L, and wherein at least one, two, or all of the following are further satisfied: $X_{H54}$ is G, $X_{H57}$ is T, and $X_{H58}$ is R, at least four of the following are further satisfied: $X_{H51}$ is A, $X_{H53}$ is L, $X_{H55}$ is M, $X_{H56}$ is T, and $X_{H59}$ is D. In another further specific embodiment wherein $X_{H61}$ is L, and wherein at least one, two, or all of the following are further satisfied: $X_{H54}$ is G, $X_{H57}$ is T, and $X_{H58}$ is R, the following is further satisfied: $X_{H51}$ is A, $X_{H53}$ is L, $X_{H55}$ is M, $X_{H56}$ is T, and $X_{H59}$ is D.

In a specific embodiment of the certain embodiments wherein $X_{H61}$ is L, at least one of the following is further satisfied: $X_{H51}$ is A, $X_{H53}$ is L, $X_{H54}$ is G, $X_{H55}$ is M, $X_{H56}$ is T, $X_{H57}$ is T, $X_{H58}$ is R, and $X_{H59}$ is D. In another specific embodiment of the certain embodiments wherein $X_{H61}$ is L, at least two of the following are further satisfied: $X_{H51}$ is A, $X_{H53}$ is L, $X_{H54}$ is G, $X_{H55}$ is M, $X_{H56}$ is T, $X_{H57}$ is T, $X_{H58}$ is R, and $X_{H59}$ is D. In another specific embodiment of the certain embodiments wherein $X_{H61}$ is L, at least three of the following are further satisfied: $X_{H51}$ is A, $X_{H53}$ is L, $X_{H54}$ is G, $X_{H55}$ is M, $X_{H56}$ is T, $X_{H57}$ is T, $X_{H58}$ is R, and $X_{H59}$ is D. In another specific embodiment of the certain embodiments wherein $X_{H61}$ is L, at least four of the following are further satisfied: $X_{H51}$ is A, $X_{H53}$ is L, $X_{H54}$ is G, $X_{H55}$ is M, $X_{H56}$ is T, $X_{H57}$ is T, $X_{H58}$ is R, and $X_{H59}$ is D. In another specific embodiment of the certain embodiments wherein $X_{H61}$ is L, at least five of the following are further satisfied:

$X_{H51}$ is A, $X_{H53}$ is L, $X_{H54}$ is G, $X_{H55}$ is M, $X_{H56}$ is T, $X_{H57}$ is T, $X_{H58}$ is R, and $X_{H59}$ is D. In another specific embodiment of the certain embodiments wherein $X_{H61}$ is L, at least six of the following are further satisfied: $X_{H51}$ is A, $X_{H53}$ is L, $X_{H54}$ is G, $X_{H55}$ is M, $X_{H56}$ is T, $X_{H57}$ is T, $X_{H58}$ is R, and $X_{H59}$ is D. In another specific embodiment of the certain embodiments wherein $X_{H61}$ is L, at least seven of the following are further satisfied: $X_{H51}$ is A, $X_{H53}$ is L, $X_{H54}$ is G, $X_{H55}$ is M, $X_{H56}$ is T, $X_{H57}$ is T, $X_{H58}$ is R, and $X_{H59}$ is D. In another specific embodiment of the certain embodiments wherein $X_{H61}$ is L, the following is further satisfied: $X_{H51}$ is A, $X_{H53}$ is L, $X_{H54}$ is G, $X_{H55}$ is M, $X_{H56}$ is T, $X_{H57}$ is T, $X_{H58}$ is R, and $X_{H59}$ is D.

In specific embodiments of the preceding aspect, $X_{H51}$ is Q, $X_{H53}$ is V, $X_{H55}$ is I, $X_{H56}$ is P, and $X_{H59}$ is E.

In another aspect, provided herein is an antibody or an antigen-binding fragment thereof, comprising a heavy chain variable region (VH) that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1, VH FR2, VH FR3 and VH FR4 comprise the amino acid sequence of $X_{H72}$QVQLVQSGSELKKPGASVKVSCKAS (SEQ ID NO: 94); WVRQAPGKGLEWMG (SEQ ID NO: 95); YAQGX$_{H63}$TGRFVX$_{H64}$SX$_{H65}$DTSX$_{H66}$STAYLQIX$_{H67}$SLKAX$_{H68}$DTAVYYC (SEQ ID NO: 96); WGX$_{H69}$GTX$_{H70}$VTVSS (SEQ ID NO: 97), respectively wherein $X_{H72}$ is M or no amino acid, $X_{H63}$ is L or F, $X_{H64}$ is M or F, $X_{H65}$ is L or T, $X_{H66}$ is V or T, $X_{H67}$ is R or C. $X_{H68}$ is D or E, $X_{H69}$ is Q or R, and $X_{H70}$ is L, M or T.

In certain embodiments of the preceding aspect, at least one of the following is satisfied: $X_{H63}$ is L, $X_{H64}$ is M, $X_{H65}$ is T, $X_{H66}$ is T, $X_{H67}$ is R, $X_{H68}$ is D, and $X_{H70}$ is L. In certain embodiments, at least two of the following are satisfied: $X_{H63}$ is L, $X_{H64}$ is M, $X_{H65}$ is T, $X_{H66}$ is T, $X_{H67}$ is R, $X_{H68}$ is D, and $X_{H70}$ is L. In certain embodiments, at least three of the following are satisfied: $X_{H63}$ is L, $X_{H64}$ is M, $X_{H65}$ is T, $X_{H66}$ is T, $X_{H67}$ is R, $X_{H68}$ is D, and $X_{H70}$ is L. In certain embodiments, at least four of the following are satisfied: $X_{H63}$ is L, $X_{H64}$ is M, $X_{H65}$ is T, $X_{H66}$ is T, $X_{H67}$ is R, $X_{H68}$ is D, and $X_{H70}$ is L. In certain embodiments, at least five of the following are satisfied: $X_{H63}$ is L, $X_{H64}$ is M, $X_{H65}$ is T, $X_{H66}$ is T, $X_{H67}$ is R, $X_{H68}$ is D, and $X_{H70}$ is L. In certain embodiments, at least six of the following are satisfied: $X_{H63}$ is L, $X_{H64}$ is M, $X_{H65}$ is T, $X_{H66}$ is T, $X_{H67}$ is R, $X_{H68}$ is D, and $X_{H70}$ is L. In certain embodiments, $X_{H63}$ is L, $X_{H64}$ is M, $X_{H65}$ is T, $X_{H66}$ is T, $X_{H67}$ is R $X_{H68}$ is D, and $X_{H70}$ is L.

In certain embodiments of the preceding aspect, at least one of the following is satisfied: $X_{H66}$ is T, $X_{H67}$ is R, and $X_{H70}$ is L. In certain embodiments, at least two of the following are satisfied: $X_{H66}$ is T, $X_{H67}$ is R, and $X_{H70}$ is L. In certain embodiments, $X_{H66}$ is T, $X_{H67}$ is R, and $X_{H70}$ is L.

In certain embodiments of the preceding aspect, $X_{H70}$ is L.

In a specific embodiment of the certain embodiments wherein $X_{H70}$ is L, at least one of the following is further satisfied: $X_{H66}$ is T, and $X_{H67}$ is R. In another specific embodiment of the certain embodiments wherein $X_{H70}$ is L, the following is further satisfied: $X_{H66}$ is T, and $X_{H67}$ is R.

In a further specific embodiment wherein $X_{H70}$ is L, and wherein at least one or both of the following are further satisfied: $X_{H66}$ is T, and $X_{H67}$ is R, at least one of the following is further satisfied: $X_{H63}$ is L, $X_{H64}$ is M, $X_{H65}$ is T, and $X_{H68}$ is D. In another further specific embodiment wherein $X_{H70}$ is L, and wherein at least one or both of the following are further satisfied: $X_{H66}$ is T, and $X_{H67}$ is R, at least two of the following are further satisfied: $X_{H63}$ is L, $X_{H64}$ is M, $X_{H65}$ is T, and $X_{H68}$ is D. In another further specific embodiment wherein $X_{H70}$ is L, and wherein at least one or both of the following are further satisfied: $X_{H66}$ is T, and $X_{H67}$ is R, at least three of the following are further satisfied: $X_{H63}$ is L, $X_{H64}$ is M, $X_{H65}$ is T, and $X_{H68}$ is D. In another further specific embodiment wherein $X_{H70}$ is L, and wherein at least one or both of the following are further satisfied: $X_{H66}$ is T, and $X_{H67}$ is R, the following are further satisfied: $X_{H63}$ is L, $X_{H64}$ is M, $X_{H65}$ is T, and $X_{H68}$ is D.

In a specific embodiment wherein $X_{H70}$ is L, at least one of the following is further satisfied: $X_{H63}$ is L, $X_{H64}$ is M, $X_{H65}$ is T, $X_{H66}$ is T, and $X_{H67}$ is R, and $X_{H68}$ is D. In another specific embodiment wherein $X_{H70}$ is L, at least two of the following are further satisfied: $X_{H63}$ is L, $X_{H64}$ is M, $X_{H65}$ is T, $X_{H66}$ is T, and $X_{H67}$ is R, and $X_{H68}$ is D. In another specific embodiment wherein $X_{H70}$ is L, at least three of the following are further satisfied: $X_{H63}$ is L, $X_{H64}$ is M, $X_{H65}$ is T, $X_{H66}$ is T, and $X_{H67}$ is R, and $X_{H68}$ is D. In another specific embodiment wherein $X_{H70}$ is L, at least four of the following are further satisfied: $X_{H63}$ is L, $X_{H64}$ is M, $X_{H65}$ is T, $X_{H66}$ is T, and $X_{H67}$ is R, and $X_{H68}$ is D. In another specific embodiment wherein $X_{H70}$ is L, at least five of the following are further satisfied: $X_{H63}$ is L, $X_{H64}$ is M, $X_{H65}$ is T, $X_{H66}$ is T, and $X_{H67}$ is R, and $X_{H68}$ is D. In another specific embodiment wherein $X_{H70}$ is L, the following are further satisfied: $X_{H63}$ is L, $X_{H64}$ is M, $X_{H65}$ is T, $X_{H66}$ is T, and $X_{H67}$ is R, and $X_{H68}$ is D.

In specific embodiments of the preceding aspect, $X_{H63}$ is F, $X_{H64}$ is F, $X_{H65}$ is L, and $X_{H68}$ is E.

In another aspect, provided herein is an antibody or antigen-binding fragment thereof comprising a VH described in Section 5.1.1, and further comprising a VL.

In another aspect, provided herein is an antibody or antigen-binding fragment thereof comprising a VH described in Section 5.1.1, and further comprising a VL described in Section 5.1.2.

In another aspect, provided herein is an antibody or antigen-binding fragment thereof which specifically binds to CD47 and comprises a VH described in Section 5.1.1, wherein the VH CDRs are as described in Section 5.1.3.

In another aspect, provided herein is an antibody or antigen-binding fragment thereof which specifically binds to CD47 and comprises a VH described in Section 5.1.1 and a VL described in Section 5.1.2, wherein the VH CDRs are as described in Section 5.1.3.

In another aspect, provided herein is an antibody or antigen-binding fragment thereof which specifically binds to CD47 and comprises a VH described in Section 5.1.1 and a VL described in Section 5.1.2, wherein the VL CDRs are as described in Section 5.1.3.

In another aspect, provided herein is an antibody or antigen-binding fragment thereof which specifically binds to CD47 and comprises a VH described in Section 5.1.1 and a VL described in Section 5.1.2, wherein the VH CDRs are as described in Section 5.1.3, and the VL CDRs are as described in Section 5.1.3.

In any of the aspects and embodiments described above, the amino acid sequence of the VH FR3 can also comprise the additional residues of NA at the C-terminus.

In any of the aspects and embodiments described above, the amino acid sequence of the corresponding VH FR3 can be shorter by four, five, six or seven residues at the N-terminus relative to the VH FR3 sequence described above.

In certain embodiments, the VH FR sequences described herein are utilized with CDRs determined in accordance with the Kabat numbering system (that is, are Kabat CDRs).

In such embodiments, the boundaries of such VH FR sequences described herein are also determined in accordance with the Kabat numbering system. In certain embodiments, the VH FR sequences described herein are utilized with CDRs determined in accordance with the Chothia numbering system (that is, are Chothia CDRs). In such embodiments, the boundaries of such VH FR sequences are also determined in accordance with the Chothia numbering system. In certain embodiments, the VH FR sequences described herein are utilized with CDRs determined in accordance with the IMGT numbering system. In such embodiments, the boundaries of such VH FR sequences are also determined in accordance with the IMGT numbering system. In certain embodiments, the VH FR sequences described herein are utilized with CDRs determined in accordance with the ABM numbering system. In such embodiments, the boundaries of such VH FR sequences are also determined in accordance with the ABM numbering system. Thus, provided herein are antibodies or antigen-binding fragments that comprise one or more of the VH FR sequences described above that are determined in accordance with the Kabat numbering scheme, the Chothia numbering scheme, the IMGT numbering system, or the ABM numbering system. As discussed herein, determination of CDRs in accordance with any of the Kabat, Chothia, IMGT, or ABM numbering systems is well known to those of skill in the art. As such, determination of boundaries of VH FR sequences described herein that can be utilized with such CDRs is also well known and routine to those of skill in the art.

5.1.2 Antibodies with Specific Light Chain Variable Region Framework Region Sequences Provided herein are antibodies and antigen-binding fragments thereof comprising specific light chain variable region framework region (VL FR) sequences.

In one aspect, provided herein is an antibody or antigen-binding fragment thereof comprising a light chain variable region (VL) that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1, VL FR2, VL FR3 and VL FR4 comprise the amino acid sequence of
NIQMTQSPSX$_{L1}$X$_{L2}$SASVGDRVTITC (SEQ ID NO: 8);
WX$_{L3}$QQKPGKX$_{L4}$PKHLIY (SEQ ID NO: 9);
GVPSRFSGSGSGTEFTLTISSLQPEDFATYYC (SEQ ID NO: 10); and
FGGGTKVEIK (SEQ ID NO: 11), respectively,
wherein X$_{L1}$ is A or S, X$_{L2}$ is M or L, X$_{L3}$ is F or Y, and X$_{L4}$ is V or A.

In certain embodiments of the preceding aspect, at least one of the following is satisfied: X$_{L1}$ is S, X$_{L2}$ is L, X$_{L3}$ is Y, and X$_{L4}$ is A. In certain embodiments, at least two of the following are satisfied: X$_{L1}$ is S, X$_{L2}$ is L, X$_{L3}$ is Y, and X$_{L4}$ is A. In certain embodiments, at least three of the following are satisfied: X$_{L1}$ is S, X$_{L2}$ is L, X$_{L3}$ is Y, and X$_{L4}$ is A. In certain embodiments, X$_{L1}$ is S, X$_{L2}$ is L, X$_{L3}$ is Y, and X$_{L4}$ is A.

In a specific embodiment, provided herein is an antibody or antigen-binding fragment thereof of any listed in Table 2, which comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence listed in the second column of Table 2 for the antibody or antigen-binding fragment, VL FR2 comprises the amino acid sequence listed in the fourth column of Table 2 for the antibody or antigen-binding fragment, VL FR3 comprises the amino acid sequence listed in the sixth column of Table 2 for the antibody or antigen-binding fragment, and VL FR4 comprises the amino acid sequence listed in the eighth column of Table 2 for the antibody or antigen-binding fragment.

TABLE 2

Exemplary Antibodies with Specific VL FR sequences.

| Antibody | VL - FR1 | SEQ ID NO: | VL - FR2 | SEQ ID NO: | VL - FR3 | SEQ ID NO: | VL - FR4 | SEQ ID NO: |
|---|---|---|---|---|---|---|---|---|
| Ab481 | NIQMTQSPSA MSASVGDRV TITC | (SEQ ID NO: 51) | WFQQKPGKV PKHLIY | (SEQ ID NO: 52) | GVPSRFSGSGS GTEFTLTISSLQ PEDFATYYC | (SEQ ID NO: 10) | FGGGTKVEIK | (SEQ ID NO: 11) |
| Ab482 | NIQMTQSPSS MSASVGDRV TITC | (SEQ ID NO: 53) | WFQQKPGKV PKHLIY | (SEQ ID NO: 52) | GVPSRFSGSGS GTEFTLTISSLQ PEDFATYYC | (SEQ ID NO: 10) | FGGGTKVEIK | (SEQ ID NO: 11) |
| Ab483 | NIQMTQSPSA LSASVGDRV TITC | (SEQ ID NO: 54) | WFQQKPGKV PKHLIY | (SEQ ID NO: 52) | GVPSRFSGSGS GTEFTLTISSLQ PEDFATYYC | (SEQ ID NO: 10) | FGGGTKVEIK | (SEQ ID NO: 11) |
| Ab484 | NIQMTQSPSA MSASVGDRV TITC | (SEQ ID NO: 51) | WYQQKPGKV PKHLIY | (SEQ ID NO: 55) | GVPSRFSGSGS GTEFTLTISSLQ PEDFATYYC | (SEQ ID NO: 10) | FGGGTKVEIK | (SEQ ID NO: 11) |
| Ab485 | NIQMTQSPSA MSASVGDRV TITC | (SEQ ID NO: 51) | WFQQKPGKA PKHLIY | (SEQ ID NO: 56) | GVPSRFSGSGS GTEFTLTISSLQ PEDFATYYC | (SEQ ID NO: 10) | FGGGTKVEIK | (SEQ ID NO: 11) |
| Ab486 | NIQMTQSPSS LSASVGDRV TITC | (SEQ ID NO: 57) | WFQQKPGKV PKHLIY | (SEQ ID NO: 52) | GVPSRFSGSGS GTEFTLTISSLQ PEDFATYYC | (SEQ ID NO: 10) | FGGGTKVEIK | (SEQ ID NO: 11) |
| Ab487 | NIQMTQSPSS MSASVGDRV TITC | (SEQ ID NO: 53) | WYQQKPGKV PKHLIY | (SEQ ID NO: 55) | GVPSRFSGSGS GTEFTLTISSLQ PEDFATYYC | (SEQ ID NO: 10) | FGGGTKVEIK | (SEQ ID NO: 11) |

TABLE 2-continued

Exemplary Antibodies with Specific VL FR sequences.

| Antibody | VL - FR1 | SEQ ID NO: | VL - FR2 | SEQ ID NO: | VL - FR3 | SEQ ID NO: | VL - FR4 | SEQ ID NO: |
|---|---|---|---|---|---|---|---|---|
| Ab488 | NIQMTQSPSS MSASVGDRV TITC | (SEQ ID NO: 53) | WFQQKPGKA PKHLIY | (SEQ ID NO: 56) | GVPSRFSGSGS GTEFTLTISSLQ PEDFATYYC | (SEQ ID NO: 10) | FGGGTKVEIK | (SEQ ID NO: 11) |
| Ab489 | NIQMTQSPSA LSASVGDRV TITC | (SEQ ID NO: 54) | WYQQKPGKV PKHLIY | (SEQ ID NO: 55) | GVPSRFSGSGS GTEFTLTISSLQ PEDFATYYC | (SEQ ID NO: 10) | FGGGTKVEIK | (SEQ ID NO: 11) |
| Ab490 | NIQMTQSPSA LSASVGDRV TITC | (SEQ ID NO: 54) | WFQQKPGKA PKHLIY | (SEQ ID NO: 56) | GVPSRFSGSGS GTEFTLTISSLQ PEDFATYYC | (SEQ ID NO: 10) | FGGGTKVEIK | (SEQ ID NO: 11) |
| Ab491 | NIQMTQSPSA MSASVGDRV TITC | (SEQ ID NO: 51) | WYQQKPGKA PKHLIY | (SEQ ID NO: 58) | GVPSRFSGSGS GTEFTLTISSLQ PEDFATYYC | (SEQ ID NO: 10) | FGGGTKVEIK | (SEQ ID NO: 11) |
| Ab492 | NIQMTQSPSS LSASVGDRV TITC | (SEQ ID NO: 57) | WYQQKPGKV PKHLIY | (SEQ ID NO: 55) | GVPSRFSGSGS GTEFTLTISSLQ PEDFATYYC | (SEQ ID NO: 10) | FGGGTKVEIK | (SEQ ID NO: 11) |
| Ab493 | NIQMTQSPSS LSASVGDRV TITC | (SEQ ID NO: 57) | WFQQKPGKA PKHLIY | (SEQ ID NO: 56) | GVPSRFSGSGS GTEFTLTISSLQ PEDFATYYC | (SEQ ID NO: 10) | FGGGTKVEIK | (SEQ ID NO: 11) |
| Ab494 | NIQMTQSPSA LSASVGDRV TITC | (SEQ ID NO: 54) | WYQQKPGKA PKHLIY | (SEQ ID NO: 58) | GVPSRFSGSGS GTEFTLTISSLQ PEDFATYYC | (SEQ ID NO: 10) | FGGGTKVEIK | (SEQ ID NO: 11) |
| Ab495 | NIQMTQSPSS LSASVGDRV TITC | (SEQ ID NO: 57) | WYQQKPGKA PKHLIY | (SEQ ID NO: 58) | GVPSRFSGSGS GTEFTLTISSLQ PEDFATYYC | (SEQ ID NO: 10) | FGGGTKVEIK | (SEQ ID NO: 11) |

In another aspect, provided herein is an antibody or antigen-binding fragment thereof which specifically binds to CD47 and comprises a VL described in Section 5.1.2, wherein the VL CDRs are as described in Section 5.1.3.

In certain embodiments, the VL FR sequences described herein are utilized with CDRs determined in accordance with the Kabat numbering system (that is, are Kabat CDRs). In such embodiments, the boundaries of such VL FR sequences described herein are also determined in accordance with the Kabat numbering system. In certain embodiments, the VL FR sequences described herein are utilized with CDRs determined in accordance with the Chothia numbering system (that is, are Chothia CDRs). In such embodiments, the boundaries of such VL FR sequences are also determined in accordance with the Chothia numbering system. In certain embodiments, the VL FR sequences described herein are utilized with CDRs determined in accordance with the IMGT numbering system. In such embodiments, the boundaries of such VL FR sequences are also determined in accordance with the IMGT numbering system. In certain embodiments, the VL FR sequences described herein are utilized with CDRs determined in accordance with the ABM numbering system. In such embodiments, the boundaries of such VL FR sequences are also determined in accordance with the ABM numbering system. Thus, provided herein are antibodies or antigen-binding fragments that comprise one or more of the VL FR sequences described above that are determined in accordance with the Kabat numbering scheme, the Chothia numbering scheme, the IMGT numbering system, or the ABM numbering system. As discussed herein, determination of CDRs in accordance with any of the Kabat, Chothia, IMGT or ABM numbering systems is well known to those of skill in the art. As such, determination of boundaries of VL FR sequences described herein that can be utilized with such CDRs is also well known and routine to those of skill in the art.

5.1.3 Antibodies with Specific Complementarity Determining Region Sequences

Provided herein are antibodies and antigen-binding fragments thereof comprising specific complementarity determining region (CDR) sequences that specifically bind to CD47 (e.g., human CD47).

In one aspect, provided herein is an antibody or an antigen-binding fragment thereof, which specifically binds to CD47 and comprises a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein at least one of the following is satisfied: (1) VH CDR1 comprises the amino acid sequence of GFNIKDYYLH (SEQ ID NO: 59); (2) VH CDR2 comprises the amino acid sequence of WIDPDQGDTE (SEQ ID NO: 60), WIDPDQGDTEYAQKFQD (SEQ ID NO: 127), or WIDPDQGDTEYAQKFQG (SEQ ID NO: 138); and (3) VH CDR3 comprises the amino acid sequence of NAAYGSSSYPMDY(SEQ ID NO: 61) or AYGSSSYPMDY (SEQ ID NO: 125).

In another aspect, provided herein is an antibody or an antigen-binding fragment thereof, which specifically binds to CD47 and comprises a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein (1) VH CDR1 comprises the amino acid sequence of GFNIKDYYLH (SEQ ID NO: 59); (2) VH CDR2 comprises the amino acid sequence of WIDPDQGDTE(SEQ ID NO: 60), WIDPDQGDTEYAQKFQD (SEQ ID NO: 127), or WIDPDQGDTEYAQKFQG (SEQ ID NO: 138); and (3) VH CDR3 comprises the amino acid sequence of NAAYGSSSYPMDY(SEQ ID NO: 61) or AYGSSSYPMDY (SEQ ID NO: 125).

In some embodiments, the antibody or antigen-binding fragment further comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein at least one of the following is satisfied: (1) VL CDR1 comprises the amino acid sequence of $X_{C1}$ASQDIHRYLS (SEQ ID NO: 62), wherein $X_{C1}$ is K or R; (2) VL CDR2 comprises the amino acid sequence of RANRLVS (SEQ ID NO: 63); and (3) VL CDR3 comprises the amino acid sequence of LQYDEFPYT (SEQ ID NO: 64).

In other embodiments, the antibody or antigen-binding fragment further comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of $X_{C1}$ASQDIHRYLS(SEQ ID NO: 62), wherein $X_{C1}$ is K or R; (2) VL CDR2 comprises the amino acid sequence of RANRLVS(SEQ ID NO: 63); and (3) VL CDR3 comprises the amino acid sequence of LQYDEFPYT(SEQ ID NO: 64).

In other embodiments, the antibody or antigen-binding fragment further comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein at least one of the following is satisfied: (1) VL CDR1 comprises the amino acid sequence of $X_{C1}$ASQDIHRYLS (SEQ ID NO: 62), wherein $X_{C1}$ is K or R; (2) VL CDR2 comprises the amino acid sequence of R$X_{C2}X_{C3}$RFVD (SEQ ID NO: 65), wherein $X_{C2}$ is any amino acid with a polar or charged side chain, and $X_{C3}$ is V, I, E, or S; and (3) VL CDR3 comprises the amino acid sequence of LQYDEFPYT (SEQ ID NO: 64). In a specific embodiment, $X_{C2}$ is Y, E, or H. In a specific embodiment, $X_{C1}$ is R.

In other embodiments, the antibody or antigen-binding fragment further comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of $X_{C1}$ASQDIHRYLS (SEQ ID NO: 62), wherein $X_{C1}$ is K or R; (2) VL CDR2 comprises the amino acid sequence of R$X_{C2}X_{C3}$RFVD (SEQ ID NO: 65), wherein $X_{C2}$ is any amino acid with a polar or charged side chain, and $X_{C3}$ is V, I, E, or S; and (3) VL CDR3 comprises the amino acid sequence of LQYDEFPYT (SEQ ID NO: 64). In a specific embodiment, $X_{C2}$ is Y, E, or H. In a specific embodiment, $X_{C1}$ is R.

In other embodiments, the antibody or antigen-binding fragment further comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL CDR2 comprises the amino acid sequence of R$X_{C2}X_{C3}$RFVD (SEQ ID NO: 65), wherein $X_{C2}$ is any amino acid with a polar or charged side chain, and $X_{C3}$ is V, I, E, or S. In specific embodiments, $X_{C2}$ is Y, E, or H. In a specific embodiment, $X_{C2}$ is Y and $X_{C3}$ is V. In another specific embodiment, $X_{C2}$ is Y and $X_{C3}$ is I. In another specific embodiment, $X_{C2}$ is Y and $X_{C3}$ is E. In another specific embodiment, $X_{C2}$ is Y and $X_{C3}$ is S. In another specific embodiment, $X_{C2}$ is E and $X_{C3}$ is V. In another specific embodiment, $X_{C2}$ is E and $X_{C3}$ is I. In another specific embodiment, $X_{C2}$ is E and $X_{C3}$ is E. In another specific embodiment, $X_{C2}$ is E and $X_{C3}$ is S. In another specific embodiment, $X_{C2}$ is H and $X_{C3}$ is V. In another specific embodiment, $X_{C2}$ is H and $X_{C3}$ is I. In another specific embodiment, $X_{C2}$ is H and $X_{C3}$ is E. In another specific embodiment, $X_{C2}$ is H and $X_{C3}$ is S. In certain embodiments, VL CDR1 comprises the amino acid sequence of $X_{C1}$ASQDIHRYLS (SEQ ID NO: 62), wherein $X_{C1}$ is K or R. In a specific embodiment, $X_{C1}$ is R. In certain embodiments, VL CDR3 comprises the amino acid sequence of LQYDEFPYT (SEQ ID NO: 64).

In another aspect, provided herein is an antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein at least one of the following is satisfied: (1) VL CDR1 comprises the amino acid sequence of $X_{C1}$ASQDIHRYLS (SEQ ID NO: 62), wherein $X_{C1}$ is K or R; (2) VL CDR2 comprises the amino acid sequence of RANRLVS (SEQ ID NO: 63); and (3) VL CDR3 comprises the amino acid sequence of LQYDEFPYT (SEQ ID NO: 64).

In another aspect, provided herein is an antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of $X_{C1}$ASQDIHRYLS(SEQ ID NO: 62), wherein $X_{C1}$ is K or R; (2) VL CDR2 comprises the amino acid sequence of RANRLVS(SEQ ID NO: 63); and (3) VL CDR3 comprises the amino acid sequence of LQYDEFPYT(SEQ ID NO: 64).

In another aspect, provided herein is an antibody or an antigen-binding fragment thereof, which specifically binds to CD47 and comprises a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein at least one of the following is satisfied: (1) VH CDR1 comprises the amino acid sequence of GFNIKDYYLH (SEQ ID NO: 98), GYTFTYYYLH (SEQ ID NO: 99), GFTFTYYYLH (SEQ ID NO: 100), GYNFTYYYLH (SEQ ID NO: 101), GYTITYYYLH (SEQ ID NO: 102), GYTFKYYYLH (SEQ ID NO: 103), GYTFTDYYLH (SEQ ID NO: 104), GFTFTDYYLH (SEQ ID NO: 105), GFTITDYYLH (SEQ ID NO: 106), GYTFKDYYLH (SEQ ID NO: 107), or GFTFKDYYLH (SEQ ID NO: 108); (2) VH CDR2 comprises the amino acid sequence of WIDPDNGDTE (SEQ ID NO: 109), WIDPDQGDTE (SEQ ID NO: 110), WIDPDYGDTE (SEQ ID NO: 111), WIDPDSGDTE (SEQ ID NO: 112), WIDPDNADTE (SEQ ID NO: 113), WIDPDNTDTE (SEQ ID NO: 114), WIDPDNGDTEFAPKFQG (SEQ ID NO: 129), WIDPDNGDTEYAEKFQG (SEQ ID NO: 130), WIDPDNGDTEYAQKFQD (SEQ ID NO: 131), WIDPDNGDTEYAQKFQG (SEQ ID NO: 132), WIDPDQGDTEYAQKFQD (SEQ ID NO: 127), WIDPDYGDTEYAQKFQD (SEQ ID NO: 133), WIDPDSGDTEYAQKFQD (SEQ ID NO: 134), WIDPDNADTEYAQKFQD (SEQ ID NO: 135), WIDPDNTDTEYAQKFQD (SEQ ID NO: 136), or WIDPDNGTEYAQKFQD (SEQ ID NO: 137); and (3) VH CDR3 comprises the amino acid sequence of NAAYGSSSYPMDY (SEQ ID NO: 115), AYGSSSYPMDY (SEQ ID NO: 125), NAAYGSSPYPMDY (SEQ ID NO: 116), or AYGSSPYPMDY (SEQ ID NO: 128).

In another aspect, provided herein is an antibody or an antigen-binding fragment thereof, which specifically binds to CD47 and comprises a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein (1) VH CDR1 comprises the amino acid sequence of GFNIKDYYLH (SEQ ID NO: 98), GYTFTYYYLH (SEQ ID NO: 99), GFTFTYYYLH (SEQ ID NO: 100), GYNFTYYYLH (SEQ ID NO: 101), GYTITYYYLH (SEQ ID NO: 102), GYTFKYYYLH (SEQ ID NO: 103), GYTFTDYYLH (SEQ ID NO: 104), GFTFTDYYLH (SEQ ID NO: 105), GFTITDYYLH (SEQ ID NO: 106), GYTFKDYYLH (SEQ ID NO: 107), or GFTFKDYYLH (SEQ ID NO: 108); (2) VH CDR2 comprises the amino acid sequence of WIDPDNGDTE (SEQ ID NO: 109), WIDPDQGDTE (SEQ ID NO: 110), WIDPDYGDTE (SEQ ID NO: 111), WIDPDSGDTE (SEQ ID NO: 112), WIDPDNADTE (SEQ ID NO: 113), WIDPDNTDTE (SEQ ID NO: 114), WIDPDNGDTEFAPKFQG (SEQ ID NO: 129), WIDPDNGDTEYAEKFQG (SEQ ID NO: 130), WIDPDNGDTEYAQKFQD (SEQ ID NO: 131), WIDPDNGDTEYAQKFQG (SEQ ID NO: 132), WIDPDQGDTEYAQKFQD (SEQ ID NO: 127), WIDPDYGDTEYAQKFQD (SEQ ID NO: 133), WIDPDSGDTEYAQKFQD (SEQ ID NO: 134), WIDPDNADTEYAQKFQD (SEQ ID NO: 135), WIDPDNTDTEYAQKFQD (SEQ ID NO: 136), or WIDPDNGTEYAQKFQD (SEQ ID NO: 137); and (3) VH CDR3 comprises the amino acid sequence of NAAYGSSSYPMDY (SEQ ID NO: 115), AYGSSSYPMDY (SEQ ID NO: 125), NAAYGSSPYPMDY (SEQ ID NO: 116) or AYGSSPYPMDY (SEQ ID NO: 128).

In some embodiments, the antibody or antigen-binding fragment further comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein at least one of the following is satisfied: (1) VL CDR1 comprises the amino acid sequence ofKASQDIHRYLS (SEQ ID NO: 117), RASQDIHRYLA (SEQ ID NO: 118), or RARQGIHRYLS (SEQ ID NO: 119); (2) VL CDR2 comprises the amino acid sequence of RANRLVD (SEQ ID NO: 120), RANRLQS (SEQ ID NO: 121), RANRRAT (SEQ ID NO: 122), or RANRLVS (SEQ ID NO: 123); and (3) VL CDR3 comprises the amino acid sequence of LQYDEFPYT (SEQ ID NO: 124).

In other embodiments, the antibody or antigen-binding fragment further comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 117), RASQDIHRYLA (SEQ ID NO: 118), or RARQGIHRYLS (SEQ ID NO: 119); (2) VL CDR2 comprises the amino acid sequence of RANRLVD (SEQ ID NO: 120), RANRLQS (SEQ ID NO: 121), RANRRAT (SEQ ID NO: 122), or RANRLVS (SEQ ID NO: 123); and (3) VL CDR3 comprises the amino acid sequence of LQYDEFPYT (SEQ ID NO: 124).

In another aspect, provided herein is an antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein at least one of the following is satisfied: (1) VL CDR1 comprises the amino acid sequence of KASQDIHRYLS (SEQ ID NO: 117), RASQDIHRYLA (SEQ ID NO: 118), or RARQGIHRYLS (SEQ ID NO: 119); (2) VL CDR2 comprises the amino acid sequence of RANRLVD (SEQ ID NO: 120), RANRLQS (SEQ ID NO: 121), RANRRAT (SEQ ID NO: 122), or RANRLVS (SEQ ID NO: 123); and (3) VL CDR3 comprises the amino acid sequence of LQYDEFPYT (SEQ ID NO: 124).

In another aspect, provided herein is an antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of KASQDIHRYLS (SEQ ID NO: 117), RASQDIHRYLA (SEQ ID NO: 118), or RARQGIHRYLS (SEQ ID NO: 119); (2) VL CDR2 comprises the amino acid sequence of RANRLVD (SEQ ID NO: 120), RANRLQS (SEQ ID NO: 121), RANRRAT (SEQ ID NO: 122), or RANRLVS (SEQ ID NO: 123); and (3) VL CDR3 comprises the amino acid sequence of LQYDEFPYT (SEQ ID NO: 124).

In another aspect, provided herein is an antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein at least one of the following is satisfied: (1) VL CDR1 comprises the amino acid sequence of $X_{C_1}$ASQDIHRYLS (SEQ ID NO: 62), wherein $X_{C_1}$ is K or R; (2) VL CDR2 comprises the amino acid sequence of $RX_{C_2}X_{C_3}$RFVD (SEQ ID NO: 65), wherein $X_{C_2}$ is any amino acid with a polar or charged side chain, and $X_{C_3}$ is V, I, E, or S; and (3) VL CDR3 comprises the amino acid sequence of LQYDEFPYT (SEQ ID NO: 64). In a specific embodiment, $X_{C_2}$ is Y, E, or H. In a specific embodiment, $X_{C_1}$ is R.

In another aspect, provided herein is an antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein (1) VL CDR1 comprises the amino acid sequence of $X_{C_1}$ASQDIHRYLS (SEQ ID NO: 62), wherein $X_{C_1}$ is K or R; (2) VL CDR2 comprises the amino acid sequence of RX$_{C2}$X$_{C3}$RFVD (SEQ ID NO: 65), wherein X$_{C2}$ is any amino acid with a polar or charged side chain, and X$_{C3}$ is V, I, E, or S; and (3) VL CDR3 comprises the amino acid sequence of LQYDEFPYT (SEQ ID NO: 64). In a specific embodiment, X$_{C2}$ is Y, E, or H. In a specific embodiment, X$_{C1}$ is R.

In another aspect, provided herein is an antibody or an antigen-binding fragment thereof, which specifically binds to CD47 and comprises a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL CDR2 comprises the amino acid sequence of RX$_{C2}$X$_{C3}$RFVD (SEQ ID NO: 65), wherein X$_{C2}$ is any amino acid with a polar or charged side chain, and X$_{C3}$ is V, I, E, or S. In specific embodiments, X$_{C2}$ is Y, E, or H. In a specific embodiment, X$_{C2}$ is Y and X$_{C3}$ is V. In another specific embodiment, X$_{C2}$ is Y and X$_{C3}$ is I. In another specific embodiment, X$_{C2}$ is Y and X$_{C3}$ is E. In another specific embodiment, X$_{C2}$ is Y and X$_{C3}$ is S. In another specific embodiment, X$_{C2}$ is E and X$_{C3}$ is V. In another specific embodiment, X$_{C2}$ is E and X$_{C3}$ is I. In another specific embodiment, X$_{C2}$ is E and X$_{C3}$ is E. In another specific embodiment, X$_{C2}$ is E and X$_{C3}$ is S. In another specific embodiment, X$_{C2}$ is H and X$_{C3}$ is V. In another specific embodiment, X$_{C2}$ is H and X$_{C3}$ is I. In another specific embodiment, X$_{C2}$ is H and X$_{C3}$ is E. In another specific embodiment, X$_{C2}$ is H and X$_{C3}$ is S. In certain embodiments, VL CDR1 comprises the amino acid sequence of X$_{C1}$ASQDIHRYLS (SEQ ID NO: 62), wherein X$_{C1}$ is K or R. In a specific embodiment, X$_{C1}$ is R. In certain embodiments, VL CDR3 comprises the amino acid sequence of LQYDEFPYT (SEQ ID NO: 64).

In a specific embodiment, provided herein is an antibody or antigen-binding fragment thereof of any listed in Table 3, which comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence listed in the second column of Table 3 for the antibody or antigen-binding fragment, VH FR2 comprises the amino acid sequence listed in the sixth column of Table 3 for the antibody or antigen-binding fragment, VH FR3 comprises the amino acid sequence listed in the 10$^{th}$ column of Table 3 for the antibody or antigen-binding fragment, VH FR4 comprises the amino acid sequence listed in the 14$^{th}$ column of Table 3 for the antibody or antigen-binding fragment, VH CDR1 comprises the amino acid sequence listed in the fourth column of Table 3 for the antibody or antigen-binding fragment, VH CDR2 comprises the amino acid sequence listed in the eighth column of Table 3 for the antibody or antigen-binding fragment, and VH CDR3 comprises the amino acid sequence listed in the 12$^{nd}$ column of Table 3 for the antibody or antigen-binding fragment.

TABLE 3

Exemplary Antibodies with Specific VH FR sequences and specific VH CDR sequences ($X_{H1}$ is M or no amino acid).

| Antibody | VH-FR1 | SEQ ID NO: | VH-CDR1 | SEQ ID NO: | VH-FR2 | SEQ ID NO: | VH-CDR2 | SEQ ID NO: | VH-FR3 | SEQ ID NO: | VH-CDR3 | SEQ ID NO: | VH-FR4 | SEQ ID NO: |
|---|---|---|---|---|---|---|---|---|---|---|---|---|---|---|
| Ab496 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRSEDTAMYYC | (SEQ ID NO: 14) | NAAYGSSSYPMDY | (SEQ ID NO: 61) | WGQGTTVTVSS | (SEQ ID NO: 15) |
| Ab497 | $X_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELSSLRSEDTAMYYC | (SEQ ID NO: 14) | NAAYGSSSYPMDY | (SEQ ID NO: 61) | WGQGTTVTVSS | (SEQ ID NO: 15) |
| Ab498 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDPDQGDTE | (SEQ ID NO: 60) | YAQKFQDRVTITRDRSMSTAYMELSSLRSEDTAMYYC | (SEQ ID NO: 14) | NAAYGSSSYPMDY | (SEQ ID NO: 61) | WGQGTTVTVSS | (SEQ ID NO: 15) |
| Ab499 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDPDQGDTE | (SEQ ID NO: 60) | YAQKFQDRVTITRDRSMSTAYMELSSLRSEDTAMYYC | (SEQ ID NO: 18) | NAAYGSSSYPMDY | (SEQ ID NO: 61) | WGQGTLVTVSS | (SEQ ID NO: 19) |
| Ab500 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQDRVTITRDRSMSTAYMELSSLRSEDTAMYYC | (SEQ ID NO: 14) | NAAYGSSSYPMDY | (SEQ ID NO: 61) | WGQGTTVTVSS | (SEQ ID NO: 15) |
| Ab501 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRAEDTAMYYC | (SEQ ID NO: 14) | NAAYGSSSYPMDY | (SEQ ID NO: 61) | WGQGTTVTVSS | (SEQ ID NO: 15) |
| Ab502 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRAEDTAMYYC | (SEQ ID NO: 18) | NAAYGSSSYPMDY | (SEQ ID NO: 61) | WGQGTLVTVSS | (SEQ ID NO: 19) |
| Ab503 | $X_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELSSLRSEDTAMYYC | (SEQ ID NO: 14) | NAAYGSSSYPMDY | (SEQ ID NO: 61) | WGQGTTVTVSS | (SEQ ID NO: 19) |
| Ab504 | $X_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELSSLRAEDTAMYYC | (SEQ ID NO: 18) | NAAYGSSSYPMDY | (SEQ ID NO: 61) | WGQGTLVTVSS | (SEQ ID NO: 19) |
| Ab505 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDPDQGDTE | (SEQ ID NO: 60) | YAQKFQDRVTITRDRSMSTAYMELSSLRAEDTAMYYC | (SEQ ID NO: 14) | NAAYGSSSYPMDY | (SEQ ID NO: 61) | WGQGTLVTVSS | (SEQ ID NO: 19) |
| Ab506 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQDRVTITRDRSMSTAYMELSSLRAEDTAMYYC | (SEQ ID NO: 18) | NAAYGSSSYPMDY | (SEQ ID NO: 61) | WGQGTTVTVSS | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab507 | X$_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQDRVTITRDRSMSTAYMELSSLRSEDTAMYYC | (SEQ ID NO: 14) | NAAYGSSSYPMDY | (SEQ ID NO: 61) | WGQGTLVTVSS | (SEQ ID NO: 19) |
| Ab508 | X$_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRAEDTAMYYC | (SEQ ID NO: 18) | NAAYGSSSYPMDY | (SEQ ID NO: 61) | WGQGTLVTVSS | (SEQ ID NO: 19) |
| Ab509 | X$_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELSSLRAEDTAMYYC | (SEQ ID NO: 18) | NAAYGSSSYPMDY | (SEQ ID NO: 61) | WGQGTLVTVSS | (SEQ ID NO: 19) |
| Ab510 | X$_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQDRVTITRDRSMSTAYMELSSLRAEDTAMYYC | (SEQ ID NO: 18) | NAAYGSSSYPMDY | (SEQ ID NO: 61) | WGQGTLVTVSS | (SEQ ID NO: 19) |
| Ab511 | X$_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRSEDTAMYYC | (SEQ ID NO: 14) | NAAYGSSSYPMDY | (SEQ ID NO: 61) | WGQGTTVTVSS | (SEQ ID NO: 15) |
| Ab512 | X$_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRSEDTAMYYC | (SEQ ID NO: 22) | NAAYGSSSYPMDY | (SEQ ID NO: 61) | WGQGTTVTVSS | (SEQ ID NO: 15) |
| Ab513 | X$_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRSEDTAMYYC | (SEQ ID NO: 23) | NAAYGSSSYPMDY | (SEQ ID NO: 61) | WGQGTTVTVSS | (SEQ ID NO: 15) |
| Ab514 | X$_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELRSSLRSEDTAMYYC | (SEQ ID NO: 24) | NAAYGSSSYPMDY | (SEQ ID NO: 61) | WGQGTTVTVSS | (SEQ ID NO: 15) |
| Ab515 | X$_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRSEDTAVYYC | (SEQ ID NO: 25) | NAAYGSSSYPMDY | (SEQ ID NO: 61) | WGQGTTVTVSS | (SEQ ID NO: 15) |
| Ab516 | X$_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELSSLRSEDTAMYYC | (SEQ ID NO: 22) | NAAYGSSSYPMDY | (SEQ ID NO: 61) | WGQGTTVTVSS | (SEQ ID NO: 15) |
| Ab517 | X$_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRSEDTAMYYC | (SEQ ID NO: 23) | NAAYGSSSYPMDY | (SEQ ID NO: 61) | WGQGTTVTVSS | (SEQ ID NO: 15) |
| Ab518 | X$_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELRSSLRSEDTAMYYC | (SEQ ID NO: 24) | NAAYGSSSYPMDY | (SEQ ID NO: 61) | WGQGTTVTVSS | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab519 | $X_{H1}$QMQLVQS GAEVKKPGS SVKVSCKAS | (SEQ ID NO: 21) | GFNIKD YYLH | (SEQ ID NO: 12) | WVRQAPG KALEWMG | (SEQ ID NO: 59) | WIDPDQ GDTE | (SEQ ID NO: 13) | (SEQ ID NO: 60) | YAQKFQDRVTITR DRSMSTAYMELSS LRSEDTAVYYC | (SEQ ID NO: 25) | NAAYGSS SYPMDY | (SEQ ID NO: 61) | WGQGTT VTVSS | (SEQ ID NO: 15) |
| Ab520 | $X_{H1}$QMQLVQS GAEVKKTGS SVKVSCKAS | (SEQ ID NO: 12) | GFNIKD YYLH | (SEQ ID NO: 12) | WVRQAPG KALEWMG | (SEQ ID NO: 59) | WIDPDQ GDTE | (SEQ ID NO: 13) | (SEQ ID NO: 60) | YAQKFQGRVTITR DRSMSTAYMELSS LRSEDTAMYYC | (SEQ ID NO: 26) | NAAYGSS SYPMDY | (SEQ ID NO: 61) | WGQGTT VTVSS | (SEQ ID NO: 15) |
| Ab521 | $X_{H1}$QMQLVQS GAEVKKTGS SVKVSCKAS | (SEQ ID NO: 12) | GFNIKD YYLH | (SEQ ID NO: 12) | WVRQAPG KALEWMG | (SEQ ID NO: 59) | WIDPDQ GDTE | (SEQ ID NO: 13) | (SEQ ID NO: 60) | YAQKFQGRVTITR DRSMSTAYMELRS LRSEDTAMYYC | (SEQ ID NO: 27) | NAAYGSS SYPMDY | (SEQ ID NO: 61) | WGQGTT VTVSS | (SEQ ID NO: 15) |
| Ab522 | $X_{H1}$QMQLVQS GAEVKKTGS SVKVSCKAS | (SEQ ID NO: 12) | GFNIKD YYLH | (SEQ ID NO: 12) | WVRQAPG KALEWMG | (SEQ ID NO: 59) | WIDPDQ GDTE | (SEQ ID NO: 13) | (SEQ ID NO: 60) | YAQKFQDRVTITR DRSMSTAYMELSS LRSEDTAVYYC | (SEQ ID NO: 28) | NAAYGSS SYPMDY | (SEQ ID NO: 61) | WGQGTT VTVSS | (SEQ ID NO: 15) |
| Ab523 | $X_{H1}$QMQLVQS GAEVKKTGS SVKVSCKAS | (SEQ ID NO: 12) | GFNIKD YYLH | (SEQ ID NO: 12) | WVRQAPG KALEWMG | (SEQ ID NO: 59) | WIDPDQ GDTE | (SEQ ID NO: 13) | (SEQ ID NO: 60) | YAQKFQGRVTITR DRSTSTAYMELSS LRSEDTAMYYC | (SEQ ID NO: 29) | NAAYGSS SYPMDY | (SEQ ID NO: 61) | WGQGTT VTVSS | (SEQ ID NO: 15) |
| Ab524 | $X_{H1}$QMQLVQS GAEVKKTGS SVKVSCKAS | (SEQ ID NO: 12) | GFNIKD YYLH | (SEQ ID NO: 12) | WVRQAPG KALEWMG | (SEQ ID NO: 59) | WIDPDQ GDTE | (SEQ ID NO: 13) | (SEQ ID NO: 60) | YAQKFQGRVTITR DRSTSTAYMELRS LRSEDTAMYYC | (SEQ ID NO: 30) | NAAYGSS SYPMDY | (SEQ ID NO: 61) | WGQGTT VTVSS | (SEQ ID NO: 15) |
| Ab525 | $X_{H1}$QMQLVQS GAEVKKTGS SVKVSCKAS | (SEQ ID NO: 12) | GFNIKD YYLH | (SEQ ID NO: 12) | WVRQAPG KALEWMG | (SEQ ID NO: 59) | WIDPDQ GDTE | (SEQ ID NO: 13) | (SEQ ID NO: 60) | YAQKFQGRVTITR DRSMSTAYMELRS LRSEDTAMYYC | (SEQ ID NO: 31) | NAAYGSS SYPMDY | (SEQ ID NO: 61) | WGQGTT VTVSS | (SEQ ID NO: 15) |
| Ab526 | $X_{H1}$QMQLVQS GAEVKKPGS SVKVSCKAS | (SEQ ID NO: 21) | GFNIKD YYLH | (SEQ ID NO: 12) | WVRQAPG KALEWMG | (SEQ ID NO: 59) | WIDPDQ GDTE | (SEQ ID NO: 13) | (SEQ ID NO: 60) | YAQKFQGRVTITR DRSMSTAYMELSS LRSEDTAMYYC | (SEQ ID NO: 26) | NAAYGSS SYPMDY | (SEQ ID NO: 61) | WGQGTT VTVSS | (SEQ ID NO: 15) |
| Ab527 | $X_{H1}$QMQLVQS GAEVKKPGS SVKVSCKAS | (SEQ ID NO: 21) | GFNIKD YYLH | (SEQ ID NO: 12) | WVRQAPG KALEWMG | (SEQ ID NO: 59) | WIDPDQ GDTE | (SEQ ID NO: 13) | (SEQ ID NO: 60) | YAQKFQGRVTITR DRSMSTAYMELRS LRSEDTAMYYC | (SEQ ID NO: 27) | NAAYGSS SYPMDY | (SEQ ID NO: 61) | WGQGTT VTVSS | (SEQ ID NO: 15) |
| Ab528 | $X_{H1}$QMQLVQS GAEVKKPGS SVKVSCKAS | (SEQ ID NO: 21) | GFNIKD YYLH | (SEQ ID NO: 12) | WVRQAPG KALEWMG | (SEQ ID NO: 59) | WIDPDQ GDTE | (SEQ ID NO: 13) | (SEQ ID NO: 60) | YAQKFQDRVTITR DRSMSTAYMELSS LRSEDTAVYYC | (SEQ ID NO: 28) | NAAYGSS SYPMDY | (SEQ ID NO: 61) | WGQGTT VTVSS | (SEQ ID NO: 15) |
| Ab529 | $X_{H1}$QMQLVQS GAEVKKPGS SVKVSCKAS | (SEQ ID NO: 21) | GFNIKD YYLH | (SEQ ID NO: 12) | WVRQAPG KALEWMG | (SEQ ID NO: 59) | WIDPDQ GDTE | (SEQ ID NO: 13) | (SEQ ID NO: 60) | YAQKFQGRVTITR DRSMSTAYMELRS LRSEDTAMYYC | (SEQ ID NO: 29) | NAAYGSS SYPMDY | (SEQ ID NO: 61) | WGQGTT VTVSS | (SEQ ID NO: 15) |

TABLE 3-continued

Exemplary Antibodies with Specific VH FR sequences and specific VH CDR sequences ($X_{H1}$ is M or no amino acid).

| Anti-body | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab530 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELSSLRSEDTAVYYC | (SEQ ID NO: 60) | NAAYGSSSYPMDY | (SEQ ID NO: 30) | WGQGTTVTVSS | (SEQ ID NO: 61) | (SEQ ID NO: 15) |
| Ab531 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELRSLRSEDTAVYYC | (SEQ ID NO: 60) | NAAYGSSSYPMDY | (SEQ ID NO: 31) | WGQGTTVTVSS | (SEQ ID NO: 61) | (SEQ ID NO: 15) |
| Ab532 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSTSTAYMELRSLRSEDTAVYYC | (SEQ ID NO: 60) | NAAYGSSSYPMDY | (SEQ ID NO: 32) | WGQGTTVTVSS | (SEQ ID NO: 61) | (SEQ ID NO: 15) |
| Ab533 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELRSLRSEDTAMYYC | (SEQ ID NO: 60) | NAAYGSSSYPMDY | (SEQ ID NO: 33) | WGQGTTVTVSS | (SEQ ID NO: 61) | (SEQ ID NO: 15) |
| Ab534 | $X_{H1}$QMQLVQSGAEVKKTGSSVKVSCKAS | (SEQ ID NO: 12) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSTSTAYMELRSLRSEDTAVYYC | (SEQ ID NO: 60) | NAAYGSSSYPMDY | (SEQ ID NO: 34) | WGQGTTVTVSS | (SEQ ID NO: 61) | (SEQ ID NO: 15) |
| Ab535 | $X_{H1}$QMQLVQSGAEVKKTGSSVKVSCKAS | (SEQ ID NO: 12) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELRSLRSEDTAVYYC | (SEQ ID NO: 60) | NAAYGSSSYPMDY | (SEQ ID NO: 35) | WGQGTTVTVSS | (SEQ ID NO: 61) | (SEQ ID NO: 15) |
| Ab536 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELRSLRSEDTAVYYC | (SEQ ID NO: 60) | NAAYGSSSYPMDY | (SEQ ID NO: 32) | WGQGTTVTVSS | (SEQ ID NO: 61) | (SEQ ID NO: 15) |
| Ab537 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSTSTAYMELRSLRSEDTAVYYC | (SEQ ID NO: 60) | NAAYGSSSYPMDY | (SEQ ID NO: 33) | WGQGTTVTVSS | (SEQ ID NO: 61) | (SEQ ID NO: 15) |
| Ab538 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELRSLRSEDTAVYYC | (SEQ ID NO: 60) | NAAYGSSSYPMDY | (SEQ ID NO: 34) | WGQGTTVTVSS | (SEQ ID NO: 61) | (SEQ ID NO: 15) |
| Ab539 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELRSLRSEDTAVYYC | (SEQ ID NO: 60) | NAAYGSSSYPMDY | (SEQ ID NO: 35) | WGQGTTVTVSS | (SEQ ID NO: 61) | (SEQ ID NO: 15) |
| Ab540 | $X_{H1}$QMQLVQSGAEVKKTGSSVKVSCKAS | (SEQ ID NO: 12) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELRSLRSEDTAVYYC | (SEQ ID NO: 60) | NAAYGSSSYPMDY | (SEQ ID NO: 36) | WGQGTTVTVSS | (SEQ ID NO: 61) | (SEQ ID NO: 15) |
| Ab541 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSTSTAYMELRSLRSEDTAMYYC | (SEQ ID NO: 60) | NAAYGSSSYPMDY | (SEQ ID NO: 36) | WGQGTTVTVSS | (SEQ ID NO: 61) | (SEQ ID NO: 15) |

TABLE 3-continued

Exemplary Antibodies with Specific VH FR sequences and specific VH CDR sequences ($X_{H1}$ is M or no amino acid).

| Anti-body | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab542 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 60) | YAQKFQDRVTITRDRSTSTAYMELSSLRSEDTAMYYC | (SEQ ID NO: 14) | NAAYGSSSYPMDY | (SEQ ID NO: 61) | WGQGTTVTVSS | (SEQ ID NO: 15) |
| Ab543 | $X_{H1}$QMQLVQSGAEVKKTGSSVKVSCKAS | (SEQ ID NO: 12) | GFNIKDYYLH | (SEQ ID NO: 12) | WVRQAPGQGLEWMG | (SEQ ID NO: 59) | WIDPDQGDTE | (SEQ ID NO: 60) | YAQKFQGRVTITRDRSMSTAYMELSSLRSEDTAMYYC | (SEQ ID NO: 22) | NAAYGSSSYPMDY | (SEQ ID NO: 61) | WGQGTTVTVSS | (SEQ ID NO: 15) |
| Ab544 | $X_{H1}$QMQLVQSGAEVKKTGSSVKVSCKAS | (SEQ ID NO: 12) | GFNIKDYYLH | (SEQ ID NO: 12) | WVRQAPGQGLEWMG | (SEQ ID NO: 59) | WIDPDQGDTE | (SEQ ID NO: 60) | YAQKFQDRVTITRDRSMSTAYMELSSLRSEDTAMYYC | (SEQ ID NO: 23) | NAAYGSSSYPMDY | (SEQ ID NO: 61) | WGQGTTVTVSS | (SEQ ID NO: 15) |
| Ab545 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 60) | YAQKFQDRVTITRDRSMSTAYMELRSLRSEDTAMYYC | (SEQ ID NO: 24) | NAAYGSSSYPMDY | (SEQ ID NO: 61) | WGQGTTVTVSS | (SEQ ID NO: 15) |
| Ab546 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 60) | YAQKFQDRVTITRDRSMSTAYMELSSLRSEDTAVYYC | (SEQ ID NO: 25) | NAAYGSSSYPMDY | (SEQ ID NO: 61) | WGQGTTVTVSS | (SEQ ID NO: 15) |
| Ab547 | $X_{H1}$QMQLVQSGAEVKKTGSSVKVSCKAS | (SEQ ID NO: 12) | GFNIKDYYLH | (SEQ ID NO: 12) | WVRQAPGQGLEWMG | (SEQ ID NO: 59) | WIDPDQGDTE | (SEQ ID NO: 60) | YAQKFQGRVTITRDRSMSTAYMELSSLRSEDTAMYYC | (SEQ ID NO: 22) | NAAYGSSSYPMDY | (SEQ ID NO: 61) | WGQGTTVTVSS | (SEQ ID NO: 15) |
| Ab548 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 60) | YAQKFQDRVTITRDRSMSTAYMELSSLRSEDTAMYYC | (SEQ ID NO: 23) | NAAYGSSSYPMDY | (SEQ ID NO: 61) | WGQGTTVTVSS | (SEQ ID NO: 15) |
| Ab549 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 60) | YAQKFQDRVTITRDRSMSTAYMELRSLRSEDTAMYYC | (SEQ ID NO: 24) | NAAYGSSSYPMDY | (SEQ ID NO: 61) | WGQGTTVTVSS | (SEQ ID NO: 15) |
| Ab550 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 60) | YAQKFQGRVTITRDRSMSTAYMELSSLRSEDTAMYYC | (SEQ ID NO: 25) | NAAYGSSSYPMDY | (SEQ ID NO: 61) | WGQGTTVTVSS | (SEQ ID NO: 15) |
| Ab551 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 60) | YAQKFQDRVTITRDRSTSTAYMELSSLRSEDTAMYYC | (SEQ ID NO: 26) | NAAYGSSSYPMDY | (SEQ ID NO: 61) | WGQGTTVTVSS | (SEQ ID NO: 15) |
| Ab552 | $X_{H1}$QMQLVQSGAEVKKTGSSVKVSCKAS | (SEQ ID NO: 12) | GFNIKDYYLH | (SEQ ID NO: 12) | WVRQAPGQGLEWMG | (SEQ ID NO: 59) | WIDPDQGDTE | (SEQ ID NO: 60) | YAQKFQGRVTITRDRSMSTAYMELRSLRSEDTAMYYC | (SEQ ID NO: 27) | NAAYGSSSYPMDY | (SEQ ID NO: 61) | WGQGTTVTVSS | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR1 | SEQ ID NO: | VH-FR2 | SEQ ID NO: | VH-CDR2 | SEQ ID NO: | VH-FR3 | SEQ ID NO: | VH-CDR3 | SEQ ID NO: | VH-FR4 | SEQ ID NO: |
|---|---|---|---|---|---|---|---|---|---|---|---|---|---|---|
| Ab553 | $X_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDDPDGDTE | (SEQ ID NO: 60) | YAQKFQGRVTITRDRSMSTAYMELSSLRSEDTAVYYC | (SEQ ID NO: 28) | NAAYGSSSYPMDY | (SEQ ID NO: 61) | WGQGTTVTVSS | (SEQ ID NO: 15) |
| Ab554 | $X_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDDPDGDTE | (SEQ ID NO: 60) | YAQKFQDRVTITRDRSMSTAYMELRSLRSEDTAVYYC | (SEQ ID NO: 29) | NAAYGSSSYPMDY | (SEQ ID NO: 61) | WGQGTTVTVSS | (SEQ ID NO: 15) |
| Ab555 | $X_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDDPDGDTE | (SEQ ID NO: 60) | YAQKFQDRVTITRDRSMSTAYMELSSLRSEDTAVYYC | (SEQ ID NO: 30) | NAAYGSSSYPMDY | (SEQ ID NO: 61) | WGQGTTVTVSS | (SEQ ID NO: 15) |
| Ab556 | $X_{H1}$QMQLVQSGAEVKKPGSSVKVSCKAS | (SEQ ID NO: 12) | GFNIKDYYLH | (SEQ ID NO: 59) | WVRQAPGQGLEWMG | (SEQ ID NO: 16) | WIDDPDGDTE | (SEQ ID NO: 60) | YAQKFQDRVTITRDRSMSTAYMELSSLRSEDTAVYYC | (SEQ ID NO: 31) | NAAYGSSSYPMDY | (SEQ ID NO: 61) | WGQGTTVTVSS | (SEQ ID NO: 15) |
| Ab557 | $X_{H1}$QMQLVQSGAEVKKPGSSVKVSCKAS | (SEQ ID NO: 21) | GFNIKDYYLH | (SEQ ID NO: 59) | WVRQAPGQGLEWMG | (SEQ ID NO: 16) | WIDDPDGDTE | (SEQ ID NO: 60) | YAQKFQDRVTITRDRSTSTAYMELSSLRSEDTAMYYC | (SEQ ID NO: 26) | NAAYGSSSYPMDY | (SEQ ID NO: 61) | WGQGTTVTVSS | (SEQ ID NO: 15) |
| Ab558 | $X_{H1}$QMQLVQSGAEVKKPGSSVKVSCKAS | (SEQ ID NO: 21) | GFNIKDYYLH | (SEQ ID NO: 59) | WVRQAPGQGLEWMG | (SEQ ID NO: 16) | WIDDPDGDTE | (SEQ ID NO: 60) | YAQKFQDRVTITRDRSMSTAYMELSSLRSEDTAMYYC | (SEQ ID NO: 27) | NAAYGSSSYPMDY | (SEQ ID NO: 61) | WGQGTTVTVSS | (SEQ ID NO: 15) |
| Ab559 | $X_{H1}$QMQLVQSGAEVKKPGSSVKVSCKAS | (SEQ ID NO: 21) | GFNIKDYYLH | (SEQ ID NO: 59) | WVRQAPGQGLEWMG | (SEQ ID NO: 16) | WIDDPDGDTE | (SEQ ID NO: 60) | YAQKFQDRVTITRDRSMSTAYMELSSLRSEDTAVYYC | (SEQ ID NO: 28) | NAAYGSSSYPMDY | (SEQ ID NO: 61) | WGQGTTVTVSS | (SEQ ID NO: 15) |
| Ab560 | $X_{H1}$QMQLVQSGAEVKKPGSSVKVSCKAS | (SEQ ID NO: 12) | GFNIKDYYLH | (SEQ ID NO: 12) | WVRQAPGQGLEWMG | (SEQ ID NO: 59) | WIDDPDGDTE | (SEQ ID NO: 60) | YAQKFQDRVTITRDRSMSTAYMELRSLRSEDTAVYYC | (SEQ ID NO: 29) | NAAYGSSSYPMDY | (SEQ ID NO: 61) | WGQGTTVTVSS | (SEQ ID NO: 15) |
| Ab561 | $X_{H1}$QMQLVQSGAEVKKPGSSVKVSCKAS | (SEQ ID NO: 12) | GFNIKDYYLH | (SEQ ID NO: 59) | WVRQAPGQGLEWMG | (SEQ ID NO: 16) | WIDDPDGDTE | (SEQ ID NO: 60) | YAQKFQDRVTITRDRSMSTAYMELSSLRSEDTAVYYC | (SEQ ID NO: 30) | NAAYGSSSYPMDY | (SEQ ID NO: 61) | WGQGTTVTVSS | (SEQ ID NO: 15) |
| Ab562 | $X_{H1}$QMQLVQSGAEVKKPGSSVKVSCKAS | (SEQ ID NO: 12) | GFNIKDYYLH | (SEQ ID NO: 59) | WVRQAPGQGLEWMG | (SEQ ID NO: 16) | WIDDPDGDTE | (SEQ ID NO: 60) | YAQKFQDRVTITRDRSMSTAYMELSSLRSEDTAVYYC | (SEQ ID NO: 31) | NAAYGSSSYPMDY | (SEQ ID NO: 61) | WGQGTTVTVSS | (SEQ ID NO: 15) |
| Ab563 | $X_{H1}$QMQLVQSGAEVKKPGSSVKVSCKAS | (SEQ ID NO: 12) | GFNIKDYYLH | (SEQ ID NO: 59) | WVRQAPGQGLEWMG | (SEQ ID NO: 16) | WIDDPDGDTE | (SEQ ID NO: 60) | YAQKFQGRVTITRDRSMSTAYMELSSLRSEDTAVYYC | (SEQ ID NO: 32) | NAAYGSSSYPMDY | (SEQ ID NO: 61) | WGQGTTVTVSS | (SEQ ID NO: 15) |
| Ab564 | $X_{H1}$QMQLVQSGAEVKKPGSSVKVSCKAS | (SEQ ID NO: 12) | GFNIKDYYLH | (SEQ ID NO: 59) | WVRQAPGQGLEWMG | (SEQ ID NO: 16) | WIDDPDGDTE | (SEQ ID NO: 60) | YAQKFQGRVTITRDRSTSTAYMELSSLRSEDTAVYYC | (SEQ ID NO: 33) | NAAYGSSSYPMDY | (SEQ ID NO: 61) | WGQGTTVTVSS | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab565 | $X_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQGRVTITRDRSMSTAYMELRSLRSEDTAVYYC | (SEQ ID NO: 34) | NAAYGSSSYPMDY | (SEQ ID NO: 61) | WGQGTTVTVSS | (SEQ ID NO: 15) |
| Ab566 | $X_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELRSLRSEDTAVYYC | (SEQ ID NO: 35) | NAAYGSSSYPMDY | (SEQ ID NO: 61) | WGQGTTVTVSS | (SEQ ID NO: 15) |
| Ab567 | $X_{H1}$QMQLVQSGAEVKKPGSSVKVSCKAS | (SEQ ID NO: 21) | GFNIKDYYLH | (SEQ ID NO: 59) | WVRQAPGQGLEWMG | (SEQ ID NO: 16) | WIDPDQGDTE | (SEQ ID NO: 60) | YAQKFQGRVTITRDRSMSTAYMELRSLRSEDTAVYYC | (SEQ ID NO: 32) | NAAYGSSSYPMDY | (SEQ ID NO: 61) | WGQGTTVTVSS | (SEQ ID NO: 15) |
| Ab568 | $X_{H1}$QMQLVQSGAEVKKPGSSVKVSCKAS | (SEQ ID NO: 21) | GFNIKDYYLH | (SEQ ID NO: 59) | WVRQAPGQGLEWMG | (SEQ ID NO: 16) | WIDPDQGDTE | (SEQ ID NO: 60) | YAQKFQGRVTITRDRSTSTAYMELSSLRSEDTAVYYC | (SEQ ID NO: 33) | NAAYGSSSYPMDY | (SEQ ID NO: 61) | WGQGTTVTVSS | (SEQ ID NO: 15) |
| Ab569 | $X_{H1}$QMQLVQSGAEVKKPGSSVKVSCKAS | (SEQ ID NO: 21) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELRSLRSEDTAVYYC | (SEQ ID NO: 34) | NAAYGSSSYPMDY | (SEQ ID NO: 61) | WGQGTTVTVSS | (SEQ ID NO: 15) |
| Ab570 | $X_{H1}$QMQLVQSGAEVKKPGSSVKVSCKAS | (SEQ ID NO: 21) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSTSTAYMELSSLRSEDTAVYYC | (SEQ ID NO: 35) | NAAYGSSSYPMDY | (SEQ ID NO: 61) | WGQGTTVTVSS | (SEQ ID NO: 15) |
| Ab571 | $X_{H1}$QMQLVQSGAEVKKPGSSVKVSCKAS | (SEQ ID NO: 21) | GFNIKDYYLH | (SEQ ID NO: 59) | WVRQAPGQGLEWMG | (SEQ ID NO: 16) | WIDPDQGDTE | (SEQ ID NO: 60) | YAQKFQGRVTITRDRSMSTAYMELRSLRSEDTAVYYC | (SEQ ID NO: 36) | NAAYGSSSYPMDY | (SEQ ID NO: 61) | WGQGTTVTVSS | (SEQ ID NO: 15) |
| Ab572 | $X_{H1}$QMQLVQSGAEVKKPGSSVKVSCKAS | (SEQ ID NO: 21) | GFNIKDYYLH | (SEQ ID NO: 59) | WVRQAPGQALEWMG | (SEQ ID NO: 17) | WIDPDQGDTE | (SEQ ID NO: 60) | YAQKFQGRVTITRDRSMSTAYMELRSLRSEDTAVYYC | (SEQ ID NO: 36) | NAAYGSSSYPMDY | (SEQ ID NO: 61) | WGQGTTVTVSS | (SEQ ID NO: 15) |
| Ab573 | $X_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQGRVTITRDRSTSTAYMELSSLRAEDTAMYYC | (SEQ ID NO: 18) | NAAYGSSSYPMDY | (SEQ ID NO: 61) | WGQGTTVTVSS | (SEQ ID NO: 15) |
| Ab574 | $X_{H1}$QMQLVQSGAEVKKPGSSVKVSCKAS | (SEQ ID NO: 21) | GFNIKDYYLH | (SEQ ID NO: 59) | WVRQAPGQALEWMG | (SEQ ID NO: 17) | WIDPDQGDTE | (SEQ ID NO: 60) | YAQKFQGRVTITRDRSMSTAYMELRSLRAEDTAMYYC | (SEQ ID NO: 37) | NAAYGSSSYPMDY | (SEQ ID NO: 61) | WGQGTTVTVSS | (SEQ ID NO: 15) |
| Ab575 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDPDQGDTE | (SEQ ID NO: 60) | YAQKFQDRVTITRDRSMSTAYMELSSLRAEDTAMYYC | (SEQ ID NO: 38) | NAAYGSSSYPMDY | (SEQ ID NO: 61) | WGQGTTVTVSS | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab576 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDDPQGDTE | (SEQ ID NO: 60) | YAQKFQDRVTITRDRSMSTAYMELSSLRAEDTAMYYC | (SEQ ID NO: 39) | NAAYGSSSYPMDY | (SEQ ID NO: 61) | WGQGTTVTVSS | (SEQ ID NO: 15) |
| Ab577 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDDPQGDTE | (SEQ ID NO: 60) | YAQKFQDRVTITRDRSTSTAYMELSSLRAEDTAMYYC | (SEQ ID NO: 40) | NAAYGSSSYPMDY | (SEQ ID NO: 61) | WGQGTTVTVSS | (SEQ ID NO: 15) |
| Ab578 | $X_{H1}$QMQLVQSGAEVKKPGSSVKVSCKAS | (SEQ ID NO: 21) | GFNIKDYYLH | (SEQ ID NO: 59) | WVRQAPGQALEWMG | (SEQ ID NO: 17) | WIDDPQGDTE | (SEQ ID NO: 60) | YAQKFQGRVTITRDRSMSTAYMELSSLRAEDTAMYYC | (SEQ ID NO: 37) | NAAYGSSSYPMDY | (SEQ ID NO: 61) | WGQGTTVTVSS | (SEQ ID NO: 15) |
| Ab579 | $X_{H1}$QMQLVQSGAEVKKPGSSVKVSCKAS | (SEQ ID NO: 21) | GFNIKDYYLH | (SEQ ID NO: 59) | WVRQAPGQALEWMG | (SEQ ID NO: 17) | WIDDPQGDTE | (SEQ ID NO: 60) | YAQKFQDRVTITRDRSMSTAYMELSSLRAEDTAMYYC | (SEQ ID NO: 38) | NAAYGSSSYPMDY | (SEQ ID NO: 61) | WGQGTTVTVSS | (SEQ ID NO: 15) |
| Ab580 | $X_{H1}$QMQLVQSGAEVKKPGSSVKVSCKAS | (SEQ ID NO: 21) | GFNIKDYYLH | (SEQ ID NO: 59) | WVRQAPGQALEWMG | (SEQ ID NO: 17) | WIDDPQGDTE | (SEQ ID NO: 60) | YAQKFQDRVTITRDRSMSTAYMELSSLRAEDTAMYYC | (SEQ ID NO: 39) | NAAYGSSSYPMDY | (SEQ ID NO: 61) | WGQGTTVTVSS | (SEQ ID NO: 15) |
| Ab581 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDDPQGDTE | (SEQ ID NO: 60) | YAQKFQDRVTITRDRSTSTAYMELSSLRAEDTAMYYC | (SEQ ID NO: 40) | NAAYGSSSYPMDY | (SEQ ID NO: 61) | WGQGTTVTVSS | (SEQ ID NO: 15) |
| Ab582 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDDPQGDTE | (SEQ ID NO: 60) | YAQKFQDRVTITRDRSMSTAYMELSSLRAEDTAMYYC | (SEQ ID NO: 41) | NAAYGSSSYPMDY | (SEQ ID NO: 61) | WGQGTTVTVSS | (SEQ ID NO: 15) |
| Ab583 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDDPQGDTE | (SEQ ID NO: 60) | YAQKFQGRVTITRDRSMSTAYMELSSLRAEDTAMYYC | (SEQ ID NO: 42) | NAAYGSSSYPMDY | (SEQ ID NO: 61) | WGQGTTVTVSS | (SEQ ID NO: 15) |
| Ab584 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDDPQGDTE | (SEQ ID NO: 60) | YAQKFQGRVTITRDRSTSTAYMELSSLRAEDTAMYYC | (SEQ ID NO: 43) | NAAYGSSSYPMDY | (SEQ ID NO: 61) | WGQGTTVTVSS | (SEQ ID NO: 15) |
| Ab585 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDDPQGDTE | (SEQ ID NO: 60) | YAQKFQDRVTITRDRSMSTAYMELSSLRAEDTAMYYC | (SEQ ID NO: 44) | NAAYGSSSYPMDY | (SEQ ID NO: 61) | WGQGTTVTVSS | (SEQ ID NO: 15) |
| Ab586 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDDPQGDTE | (SEQ ID NO: 60) | YAQKFQDRVTITRDRSMSTAYMELSSLRAEDTAMYYC | (SEQ ID NO: 45) | NAAYGSSSYPMDY | (SEQ ID NO: 61) | WGQGTTVTVSS | (SEQ ID NO: 15) |
| Ab587 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDDPQGDTE | (SEQ ID NO: 60) | YAQKFQDRVTITRDRSMSTAYMELSSLRAEDTAMYYC | (SEQ ID NO: 46) | NAAYGSSSYPMDY | (SEQ ID NO: 61) | WGQGTTVTVSS | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab588 | $X_{H1}$QMQLVQSGAEVKKPGSSVKVSCKAS | (SEQ ID NO: 21) | GFNIKDYYLH | (SEQ ID NO: 59) | WVRQAPGQALEWMG | (SEQ ID NO: 17) | WIDPDQGDTE | (SEQ ID NO: 60) | YAQKFQGRVTITRDRSTSTAYMELSSLRAEDTAMYYC | (SEQ ID NO: 41) | NAAYGSSSYPMDY | (SEQ ID NO: 61) | WGQGTTVTVSS | (SEQ ID NO: 15) |
| Ab589 | $X_{H1}$QMQLVQSGAEVKKPGSSVKVSCKAS | (SEQ ID NO: 21) | GFNIKDYYLH | (SEQ ID NO: 59) | WVRQAPGQALEWMG | (SEQ ID NO: 17) | WIDPDQGDTE | (SEQ ID NO: 60) | YAQKFQGRVTITRDRSMSTAYMELRSLRAEDTAMYYC | (SEQ ID NO: 42) | NAAYGSSSYPMDY | (SEQ ID NO: 61) | WGQGTTVTVSS | (SEQ ID NO: 15) |
| Ab590 | $X_{H1}$QMQLVQSGAEVKKPGSSVKVSCKAS | (SEQ ID NO: 21) | GFNIKDYYLH | (SEQ ID NO: 59) | WVRQAPGQALEWMG | (SEQ ID NO: 17) | WIDPDQGDTE | (SEQ ID NO: 60) | YAQKFQGRVTITRDRSMSTAYMELSSLRAEDTAMYYC | (SEQ ID NO: 43) | NAAYGSSSYPMDY | (SEQ ID NO: 61) | WGQGTTVTVSS | (SEQ ID NO: 15) |
| Ab591 | $X_{H1}$QMQLVQSGAEVKKPGSSVKVSCKAS | (SEQ ID NO: 21) | GFNIKDYYLH | (SEQ ID NO: 59) | WVRQAPGQALEWMG | (SEQ ID NO: 17) | WIDPDQGDTE | (SEQ ID NO: 60) | YAQKFQDRVTITRDRSMSTAYMELRSLRAEDTAMYYC | (SEQ ID NO: 44) | NAAYGSSSYPMDY | (SEQ ID NO: 61) | WGQGTTVTVSS | (SEQ ID NO: 15) |
| Ab592 | $X_{H1}$QMQLVQSGAEVKKPGSSVKVSCKAS | (SEQ ID NO: 21) | GFNIKDYYLH | (SEQ ID NO: 59) | WVRQAPGQALEWMG | (SEQ ID NO: 17) | WIDPDQGDTE | (SEQ ID NO: 60) | YAQKFQGRVTITRDRSTSTAYMELSSLRAEDTAMYYC | (SEQ ID NO: 45) | NAAYGSSSYPMDY | (SEQ ID NO: 61) | WGQGTTVTVSS | (SEQ ID NO: 15) |
| Ab593 | $X_{H1}$QMQLVQSGAEVKKPGSSVKVSCKAS | (SEQ ID NO: 21) | GFNIKDYYLH | (SEQ ID NO: 59) | WVRQAPGQALEWMG | (SEQ ID NO: 17) | WIDPDQGDTE | (SEQ ID NO: 60) | YAQKFQGRVTITRDRSMSTAYMELRSLRAEDTAMYYC | (SEQ ID NO: 46) | NAAYGSSSYPMDY | (SEQ ID NO: 61) | WGQGTTVTVSS | (SEQ ID NO: 15) |
| Ab594 | $X_{H1}$QMQLVQSGAEVKKTGSSVKVSCKAS | (SEQ ID NO: 21) | GFNIKDYYLH | (SEQ ID NO: 59) | WVRQAPGQALEWMG | (SEQ ID NO: 17) | WIDPDQGDTE | (SEQ ID NO: 60) | YAQKFQGRVTITRDRSMSTAYMELSSLRAEDTAVYYC | (SEQ ID NO: 47) | NAAYGSSSYPMDY | (SEQ ID NO: 61) | WGQGTTVTVSS | (SEQ ID NO: 15) |
| Ab595 | $X_{H1}$QMQLVQSGAEVKKTGSSVKVSCKAS | (SEQ ID NO: 21) | GFNIKDYYLH | (SEQ ID NO: 59) | WVRQAPGQALEWMG | (SEQ ID NO: 17) | WIDPDQGDTE | (SEQ ID NO: 60) | YAQKFQGRVTITRDRSTSTAYMELSSLRAEDTAVYYC | (SEQ ID NO: 48) | NAAYGSSSYPMDY | (SEQ ID NO: 61) | WGQGTTVTVSS | (SEQ ID NO: 15) |
| Ab596 | $X_{H1}$QMQLVQSGAEVKKTGSSVKVSCKAS | (SEQ ID NO: 21) | GFNIKDYYLH | (SEQ ID NO: 59) | WVRQAPGQALEWMG | (SEQ ID NO: 17) | WIDPDQGDTE | (SEQ ID NO: 60) | YAQKFQDRVTITRDRSMSTAYMELRSLRAEDTAMYYC | (SEQ ID NO: 49) | NAAYGSSSYPMDY | (SEQ ID NO: 61) | WGQGTTVTVSS | (SEQ ID NO: 15) |
| Ab597 | $X_{H1}$QMQLVQSGAEVKKTGSSVKVSCKAS | (SEQ ID NO: 12) | GFNIKDYYLH | (SEQ ID NO: 59) | WVRQAPGQALEWMG | (SEQ ID NO: 17) | WIDPDQGDTE | (SEQ ID NO: 60) | YAQKFQDRVTITRDRSTSTAYMELRSLRAEDTAVYYC | (SEQ ID NO: 50) | NAAYGSSSYPMDY | (SEQ ID NO: 61) | WGQGTTVTVSS | (SEQ ID NO: 15) |
| Ab598 | $X_{H1}$QMQLVQSGAEVKKPGSSVKVSCKAS | (SEQ ID NO: 21) | GFNIKDYYLH | (SEQ ID NO: 59) | WVRQAPGQALEWMG | (SEQ ID NO: 17) | WIDPDQGDTE | (SEQ ID NO: 60) | YAQKFQDRVTITRDRSMSTAYMELRSLRAEDTAMYYC | (SEQ ID NO: 47) | NAAYGSSSYPMDY | (SEQ ID NO: 61) | WGQGTTVTVSS | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab599 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSTSTAYMELSSLRAEDTAVYYC | (SEQ ID NO: 48) | NAAYGSSYPMDY | (SEQ ID NO: 61) | WGQGTTVTVSS | (SEQ ID NO: 15) |
| Ab600 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSMSTAYMELRSLRAEDTAVYYC | (SEQ ID NO: 49) | NAAYGSSYPMDY | (SEQ ID NO: 61) | WGQGTTVTVSS | (SEQ ID NO: 15) |
| Ab601 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQDRVTITRDRSTSTAYMELRSLRAEDTAVYYC | (SEQ ID NO: 50) | NAAYGSSYPMDY | (SEQ ID NO: 61) | WGQGTTVTVSS | (SEQ ID NO: 15) |
| Ab602 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSMSTAYMELRSLRAEDTAVYYC | (SEQ ID NO: 139) | NAAYGSSYPMDY | (SEQ ID NO: 61) | WGQGTTVTVSS | (SEQ ID NO: 15) |
| Ab603 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSMSTAYMELRSLRAEDTAVYYC | (SEQ ID NO: 139) | NAAYGSSYPMDY | (SEQ ID NO: 61) | WGQGTTVTVSS | (SEQ ID NO: 15) |
| Ab604 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSMSTAYMELRSLRSEDTAMYYC | (SEQ ID NO: 14) | NAAYGSSYPMDY | (SEQ ID NO: 61) | WGQGTLVTVSS | (SEQ ID NO: 19) |
| Ab605 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSMSTAYMELRSLRSEDTAMYYC | (SEQ ID NO: 22) | NAAYGSSYPMDY | (SEQ ID NO: 61) | WGQGTLVTVSS | (SEQ ID NO: 19) |
| Ab606 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSMSTAYMELRSLRSEDTAMYYC | (SEQ ID NO: 23) | NAAYGSSYPMDY | (SEQ ID NO: 61) | WGQGTLVTVSS | (SEQ ID NO: 19) |
| Ab607 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSMSTAYMELRSLRSEDTAMYYC | (SEQ ID NO: 24) | NAAYGSSYPMDY | (SEQ ID NO: 61) | WGQGTLVTVSS | (SEQ ID NO: 19) |
| Ab608 | $X_{H1}$QMQLVQSGAEVKKTGSSVKVSCKAS | (SEQ ID NO: 12) | GFNIKDYYLH | (SEQ ID NO: 12) | WVRQAPGQALEWMG | (SEQ ID NO: 59) | WIDPDQGDTE | (SEQ ID NO: 60) | YAQKFQDRVTITRDRSMSTAYMELSSLRSEDTAVYYC | (SEQ ID NO: 25) | NAAYGSSYPMDY | (SEQ ID NO: 61) | WGQGTLVTVSS | (SEQ ID NO: 19) |
| Ab609 | $X_{H1}$QMQLVQSGAEVKKTGSSVKVSCKAS | (SEQ ID NO: 12) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSMSTAYMELSSLRSEDTAMYYC | (SEQ ID NO: 22) | NAAYGSSYPMDY | (SEQ ID NO: 61) | WGQGTLVTVSS | (SEQ ID NO: 19) |
| Ab610 | $X_{H1}$QMQLVQSGAEVKKTGSSVKVSCKAS | (SEQ ID NO: 12) | GFNIKDYYLH | (SEQ ID NO: 12) | WVRQAPGQALEWMG | (SEQ ID NO: 59) | WIDPDQGDTE | (SEQ ID NO: 60) | YAQKFQDRVTITRDRSMSTAYMELSSLRSEDTAMYYC | (SEQ ID NO: 23) | NAAYGSSYPMDY | (SEQ ID NO: 61) | WGQGTLVTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab611 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQDRVTITRDRSMSTAYMELSSLRSEDTAMYYC | (SEQ ID NO: 24) | NAAYGSSSYPMDY | (SEQ ID NO: 61) | WGQGTLVTVSS | (SEQ ID NO: 19) |
| Ab612 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQDRVTITRDRSMSTAYMELSSLRSEDTAVYYC | (SEQ ID NO: 25) | NAAYGSSSYPMDY | (SEQ ID NO: 61) | WGQGTLVTVSS | (SEQ ID NO: 19) |
| Ab613 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSTSTAYMELSSLRSEDTAMYYC | (SEQ ID NO: 26) | NAAYGSSSYPMDY | (SEQ ID NO: 61) | WGQGTLVTVSS | (SEQ ID NO: 19) |
| Ab614 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSTSTAYMELSSLRSEDTAVYYC | (SEQ ID NO: 27) | NAAYGSSSYPMDY | (SEQ ID NO: 61) | WGQGTLVTVSS | (SEQ ID NO: 19) |
| Ab615 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQDRVTITRDRSMSTAYMELSSLRSEDTAVYYC | (SEQ ID NO: 28) | NAAYGSSSYPMDY | (SEQ ID NO: 61) | WGQGTLVTVSS | (SEQ ID NO: 19) |
| Ab616 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSMSTAYMELSSLRSEDTAVYYC | (SEQ ID NO: 29) | NAAYGSSSYPMDY | (SEQ ID NO: 61) | WGQGTLVTVSS | (SEQ ID NO: 19) |
| Ab617 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSMSTAYMELSSLRSEDTAVYYC | (SEQ ID NO: 30) | NAAYGSSSYPMDY | (SEQ ID NO: 61) | WGQGTLVTVSS | (SEQ ID NO: 19) |
| Ab618 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQDRVTITRDRSMSTAYMELSSLRSEDTAMYYC | (SEQ ID NO: 31) | NAAYGSSSYPMDY | (SEQ ID NO: 61) | WGQGTLVTVSS | (SEQ ID NO: 19) |
| Ab619 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSTSTAYMELSSLRSEDTAMYYC | (SEQ ID NO: 26) | NAAYGSSSYPMDY | (SEQ ID NO: 61) | WGQGTLVTVSS | (SEQ ID NO: 19) |
| Ab620 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSTSTAYMELSSLRSEDTAVYYC | (SEQ ID NO: 27) | NAAYGSSSYPMDY | (SEQ ID NO: 61) | WGQGTLVTVSS | (SEQ ID NO: 19) |
| Ab621 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 60) | YAQKFQGRVTITRDRSMSTAYMELSSLRSEDTAVYYC | (SEQ ID NO: 28) | NAAYGSSSYPMDY | (SEQ ID NO: 61) | WGQGTLVTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab622 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELSSLRSEDTAMYYC | (SEQ ID NO: 29) | NAAYGSSSYPMDY | (SEQ ID NO: 60) | WGQGTLVTVSS | (SEQ ID NO: 61) | (SEQ ID NO: 19) |
| Ab623 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELSSLRSEDTAVYYC | (SEQ ID NO: 30) | NAAYGSSSYPMDY | (SEQ ID NO: 60) | WGQGTLVTVSS | (SEQ ID NO: 61) | (SEQ ID NO: 19) |
| Ab624 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELRSLRSEDTAVYYC | (SEQ ID NO: 31) | NAAYGSSSYPMDY | (SEQ ID NO: 60) | WGQGTLVTVSS | (SEQ ID NO: 61) | (SEQ ID NO: 19) |
| Ab625 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSMSTAYMELSSLRSEDTAMYYC | (SEQ ID NO: 32) | NAAYGSSSYPMDY | (SEQ ID NO: 60) | WGQGTLVTVSS | (SEQ ID NO: 61) | (SEQ ID NO: 19) |
| Ab626 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSTSTAYMELSSLRSEDTAVYYC | (SEQ ID NO: 33) | NAAYGSSSYPMDY | (SEQ ID NO: 60) | WGQGTLVTVSS | (SEQ ID NO: 61) | (SEQ ID NO: 19) |
| Ab627 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSMSTAYMELRSLRSEDTAVYYC | (SEQ ID NO: 34) | NAAYGSSSYPMDY | (SEQ ID NO: 60) | WGQGTLVTVSS | (SEQ ID NO: 61) | (SEQ ID NO: 19) |
| Ab628 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSMSTAYMELRSLRSEDTAVYYC | (SEQ ID NO: 35) | NAAYGSSSYPMDY | (SEQ ID NO: 60) | WGQGTLVTVSS | (SEQ ID NO: 61) | (SEQ ID NO: 19) |
| Ab629 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSMSTAYMELRSLRSEDTAMYYC | (SEQ ID NO: 32) | NAAYGSSSYPMDY | (SEQ ID NO: 60) | WGQGTLVTVSS | (SEQ ID NO: 61) | (SEQ ID NO: 19) |
| Ab630 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSTSTAYMELSSLRSEDTAVYYC | (SEQ ID NO: 33) | NAAYGSSSYPMDY | (SEQ ID NO: 60) | WGQGTLVTVSS | (SEQ ID NO: 61) | (SEQ ID NO: 19) |
| Ab631 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELRSLRSEDTAVYYC | (SEQ ID NO: 34) | NAAYGSSSYPMDY | (SEQ ID NO: 60) | WGQGTLVTVSS | (SEQ ID NO: 61) | (SEQ ID NO: 19) |
| Ab632 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELRSLRSEDTAVYYC | (SEQ ID NO: 35) | NAAYGSSSYPMDY | (SEQ ID NO: 60) | WGQGTLVTVSS | (SEQ ID NO: 61) | (SEQ ID NO: 19) |
| Ab633 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELRSLRSEDTAVYYC | (SEQ ID NO: 36) | NAAYGSSSYPMDY | (SEQ ID NO: 60) | WGQGTLVTVSS | (SEQ ID NO: 61) | (SEQ ID NO: 19) |

TABLE 3-continued

Exemplary Antibodies with Specific VH FR sequences and specific VH CDR sequences ($X_{H1}$ is M or no amino acid).

| Anti-body | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab634 | $X_{X1}$QMQLVQS GAEVKKPGS SVKVSCKAS | (SEQ ID NO: 21) | GFNIKD YYLH | (SEQ ID NO: 12) | WVRQAPG QALEWMG | (SEQ ID NO: 59) | WIDDPDQ GDTE | (SEQ ID NO: 17) | YAQKFQDRVTITR DRSMSTAYMELRS LRSEDTANYYC | (SEQ ID NO: 326) | NAAYGSS SYPMDY | (SEQ ID NO: 60) | WGQGTL VTVSS | (SEQ ID NO: 61) | (SEQ ID NO: 19) |
| Ab635 | $X_{X1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDDPDQ GDTE | (SEQ ID NO: 20) | YAQKFQDRVTITR DRSTSTAYMELSS LRSEDTAMYYC | (SEQ ID NO: 14) | NAAYGSS SYPMDY | (SEQ ID NO: 60) | WGQGTT VTVSS | (SEQ ID NO: 61) | (SEQ ID NO: 15) |
| Ab636 | $X_{X1}$QMQLVQS GAEVKKTGS SVKVSCKAS | (SEQ ID NO: 21) | GFNIKD YYLH | (SEQ ID NO: 12) | WVRQAPG KGLEWMG | (SEQ ID NO: 59) | WIDDPDQ GDTE | (SEQ ID NO: 20) | YAQKFQDRVTITR DRSMSTAYMELSS LRSEDTAMYYC | (SEQ ID NO: 22) | NAAYGSS SYPMDY | (SEQ ID NO: 60) | WGQGTT VTVSS | (SEQ ID NO: 61) | (SEQ ID NO: 15) |
| Ab637 | $X_{X1}$QMQLVQS GAEVKKTGS SVKVSCKAS | (SEQ ID NO: 21) | GFNIKD YYLH | (SEQ ID NO: 12) | WVRQAPG KGLEWMG | (SEQ ID NO: 59) | WIDDPDQ GDTE | (SEQ ID NO: 20) | YAQKFQDRVTITR DRSMSTAYMELSS LRSEDTAMYYC | (SEQ ID NO: 23) | NAAYGSS SYPMDY | (SEQ ID NO: 60) | WGQGTT VTVSS | (SEQ ID NO: 61) | (SEQ ID NO: 15) |
| Ab638 | $X_{X1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDDPDQ GDTE | (SEQ ID NO: 20) | YAQKFQDRVTITR DRSMSTAYMELSS LRSEDTAMYYC | (SEQ ID NO: 24) | NAAYGSS SYPMDY | (SEQ ID NO: 60) | WGQGTT VTVSS | (SEQ ID NO: 61) | (SEQ ID NO: 15) |
| Ab639 | $X_{X1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDDPDQ GDTE | (SEQ ID NO: 20) | YAQKFQGRVTITR DRSMSTAYMELSS LRSEDTAMYYC | (SEQ ID NO: 25) | NAAYGSS SYPMDY | (SEQ ID NO: 60) | WGQGTT VTVSS | (SEQ ID NO: 61) | (SEQ ID NO: 15) |
| Ab640 | $X_{X1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDDPDQ GDTE | (SEQ ID NO: 20) | YAQKFQDRVTITR DRSMSTAYMELSS LRSEDTAMYYC | (SEQ ID NO: 22) | NAAYGSS SYPMDY | (SEQ ID NO: 60) | WGQGTT VTVSS | (SEQ ID NO: 61) | (SEQ ID NO: 15) |
| Ab641 | $X_{X1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDDPDQ GDTE | (SEQ ID NO: 20) | YAQKFQDRVTITR DRSMSTAYMELSS LRSEDTAMYYC | (SEQ ID NO: 23) | NAAYGSS SYPMDY | (SEQ ID NO: 60) | WGQGTT VTVSS | (SEQ ID NO: 61) | (SEQ ID NO: 15) |
| Ab642 | $X_{X1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDDPDQ GDTE | (SEQ ID NO: 20) | YAQKFQDRVTITR DRSMSTAYMELSS LRSEDTAMYYC | (SEQ ID NO: 24) | NAAYGSS SYPMDY | (SEQ ID NO: 60) | WGQGTT VTVSS | (SEQ ID NO: 61) | (SEQ ID NO: 15) |
| Ab643 | $X_{X1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDDPDQ GDTE | (SEQ ID NO: 20) | YAQKFQDRVTITR DRSTSTAYMELSS LRSEDTAVYYC | (SEQ ID NO: 25) | NAAYGSS SYPMDY | (SEQ ID NO: 60) | WGQGTT VTVSS | (SEQ ID NO: 61) | (SEQ ID NO: 15) |
| Ab644 | $X_{X1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDDPDQ GDTE | (SEQ ID NO: 20) | YAQKFQGRVTITR DRSTSTAYMELSS LRSEDTAMYYC | (SEQ ID NO: 26) | NAAYGSS SYPMDY | (SEQ ID NO: 60) | WGQGTT VTVSS | (SEQ ID NO: 61) | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab645 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSTSTAYMELRSLRSEDTAMYYC | (SEQ ID NO: 60) | NAAYGSSSYPMDY | (SEQ ID NO: 27) | WGQGTTVTVSS | (SEQ ID NO: 61) | (SEQ ID NO: 15) |
| Ab646 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSMSTAYMELSSLRSEDTAMYYC | (SEQ ID NO: 60) | NAAYGSSSYPMDY | (SEQ ID NO: 28) | WGQGTTVTVSS | (SEQ ID NO: 61) | (SEQ ID NO: 15) |
| Ab647 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQDRVTITRDRSMSTAYMELRSLRSEDTAMYYC | (SEQ ID NO: 60) | NAAYGSSSYPMDY | (SEQ ID NO: 29) | WGQGTTVTVSS | (SEQ ID NO: 61) | (SEQ ID NO: 15) |
| Ab648 | $X_{H1}$QMQLVQSGAEVKKPGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQDRVTITRDRSMSTAYMELSSLRSEDTAMYYC | (SEQ ID NO: 60) | NAAYGSSSYPMDY | (SEQ ID NO: 30) | WGQGTTVTVSS | (SEQ ID NO: 61) | (SEQ ID NO: 15) |
| Ab649 | $X_{H1}$QMQLVQSGAEVKKPGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSMSTAYMELSSLRSEDTAVYYC | (SEQ ID NO: 60) | NAAYGSSSYPMDY | (SEQ ID NO: 31) | WGQGTTVTVSS | (SEQ ID NO: 61) | (SEQ ID NO: 15) |
| Ab650 | $X_{H1}$QMQLVQSGAEVKKPGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSTSTAYMELRSLRSEDTAMYYC | (SEQ ID NO: 60) | NAAYGSSSYPMDY | (SEQ ID NO: 26) | WGQGTTVTVSS | (SEQ ID NO: 61) | (SEQ ID NO: 15) |
| Ab651 | $X_{H1}$QMQLVQSGAEVKKPGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSTSTAYMELRSLRSEDTAMYYC | (SEQ ID NO: 60) | NAAYGSSSYPMDY | (SEQ ID NO: 27) | WGQGTTVTVSS | (SEQ ID NO: 61) | (SEQ ID NO: 15) |
| Ab652 | $X_{H1}$QMQLVQSGAEVKKPGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSMSTAYMELSSLRSEDTAMYYC | (SEQ ID NO: 60) | NAAYGSSSYPMDY | (SEQ ID NO: 28) | WGQGTTVTVSS | (SEQ ID NO: 61) | (SEQ ID NO: 15) |
| Ab653 | $X_{H1}$QMQLVQSGAEVKKPGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQDRVTITRDRSTSTAYMELRSLRSEDTAMYYC | (SEQ ID NO: 60) | NAAYGSSSYPMDY | (SEQ ID NO: 29) | WGQGTTVTVSS | (SEQ ID NO: 61) | (SEQ ID NO: 15) |
| Ab654 | $X_{H1}$QMQLVQSGAEVKKPGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQDRVTITRDRSMSTAYMELSSLRSEDTAVYYC | (SEQ ID NO: 60) | NAAYGSSSYPMDY | (SEQ ID NO: 30) | WGQGTTVTVSS | (SEQ ID NO: 61) | (SEQ ID NO: 15) |
| Ab655 | $X_{H1}$QMQLVQSGAEVKKPGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSMSTAYMELRSLRSEDTAVYYC | (SEQ ID NO: 60) | NAAYGSSSYPMDY | (SEQ ID NO: 31) | WGQGTTVTVSS | (SEQ ID NO: 61) | (SEQ ID NO: 15) |
| Ab656 | $X_{H1}$QMQLVQSGAEVKKPGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSMSTAYMELRSLRSEDTAMYYC | (SEQ ID NO: 60) | NAAYGSSSYPMDY | (SEQ ID NO: 32) | WGQGTTVTVSS | (SEQ ID NO: 61) | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab657 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSTSTAYMELSSLRSEDTAVYYC | (SEQ ID NO: 33) | NAAYGSSSYPMDY | (SEQ ID NO: 61) | WGQGTTVTVSS | (SEQ ID NO: 15) |
| Ab658 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRSEDTAVYYC | (SEQ ID NO: 34) | NAAYGSSSYPMDY | (SEQ ID NO: 61) | WGQGTTVTVSS | (SEQ ID NO: 15) |
| Ab659 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRSEDTAVYYC | (SEQ ID NO: 35) | NAAYGSSSYPMDY | (SEQ ID NO: 61) | WGQGTTVTVSS | (SEQ ID NO: 15) |
| Ab660 | $X_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSTSTAYMELSSLRSEDTAVYYC | (SEQ ID NO: 32) | NAAYGSSSYPMDY | (SEQ ID NO: 61) | WGQGTTVTVSS | (SEQ ID NO: 15) |
| Ab661 | $X_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSTSTAYMELSSLRSEDTAVYYC | (SEQ ID NO: 33) | NAAYGSSSYPMDY | (SEQ ID NO: 61) | WGQGTTVTVSS | (SEQ ID NO: 15) |
| Ab662 | $X_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRSEDTAVYYC | (SEQ ID NO: 34) | NAAYGSSSYPMDY | (SEQ ID NO: 61) | WGQGTTVTVSS | (SEQ ID NO: 15) |
| Ab663 | $X_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRSEDTAVYYC | (SEQ ID NO: 35) | NAAYGSSSYPMDY | (SEQ ID NO: 61) | WGQGTTVTVSS | (SEQ ID NO: 15) |
| Ab664 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSTSTAYMELSSLRSEDTAVYYC | (SEQ ID NO: 36) | NAAYGSSSYPMDY | (SEQ ID NO: 61) | WGQGTTVTVSS | (SEQ ID NO: 15) |
| Ab665 | $X_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSTSTAYMELSSLRSEDTAVYYC | (SEQ ID NO: 36) | NAAYGSSSYPMDY | (SEQ ID NO: 61) | WGQGTTVTVSS | (SEQ ID NO: 15) |
| Ab666 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSTSTAYMELRSLRAEDTAMYYC | (SEQ ID NO: 18) | NAAYGSSSYPMDY | (SEQ ID NO: 61) | WGQGTTVTVSS | (SEQ ID NO: 15) |
| Ab667 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRAEDTAMYYC | (SEQ ID NO: 37) | NAAYGSSSYPMDY | (SEQ ID NO: 61) | WGQGTTVTVSS | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab668 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRAEDTAMYYC | (SEQ ID NO: 38) | NAAYGSSSYPMDY | (SEQ ID NO: 61) | WGQGTTVTVSS | (SEQ ID NO: 15) |
| Ab669 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELRSLRAEDTAMYYC | (SEQ ID NO: 39) | NAAYGSSSYPMDY | (SEQ ID NO: 61) | WGQGTTVTVSS | (SEQ ID NO: 15) |
| Ab670 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSTSTAYMELSSLRAEDTAVYYC | (SEQ ID NO: 40) | NAAYGSSSYPMDY | (SEQ ID NO: 61) | WGQGTTVTVSS | (SEQ ID NO: 15) |
| Ab671 | $X_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELSSLRAEDTAMYYC | (SEQ ID NO: 37) | NAAYGSSSYPMDY | (SEQ ID NO: 61) | WGQGTTVTVSS | (SEQ ID NO: 15) |
| Ab672 | $X_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRAEDTAMYYC | (SEQ ID NO: 38) | NAAYGSSSYPMDY | (SEQ ID NO: 61) | WGQGTTVTVSS | (SEQ ID NO: 15) |
| Ab673 | $X_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELRSLRAEDTAMYYC | (SEQ ID NO: 39) | NAAYGSSSYPMDY | (SEQ ID NO: 61) | WGQGTTVTVSS | (SEQ ID NO: 15) |
| Ab674 | $X_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSTSTAYMELSSLRAEDTAVYYC | (SEQ ID NO: 40) | NAAYGSSSYPMDY | (SEQ ID NO: 61) | WGQGTTVTVSS | (SEQ ID NO: 15) |
| Ab675 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRAEDTAMYYC | (SEQ ID NO: 41) | NAAYGSSSYPMDY | (SEQ ID NO: 61) | WGQGTTVTVSS | (SEQ ID NO: 15) |
| Ab676 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELRSLRAEDTAMYYC | (SEQ ID NO: 42) | NAAYGSSSYPMDY | (SEQ ID NO: 61) | WGQGTTVTVSS | (SEQ ID NO: 15) |
| Ab677 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELRSLRAEDTAMYYC | (SEQ ID NO: 43) | NAAYGSSSYPMDY | (SEQ ID NO: 61) | WGQGTTVTVSS | (SEQ ID NO: 15) |
| Ab678 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELRSLRAEDTAMYYC | (SEQ ID NO: 44) | NAAYGSSSYPMDY | (SEQ ID NO: 61) | WGQGTTVTVSS | (SEQ ID NO: 15) |
| Ab679 | $X_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSTSTAYMELSSLRAEDTAMYYC | (SEQ ID NO: 45) | NAAYGSSSYPMDY | (SEQ ID NO: 61) | WGQGTTVTVSS | (SEQ ID NO: 15) |

TABLE 3-continued

Exemplary Antibodies with Specific VH FR sequences and specific VH CDR sequences ($X_{H1}$ is M or no amino acid).

| Anti-body | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab680 | $X_{H1}$QMQLVQSGAEVKKTGSSVKVSCKAS | (SEQ ID NO: 12) | GFNIKDYYLH | (SEQ ID NO: 21) | WVRQAPGKALEWMG | (SEQ ID NO: 59) | WIDPDQGDTE | (SEQ ID NO: 13) | YAQKFQDRVTITRDRSMSTAYMELRSLRAEDTAMYYC | (SEQ ID NO: 46) | NAAYGSSSYPMDY | (SEQ ID NO: 61) | WGQGTTVTVSS | (SEQ ID NO: 15) |
| Ab681 | $X_{H1}$QMQLVQSGAEVKKPGSSVKVSCKAS | (SEQ ID NO: 21) | GFNIKDYYLH | (SEQ ID NO: 21) | WVRQAPGKALEWMG | (SEQ ID NO: 59) | WIDPDQGDTE | (SEQ ID NO: 13) | YAQKFQGRVTITRDRSTSTAYMELSSLRAEDTAMYYC | (SEQ ID NO: 41) | NAAYGSSSYPMDY | (SEQ ID NO: 61) | WGQGTTVTVSS | (SEQ ID NO: 15) |
| Ab682 | $X_{H1}$QMQLVQSGAEVKKPGSSVKVSCKAS | (SEQ ID NO: 21) | GFNIKDYYLH | (SEQ ID NO: 21) | WVRQAPGKALEWMG | (SEQ ID NO: 59) | WIDPDQGDTE | (SEQ ID NO: 13) | YAQKFQGRVTITRDRSMSTAYMELRSLRAEDTAMYYC | (SEQ ID NO: 42) | NAAYGSSSYPMDY | (SEQ ID NO: 61) | WGQGTTVTVSS | (SEQ ID NO: 15) |
| Ab683 | $X_{H1}$QMQLVQSGAEVKKPGSSVKVSCKAS | (SEQ ID NO: 21) | GFNIKDYYLH | (SEQ ID NO: 21) | WVRQAPGKALEWMG | (SEQ ID NO: 59) | WIDPDQGDTE | (SEQ ID NO: 13) | YAQKFQDRVTITRDRSTSTAYMELSSLRAEDTAMYYC | (SEQ ID NO: 43) | NAAYGSSSYPMDY | (SEQ ID NO: 61) | WGQGTTVTVSS | (SEQ ID NO: 15) |
| Ab684 | $X_{H1}$QMQLVQSGAEVKKPGSSVKVSCKAS | (SEQ ID NO: 21) | GFNIKDYYLH | (SEQ ID NO: 21) | WVRQAPGKALEWMG | (SEQ ID NO: 59) | WIDPDQGDTE | (SEQ ID NO: 13) | YAQKFQDRVTITRDRSMSTAYMELRSLRAEDTAMYYC | (SEQ ID NO: 44) | NAAYGSSSYPMDY | (SEQ ID NO: 61) | WGQGTTVTVSS | (SEQ ID NO: 15) |
| Ab685 | $X_{H1}$QMQLVQSGAEVKKPGSSVKVSCKAS | (SEQ ID NO: 21) | GFNIKDYYLH | (SEQ ID NO: 21) | WVRQAPGKALEWMG | (SEQ ID NO: 59) | WIDPDQGDTE | (SEQ ID NO: 13) | YAQKFQGRVTITRDRSTSTAYMELSSLRAEDTAMYYC | (SEQ ID NO: 45) | NAAYGSSSYPMDY | (SEQ ID NO: 61) | WGQGTTVTVSS | (SEQ ID NO: 15) |
| Ab686 | $X_{H1}$QMQLVQSGAEVKKTGSSVKVSCKAS | (SEQ ID NO: 12) | GFNIKDYYLH | (SEQ ID NO: 21) | WVRQAPGKALEWMG | (SEQ ID NO: 59) | WIDPDQGDTE | (SEQ ID NO: 13) | YAQKFQGRVTITRDRSMSTAYMELRSLRAEDTAMYYC | (SEQ ID NO: 46) | NAAYGSSSYPMDY | (SEQ ID NO: 61) | WGQGTTVTVSS | (SEQ ID NO: 15) |
| Ab687 | $X_{H1}$QMQLVQSGAEVKKTGSSVKVSCKAS | (SEQ ID NO: 12) | GFNIKDYYLH | (SEQ ID NO: 21) | WVRQAPGKALEWMG | (SEQ ID NO: 59) | WIDPDQGDTE | (SEQ ID NO: 13) | YAQKFQGRVTITRDRSMSTAYMELRSLRAEDTAMYYC | (SEQ ID NO: 47) | NAAYGSSSYPMDY | (SEQ ID NO: 61) | WGQGTTVTVSS | (SEQ ID NO: 15) |
| Ab688 | $X_{H1}$QMQLVQSGAEVKKTGSSVKVSCKAS | (SEQ ID NO: 12) | GFNIKDYYLH | (SEQ ID NO: 21) | WVRQAPGKALEWMG | (SEQ ID NO: 59) | WIDPDQGDTE | (SEQ ID NO: 13) | YAQKFQGRVTITRDRSTSTAYMELSSLRAEDTAVYYC | (SEQ ID NO: 48) | NAAYGSSSYPMDY | (SEQ ID NO: 61) | WGQGTTVTVSS | (SEQ ID NO: 15) |
| Ab689 | $X_{H1}$QMQLVQSGAEVKKTGSSVKVSCKAS | (SEQ ID NO: 12) | GFNIKDYYLH | (SEQ ID NO: 21) | WVRQAPGKALEWMG | (SEQ ID NO: 59) | WIDPDQGDTE | (SEQ ID NO: 13) | YAQKFQGRVTITRDRSMSTAYMELRSLRAEDTAVYYC | (SEQ ID NO: 49) | NAAYGSSSYPMDY | (SEQ ID NO: 61) | WGQGTTVTVSS | (SEQ ID NO: 15) |
| Ab690 | $X_{H1}$QMQLVQSGAEVKKTGSSVKVSCKAS | (SEQ ID NO: 12) | GFNIKDYYLH | (SEQ ID NO: 21) | WVRQAPGKALEWMG | (SEQ ID NO: 59) | WIDPDQGDTE | (SEQ ID NO: 13) | YAQKFQGRVTITRDRSTSTAYMELSSLRAEDTAVYYC | (SEQ ID NO: 50) | NAAYGSSSYPMDY | (SEQ ID NO: 61) | WGQGTTVTVSS | (SEQ ID NO: 15) |

TABLE 3-continued

Exemplary Antibodies with Specific VH FR sequences and specific VH CDR sequences ($X_{H1}$ is M or no amino acid).

| Anti-body | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab691 | X$_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELRSLRAEDTAVYYC | (SEQ ID NO: 47) | NAAYGSSSYPMDY | (SEQ ID NO: 61) | WGQGTTVTVSS | (SEQ ID NO: 15) |
| Ab692 | X$_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSTSTAYMELRSLRAEDTAVYYC | (SEQ ID NO: 48) | NAAYGSSSYPMDY | (SEQ ID NO: 61) | WGQGTTVTVSS | (SEQ ID NO: 15) |
| Ab693 | X$_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELRSLRAEDTAVYYC | (SEQ ID NO: 49) | NAAYGSSSYPMDY | (SEQ ID NO: 61) | WGQGTTVTVSS | (SEQ ID NO: 15) |
| Ab694 | X$_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELRSLRAEDTAVYYC | (SEQ ID NO: 50) | NAAYGSSSYPMDY | (SEQ ID NO: 61) | WGQGTTVTVSS | (SEQ ID NO: 15) |
| Ab695 | X$_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSTSTAYMELSSLRAEDTAVYYC | (SEQ ID NO: 139) | NAAYGSSSYPMDY | (SEQ ID NO: 61) | WGQGTTVTVSS | (SEQ ID NO: 15) |
| Ab696 | X$_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELSSLRAEDTAVYYC | (SEQ ID NO: 139) | NAAYGSSSYPMDY | (SEQ ID NO: 61) | WGQGTTVTVSS | (SEQ ID NO: 15) |
| Ab697 | X$_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELSSLRSEDTAMYYC | (SEQ ID NO: 14) | NAAYGSSSYPMDY | (SEQ ID NO: 61) | WGQGTLVTVSS | (SEQ ID NO: 19) |
| Ab698 | X$_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELSSLRSEDTAMYYC | (SEQ ID NO: 22) | NAAYGSSSYPMDY | (SEQ ID NO: 61) | WGQGTLVTVSS | (SEQ ID NO: 19) |
| Ab699 | X$_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSTSTAYMELSSLRSEDTAMYYC | (SEQ ID NO: 23) | NAAYGSSSYPMDY | (SEQ ID NO: 61) | WGQGTLVTVSS | (SEQ ID NO: 19) |
| Ab700 | X$_{H1}$QMQLVQSGAEVKKTGSSVKVSCKAS | (SEQ ID NO: 12) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELSSLRSEDTAMYYC | (SEQ ID NO: 24) | NAAYGSSSYPMDY | (SEQ ID NO: 61) | WGQGTLVTVSS | (SEQ ID NO: 19) |
| Ab701 | X$_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRSEDTAMYYC | (SEQ ID NO: 25) | NAAYGSSSYPMDY | (SEQ ID NO: 61) | WGQGTLVTVSS | (SEQ ID NO: 19) |
| Ab702 | X$_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELSSLRSEDTAMYYC | (SEQ ID NO: 22) | NAAYGSSSYPMDY | (SEQ ID NO: 61) | WGQGTLVTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab703 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELSSLRSEDTAMYYC | (SEQ ID NO: 23) | NAAYGSSSYPMDY | (SEQ ID NO: 60) | WGQGTLVTVSS | (SEQ ID NO: 61) | (SEQ ID NO: 19) |
| Ab704 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELRSLRSEDTAMYYC | (SEQ ID NO: 24) | NAAYGSSSYPMDY | (SEQ ID NO: 60) | WGQGTLVTVSS | (SEQ ID NO: 61) | (SEQ ID NO: 19) |
| Ab705 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSTSTAYMELSSLRSEDTAMYYC | (SEQ ID NO: 25) | NAAYGSSSYPMDY | (SEQ ID NO: 60) | WGQGTLVTVSS | (SEQ ID NO: 61) | (SEQ ID NO: 19) |
| Ab706 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELSSLRSEDTAVYYC | (SEQ ID NO: 26) | NAAYGSSSYPMDY | (SEQ ID NO: 60) | WGQGTLVTVSS | (SEQ ID NO: 61) | (SEQ ID NO: 19) |
| Ab707 | $X_{H1}$QMQLVQSGAEVKKTGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELSSLRSEDTAMYYC | (SEQ ID NO: 27) | NAAYGSSSYPMDY | (SEQ ID NO: 60) | WGQGTLVTVSS | (SEQ ID NO: 61) | (SEQ ID NO: 19) |
| Ab708 | $X_{H1}$QMQLVQSGAEVKKTGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELSSLRSEDTAMYYC | (SEQ ID NO: 28) | NAAYGSSSYPMDY | (SEQ ID NO: 60) | WGQGTLVTVSS | (SEQ ID NO: 61) | (SEQ ID NO: 19) |
| Ab709 | $X_{H1}$QMQLVQSGAEVKKTGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELSSLRSEDTAMYYC | (SEQ ID NO: 29) | NAAYGSSSYPMDY | (SEQ ID NO: 60) | WGQGTLVTVSS | (SEQ ID NO: 61) | (SEQ ID NO: 19) |
| Ab710 | $X_{H1}$QMQLVQSGAEVKKTGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELSSLRSEDTAMYYC | (SEQ ID NO: 30) | NAAYGSSSYPMDY | (SEQ ID NO: 60) | WGQGTLVTVSS | (SEQ ID NO: 61) | (SEQ ID NO: 19) |
| Ab711 | $X_{H1}$QMQLVQSGAEVKKTGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQCRVTITRDRSTSTAYMELSSLRSEDTAVYYC | (SEQ ID NO: 31) | NAAYGSSSYPMDY | (SEQ ID NO: 60) | WGQGTLVTVSS | (SEQ ID NO: 61) | (SEQ ID NO: 19) |
| Ab712 | $X_{H1}$QMQLVQSGAEVKKTGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELSSLRSEDTAMYYC | (SEQ ID NO: 26) | NAAYGSSSYPMDY | (SEQ ID NO: 60) | WGQGTLVTVSS | (SEQ ID NO: 61) | (SEQ ID NO: 19) |
| Ab713 | $X_{H1}$QMQLVQSGAEVKKTGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSTSTAYMELRSLRSEDTAMYYC | (SEQ ID NO: 27) | NAAYGSSSYPMDY | (SEQ ID NO: 60) | WGQGTLVTVSS | (SEQ ID NO: 61) | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab714 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELSSLRSEDTAVYYC | (SEQ ID NO: 60) | NAAYGSSYPMDY | (SEQ ID NO: 28) | WGQGTLVTVSS | (SEQ ID NO: 61) | (SEQ ID NO: 19) |
| Ab715 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELSSLRSEDTAVYYC | (SEQ ID NO: 60) | NAAYGSSYPMDY | (SEQ ID NO: 29) | WGQGTLVTVSS | (SEQ ID NO: 61) | (SEQ ID NO: 19) |
| Ab716 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELSSLRSEDTAMYYC | (SEQ ID NO: 60) | NAAYGSSYPMDY | (SEQ ID NO: 30) | WGQGTLVTVSS | (SEQ ID NO: 61) | (SEQ ID NO: 19) |
| Ab717 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTITRDRSMSTAYMELRSLRSEDTAVYYC | (SEQ ID NO: 60) | NAAYGSSYPMDY | (SEQ ID NO: 31) | WGQGTLVTVSS | (SEQ ID NO: 61) | (SEQ ID NO: 19) |
| Ab718 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELRSLRSEDTAVYYC | (SEQ ID NO: 60) | NAAYGSSYPMDY | (SEQ ID NO: 32) | WGQGTLVTVSS | (SEQ ID NO: 61) | (SEQ ID NO: 19) |
| Ab719 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQDRVTSTAYMELRSLRSEDTAVYYC | (SEQ ID NO: 60) | NAAYGSSYPMDY | (SEQ ID NO: 33) | WGQGTLVTVSS | (SEQ ID NO: 61) | (SEQ ID NO: 19) |
| Ab720 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELRSLRSEDTAVYYC | (SEQ ID NO: 60) | NAAYGSSYPMDY | (SEQ ID NO: 34) | WGQGTLVTVSS | (SEQ ID NO: 61) | (SEQ ID NO: 19) |
| Ab721 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELRSLRSEDTAVYYC | (SEQ ID NO: 60) | NAAYGSSYPMDY | (SEQ ID NO: 35) | WGQGTLVTVSS | (SEQ ID NO: 61) | (SEQ ID NO: 19) |
| Ab722 | $X_{H1}$QMQLVQSGAEVKKTGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELRSLRSEDTAMYYC | (SEQ ID NO: 60) | NAAYGSSYPMDY | (SEQ ID NO: 32) | WGQGTLVTVSS | (SEQ ID NO: 61) | (SEQ ID NO: 19) |
| Ab723 | $X_{H1}$QMQLVQSGAEVKKTGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTSTAYMELRSLRSEDTAVYYC | (SEQ ID NO: 60) | NAAYGSSYPMDY | (SEQ ID NO: 33) | WGQGTLVTVSS | (SEQ ID NO: 61) | (SEQ ID NO: 19) |
| Ab724 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELRSLRSEDTAVYYC | (SEQ ID NO: 60) | NAAYGSSYPMDY | (SEQ ID NO: 34) | WGQGTLVTVSS | (SEQ ID NO: 61) | (SEQ ID NO: 19) |
| Ab725 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 13) | YAQKFQGRVTITRDRSMSTAYMELRSLRSEDTAVYYC | (SEQ ID NO: 60) | NAAYGSSYPMDY | (SEQ ID NO: 35) | WGQGTLVTVSS | (SEQ ID NO: 61) | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab726 | $X_{X1}$QMQLVQSGAEVKKTGSSVKVSCKAS | (SEQ ID NO: 12) | GFNIKDYYLH | (SEQ ID NO: 21) | WVRQAPGKALEWMG | (SEQ ID NO: 59) | WIDPDQGDTE | (SEQ ID NO: 60) | YAQKFQGRVTITRDRSMSTAYMELRSLRSEDTAVYYC | (SEQ ID NO: 36) | NAAYGSSYPMDY | (SEQ ID NO: 61) | WGQGTLVTVSS | (SEQ ID NO: 19) |
| Ab727 | $X_{X1}$QMQLVQSGAEVKKTGSSVKVSCKAS | (SEQ ID NO: 12) | GFNIKDYYLH | (SEQ ID NO: 21) | WVRQAPGKALEWMG | (SEQ ID NO: 59) | WIDPDQGDTE | (SEQ ID NO: 60) | YAQKFQGRVTITRDRSTSTAYMELRSLRSEDTAMYYC | (SEQ ID NO: 36) | NAAYGSSYPMDY | (SEQ ID NO: 61) | WGQGTLVTVSS | (SEQ ID NO: 19) |
| Ab728 | $X_{X1}$QMQLVQSGAEVKKPGSSVKVSCKAS | (SEQ ID NO: 12) | GFNIKDYYLH | (SEQ ID NO: 21) | WVRQAPGQGLEWMG | (SEQ ID NO: 59) | WIDPDQGDTE | (SEQ ID NO: 16) | YAQKFQDRVTITRDRSTSTAYMELRSLRAEDTAMYYC | (SEQ ID NO: 18) | NAAYGSSYPMDY | (SEQ ID NO: 61) | WGQGTTVTVSS | (SEQ ID NO: 15) |
| Ab729 | $X_{X1}$QMQLVQSGAEVKKTGSSVKVSCKAS | (SEQ ID NO: 12) | GFNIKDYYLH | (SEQ ID NO: 21) | WVRQAPGQGLEWMG | (SEQ ID NO: 59) | WIDPDQGDTE | (SEQ ID NO: 16) | YAQKFQGRVTITRDRSMSTAYMELSSLRAEDTAMYYC | (SEQ ID NO: 37) | NAAYGSSYPMDY | (SEQ ID NO: 61) | WGQGTTVTVSS | (SEQ ID NO: 15) |
| Ab730 | $X_{X1}$QMQLVQSGAEVKKTGSSVKVSCKAS | (SEQ ID NO: 12) | GFNIKDYYLH | (SEQ ID NO: 21) | WVRQAPGQGLEWMG | (SEQ ID NO: 59) | WIDPDQGDTE | (SEQ ID NO: 16) | YAQKFQGRVTITRDRSTSTAYMELSSLRAEDTAMYYC | (SEQ ID NO: 38) | NAAYGSSYPMDY | (SEQ ID NO: 61) | WGQGTTVTVSS | (SEQ ID NO: 15) |
| Ab731 | $X_{X1}$QMQLVQSGAEVKKPGSSVKVSCKAS | (SEQ ID NO: 12) | GFNIKDYYLH | (SEQ ID NO: 21) | WVRQAPGQGLEWMG | (SEQ ID NO: 59) | WIDPDQGDTE | (SEQ ID NO: 16) | YAQKFQDRVTITRDRSMSTAYMELSSLRAEDTAMYYC | (SEQ ID NO: 39) | NAAYGSSYPMDY | (SEQ ID NO: 61) | WGQGTTVTVSS | (SEQ ID NO: 15) |
| Ab732 | $X_{X1}$QMQLVQSGAEVKKPGSSVKVSCKAS | (SEQ ID NO: 12) | GFNIKDYYLH | (SEQ ID NO: 21) | WVRQAPGQGLEWMG | (SEQ ID NO: 59) | WIDPDQGDTE | (SEQ ID NO: 16) | YAQKFQDRVTITRDRSTSTAYMELSSLRAEDTAMYYC | (SEQ ID NO: 40) | NAAYGSSYPMDY | (SEQ ID NO: 61) | WGQGTTVTVSS | (SEQ ID NO: 15) |
| Ab733 | $X_{X1}$QMQLVQSGAEVKKTGSSVKVSCKAS | (SEQ ID NO: 12) | GFNIKDYYLH | (SEQ ID NO: 21) | WVRQAPGQGLEWMG | (SEQ ID NO: 59) | WIDPDQGDTE | (SEQ ID NO: 16) | YAQKFQGRVTITRDRSMSTAYMELSSLRAEDTAMYYC | (SEQ ID NO: 37) | NAAYGSSYPMDY | (SEQ ID NO: 61) | WGQGTTVTVSS | (SEQ ID NO: 15) |
| Ab734 | $X_{X1}$QMQLVQSGAEVKKTGSSVKVSCKAS | (SEQ ID NO: 12) | GFNIKDYYLH | (SEQ ID NO: 21) | WVRQAPGQGLEWMG | (SEQ ID NO: 59) | WIDPDQGDTE | (SEQ ID NO: 16) | YAQKFQGRVTITRDRSTSTAYMELSSLRAEDTAMYYC | (SEQ ID NO: 38) | NAAYGSSYPMDY | (SEQ ID NO: 61) | WGQGTTVTVSS | (SEQ ID NO: 15) |
| Ab735 | $X_{X1}$QMQLVQSGAEVKKPGSSVKVSCKAS | (SEQ ID NO: 12) | GFNIKDYYLH | (SEQ ID NO: 21) | WVRQAPGQGLEWMG | (SEQ ID NO: 59) | WIDPDQGDTE | (SEQ ID NO: 16) | YAQKFQDRVTITRDRSMSTAYMELSSLRAEDTAMYYC | (SEQ ID NO: 39) | NAAYGSSYPMDY | (SEQ ID NO: 61) | WGQGTTVTVSS | (SEQ ID NO: 15) |
| Ab736 | $X_{X1}$QMQLVQSGAEVKKPGSSVKVSCKAS | (SEQ ID NO: 12) | GFNIKDYYLH | (SEQ ID NO: 21) | WVRQAPGQGLEWMG | (SEQ ID NO: 59) | WIDPDQGDTE | (SEQ ID NO: 16) | YAQKFQDRVTITRDRSTSTAYMELSSLRAEDTAVYYC | (SEQ ID NO: 40) | NAAYGSSYPMDY | (SEQ ID NO: 61) | WGQGTTVTVSS | (SEQ ID NO: 15) |

TABLE 3-continued

Exemplary Antibodies with Specific VH FR sequences and specific VH CDR sequences ($X_{H1}$ is M or no amino acid).

| Anti-body | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab737 | $X_{H1}$QMQLVQSGAEVKKTGSSVKVSCKAS | (SEQ ID NO: 12) | GFNIKDYYLH | (SEQ ID NO: 21) | WVRQAPGQGLEWMG | (SEQ ID NO: 59) | WIDDPDGDTE | (SEQ ID NO: 16) | YAQKFQGRVTITRDRSTSTAYMELSSLRAEDTAMYYC | (SEQ ID NO: 60) | NAAYGSSSYPMDY | (SEQ ID NO: 41) | WGQGTTVTVSS | (SEQ ID NO: 61) | (SEQ ID NO: 15) |
| Ab738 | $X_{H1}$QMQLVQSGAEVKKTGSSVKVSCKAS | (SEQ ID NO: 12) | GFNIKDYYLH | (SEQ ID NO: 21) | WVRQAPGQGLEWMG | (SEQ ID NO: 59) | WIDDPDGDTE | (SEQ ID NO: 16) | YAQKFQGRVTITRDRSMSTAYMELRSLRAEDTAMYYC | (SEQ ID NO: 60) | NAAYGSSSYPMDY | (SEQ ID NO: 42) | WGQGTTVTVSS | (SEQ ID NO: 61) | (SEQ ID NO: 15) |
| Ab739 | $X_{H1}$QMQLVQSGAEVKKTGSSVKVSCKAS | (SEQ ID NO: 12) | GFNIKDYYLH | (SEQ ID NO: 21) | WVRQAPGQGLEWMG | (SEQ ID NO: 59) | WIDDPDGDTE | (SEQ ID NO: 16) | YAQKFQGRVTITRDRSMSTAYMELSSLRAEDTAMYYC | (SEQ ID NO: 60) | NAAYGSSSYPMDY | (SEQ ID NO: 43) | WGQGTTVTVSS | (SEQ ID NO: 61) | (SEQ ID NO: 15) |
| Ab740 | $X_{H1}$QMQLVQSGAEVKKTGSSVKVSCKAS | (SEQ ID NO: 12) | GFNIKDYYLH | (SEQ ID NO: 21) | WVRQAPGQGLEWMG | (SEQ ID NO: 59) | WIDDPDGDTE | (SEQ ID NO: 16) | YAQKFQDRVTITRDRSTSTAYMELSSLRAEDTAMYYC | (SEQ ID NO: 60) | NAAYGSSSYPMDY | (SEQ ID NO: 44) | WGQGTTVTVSS | (SEQ ID NO: 61) | (SEQ ID NO: 15) |
| Ab741 | $X_{H1}$QMQLVQSGAEVKKTGSSVKVSCKAS | (SEQ ID NO: 12) | GFNIKDYYLH | (SEQ ID NO: 21) | WVRQAPGQGLEWMG | (SEQ ID NO: 59) | WIDDPDGDTE | (SEQ ID NO: 16) | YAQKFQGRVTITRDRSMSTAYMELSSLRAEDTAMYYC | (SEQ ID NO: 60) | NAAYGSSSYPMDY | (SEQ ID NO: 45) | WGQGTTVTVSS | (SEQ ID NO: 61) | (SEQ ID NO: 15) |
| Ab742 | $X_{H1}$QMQLVQSGAEVKKTGSSVKVSCKAS | (SEQ ID NO: 12) | GFNIKDYYLH | (SEQ ID NO: 21) | WVRQAPGQGLEWMG | (SEQ ID NO: 59) | WIDDPDGDTE | (SEQ ID NO: 16) | YAQKFQGRVTITRDRSMSTAYMELRSLRAEDTAVYYC | (SEQ ID NO: 60) | NAAYGSSSYPMDY | (SEQ ID NO: 46) | WGQGTTVTVSS | (SEQ ID NO: 61) | (SEQ ID NO: 15) |
| Ab743 | $X_{H1}$QMQLVQSGAEVKKPGSSVKVSCKAS | (SEQ ID NO: 12) | GFNIKDYYLH | (SEQ ID NO: 21) | WVRQAPGQGLEWMG | (SEQ ID NO: 59) | WIDDPDGDTE | (SEQ ID NO: 16) | YAQKFQGRVTITRDRSTSTAYMELSSLRAEDTAMYYC | (SEQ ID NO: 60) | NAAYGSSSYPMDY | (SEQ ID NO: 41) | WGQGTTVTVSS | (SEQ ID NO: 61) | (SEQ ID NO: 15) |
| Ab744 | $X_{H1}$QMQLVQSGAEVKKPGSSVKVSCKAS | (SEQ ID NO: 12) | GFNIKDYYLH | (SEQ ID NO: 21) | WVRQAPGQGLEWMG | (SEQ ID NO: 59) | WIDDPDGDTE | (SEQ ID NO: 16) | YAQKFQGRVTITRDRSMSTAYMELSSLRAEDTAMYYC | (SEQ ID NO: 60) | NAAYGSSSYPMDY | (SEQ ID NO: 42) | WGQGTTVTVSS | (SEQ ID NO: 61) | (SEQ ID NO: 15) |
| Ab745 | $X_{H1}$QMQLVQSGAEVKKPGSSVKVSCKAS | (SEQ ID NO: 12) | GFNIKDYYLH | (SEQ ID NO: 21) | WVRQAPGQGLEWMG | (SEQ ID NO: 59) | WIDDPDGDTE | (SEQ ID NO: 16) | YAQKFQGRVTITRDRSMSTAYMELSSLRAEDTAMYYC | (SEQ ID NO: 60) | NAAYGSSSYPMDY | (SEQ ID NO: 43) | WGQGTTVTVSS | (SEQ ID NO: 61) | (SEQ ID NO: 15) |
| Ab746 | $X_{H1}$QMQLVQSGAEVKKPGSSVKVSCKAS | (SEQ ID NO: 12) | GFNIKDYYLH | (SEQ ID NO: 21) | WVRQAPGQGLEWMG | (SEQ ID NO: 59) | WIDDPDGDTE | (SEQ ID NO: 16) | YAQKFQDRVTITRDRSMSTAYMELSSLRAEDTAMYYC | (SEQ ID NO: 60) | NAAYGSSSYPMDY | (SEQ ID NO: 44) | WGQGTTVTVSS | (SEQ ID NO: 61) | (SEQ ID NO: 15) |
| Ab747 | $X_{H1}$QMQLVQSGAEVKKPGSSVKVSCKAS | (SEQ ID NO: 12) | GFNIKDYYLH | (SEQ ID NO: 21) | WVRQAPGQGLEWMG | (SEQ ID NO: 59) | WIDDPDGDTE | (SEQ ID NO: 16) | YAQKFQGRVTITRDRSMSTAYMELSSLRAEDTAMYYC | (SEQ ID NO: 60) | NAAYGSSSYPMDY | (SEQ ID NO: 45) | WGQGTTVTVSS | (SEQ ID NO: 61) | (SEQ ID NO: 15) |
| Ab748 | $X_{H1}$QMQLVQSGAEVKKPGSSVKVSCKAS | (SEQ ID NO: 12) | GFNIKDYYLH | (SEQ ID NO: 21) | WVRQAPGQGLEWMG | (SEQ ID NO: 59) | WIDDPDGDTE | (SEQ ID NO: 16) | YAQKFQGRVTITRDRSMSTAYMELRSLRAEDTAMYYC | (SEQ ID NO: 60) | NAAYGSSSYPMDY | (SEQ ID NO: 46) | WGQGTTVTVSS | (SEQ ID NO: 61) | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab749 | $X_{H1}$QMQLVQSGAEVKKTGSSVKVSCKAS | (SEQ ID NO: 12) | GFNIKDYYLH | (SEQ ID NO: 12) | WVRQAPGQGLEWMG | (SEQ ID NO: 59) | WIDPDQGDTE | (SEQ ID NO: 60) | YAQKFQGRVTITRDRSMSTAYMELRSLRAEDTAMYYC | (SEQ ID NO: 47) | NAAYGSSSYPMDY | (SEQ ID NO: 61) | WGQGTTVTVSS | (SEQ ID NO: 15) |
| Ab750 | $X_{H1}$QMQLVQSGAEVKKTGSSVKVSCKAS | (SEQ ID NO: 12) | GFNIKDYYLH | (SEQ ID NO: 12) | WVRQAPGQGLEWMG | (SEQ ID NO: 59) | WIDPDQGDTE | (SEQ ID NO: 60) | YAQKFQGRVTITRDRSTSTAYMELSSLRAEDTAVYYC | (SEQ ID NO: 48) | NAAYGSSSYPMDY | (SEQ ID NO: 61) | WGQGTTVTVSS | (SEQ ID NO: 15) |
| Ab751 | $X_{H1}$QMQLVQSGAEVKKTGSSVKVSCKAS | (SEQ ID NO: 12) | GFNIKDYYLH | (SEQ ID NO: 12) | WVRQAPGQGLEWMG | (SEQ ID NO: 59) | WIDPDQGDTE | (SEQ ID NO: 60) | YAQKFQGRVTITRDRSMSTAYMELRSLRAEDTAVYYC | (SEQ ID NO: 49) | NAAYGSSSYPMDY | (SEQ ID NO: 61) | WGQGTTVTVSS | (SEQ ID NO: 15) |
| Ab752 | $X_{H1}$QMQLVQSGAEVKKTGSSVKVSCKAS | (SEQ ID NO: 12) | GFNIKDYYLH | (SEQ ID NO: 12) | WVRQAPGQGLEWMG | (SEQ ID NO: 59) | WIDPDQGDTE | (SEQ ID NO: 60) | YAQKFQDRVTITRDRSTSTAYMELRSLRAEDTAVYYC | (SEQ ID NO: 50) | NAAYGSSSYPMDY | (SEQ ID NO: 61) | WGQGTTVTVSS | (SEQ ID NO: 15) |
| Ab753 | $X_{H1}$QMQLVQSGAEVKKPGSSVKVSCKAS | (SEQ ID NO: 21) | GFNIKDYYLH | (SEQ ID NO: 21) | WVRQAPGQGLEWMG | (SEQ ID NO: 59) | WIDPDQGDTE | (SEQ ID NO: 60) | YAQKFQGRVTITRDRSMSTAYMELRSLRAEDTAMYYC | (SEQ ID NO: 47) | NAAYGSSSYPMDY | (SEQ ID NO: 61) | WGQGTTVTVSS | (SEQ ID NO: 15) |
| Ab754 | $X_{H1}$QMQLVQSGAEVKKPGSSVKVSCKAS | (SEQ ID NO: 21) | GFNIKDYYLH | (SEQ ID NO: 21) | WVRQAPGQGLEWMG | (SEQ ID NO: 59) | WIDPDQGDTE | (SEQ ID NO: 60) | YAQKFQGRVTITRDRSTSTAYMELSSLRAEDTAVYYC | (SEQ ID NO: 48) | NAAYGSSSYPMDY | (SEQ ID NO: 61) | WGQGTTVTVSS | (SEQ ID NO: 15) |
| Ab755 | $X_{H1}$QMQLVQSGAEVKKPGSSVKVSCKAS | (SEQ ID NO: 21) | GFNIKDYYLH | (SEQ ID NO: 21) | WVRQAPGQGLEWMG | (SEQ ID NO: 59) | WIDPDQGDTE | (SEQ ID NO: 60) | YAQKFQGRVTITRDRSMSTAYMELRSLRAEDTAVYYC | (SEQ ID NO: 49) | NAAYGSSSYPMDY | (SEQ ID NO: 61) | WGQGTTVTVSS | (SEQ ID NO: 15) |
| Ab756 | $X_{H1}$QMQLVQSGAEVKKPGSSVKVSCKAS | (SEQ ID NO: 21) | GFNIKDYYLH | (SEQ ID NO: 21) | WVRQAPGQGLEWMG | (SEQ ID NO: 59) | WIDPDQGDTE | (SEQ ID NO: 60) | YAQKFQDRVTITRDRSTSTAYMELRSLRAEDTAVYYC | (SEQ ID NO: 50) | NAAYGSSSYPMDY | (SEQ ID NO: 61) | WGQGTTVTVSS | (SEQ ID NO: 15) |
| Ab757 | $X_{H1}$QMQLVQSGAEVKKPGSSVKVSCKAS | (SEQ ID NO: 12) | GFNIKDYYLH | (SEQ ID NO: 12) | WVRQAPGQGLEWMG | (SEQ ID NO: 59) | WIDPDQGDTE | (SEQ ID NO: 60) | YAQKFQGRVTITRDRSMSTAYMELRSLRAEDTAVYYC | (SEQ ID NO: 139) | NAAYGSSSYPMDY | (SEQ ID NO: 61) | WGQGTTVTVSS | (SEQ ID NO: 15) |
| Ab758 | $X_{H1}$QMQLVQSGAEVKKPGSSVKVSCKAS | (SEQ ID NO: 21) | GFNIKDYYLH | (SEQ ID NO: 21) | WVRQAPGQGLEWMG | (SEQ ID NO: 59) | WIDPDQGDTE | (SEQ ID NO: 60) | YAQKFQGRVTITRDRSMSTAYMELRSLRAEDTAVYYC | (SEQ ID NO: 139) | NAAYGSSSYPMDY | (SEQ ID NO: 61) | WGQGTTVTVSS | (SEQ ID NO: 15) |
| Ab759 | $X_{H1}$QMQLVQSGAEVKKPGSSVKVSCKAS | (SEQ ID NO: 21) | GFNIKDYYLH | (SEQ ID NO: 21) | WVRQAPGQGLEWMG | (SEQ ID NO: 59) | WIDPDQGDTE | (SEQ ID NO: 60) | YAQKFQDRVTITRDRSTSTAYMELSSLRSEDTAMYYC | (SEQ ID NO: 14) | NAAYGSSSYPMDY | (SEQ ID NO: 61) | WGQGTLVTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab760 | $X_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQGRVTITRDRSMSTAYMELSSLRSEDTAMYYC | (SEQ ID NO: 22) | NAAYGSSSYPMDY | (SEQ ID NO: 61) | WGQGTLVTVSS | (SEQ ID NO: 19) |
| Ab761 | $X_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELSSLRSEDTAMYYC | (SEQ ID NO: 23) | NAAYGSSSYPMDY | (SEQ ID NO: 61) | WGQGTLVTVSS | (SEQ ID NO: 19) |
| Ab762 | $X_{H1}$QMQLVQSGAEVKKTGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELRSLRSEDTAMYYC | (SEQ ID NO: 24) | NAAYGSSSYPMDY | (SEQ ID NO: 61) | WGQGTLVTVSS | (SEQ ID NO: 19) |
| Ab763 | $X_{H1}$QMQLVQSGAEVKKPGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELSSLRSEDTAMYYC | (SEQ ID NO: 25) | NAAYGSSSYPMDY | (SEQ ID NO: 61) | WGQGTLVTVSS | (SEQ ID NO: 19) |
| Ab764 | $X_{H1}$QMQLVQSGAEVKKPGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQGRVTITRDRSMSTAYMELSSLRSEDTAMYYC | (SEQ ID NO: 22) | NAAYGSSSYPMDY | (SEQ ID NO: 61) | WGQGTLVTVSS | (SEQ ID NO: 19) |
| Ab765 | $X_{H1}$QMQLVQSGAEVKKPGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELSSLRSEDTAMYYC | (SEQ ID NO: 23) | NAAYGSSSYPMDY | (SEQ ID NO: 61) | WGQGTLVTVSS | (SEQ ID NO: 19) |
| Ab766 | $X_{H1}$QMQLVQSGAEVKKPGSSVKVSCKAS | (SEQ ID NO: 21) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELRSLRSEDTAMYYC | (SEQ ID NO: 24) | NAAYGSSSYPMDY | (SEQ ID NO: 61) | WGQGTLVTVSS | (SEQ ID NO: 19) |
| Ab767 | $X_{H1}$QMQLVQSGAEVKKPGSSVKVSCKAS | (SEQ ID NO: 21) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELSSLRSEDTAMYYC | (SEQ ID NO: 25) | NAAYGSSSYPMDY | (SEQ ID NO: 61) | WGQGTLVTVSS | (SEQ ID NO: 19) |
| Ab768 | $X_{H1}$QMQLVQSGAEVKKPGSSVKVSCKAS | (SEQ ID NO: 21) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSTSTAYMELSSLRSEDTAMYYC | (SEQ ID NO: 26) | NAAYGSSSYPMDY | (SEQ ID NO: 61) | WGQGTLVTVSS | (SEQ ID NO: 19) |
| Ab769 | $X_{H1}$QMQLVQSGAEVKKPGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSTSTAYMELRSLRSEDTAMYYC | (SEQ ID NO: 27) | NAAYGSSSYPMDY | (SEQ ID NO: 61) | WGQGTLVTVSS | (SEQ ID NO: 19) |
| Ab770 | $X_{H1}$QMQLVQSGAEVKKPGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELSSLRSEDTAVYYC | (SEQ ID NO: 28) | NAAYGSSSYPMDY | (SEQ ID NO: 61) | WGQGTLVTVSS | (SEQ ID NO: 19) |
| Ab771 | $X_{H1}$QMQLVQSGAEVKKPGSSVKVSCKAS | (SEQ ID NO: 12) | GFNIKDYYLH | (SEQ ID NO: 59) | WVRQAPGQGLEWMG | (SEQ ID NO: 16) | WIDPDQGDTE | (SEQ ID NO: 60) | YAQKFQDRVTITRDRSMSTAYMELRSLRSEDTAMYYC | (SEQ ID NO: 29) | NAAYGSSSYPMDY | (SEQ ID NO: 61) | WGQGTLVTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab772 | $X_{H1}$QMQLVQS GAEVKKTGS SVKVSCKAS | (SEQ ID NO: 12) | GFNIKD YYLH | (SEQ ID NO: 21) | WVRQAPG QGLEWMG | (SEQ ID NO: 59) | WIDPDQ GDTE | (SEQ ID NO: 16) | YAQKFQDRVTITR DRSMSTAYMELSS LRSEDTAVYYC | (SEQ ID NO: 60) | NAAYGSS SYPMDY | (SEQ ID NO: 30) | WGQGTL VTVSS | (SEQ ID NO: 61) | (SEQ ID NO: 19) |
| Ab773 | $X_{H1}$QMQLVQS GAEVKKTGS SVKVSCKAS | (SEQ ID NO: 12) | GFNIKD YYLH | (SEQ ID NO: 21) | WVRQAPG QGLEWMG | (SEQ ID NO: 59) | WIDPDQ GDTE | (SEQ ID NO: 16) | YAQKFQDRVTITR DRSMSTAYMELRS LRSEDTAVYYC | (SEQ ID NO: 60) | NAAYGSS SYPMDY | (SEQ ID NO: 31) | WGQGTL VTVSS | (SEQ ID NO: 61) | (SEQ ID NO: 19) |
| Ab774 | $X_{H1}$QMQLVQS GAEVKKPGS SVKVSCKAS | (SEQ ID NO: 21) | GFNIKD YYLH | (SEQ ID NO: 21) | WVRQAPG QGLEWMG | (SEQ ID NO: 59) | WIDPDQ GDTE | (SEQ ID NO: 16) | YAQKFQGRVTITR DRSTSTAYMELSS LRSEDTAMYYC | (SEQ ID NO: 60) | NAAYGSS SYPMDY | (SEQ ID NO: 26) | WGQGTL VTVSS | (SEQ ID NO: 61) | (SEQ ID NO: 19) |
| Ab775 | $X_{H1}$QMQLVQS GAEVKKPGS SVKVSCKAS | (SEQ ID NO: 21) | GFNIKD YYLH | (SEQ ID NO: 21) | WVRQAPG QGLEWMG | (SEQ ID NO: 59) | WIDPDQ GDTE | (SEQ ID NO: 16) | YAQKFQGRVTITR DRSTSTAYMELRS LRSEDTAMYYC | (SEQ ID NO: 60) | NAAYGSS SYPMDY | (SEQ ID NO: 27) | WGQGTL VTVSS | (SEQ ID NO: 61) | (SEQ ID NO: 19) |
| Ab776 | $X_{H1}$QMQLVQS GAEVKKPGS SVKVSCKAS | (SEQ ID NO: 21) | GFNIKD YYLH | (SEQ ID NO: 21) | WVRQAPG QGLEWMG | (SEQ ID NO: 59) | WIDPDQ GDTE | (SEQ ID NO: 16) | YAQKFQDRVTITR DRSMSTAYMELSS LRSEDTAVYYC | (SEQ ID NO: 60) | NAAYGSS SYPMDY | (SEQ ID NO: 28) | WGQGTL VTVSS | (SEQ ID NO: 61) | (SEQ ID NO: 19) |
| Ab777 | $X_{H1}$QMQLVQS GAEVKKPGS SVKVSCKAS | (SEQ ID NO: 21) | GFNIKD YYLH | (SEQ ID NO: 21) | WVRQAPG QGLEWMG | (SEQ ID NO: 59) | WIDPDQ GDTE | (SEQ ID NO: 16) | YAQKFQDRVTITR DRSMSTAYMELRS LRSEDTAVYYC | (SEQ ID NO: 60) | NAAYGSS SYPMDY | (SEQ ID NO: 29) | WGQGTL VTVSS | (SEQ ID NO: 61) | (SEQ ID NO: 19) |
| Ab778 | $X_{H1}$QMQLVQS GAEVKKPGS SVKVSCKAS | (SEQ ID NO: 21) | GFNIKD YYLH | (SEQ ID NO: 21) | WVRQAPG QGLEWMG | (SEQ ID NO: 59) | WIDPDQ GDTE | (SEQ ID NO: 16) | YAQKFQDRVTITR DRSMSTAYMELSS LRSEDTAVYYC | (SEQ ID NO: 60) | NAAYGSS SYPMDY | (SEQ ID NO: 30) | WGQGTL VTVSS | (SEQ ID NO: 61) | (SEQ ID NO: 19) |
| Ab779 | $X_{H1}$QMQLVQS GAEVKKTGS SVKVSCKAS | (SEQ ID NO: 12) | GFNIKD YYLH | (SEQ ID NO: 21) | WVRQAPG QGLEWMG | (SEQ ID NO: 59) | WIDPDQ GDTE | (SEQ ID NO: 16) | YAQKFQDRVTITR DRSMSTAYMELRS LRSEDTAVYYC | (SEQ ID NO: 60) | NAAYGSS SYPMDY | (SEQ ID NO: 31) | WGQGTL VTVSS | (SEQ ID NO: 61) | (SEQ ID NO: 19) |
| Ab780 | $X_{H1}$QMQLVQS GAEVKKTGS SVKVSCKAS | (SEQ ID NO: 12) | GFNIKD YYLH | (SEQ ID NO: 12) | WVRQAPG QGLEWMG | (SEQ ID NO: 59) | WIDPDQ GDTE | (SEQ ID NO: 16) | YAQKFQGRVTITR DRSMSTAYMELSS LRSEDTAMYYC | (SEQ ID NO: 60) | NAAYGSS SYPMDY | (SEQ ID NO: 32) | WGQGTL VTVSS | (SEQ ID NO: 61) | (SEQ ID NO: 19) |
| Ab781 | $X_{H1}$QMQLVQS GAEVKKTGS SVKVSCKAS | (SEQ ID NO: 12) | GFNIKD YYLH | (SEQ ID NO: 12) | WVRQAPG QGLEWMG | (SEQ ID NO: 59) | WIDPDQ GDTE | (SEQ ID NO: 16) | YAQKFQGRVTITR DRSTSTAYMELSS LRSEDTAVYYC | (SEQ ID NO: 60) | NAAYGSS SYPMDY | (SEQ ID NO: 33) | WGQGTL VTVSS | (SEQ ID NO: 61) | (SEQ ID NO: 19) |
| Ab782 | $X_{H1}$QMQLVQS GAEVKKTGS SVKVSCKAS | (SEQ ID NO: 12) | GFNIKD YYLH | (SEQ ID NO: 12) | WVRQAPG QGLEWMG | (SEQ ID NO: 59) | WIDPDQ GDTE | (SEQ ID NO: 16) | YAQKFQGRVTITR DRSMSTAYMELRS LRSEDTAVYYC | (SEQ ID NO: 60) | NAAYGSS SYPMDY | (SEQ ID NO: 34) | WGQGTL VTVSS | (SEQ ID NO: 61) | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab783 | $X_{H1}$QMQLVQS GAEVKKTGS SVKVSCKAS | (SEQ ID NO: 12) | GFNIKD YYLH | (SEQ ID NO: 21) | WVRQAPG QGLEWMG | (SEQ ID NO: 59) | WIDPDQ GDTE | (SEQ ID NO: 60) | YAQKFQDRVTITR DRSMSTAYMELRS LRSEDTAVYYC | (SEQ ID NO: 35) | NAAYGSS SYPMDY | (SEQ ID NO: 61) | WGQGTL VTVSS | (SEQ ID NO: 19) |
| Ab784 | $X_{H1}$QMQLVQS GAEVKKPGS SVKVSCKAS | (SEQ ID NO: 21) | GFNIKD YYLH | (SEQ ID NO: 21) | WVRQAPG QGLEWMG | (SEQ ID NO: 59) | WIDPDQ GDTE | (SEQ ID NO: 60) | YAQKFQGRVTITR DRSMSTAYMELRS LRSEDTAVYYC | (SEQ ID NO: 32) | NAAYGSS SYPMDY | (SEQ ID NO: 61) | WGQGTL VTVSS | (SEQ ID NO: 19) |
| Ab785 | $X_{H1}$QMQLVQS GAEVKKPGS SVKVSCKAS | (SEQ ID NO: 21) | GFNIKD YYLH | (SEQ ID NO: 21) | WVRQAPG QGLEWMG | (SEQ ID NO: 59) | WIDPDQ GDTE | (SEQ ID NO: 60) | YAQKFQGRVTITR DRSTSTAYMELSS LRSEDTAVYYC | (SEQ ID NO: 33) | NAAYGSS SYPMDY | (SEQ ID NO: 61) | WGQGTL VTVSS | (SEQ ID NO: 19) |
| Ab786 | $X_{H1}$QMQLVQS GAEVKKPGS SVKVSCKAS | (SEQ ID NO: 21) | GFNIKD YYLH | (SEQ ID NO: 21) | WVRQAPG QGLEWMG | (SEQ ID NO: 59) | WIDPDQ GDTE | (SEQ ID NO: 60) | YAQKFQDRVTITR DRSMSTAYMELRS LRSEDTAMYYC | (SEQ ID NO: 34) | NAAYGSS SYPMDY | (SEQ ID NO: 61) | WGQGTL VTVSS | (SEQ ID NO: 19) |
| Ab787 | $X_{H1}$QMQLVQS GAEVKKTGS SVKVSCKAS | (SEQ ID NO: 12) | GFNIKD YYLH | (SEQ ID NO: 21) | WVRQAPG QGLEWMG | (SEQ ID NO: 59) | WIDPDQ GDTE | (SEQ ID NO: 60) | YAQKFQGRVTITR DRSMSTAYMELRS LRSEDTAVYYC | (SEQ ID NO: 35) | NAAYGSS SYPMDY | (SEQ ID NO: 61) | WGQGTL VTVSS | (SEQ ID NO: 19) |
| Ab788 | $X_{H1}$QMQLVQS GAEVKKPGS SVKVSCKAS | (SEQ ID NO: 21) | GFNIKD YYLH | (SEQ ID NO: 21) | WVRQAPG QGLEWMG | (SEQ ID NO: 59) | WIDPDQ GDTE | (SEQ ID NO: 60) | YAQKFQGRVTITR DRSMSTAYMELRS LRSEDTAVYYC | (SEQ ID NO: 36) | NAAYGSS SYPMDY | (SEQ ID NO: 61) | WGQGTL VTVSS | (SEQ ID NO: 19) |
| Ab789 | $X_{H1}$QMQLVQS GAEVKKTGS SVKVSCKAS | (SEQ ID NO: 12) | GFNIKD YYLH | (SEQ ID NO: 21) | WVRQAPG QGLEWMG | (SEQ ID NO: 59) | WIDPDQ GDTE | (SEQ ID NO: 60) | YAQKFQGRVTITR DRSMSTAYMELRS LRSEDTAVYYC | (SEQ ID NO: 36) | NAAYGSS SYPMDY | (SEQ ID NO: 61) | WGQGTL VTVSS | (SEQ ID NO: 19) |
| Ab790 | $X_{H1}$QMQLVQS GAEVKKPGS SVKVSCKAS | (SEQ ID NO: 21) | GFNIKD YYLH | (SEQ ID NO: 21) | WVRQAPG QALEWMG | (SEQ ID NO: 59) | WIDPDQ GDTE | (SEQ ID NO: 17) | YAQKFQDRVTITR DRSTSTAYMELSS LRAEDTAMYYC | (SEQ ID NO: 33) | NAAYGSS SYPMDY | (SEQ ID NO: 61) | WGQGTL VTVSS | (SEQ ID NO: 19) |
| Ab791 | $X_{H1}$QMQLVQS GAEVKKPGS SVKVSCKAS | (SEQ ID NO: 21) | GFNIKD YYLH | (SEQ ID NO: 21) | WVRQAPG QALEWMG | (SEQ ID NO: 59) | WIDPDQ GDTE | (SEQ ID NO: 17) | YAQKFQGRVTITR DRSMSTAYMELSS LRAEDTAMYYC | (SEQ ID NO: 37) | NAAYGSS SYPMDY | (SEQ ID NO: 61) | WGQGTL VTVSS | (SEQ ID NO: 19) |
| Ab792 | $X_{H1}$QMQLVQS GAEVKKTGS SVKVSCKAS | (SEQ ID NO: 12) | GFNIKD YYLH | (SEQ ID NO: 21) | WVRQAPG QALEWMG | (SEQ ID NO: 59) | WIDPDQ GDTE | (SEQ ID NO: 17) | YAQKFQGRVTITR DRSMSTAYMELSS LRAEDTAMYYC | (SEQ ID NO: 38) | NAAYGSS SYPMDY | (SEQ ID NO: 61) | WGQGTL VTVSS | (SEQ ID NO: 19) |
| Ab793 | $X_{H1}$QMQLVQS GAEVKKTGS SVKVSCKAS | (SEQ ID NO: 12) | GFNIKD YYLH | (SEQ ID NO: 21) | WVRQAPG QALEWMG | (SEQ ID NO: 59) | WIDPDQ GDTE | (SEQ ID NO: 17) | YAQKFQGRVTITR DRSMSTAYMELSS LRAEDTAVYYC | (SEQ ID NO: 39) | NAAYGSS SYPMDY | (SEQ ID NO: 61) | WGQGTL VTVSS | (SEQ ID NO: 19) |
| Ab794 | $X_{H1}$QMQLVQS GAEVKKTGS SVKVSCKAS | (SEQ ID NO: 12) | GFNIKD YYLH | (SEQ ID NO: 21) | WVRQAPG QALEWMG | (SEQ ID NO: 59) | WIDPDQ GDTE | (SEQ ID NO: 17) | YAQKFQDRVTITR DRSTSTAYMELSS LRAEDTAMYYC | (SEQ ID NO: 40) | NAAYGSS SYPMDY | (SEQ ID NO: 61) | WGQGTL VTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab795 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSMSTAYMELSSLRAEDTAMYYC | (SEQ ID NO: 60) | NAAYGSSSYPMDY | (SEQ ID NO: 37) | WGQGTLVTVSS | (SEQ ID NO: 61) | (SEQ ID NO: 19) |
| Ab796 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELSSLRAEDTAMYYC | (SEQ ID NO: 60) | NAAYGSSSYPMDY | (SEQ ID NO: 38) | WGQGTLVTVSS | (SEQ ID NO: 61) | (SEQ ID NO: 19) |
| Ab797 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELRSLRAEDTAMYYC | (SEQ ID NO: 60) | NAAYGSSSYPMDY | (SEQ ID NO: 39) | WGQGTLVTVSS | (SEQ ID NO: 61) | (SEQ ID NO: 19) |
| Ab798 | $X_{H1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSTSTAYMELSSLRAEDTAMYYC | (SEQ ID NO: 60) | NAAYGSSSYPMDY | (SEQ ID NO: 40) | WGQGTLVTVSS | (SEQ ID NO: 61) | (SEQ ID NO: 19) |
| Ab799 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELSSLRAEDTAMYYC | (SEQ ID NO: 60) | NAAYGSSSYPMDY | (SEQ ID NO: 41) | WGQGTLVTVSS | (SEQ ID NO: 61) | (SEQ ID NO: 19) |
| Ab800 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELRSLRAEDTAMYYC | (SEQ ID NO: 60) | NAAYGSSSYPMDY | (SEQ ID NO: 42) | WGQGTLVTVSS | (SEQ ID NO: 61) | (SEQ ID NO: 19) |
| Ab801 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELSSLRAEDTAMYYC | (SEQ ID NO: 60) | NAAYGSSSYPMDY | (SEQ ID NO: 43) | WGQGTLVTVSS | (SEQ ID NO: 61) | (SEQ ID NO: 19) |
| Ab802 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELRSLRAEDTAMYYC | (SEQ ID NO: 60) | NAAYGSSSYPMDY | (SEQ ID NO: 44) | WGQGTLVTVSS | (SEQ ID NO: 61) | (SEQ ID NO: 19) |
| Ab803 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSTSTAYMELSSLRAEDTAMYYC | (SEQ ID NO: 60) | NAAYGSSSYPMDY | (SEQ ID NO: 45) | WGQGTLVTVSS | (SEQ ID NO: 61) | (SEQ ID NO: 19) |
| Ab804 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELRSLRAEDTAMYYC | (SEQ ID NO: 60) | NAAYGSSSYPMDY | (SEQ ID NO: 46) | WGQGTLVTVSS | (SEQ ID NO: 61) | (SEQ ID NO: 19) |
| Ab805 | $X_{H1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSTSTAYMELSSLRAEDTAVYYC | (SEQ ID NO: 60) | NAAYGSSSYPMDY | (SEQ ID NO: 41) | WGQGTLVTVSS | (SEQ ID NO: 61) | (SEQ ID NO: 19) |

TABLE 3-continued

Exemplary Antibodies with Specific VH FR sequences and specific VH CDR sequences ($X_{H1}$ is M or no amino acid).

| Anti-body | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab806 | X$_{X1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSMSTAYMELSSLRAEDTAMYYC | (SEQ ID NO: 42) | NAAYGSSSYPMDY | (SEQ ID NO: 60) | WGQGTLVTVSS | (SEQ ID NO: 61) | (SEQ ID NO: 19) |
| Ab807 | X$_{X1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSMSTAYMELSSLRAEDTAMYYC | (SEQ ID NO: 43) | NAAYGSSSYPMDY | (SEQ ID NO: 60) | WGQGTLVTVSS | (SEQ ID NO: 61) | (SEQ ID NO: 19) |
| Ab808 | X$_{X1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSMSTAYMELSSLRAEDTAMYYC | (SEQ ID NO: 44) | NAAYGSSSYPMDY | (SEQ ID NO: 60) | WGQGTLVTVSS | (SEQ ID NO: 61) | (SEQ ID NO: 19) |
| Ab809 | X$_{X1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELSSLRAEDTAMYYC | (SEQ ID NO: 45) | NAAYGSSSYPMDY | (SEQ ID NO: 60) | WGQGTLVTVSS | (SEQ ID NO: 61) | (SEQ ID NO: 19) |
| Ab810 | X$_{X1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSMSTAYMELSSLRAEDTAMYYC | (SEQ ID NO: 46) | NAAYGSSSYPMDY | (SEQ ID NO: 60) | WGQGTLVTVSS | (SEQ ID NO: 61) | (SEQ ID NO: 19) |
| Ab811 | X$_{X1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQDRVTITRDRSTSTAYMELSSLRAEDTAMYYC | (SEQ ID NO: 47) | NAAYGSSSYPMDY | (SEQ ID NO: 60) | WGQGTLVTVSS | (SEQ ID NO: 61) | (SEQ ID NO: 19) |
| Ab812 | X$_{X1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSMSTAYMELSSLRAEDTAVYYC | (SEQ ID NO: 48) | NAAYGSSSYPMDY | (SEQ ID NO: 60) | WGQGTLVTVSS | (SEQ ID NO: 61) | (SEQ ID NO: 19) |
| Ab813 | X$_{X1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSMSTAYMELSSLRAEDTAVYYC | (SEQ ID NO: 49) | NAAYGSSSYPMDY | (SEQ ID NO: 60) | WGQGTLVTVSS | (SEQ ID NO: 61) | (SEQ ID NO: 19) |
| Ab814 | X$_{X1}$QMQLVQSGAEVKKTGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSTSTAYMELSSLRAEDTAMYYC | (SEQ ID NO: 50) | NAAYGSSSYPMDY | (SEQ ID NO: 60) | WGQGTLVTVSS | (SEQ ID NO: 61) | (SEQ ID NO: 19) |
| Ab815 | X$_{X1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSTSTAYMELSSLRAEDTAMYYC | (SEQ ID NO: 47) | NAAYGSSSYPMDY | (SEQ ID NO: 60) | WGQGTLVTVSS | (SEQ ID NO: 61) | (SEQ ID NO: 19) |
| Ab816 | X$_{X1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSMSTAYMELSSLRAEDTAVYYC | (SEQ ID NO: 48) | NAAYGSSSYPMDY | (SEQ ID NO: 60) | WGQGTLVTVSS | (SEQ ID NO: 61) | (SEQ ID NO: 19) |
| Ab817 | X$_{X1}$QMQLVQSGAEVKKPGSSVKVSCKAS | (SEQ ID NO: 21) | GFNIKDYYLH | (SEQ ID NO: 12) | WVRQAPGQALEWMG | (SEQ ID NO: 59) | WIDPDQGDTE | (SEQ ID NO: 17) | YAQKFQGRVTITRDRSMSTAYMELSSLRAEDTAVYYC | (SEQ ID NO: 49) | NAAYGSSSYPMDY | (SEQ ID NO: 60) | WGQGTLVTVSS | (SEQ ID NO: 61) | (SEQ ID NO: 19) |

TABLE 3-continued

Exemplary Antibodies with Specific VH FR sequences and specific VH CDR sequences ($X_{H1}$ is M or no amino acid).

| Anti-body | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab818 | $X_{H1}$QMQLVQS GAEVKKPGS SVKVSCKAS | (SEQ ID NO: 21) | GFNIKD YYLH | (SEQ ID NO: 12) | WVRQAPG QALEWMG | (SEQ ID NO: 59) | WIDPDQ GDTE | (SEQ ID NO: 17) | YAQKFQDRVTITR DRSTSTAYMELRS LRAEDTAVYYC | (SEQ ID NO: 60) | NAAYGSS SYPMDY | (SEQ ID NO: 50) | WGQGTL VTVSS | (SEQ ID NO: 61) | (SEQ ID NO: 19) |
| Ab819 | $X_{H1}$QMQLVQS GAEVKKTGS SVKVSCKAS | (SEQ ID NO: 21) | GFNIKD YYLH | (SEQ ID NO: 12) | WVRQAPG QALEWMG | (SEQ ID NO: 59) | WIDPDQ GDTE | (SEQ ID NO: 17) | YAQKFQGRVTITR DRSMSTAYMELRS LRAEDTAVYYC | (SEQ ID NO: 60) | NAAYGSS SYPMDY | (SEQ ID NO: 139) | WGQGTL VTVSS | (SEQ ID NO: 61) | (SEQ ID NO: 19) |
| Ab820 | $X_{H1}$QMQLVQS GAEVKKPGS SVKVSCKAS | (SEQ ID NO: 21) | GFNIKD YYLH | (SEQ ID NO: 12) | WVRQAPG QALEWMG | (SEQ ID NO: 59) | WIDPDQ GDTE | (SEQ ID NO: 17) | YAQKFQGRVTITR DRSMSTAYMELRS LRAEDTAVYYC | (SEQ ID NO: 60) | NAAYGSS SYPMDY | (SEQ ID NO: 139) | WGQGTL VTVSS | (SEQ ID NO: 61) | (SEQ ID NO: 19) |
| Ab821 | $X_{H1}$QMQLVQS GAEVKKTGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQDRVTITR DRSTSTAYMELSS LRAEDTAMYYC | (SEQ ID NO: 60) | NAAYGSS SYPMDY | (SEQ ID NO: 18) | WGQGTT VTVSS | (SEQ ID NO: 61) | (SEQ ID NO: 15) |
| Ab822 | $X_{H1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELSS LRAEDTAMYYC | (SEQ ID NO: 60) | NAAYGSS SYPMDY | (SEQ ID NO: 37) | WGQGTT VTVSS | (SEQ ID NO: 61) | (SEQ ID NO: 15) |
| Ab823 | $X_{H1}$QMQLVQS GAEVKKTGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELSS LRAEDTAMYYC | (SEQ ID NO: 60) | NAAYGSS SYPMDY | (SEQ ID NO: 38) | WGQGTT VTVSS | (SEQ ID NO: 61) | (SEQ ID NO: 15) |
| Ab824 | $X_{H1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELSS LRAEDTAMYYC | (SEQ ID NO: 60) | NAAYGSS SYPMDY | (SEQ ID NO: 39) | WGQGTT VTVSS | (SEQ ID NO: 61) | (SEQ ID NO: 15) |
| Ab825 | $X_{H1}$QMQLVQS GAEVKKTGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQDRVTITR DRSTSTAYMELSS LRAEDTAMYYC | (SEQ ID NO: 60) | NAAYGSS SYPMDY | (SEQ ID NO: 40) | WGQGTT VTVSS | (SEQ ID NO: 61) | (SEQ ID NO: 15) |
| Ab826 | $X_{H1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELSS LRAEDTAMYYC | (SEQ ID NO: 60) | NAAYGSS SYPMDY | (SEQ ID NO: 37) | WGQGTT VTVSS | (SEQ ID NO: 61) | (SEQ ID NO: 15) |
| Ab827 | $X_{H1}$QMQLVQS GAEVKKTGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELSS LRAEDTAMYYC | (SEQ ID NO: 60) | NAAYGSS SYPMDY | (SEQ ID NO: 38) | WGQGTT VTVSS | (SEQ ID NO: 61) | (SEQ ID NO: 15) |
| Ab828 | $X_{H1}$QMQLVQS GAEVKKTGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELSS LRAEDTAMYYC | (SEQ ID NO: 60) | NAAYGSS SYPMDY | (SEQ ID NO: 39) | WGQGTT VTVSS | (SEQ ID NO: 61) | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab829 | $X_{H1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQDRVTITR DRSTSTAYMELSS LRAEDTAVYYC | (SEQ ID NO: 60) | NAAYGSS SYPMDY | (SEQ ID NO: 40) | WGQGTT VTVSS | (SEQ ID NO: 61) | (SEQ ID NO: 15) |
| Ab830 | $X_{H1}$QMQLVQS GAEVKKPGS SVKVSCKAS | (SEQ ID NO: 12) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSTSTAYMELSS LRAEDTAMYYC | (SEQ ID NO: 60) | NAAYGSS SYPMDY | (SEQ ID NO: 41) | WGQGTT VTVSS | (SEQ ID NO: 61) | (SEQ ID NO: 15) |
| Ab831 | $X_{H1}$QMQLVQS GAEVKKTGS SVKVSCKAS | (SEQ ID NO: 12) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELSS LRAEDTAMYYC | (SEQ ID NO: 60) | NAAYGSS SYPMDY | (SEQ ID NO: 42) | WGQGTT VTVSS | (SEQ ID NO: 61) | (SEQ ID NO: 15) |
| Ab832 | $X_{H1}$QMQLVQS GAEVKKTGS SVKVSCKAS | (SEQ ID NO: 12) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELSS LRAEDTAMYYC | (SEQ ID NO: 60) | NAAYGSS SYPMDY | (SEQ ID NO: 43) | WGQGTT VTVSS | (SEQ ID NO: 61) | (SEQ ID NO: 15) |
| Ab833 | $X_{H1}$QMQLVQS GAEVKKTGS SVKVSCKAS | (SEQ ID NO: 12) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELSS LRAEDTAMYYC | (SEQ ID NO: 60) | NAAYGSS SYPMDY | (SEQ ID NO: 44) | WGQGTT VTVSS | (SEQ ID NO: 61) | (SEQ ID NO: 15) |
| Ab834 | $X_{H1}$QMQLVQS GAEVKKTGS SVKVSCKAS | (SEQ ID NO: 12) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELSS LRAEDTAMYYC | (SEQ ID NO: 60) | NAAYGSS SYPMDY | (SEQ ID NO: 45) | WGQGTT VTVSS | (SEQ ID NO: 61) | (SEQ ID NO: 15) |
| Ab835 | $X_{H1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQDRVTITR DRSTSTAYMELSS LRAEDTAVYYC | (SEQ ID NO: 60) | NAAYGSS SYPMDY | (SEQ ID NO: 46) | WGQGTT VTVSS | (SEQ ID NO: 61) | (SEQ ID NO: 15) |
| Ab836 | $X_{H1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELRS LRAEDTAMYYC | (SEQ ID NO: 60) | NAAYGSS SYPMDY | (SEQ ID NO: 41) | WGQGTT VTVSS | (SEQ ID NO: 61) | (SEQ ID NO: 15) |
| Ab837 | $X_{H1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELRS LRAEDTAMYYC | (SEQ ID NO: 60) | NAAYGSS SYPMDY | (SEQ ID NO: 42) | WGQGTT VTVSS | (SEQ ID NO: 61) | (SEQ ID NO: 15) |
| Ab838 | $X_{H1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELRS LRAEDTAMYYC | (SEQ ID NO: 60) | NAAYGSS SYPMDY | (SEQ ID NO: 43) | WGQGTT VTVSS | (SEQ ID NO: 61) | (SEQ ID NO: 15) |
| Ab839 | $X_{H1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQGRVTITR DRSMSTAYMELRS LRAEDTAMYYC | (SEQ ID NO: 60) | NAAYGSS SYPMDY | (SEQ ID NO: 44) | WGQGTT VTVSS | (SEQ ID NO: 61) | (SEQ ID NO: 15) |
| Ab840 | $X_{H1}$QMQLVQS GAEVKKPGS SVKVSCKAS | (SEQ ID NO: 21) | GFNIKD YYLH | (SEQ ID NO: 12) | WVRQAPG KGLEWMG | (SEQ ID NO: 59) | WIDPDQ GDTE | (SEQ ID NO: 20) | YAQKFQDRVTITR DRSTSTAYMELSS LRAEDTAVYYC | (SEQ ID NO: 60) | NAAYGSS SYPMDY | (SEQ ID NO: 45) | WGQGTT VTVSS | (SEQ ID NO: 61) | (SEQ ID NO: 15) |

TABLE 3-continued

Exemplary Antibodies with Specific VH FR sequences and specific VH CDR sequences ($X_{H1}$ is M or no amino acid).

| Anti-body | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab841 | $X_{H1}$QMQLVQSGAEVKKPGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 20) | YAQKFQDRVTITRDRSMSTAYMELRSLRAEDTAMYYC | (SEQ ID NO: 60) | NAAYGSSSYPMDY | (SEQ ID NO: 46) | WGQGTTVTVSS | (SEQ ID NO: 61) | (SEQ ID NO: 15) |
| Ab842 | $X_{H1}$QMQLVQSGAEVKKTGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSMSTAYMELRSLRAEDTAMYYC | (SEQ ID NO: 60) | NAAYGSSSYPMDY | (SEQ ID NO: 47) | WGQGTTVTVSS | (SEQ ID NO: 61) | (SEQ ID NO: 15) |
| Ab843 | $X_{H1}$QMQLVQSGAEVKKTGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSTSTAYMELRSLRAEDTAMYYC | (SEQ ID NO: 60) | NAAYGSSSYPMDY | (SEQ ID NO: 48) | WGQGTTVTVSS | (SEQ ID NO: 61) | (SEQ ID NO: 15) |
| Ab844 | $X_{H1}$QMQLVQSGAEVKKTGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSMSTAYMELRSLRAEDTAVYYC | (SEQ ID NO: 60) | NAAYGSSSYPMDY | (SEQ ID NO: 49) | WGQGTTVTVSS | (SEQ ID NO: 61) | (SEQ ID NO: 15) |
| Ab845 | $X_{H1}$QMQLVQSGAEVKKPGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSTSTAYMELRSLRAEDTAVYYC | (SEQ ID NO: 60) | NAAYGSSSYPMDY | (SEQ ID NO: 50) | WGQGTTVTVSS | (SEQ ID NO: 61) | (SEQ ID NO: 15) |
| Ab846 | $X_{H1}$QMQLVQSGAEVKKTGSSVKVSCKAS | (SEQ ID NO: 12) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSMSTAYMELRSLRAEDTAMYYC | (SEQ ID NO: 60) | NAAYGSSSYPMDY | (SEQ ID NO: 47) | WGQGTTVTVSS | (SEQ ID NO: 61) | (SEQ ID NO: 15) |
| Ab847 | $X_{H1}$QMQLVQSGAEVKKTGSSVKVSCKAS | (SEQ ID NO: 12) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSTSTAYMELRSLRAEDTAMYYC | (SEQ ID NO: 60) | NAAYGSSSYPMDY | (SEQ ID NO: 48) | WGQGTTVTVSS | (SEQ ID NO: 61) | (SEQ ID NO: 15) |
| Ab848 | $X_{H1}$QMQLVQSGAEVKKTGSSVKVSCKAS | (SEQ ID NO: 12) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSMSTAYMELRSLRAEDTAVYYC | (SEQ ID NO: 60) | NAAYGSSSYPMDY | (SEQ ID NO: 49) | WGQGTTVTVSS | (SEQ ID NO: 61) | (SEQ ID NO: 15) |
| Ab849 | $X_{H1}$QMQLVQSGAEVKKPGSSVKVSCKAS | (SEQ ID NO: 12) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSTSTAYMELRSLRAEDTAVYYC | (SEQ ID NO: 60) | NAAYGSSSYPMDY | (SEQ ID NO: 50) | WGQGTTVTVSS | (SEQ ID NO: 61) | (SEQ ID NO: 15) |
| Ab850 | $X_{H1}$QMQLVQSGAEVKKPGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSMSTAYMELRSLRAEDTAVYYC | (SEQ ID NO: 60) | NAAYGSSSYPMDY | (SEQ ID NO: 139) | WGQGTTVTVSS | (SEQ ID NO: 61) | (SEQ ID NO: 15) |
| Ab851 | $X_{H1}$QMQLVQSGAEVKKPGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSMSTAYMELRSLRAEDTAVYYC | (SEQ ID NO: 60) | NAAYGSSSYPMDY | (SEQ ID NO: 139) | WGQGTTVTVSS | (SEQ ID NO: 61) | (SEQ ID NO: 15) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR1 | SEQ ID NO: | VH-FR2 | SEQ ID NO: | VH-CDR2 | SEQ ID NO: | VH-FR3 | SEQ ID NO: | VH-CDR3 | SEQ ID NO: | VH-FR4 | SEQ ID NO: |
|---|---|---|---|---|---|---|---|---|---|---|---|---|---|---|
| Ab852 | X$_{H1}$QMQLVQSGAEVKKPGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 20) | YAQKFQDRVTITRDRSTSTAYMELSSLRSEDTAMYYC | (SEQ ID NO: 14) | NAAYGSSSYPMDY | (SEQ ID NO: 61) | WGQGTLVTVSS | (SEQ ID NO: 19) |
| Ab853 | X$_{H1}$QMQLVQSGAEVKKTGSSVKVSCKAS | (SEQ ID NO: 12) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSMSTAYMELSSLRSEDTAMYYC | (SEQ ID NO: 22) | NAAYGSSSYPMDY | (SEQ ID NO: 61) | WGQGTLVTVSS | (SEQ ID NO: 19) |
| Ab854 | X$_{H1}$QMQLVQSGAEVKKTGSSVKVSCKAS | (SEQ ID NO: 12) | GFNIKDYYLH | (SEQ ID NO: 12) | WVRQAPGKGLEWMG | (SEQ ID NO: 59) | WIDPDQGDTE | (SEQ ID NO: 20) | YAQKFQDRVTITRDRSMSTAYMELSSLRSEDTAMYYC | (SEQ ID NO: 23) | NAAYGSSSYPMDY | (SEQ ID NO: 61) | WGQGTLVTVSS | (SEQ ID NO: 19) |
| Ab855 | X$_{H1}$QMQLVQSGAEVKKPGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 20) | YAQKFQDRVTITRDRSMSTAYMELRSLRSEDTAMYYC | (SEQ ID NO: 24) | NAAYGSSSYPMDY | (SEQ ID NO: 61) | WGQGTLVTVSS | (SEQ ID NO: 19) |
| Ab856 | X$_{H1}$QMQLVQSGAEVKKPGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSMSTAYMELSSLRSEDTAMYYC | (SEQ ID NO: 25) | NAAYGSSSYPMDY | (SEQ ID NO: 61) | WGQGTLVTVSS | (SEQ ID NO: 19) |
| Ab857 | X$_{H1}$QMQLVQSGAEVKKTGSSVKVSCKAS | (SEQ ID NO: 12) | GFNIKDYYLH | (SEQ ID NO: 12) | WVRQAPGKGLEWMG | (SEQ ID NO: 59) | WIDPDQGDTE | (SEQ ID NO: 20) | YAQKFQDRVTITRDRSMSTAYMELSSLRSEDTAMYYC | (SEQ ID NO: 22) | NAAYGSSSYPMDY | (SEQ ID NO: 61) | WGQGTLVTVSS | (SEQ ID NO: 19) |
| Ab858 | X$_{H1}$QMQLVQSGAEVKKTGSSVKVSCKAS | (SEQ ID NO: 12) | GFNIKDYYLH | (SEQ ID NO: 12) | WVRQAPGKGLEWMG | (SEQ ID NO: 59) | WIDPDQGDTE | (SEQ ID NO: 20) | YAQKFQDRVTITRDRSMSTAYMELSSLRSEDTAMYYC | (SEQ ID NO: 23) | NAAYGSSSYPMDY | (SEQ ID NO: 61) | WGQGTLVTVSS | (SEQ ID NO: 19) |
| Ab859 | X$_{H1}$QMQLVQSGAEVKKPGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 20) | YAQKFQDRVTITRDRSMSTAYMELRSLRSEDTAMYYC | (SEQ ID NO: 24) | NAAYGSSSYPMDY | (SEQ ID NO: 61) | WGQGTLVTVSS | (SEQ ID NO: 19) |
| Ab860 | X$_{H1}$QMQLVQSGAEVKKPGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSMSTAYMELSSLRSEDTAMYYC | (SEQ ID NO: 25) | NAAYGSSSYPMDY | (SEQ ID NO: 61) | WGQGTLVTVSS | (SEQ ID NO: 19) |
| Ab861 | X$_{H1}$QMQLVQSGAEVKKTGSSVKVSCKAS | (SEQ ID NO: 12) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSTSTAYMELSSLRSEDTAMYYC | (SEQ ID NO: 26) | NAAYGSSSYPMDY | (SEQ ID NO: 61) | WGQGTLVTVSS | (SEQ ID NO: 19) |
| Ab862 | X$_{H1}$QMQLVQSGAEVKKTGSSVKVSCKAS | (SEQ ID NO: 12) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSMSTAYMELRSLRSEDTAVYYC | (SEQ ID NO: 27) | NAAYGSSSYPMDY | (SEQ ID NO: 61) | WGQGTLVTVSS | (SEQ ID NO: 19) |
| Ab863 | X$_{H1}$QMQLVQSGAEVKKTGSSVKVSCKAS | (SEQ ID NO: 12) | GFNIKDYYLH | (SEQ ID NO: 12) | WVRQAPGKGLEWMG | (SEQ ID NO: 59) | WIDPDQGDTE | (SEQ ID NO: 20) | YAQKFQGRVTITRDRSMSTAYMELSSLRSEDTAVYYC | (SEQ ID NO: 28) | NAAYGSSSYPMDY | (SEQ ID NO: 61) | WGQGTLVTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab864 | X$_{X1}$QMQLVQS GAEVKKTGS SVKVSCKAS | (SEQ ID NO: 12) | GFNIKD YYLH | (SEQ ID NO: 59) | WVRQAPG KGLEWMG | (SEQ ID NO: 20) | WIDDPDQ GDTE | (SEQ ID NO: 60) | YAQKFQDRVTITR DRSMSTAYMELRS LRSEDTAMYYC | (SEQ ID NO: 29) | NAAYGSS SYPMDY | (SEQ ID NO: 61) | WGQGTL VTVSS | (SEQ ID NO: 19) |
| Ab865 | X$_{X1}$QMQLVQS GAEVKKTGS SVKVSCKAS | (SEQ ID NO: 12) | GFNIKD YYLH | (SEQ ID NO: 59) | WVRQAPG KGLEWMG | (SEQ ID NO: 20) | WIDDPDQ GDTE | (SEQ ID NO: 60) | YAQKFQDRVTITR DRSMSTAYMELSS LRSEDTAMYYC | (SEQ ID NO: 30) | NAAYGSS SYPMDY | (SEQ ID NO: 61) | WGQGTL VTVSS | (SEQ ID NO: 19) |
| Ab866 | X$_{X1}$QMQLVQS GAEVKKTGS SVKVSCKAS | (SEQ ID NO: 12) | GFNIKD YYLH | (SEQ ID NO: 59) | WVRQAPG KGLEWMG | (SEQ ID NO: 20) | WIDDPDQ GDTE | (SEQ ID NO: 60) | YAQKFQDRVTITR DRSMSTAYMELRS LRSEDTAVYYC | (SEQ ID NO: 31) | NAAYGSS SYPMDY | (SEQ ID NO: 61) | WGQGTL VTVSS | (SEQ ID NO: 19) |
| Ab867 | X$_{X1}$QMQLVQS GAEVKKPGS SVKVSCKAS | (SEQ ID NO: 21) | GFNIKD YYLH | (SEQ ID NO: 59) | WVRQAPG KGLEWMG | (SEQ ID NO: 20) | WIDDPDQ GDTE | (SEQ ID NO: 60) | YAQKFQGRVTITR DRSTSTAYMELSS LRSEDTAMYYC | (SEQ ID NO: 26) | NAAYGSS SYPMDY | (SEQ ID NO: 61) | WGQGTL VTVSS | (SEQ ID NO: 19) |
| Ab868 | X$_{X1}$QMQLVQS GAEVKKPGS SVKVSCKAS | (SEQ ID NO: 21) | GFNIKD YYLH | (SEQ ID NO: 59) | WVRQAPG KGLEWMG | (SEQ ID NO: 20) | WIDDPDQ GDTE | (SEQ ID NO: 60) | YAQKFQGRVTITR DRSTSTAYMELRS LRSEDTAVYYC | (SEQ ID NO: 27) | NAAYGSS SYPMDY | (SEQ ID NO: 61) | WGQGTL VTVSS | (SEQ ID NO: 19) |
| Ab869 | X$_{X1}$QMQLVQS GAEVKKPGS SVKVSCKAS | (SEQ ID NO: 21) | GFNIKD YYLH | (SEQ ID NO: 59) | WVRQAPG KGLEWMG | (SEQ ID NO: 20) | WIDDPDQ GDTE | (SEQ ID NO: 60) | YAQKFQGRVTITR DRSMSTAYMELSS LRSEDTAVYYC | (SEQ ID NO: 28) | NAAYGSS SYPMDY | (SEQ ID NO: 61) | WGQGTL VTVSS | (SEQ ID NO: 19) |
| Ab870 | X$_{X1}$QMQLVQS GAEVKKPGS SVKVSCKAS | (SEQ ID NO: 21) | GFNIKD YYLH | (SEQ ID NO: 59) | WVRQAPG KGLEWMG | (SEQ ID NO: 20) | WIDDPDQ GDTE | (SEQ ID NO: 60) | YAQKFQDRVTITR DRSMSTAYMELRS LRSEDTAMYYC | (SEQ ID NO: 29) | NAAYGSS SYPMDY | (SEQ ID NO: 61) | WGQGTL VTVSS | (SEQ ID NO: 19) |
| Ab871 | X$_{X1}$QMQLVQS GAEVKKPGS SVKVSCKAS | (SEQ ID NO: 21) | GFNIKD YYLH | (SEQ ID NO: 59) | WVRQAPG KGLEWMG | (SEQ ID NO: 20) | WIDDPDQ GDTE | (SEQ ID NO: 60) | YAQKFQDRVTITR DRSMSTAYMELSS LRSEDTAMYYC | (SEQ ID NO: 30) | NAAYGSS SYPMDY | (SEQ ID NO: 61) | WGQGTL VTVSS | (SEQ ID NO: 19) |
| Ab872 | X$_{X1}$QMQLVQS GAEVKKPGS SVKVSCKAS | (SEQ ID NO: 21) | GFNIKD YYLH | (SEQ ID NO: 59) | WVRQAPG KGLEWMG | (SEQ ID NO: 20) | WIDDPDQ GDTE | (SEQ ID NO: 60) | YAQKFQDRVTITR DRSMSTAYMELRS LRSEDTAVYYC | (SEQ ID NO: 31) | NAAYGSS SYPMDY | (SEQ ID NO: 61) | WGQGTL VTVSS | (SEQ ID NO: 19) |
| Ab873 | X$_{X1}$QMQLVQS GAEVKKTGS SVKVSCKAS | (SEQ ID NO: 12) | GFNIKD YYLH | (SEQ ID NO: 59) | WVRQAPG KGLEWMG | (SEQ ID NO: 20) | WIDDPDQ GDTE | (SEQ ID NO: 60) | YAQKFQGRVTITR DRSMSTAYMELRS LRSEDTAMYYC | (SEQ ID NO: 32) | NAAYGSS SYPMDY | (SEQ ID NO: 61) | WGQGTL VTVSS | (SEQ ID NO: 19) |
| Ab874 | X$_{X1}$QMQLVQS GAEVKKTGS SVKVSCKAS | (SEQ ID NO: 12) | GFNIKD YYLH | (SEQ ID NO: 59) | WVRQAPG KGLEWMG | (SEQ ID NO: 20) | WIDDPDQ GDTE | (SEQ ID NO: 60) | YAQKFQGRVTITR DRSTSTAYMELSS LRSEDTAVYYC | (SEQ ID NO: 33) | NAAYGSS SYPMDY | (SEQ ID NO: 61) | WGQGTL VTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab875 | X$_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRSEDTAVYYC | (SEQ ID NO: 34) | NAAYGSSSYPMDY | (SEQ ID NO: 61) | WGQGTLVTVSS | (SEQ ID NO: 19) |
| Ab876 | X$_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRSEDTAVYYC | (SEQ ID NO: 35) | NAAYGSSSYPMDY | (SEQ ID NO: 61) | WGQGTLVTVSS | (SEQ ID NO: 19) |
| Ab877 | X$_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRSEDTAVYYC | (SEQ ID NO: 32) | NAAYGSSSYPMDY | (SEQ ID NO: 61) | WGQGTLVTVSS | (SEQ ID NO: 19) |
| Ab878 | X$_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSTSTAYMELSSLRSEDTAVYYC | (SEQ ID NO: 33) | NAAYGSSSYPMDY | (SEQ ID NO: 61) | WGQGTLVTVSS | (SEQ ID NO: 19) |
| Ab879 | X$_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRSEDTAVYYC | (SEQ ID NO: 34) | NAAYGSSSYPMDY | (SEQ ID NO: 61) | WGQGTLVTVSS | (SEQ ID NO: 19) |
| Ab880 | X$_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRSEDTAVYYC | (SEQ ID NO: 35) | NAAYGSSSYPMDY | (SEQ ID NO: 61) | WGQGTLVTVSS | (SEQ ID NO: 19) |
| Ab881 | X$_{H1}$QMQLVQSGAEVKKPGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 13) | YAQKFQGRVTITRDRSMSTAYMELRSLRSEDTAVYYC | (SEQ ID NO: 36) | NAAYGSSSYPMDY | (SEQ ID NO: 61) | WGQGTLVTVSS | (SEQ ID NO: 19) |
| Ab882 | X$_{H1}$QMQLVQSGAEVKKPGSSVKVSCKAS | (SEQ ID NO: 12) | GFNIKDYYLH | (SEQ ID NO: 59) | WVRQAPGKALEWMG | (SEQ ID NO: 20) | WIDPDQGDTE | (SEQ ID NO: 13) | YAQKFQGRVTITRDRSMSTAYMELRSLRSEDTAVYYC | (SEQ ID NO: 36) | NAAYGSSSYPMDY | (SEQ ID NO: 61) | WGQGTLVTVSS | (SEQ ID NO: 19) |
| Ab883 | X$_{H1}$QMQLVQSGAEVKKPGSSVKVSCKAS | (SEQ ID NO: 12) | GFNIKDYYLH | (SEQ ID NO: 59) | WVRQAPGKALEWMG | (SEQ ID NO: 20) | WIDPDQGDTE | (SEQ ID NO: 13) | YAQKFQGRVTITRDRSMSTAYMELSSLRSEDTAVYYC | (SEQ ID NO: 18) | NAAYGSSSYPMDY | (SEQ ID NO: 61) | WGQGTLVTVSS | (SEQ ID NO: 19) |
| Ab884 | X$_{H1}$QMQLVQSGAEVKKPGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 13) | YAQKFQDRVTITRDRSMSTAYMELRSLRAEDTAMYYC | (SEQ ID NO: 37) | NAAYGSSSYPMDY | (SEQ ID NO: 61) | WGQGTLVTVSS | (SEQ ID NO: 19) |
| Ab885 | X$_{H1}$QMQLVQSGAEVKKPGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 13) | YAQKFQDRVTITRDRSMSTAYMELRSLRAEDTAMYYC | (SEQ ID NO: 38) | NAAYGSSSYPMDY | (SEQ ID NO: 61) | WGQGTLVTVSS | (SEQ ID NO: 19) |
| Ab886 | X$_{H1}$QMQLVQSGAEVKKPGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 13) | YAQKFQDRVTITRDRSMSTAYMELSSLRAEDTAMYYC | (SEQ ID NO: 39) | NAAYGSSSYPMDY | (SEQ ID NO: 61) | WGQGTLVTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab887 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 13) | YAQKFQDRVTITRDRSTSTAYMELSSLRAEDTAVYYC | (SEQ ID NO: 40) | NAAYGSSYPMDY | (SEQ ID NO: 61) | WGQGTLVTVSS | (SEQ ID NO: 19) |
| Ab888 | $X_{H1}$QMQLVQSGAEVKKPGSSVKVSCKAS | (SEQ ID NO: 21) | GFNIKDYYLH | (SEQ ID NO: 21) | WVRQAPGKGLEWMG | (SEQ ID NO: 59) | WIDPDQGDTE | (SEQ ID NO: 13) | YAQKFQGRVTITRDRSMSTAYMELSSLRAEDTAMYYC | (SEQ ID NO: 37) | NAAYGSSYPMDY | (SEQ ID NO: 61) | WGQGTLVTVSS | (SEQ ID NO: 19) |
| Ab889 | $X_{H1}$QMQLVQSGAEVKKPGSSVKVSCKAS | (SEQ ID NO: 21) | GFNIKDYYLH | (SEQ ID NO: 21) | WVRQAPGKGLEWMG | (SEQ ID NO: 59) | WIDPDQGDTE | (SEQ ID NO: 13) | YAQKFQDRVTITRDRSMSTAYMELSSLRAEDTAMYYC | (SEQ ID NO: 38) | NAAYGSSYPMDY | (SEQ ID NO: 61) | WGQGTLVTVSS | (SEQ ID NO: 19) |
| Ab890 | $X_{H1}$QMQLVQSGAEVKKPGSSVKVSCKAS | (SEQ ID NO: 21) | GFNIKDYYLH | (SEQ ID NO: 21) | WVRQAPGKGLEWMG | (SEQ ID NO: 59) | WIDPDQGDTE | (SEQ ID NO: 13) | YAQKFQDRVTITRDRSMSTAYMELRSLRAEDTAMYYC | (SEQ ID NO: 39) | NAAYGSSYPMDY | (SEQ ID NO: 61) | WGQGTLVTVSS | (SEQ ID NO: 19) |
| Ab891 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 13) | YAQKFQDRVTITRDRSTSTAYMELSSLRAEDTAVYYC | (SEQ ID NO: 40) | NAAYGSSYPMDY | (SEQ ID NO: 61) | WGQGTLVTVSS | (SEQ ID NO: 19) |
| Ab892 | $X_{H1}$QMQLVQSGAEVKKTGSSVKVSCKAS | (SEQ ID NO: 12) | GFNIKDYYLH | (SEQ ID NO: 21) | WVRQAPGKALEWMG | (SEQ ID NO: 59) | WIDPDQGDTE | (SEQ ID NO: 13) | YAQKFQGRVTITRDRSMSTAYMELSSLRAEDTAMYYC | (SEQ ID NO: 41) | NAAYGSSYPMDY | (SEQ ID NO: 61) | WGQGTLVTVSS | (SEQ ID NO: 19) |
| Ab893 | $X_{H1}$QMQLVQSGAEVKKTGSSVKVSCKAS | (SEQ ID NO: 12) | GFNIKDYYLH | (SEQ ID NO: 21) | WVRQAPGKALEWMG | (SEQ ID NO: 59) | WIDPDQGDTE | (SEQ ID NO: 13) | YAQKFQGRVTITRDRSMSTAYMELRSLRAEDTAMYYC | (SEQ ID NO: 42) | NAAYGSSYPMDY | (SEQ ID NO: 61) | WGQGTLVTVSS | (SEQ ID NO: 19) |
| Ab894 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 13) | YAQKFQDRVTITRDRSMSTAYMELSSLRAEDTAMYYC | (SEQ ID NO: 43) | NAAYGSSYPMDY | (SEQ ID NO: 61) | WGQGTLVTVSS | (SEQ ID NO: 19) |
| Ab895 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 13) | YAQKFQDRVTITRDRSTSTAYMELRSLRAEDTAMYYC | (SEQ ID NO: 44) | NAAYGSSYPMDY | (SEQ ID NO: 61) | WGQGTLVTVSS | (SEQ ID NO: 19) |
| Ab896 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 13) | YAQKFQDRVTITRDRSMSTAYMELRSLRAEDTAMYYC | (SEQ ID NO: 45) | NAAYGSSYPMDY | (SEQ ID NO: 61) | WGQGTLVTVSS | (SEQ ID NO: 19) |
| Ab897 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 13) | YAQKFQDRVTITRDRSMSTAYMELRSLRAEDTAMYYC | (SEQ ID NO: 46) | NAAYGSSYPMDY | (SEQ ID NO: 61) | WGQGTLVTVSS | (SEQ ID NO: 19) |

TABLE 3-continued

Exemplary Antibodies with Specific VH FR sequences and specific VH CDR sequences ($X_{H1}$ is M or no amino acid).

| Anti-body | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab898 | $X_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 13) | WIDPDQGDTE | (SEQ ID NO: 60) | YAQKFQGRVTITRDRSMSTAYMELSSLRAEDTAMYYC | (SEQ ID NO: 41) | NAAYGSSSYPMDY | (SEQ ID NO: 61) | WGQGTLVTVSS | (SEQ ID NO: 19) |
| Ab899 | $X_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 13) | WIDPDQGDTE | (SEQ ID NO: 60) | YAQKFQGRVTITRDRSMSTAYMELSSLRAEDTAMYYC | (SEQ ID NO: 42) | NAAYGSSSYPMDY | (SEQ ID NO: 61) | WGQGTLVTVSS | (SEQ ID NO: 19) |
| Ab900 | $X_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 13) | WIDPDQGDTE | (SEQ ID NO: 60) | YAQKFQGRVTITRDRSMSTAYMELSSLRAEDTAMYYC | (SEQ ID NO: 43) | NAAYGSSSYPMDY | (SEQ ID NO: 61) | WGQGTLVTVSS | (SEQ ID NO: 19) |
| Ab901 | $X_{H1}$QMQLVQSGAEVKKPGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQDRVTITRDRSMSTAYMELSSLRAEDTAMYYC | (SEQ ID NO: 44) | NAAYGSSSYPMDY | (SEQ ID NO: 61) | WGQGTLVTVSS | (SEQ ID NO: 19) |
| Ab902 | $X_{H1}$QMQLVQSGAEVKKTGSSVKVSCKAS | (SEQ ID NO: 21) | GFNIKDYYLH | (SEQ ID NO: 59) | WVRQAPGKALEWMG | (SEQ ID NO: 13) | WIDPDQGDTE | (SEQ ID NO: 60) | YAQKFQGRVTITRDRSMSTAYMELRSLRAEDTAMYYC | (SEQ ID NO: 45) | NAAYGSSSYPMDY | (SEQ ID NO: 61) | WGQGTLVTVSS | (SEQ ID NO: 19) |
| Ab903 | $X_{H1}$QMQLVQSGAEVKKTGSSVKVSCKAS | (SEQ ID NO: 21) | GFNIKDYYLH | (SEQ ID NO: 59) | WVRQAPGKGLEWMG | (SEQ ID NO: 13) | WIDPDQGDTE | (SEQ ID NO: 60) | YAQKFQGRVTITRDRSMSTAYMELSSLRAEDTAMYYC | (SEQ ID NO: 46) | NAAYGSSSYPMDY | (SEQ ID NO: 61) | WGQGTLVTVSS | (SEQ ID NO: 19) |
| Ab904 | $X_{H1}$QMQLVQSGAEVKKTGSSVKVSCKAS | (SEQ ID NO: 21) | GFNIKDYYLH | (SEQ ID NO: 59) | WVRQAPGKGLEWMG | (SEQ ID NO: 13) | WIDPDQGDTE | (SEQ ID NO: 60) | YAQKFQGRVTITRDRSTSTAYMELRSLRAEDTAVYYC | (SEQ ID NO: 47) | NAAYGSSSYPMDY | (SEQ ID NO: 61) | WGQGTLVTVSS | (SEQ ID NO: 19) |
| Ab905 | $X_{H1}$QMQLVQSGAEVKKTGSSVKVSCKAS | (SEQ ID NO: 21) | GFNIKDYYLH | (SEQ ID NO: 59) | WVRQAPGKGLEWMG | (SEQ ID NO: 13) | WIDPDQGDTE | (SEQ ID NO: 60) | YAQKFQGRVTITRDRSMSTAYMELRSLRAEDTAMYYC | (SEQ ID NO: 48) | NAAYGSSSYPMDY | (SEQ ID NO: 61) | WGQGTLVTVSS | (SEQ ID NO: 19) |
| Ab906 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 13) | WIDPDQGDTE | (SEQ ID NO: 60) | YAQKFQGRVTITRDRSTSTAYMELRSLRAEDTAVYYC | (SEQ ID NO: 49) | NAAYGSSSYPMDY | (SEQ ID NO: 61) | WGQGTLVTVSS | (SEQ ID NO: 19) |
| Ab907 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 13) | WIDPDQGDTE | (SEQ ID NO: 60) | YAQKFQGRVTITRDRSMSTAYMELRSLRAEDTAVYYC | (SEQ ID NO: 50) | NAAYGSSSYPMDY | (SEQ ID NO: 61) | WGQGTLVTVSS | (SEQ ID NO: 19) |
| Ab908 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 13) | WIDPDQGDTE | (SEQ ID NO: 60) | YAQKFQGRVTITRDRSMSTAYMELRSLRAEDTAVYYC | (SEQ ID NO: 47) | NAAYGSSSYPMDY | (SEQ ID NO: 61) | WGQGTLVTVSS | (SEQ ID NO: 19) |
| Ab909 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 13) | WIDPDQGDTE | (SEQ ID NO: 60) | YAQKFQGRVTITRDRSTSTAYMELRSLRAEDTAVYYC | (SEQ ID NO: 48) | NAAYGSSSYPMDY | (SEQ ID NO: 61) | WGQGTLVTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab910 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 60) | YAQKFQGRVTITRDRSMSTAYMELRSLRAEDTAVYYC | (SEQ ID NO: 49) | NAAYGSSYPMDY | (SEQ ID NO: 61) | WGQGTLVTVSS | (SEQ ID NO: 19) |
| Ab911 | $X_{H1}$QMQLVQSGAEVKKPGSSVKVSCKAS | (SEQ ID NO: 21) | GFNIKDYYLH | (SEQ ID NO: 12) | WVRQAPGKALEWMG | (SEQ ID NO: 59) | WIDPDQGDTE | (SEQ ID NO: 60) | YAQKFQDRVTITRDRSTSTAYMELRSLRAEDTAVYYC | (SEQ ID NO: 50) | NAAYGSSYPMDY | (SEQ ID NO: 61) | WGQGTLVTVSS | (SEQ ID NO: 19) |
| Ab912 | $X_{H1}$QMQLVQSGAEVKKPGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 60) | YAQKFQGRVTITRDRSMSTAYMELRSLRAEDTAVYYC | (SEQ ID NO: 139) | NAAYGSSYPMDY | (SEQ ID NO: 61) | WGQGTLVTVSS | (SEQ ID NO: 19) |
| Ab913 | $X_{H1}$QMQLVQSGAEVKKTGSSVKVSCKAS | (SEQ ID NO: 21) | GFNIKDYYLH | (SEQ ID NO: 12) | WVRQAPGKGLEWMG | (SEQ ID NO: 59) | WIDPDQGDTE | (SEQ ID NO: 60) | YAQKFQDRVTITRDRSTSTAYMELRSLRAEDTAVYYC | (SEQ ID NO: 139) | NAAYGSSYPMDY | (SEQ ID NO: 61) | WGQGTLVTVSS | (SEQ ID NO: 19) |
| Ab914 | $X_{H1}$QMQLVQSGAEVKKPGSSVKVSCKAS | (SEQ ID NO: 21) | GFNIKDYYLH | (SEQ ID NO: 16) | WVRQAPGQGLEWMG | (SEQ ID NO: 59) | WIDPDQGDTE | (SEQ ID NO: 60) | YAQKFQGRVTITRDRSMSTAYMELSSLRAEDTAVYYC | (SEQ ID NO: 18) | NAAYGSSYPMDY | (SEQ ID NO: 61) | WGQGTLVTVSS | (SEQ ID NO: 19) |
| Ab915 | $X_{H1}$QMQLVQSGAEVKKPGSSVKVSCKAS | (SEQ ID NO: 21) | GFNIKDYYLH | (SEQ ID NO: 16) | WVRQAPGQGLEWMG | (SEQ ID NO: 59) | WIDPDQGDTE | (SEQ ID NO: 60) | YAQKFQDRVTITRDRSTSTAYMELSSLRAEDTAVYYC | (SEQ ID NO: 37) | NAAYGSSYPMDY | (SEQ ID NO: 61) | WGQGTLVTVSS | (SEQ ID NO: 19) |
| Ab916 | $X_{H1}$QMQLVQSGAEVKKTGSSVKVSCKAS | (SEQ ID NO: 21) | GFNIKDYYLH | (SEQ ID NO: 16) | WVRQAPGQGLEWMG | (SEQ ID NO: 59) | WIDPDQGDTE | (SEQ ID NO: 60) | YAQKFQGRVTITRDRSMSTAYMELSSLRAEDTAMYYC | (SEQ ID NO: 38) | NAAYGSSYPMDY | (SEQ ID NO: 61) | WGQGTLVTVSS | (SEQ ID NO: 19) |
| Ab917 | $X_{H1}$QMQLVQSGAEVKKTGSSVKVSCKAS | (SEQ ID NO: 21) | GFNIKDYYLH | (SEQ ID NO: 16) | WVRQAPGQGLEWMG | (SEQ ID NO: 59) | WIDPDQGDTE | (SEQ ID NO: 60) | YAQKFQDRVTITRDRSTSTAYMELSSLRAEDTAMYYC | (SEQ ID NO: 39) | NAAYGSSYPMDY | (SEQ ID NO: 61) | WGQGTLVTVSS | (SEQ ID NO: 19) |
| Ab918 | $X_{H1}$QMQLVQSGAEVKKPGSSVKVSCKAS | (SEQ ID NO: 21) | GFNIKDYYLH | (SEQ ID NO: 16) | WVRQAPGQGLEWMG | (SEQ ID NO: 59) | WIDPDQGDTE | (SEQ ID NO: 60) | YAQKFQGRVTITRDRSMSTAYMELRSLRAEDTAMYYC | (SEQ ID NO: 40) | NAAYGSSYPMDY | (SEQ ID NO: 61) | WGQGTLVTVSS | (SEQ ID NO: 19) |
| Ab919 | $X_{H1}$QMQLVQSGAEVKKTGSSVKVSCKAS | (SEQ ID NO: 21) | GFNIKDYYLH | (SEQ ID NO: 16) | WVRQAPGQGLEWMG | (SEQ ID NO: 59) | WIDPDQGDTE | (SEQ ID NO: 60) | YAQKFQGRVTITRDRSMSTAYMELSSLRAEDTAMYYC | (SEQ ID NO: 37) | NAAYGSSYPMDY | (SEQ ID NO: 61) | WGQGTLVTVSS | (SEQ ID NO: 19) |
| Ab920 | $X_{H1}$QMQLVQSGAEVKKTGSSVKVSCKAS | (SEQ ID NO: 21) | GFNIKDYYLH | (SEQ ID NO: 16) | WVRQAPGQGLEWMG | (SEQ ID NO: 59) | WIDPDQGDTE | (SEQ ID NO: 60) | YAQKFQDRVTITRDRSMSTAYMELSSLRAEDTAMYYC | (SEQ ID NO: 38) | NAAYGSSYPMDY | (SEQ ID NO: 61) | WGQGTLVTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab921 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSMSTAYMELRSLRAEDTAMYYC | (SEQ ID NO: 60) | NAAYGSSYPMDY | (SEQ ID NO: 39) | WGQGTLVTVSS | (SEQ ID NO: 61) | (SEQ ID NO: 19) |
| Ab922 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSTSTAYMELSSLRAEDTAMYYC | (SEQ ID NO: 60) | NAAYGSSYPMDY | (SEQ ID NO: 40) | WGQGTLVTVSS | (SEQ ID NO: 61) | (SEQ ID NO: 19) |
| Ab923 | $X_{H1}$QMQLVQSGAEVKKTGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQGRVTITRDRSMSTAYMELSSLRAEDTAMYYC | (SEQ ID NO: 60) | NAAYGSSYPMDY | (SEQ ID NO: 41) | WGQGTLVTVSS | (SEQ ID NO: 61) | (SEQ ID NO: 19) |
| Ab924 | $X_{H1}$QMQLVQSGAEVKKTGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSMSTAYMELRSLRAEDTAMYYC | (SEQ ID NO: 60) | NAAYGSSYPMDY | (SEQ ID NO: 42) | WGQGTLVTVSS | (SEQ ID NO: 61) | (SEQ ID NO: 19) |
| Ab925 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQGRVTITRDRSTSTAYMELSSLRAEDTAVYYC | (SEQ ID NO: 60) | NAAYGSSYPMDY | (SEQ ID NO: 43) | WGQGTLVTVSS | (SEQ ID NO: 61) | (SEQ ID NO: 19) |
| Ab926 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQGRVTITRDRSMSTAYMELSSLRAEDTAMYYC | (SEQ ID NO: 60) | NAAYGSSYPMDY | (SEQ ID NO: 44) | WGQGTLVTVSS | (SEQ ID NO: 61) | (SEQ ID NO: 19) |
| Ab927 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSMSTAYMELRSLRAEDTAMYYC | (SEQ ID NO: 60) | NAAYGSSYPMDY | (SEQ ID NO: 45) | WGQGTLVTVSS | (SEQ ID NO: 61) | (SEQ ID NO: 19) |
| Ab928 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSMSTAYMELRSLRAEDTAMYYC | (SEQ ID NO: 60) | NAAYGSSYPMDY | (SEQ ID NO: 46) | WGQGTLVTVSS | (SEQ ID NO: 61) | (SEQ ID NO: 19) |
| Ab929 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSMSTAYMELSSLRAEDTAMYYC | (SEQ ID NO: 60) | NAAYGSSYPMDY | (SEQ ID NO: 41) | WGQGTLVTVSS | (SEQ ID NO: 61) | (SEQ ID NO: 19) |
| Ab930 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSMSTAYMELRSLRAEDTAMYYC | (SEQ ID NO: 60) | NAAYGSSYPMDY | (SEQ ID NO: 42) | WGQGTLVTVSS | (SEQ ID NO: 61) | (SEQ ID NO: 19) |
| Ab931 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSMSTAYMELRSLRAEDTAMYYC | (SEQ ID NO: 60) | NAAYGSSYPMDY | (SEQ ID NO: 43) | WGQGTLVTVSS | (SEQ ID NO: 61) | (SEQ ID NO: 19) |
| Ab932 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSMSTAYMELRSLRAEDTAMYYC | (SEQ ID NO: 60) | NAAYGSSYPMDY | (SEQ ID NO: 44) | WGQGTLVTVSS | (SEQ ID NO: 61) | (SEQ ID NO: 19) |

TABLE 3-continued

Exemplary Antibodies with Specific VH FR sequences and specific VH CDR sequences ($X_{H1}$ is M or no amino acid).

| Anti-body | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab933 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSTSTAYMELSSLRAEDTAVYYC | (SEQ ID NO: 45) | NAAYGSSSYPMDY | (SEQ ID NO: 61) | WGQGTLVTVSS | (SEQ ID NO: 19) |
| Ab934 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQGRVTITRDRSMSTAYMELRSLRAEDTAVYYC | (SEQ ID NO: 46) | NAAYGSSSYPMDY | (SEQ ID NO: 61) | WGQGTLVTVSS | (SEQ ID NO: 19) |
| Ab935 | $X_{H1}$QMQLVQSGAEVKKTGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSMSTAYMELRSLRAEDTAMYYC | (SEQ ID NO: 47) | NAAYGSSSYPMDY | (SEQ ID NO: 61) | WGQGTLVTVSS | (SEQ ID NO: 19) |
| Ab936 | $X_{H1}$QMQLVQSGAEVKKTGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSTSTAYMELSSLRAEDTAVYYC | (SEQ ID NO: 48) | NAAYGSSSYPMDY | (SEQ ID NO: 61) | WGQGTLVTVSS | (SEQ ID NO: 19) |
| Ab937 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQGRVTITRDRSMSTAYMELRSLRAEDTAVYYC | (SEQ ID NO: 49) | NAAYGSSSYPMDY | (SEQ ID NO: 61) | WGQGTLVTVSS | (SEQ ID NO: 19) |
| Ab938 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQGRVTITRDRSMSTAYMELRSLRAEDTAVYYC | (SEQ ID NO: 50) | NAAYGSSSYPMDY | (SEQ ID NO: 61) | WGQGTLVTVSS | (SEQ ID NO: 19) |
| Ab939 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSMSTAYMELRSLRAEDTAMYYC | (SEQ ID NO: 47) | NAAYGSSSYPMDY | (SEQ ID NO: 61) | WGQGTLVTVSS | (SEQ ID NO: 19) |
| Ab940 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSTSTAYMELSSLRAEDTAVYYC | (SEQ ID NO: 48) | NAAYGSSSYPMDY | (SEQ ID NO: 61) | WGQGTLVTVSS | (SEQ ID NO: 19) |
| Ab941 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQGRVTITRDRSMSTAYMELRSLRAEDTAVYYC | (SEQ ID NO: 49) | NAAYGSSSYPMDY | (SEQ ID NO: 61) | WGQGTLVTVSS | (SEQ ID NO: 19) |
| Ab942 | $X_{H1}$QMQLVQSGAEVKKPGSSVKVSCKAS | (SEQ ID NO: 21) | GFNIKDYYLH | (SEQ ID NO: 12) | WVRQAPGQGLEWMG | (SEQ ID NO: 59) | WIDPDQGDTE | (SEQ ID NO: 16) | YAQKFQDRVTITRDRSTSTAYMELSSLRAEDTAVYYC | (SEQ ID NO: 50) | NAAYGSSSYPMDY | (SEQ ID NO: 61) | WGQGTLVTVSS | (SEQ ID NO: 19) |
| Ab943 | $X_{H1}$QMQLVQSGAEVKKPGSSVKVSCKAS | (SEQ ID NO: 12) | GFNIKDYYLH | (SEQ ID NO: 12) | WVRQAPGQGLEWMG | (SEQ ID NO: 59) | WIDPDQGDTE | (SEQ ID NO: 16) | YAQKFQGRVTITRDRSMSTAYMELRSLRAEDTAVYYC | (SEQ ID NO: 139) | NAAYGSSSYPMDY | (SEQ ID NO: 61) | WGQGTLVTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab944 | $X_{H1}$QMQLVQSGAEVKKTGSSVKVSCKAS | (SEQ ID NO: 12) | GFNIKDYYLH | (SEQ ID NO: 21) | WVRQAPGQGLEWMG | (SEQ ID NO: 59) | WIDPDQGDTE | (SEQ ID NO: 16) | YAQKFQGRVTITRDRSMSTAYMELSSLRAEDTAVYYC | (SEQ ID NO: 139) | NAAYGSSYPMDY | (SEQ ID NO: 61) | WGQGTLVTVSS | (SEQ ID NO: 19) |
| Ab945 | $X_{H1}$QMQLVQSGAEVKKPGSSVKVSCKAS | (SEQ ID NO: 21) | GFNIKDYYLH | (SEQ ID NO: 21) | WVRQAPGKGLEWMG | (SEQ ID NO: 59) | WIDPDQGDTE | (SEQ ID NO: 20) | YAQKFQDRVTITRDRSTSTAYMELSSLRAEDTAMYYC | (SEQ ID NO: 18) | NAAYGSSYPMDY | (SEQ ID NO: 61) | WGQGTLVTVSS | (SEQ ID NO: 19) |
| Ab946 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSMSTAYMELSSLRAEDTAMYYC | (SEQ ID NO: 37) | NAAYGSSYPMDY | (SEQ ID NO: 61) | WGQGTLVTVSS | (SEQ ID NO: 19) |
| Ab947 | $X_{H1}$QMQLVQSGAEVKKPGSSVKVSCKAS | (SEQ ID NO: 21) | GFNIKDYYLH | (SEQ ID NO: 21) | WVRQAPGKGLEWMG | (SEQ ID NO: 59) | WIDPDQGDTE | (SEQ ID NO: 20) | YAQKFQDRVTITRDRSMSTAYMELSSLRAEDTAMYYC | (SEQ ID NO: 38) | NAAYGSSYPMDY | (SEQ ID NO: 61) | WGQGTLVTVSS | (SEQ ID NO: 19) |
| Ab948 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQDRVTITRDRSMSTAYMELSSLRAEDTAMYYC | (SEQ ID NO: 39) | NAAYGSSYPMDY | (SEQ ID NO: 61) | WGQGTLVTVSS | (SEQ ID NO: 19) |
| Ab949 | $X_{H1}$QMQLVQSGAEVKKPGSSVKVSCKAS | (SEQ ID NO: 21) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSTSTAYMELSSLRAEDTAMYYC | (SEQ ID NO: 40) | NAAYGSSYPMDY | (SEQ ID NO: 61) | WGQGTLVTVSS | (SEQ ID NO: 19) |
| Ab950 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSMSTAYMELSSLRAEDTAMYYC | (SEQ ID NO: 37) | NAAYGSSYPMDY | (SEQ ID NO: 61) | WGQGTLVTVSS | (SEQ ID NO: 19) |
| Ab951 | $X_{H1}$QMQLVQSGAEVKKPGSSVKVSCKAS | (SEQ ID NO: 21) | GFNIKDYYLH | (SEQ ID NO: 21) | WVRQAPGKGLEWMG | (SEQ ID NO: 59) | WIDPDQGDTE | (SEQ ID NO: 20) | YAQKFQDRVTITRDRSMSTAYMELSSLRAEDTAMYYC | (SEQ ID NO: 38) | NAAYGSSYPMDY | (SEQ ID NO: 61) | WGQGTLVTVSS | (SEQ ID NO: 19) |
| Ab952 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQDRVTITRDRSMSTAYMELSSLRAEDTAMYYC | (SEQ ID NO: 39) | NAAYGSSYPMDY | (SEQ ID NO: 61) | WGQGTLVTVSS | (SEQ ID NO: 19) |
| Ab953 | $X_{H1}$QMQLVQSGAEVKKPGSSVKVSCKAS | (SEQ ID NO: 21) | GFNIKDYYLH | (SEQ ID NO: 21) | WVRQAPGKGLEWMG | (SEQ ID NO: 59) | WIDPDQGDTE | (SEQ ID NO: 20) | YAQKFQDRVTITRDRSTSTAYMELSSLRAEDTAVYYC | (SEQ ID NO: 40) | NAAYGSSYPMDY | (SEQ ID NO: 61) | WGQGTLVTVSS | (SEQ ID NO: 19) |
| Ab954 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSMSTAYMELSSLRAEDTAMYYC | (SEQ ID NO: 41) | NAAYGSSYPMDY | (SEQ ID NO: 61) | WGQGTLVTVSS | (SEQ ID NO: 19) |
| Ab955 | $X_{H1}$QMQLVQSGAEVKKTGSSVKVSCKAS | (SEQ ID NO: 12) | GFNIKDYYLH | (SEQ ID NO: 21) | WVRQAPGKGLEWMG | (SEQ ID NO: 59) | WIDPDQGDTE | (SEQ ID NO: 20) | YAQKFQGRVTITRDRSMSTAYMELRSLRAEDTAMYYC | (SEQ ID NO: 42) | NAAYGSSYPMDY | (SEQ ID NO: 61) | WGQGTLVTVSS | (SEQ ID NO: 19) |

TABLE 3-continued

Exemplary Antibodies with Specific VH FR sequences and specific VH CDR sequences ($X_{H1}$ is M or no amino acid).

| Anti-body | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab956 | $X_{H1}$QMQLVQS GAEVKKTGS SVKVSCKAS | (SEQ ID NO: 12) | GFNIKD YYLH | (SEQ ID NO: 59) | WVRQAPG KGLEWMG | (SEQ ID NO: 20) | WIDPDQ GDTE | (SEQ ID NO: 60) | YAQKFQGRVTITR DRSMSTAYMELSS LRAEDTAMYYC | (SEQ ID NO: 43) | NAAYGSS SYPMDY | (SEQ ID NO: 61) | WGQGTL VTVSS | (SEQ ID NO: 19) |
| Ab957 | $X_{H1}$QMQLVQS GAEVKKTGS SVKVSCKAS | (SEQ ID NO: 12) | GFNIKD YYLH | (SEQ ID NO: 59) | WVRQAPG KGLEWMG | (SEQ ID NO: 20) | WIDPDQ GDTE | (SEQ ID NO: 60) | YAQKFQDRVTITR DRSMSTAYMELRS LRAEDTAMYYC | (SEQ ID NO: 44) | NAAYGSS SYPMDY | (SEQ ID NO: 61) | WGQGTL VTVSS | (SEQ ID NO: 19) |
| Ab958 | $X_{H1}$QMQLVQS GAEVKKTGS SVKVSCKAS | (SEQ ID NO: 12) | GFNIKD YYLH | (SEQ ID NO: 59) | WVRQAPG KGLEWMG | (SEQ ID NO: 20) | WIDPDQ GDTE | (SEQ ID NO: 60) | YAQKFQDRVTITR DRSTSTAYMELSS LRAEDTAMYYC | (SEQ ID NO: 45) | NAAYGSS SYPMDY | (SEQ ID NO: 61) | WGQGTL VTVSS | (SEQ ID NO: 19) |
| Ab959 | $X_{H1}$QMQLVQS GAEVKKTGS SVKVSCKAS | (SEQ ID NO: 12) | GFNIKD YYLH | (SEQ ID NO: 59) | WVRQAPG KGLEWMG | (SEQ ID NO: 20) | WIDPDQ GDTE | (SEQ ID NO: 60) | YAQKFQDRVTITR DRSMSTAYMELSS LRAEDTAVYYC | (SEQ ID NO: 46) | NAAYGSS SYPMDY | (SEQ ID NO: 61) | WGQGTL VTVSS | (SEQ ID NO: 19) |
| Ab960 | $X_{H1}$QMQLVQS GAEVKKPGS SVKVSCKAS | (SEQ ID NO: 21) | GFNIKD YYLH | (SEQ ID NO: 59) | WVRQAPG KGLEWMG | (SEQ ID NO: 20) | WIDPDQ GDTE | (SEQ ID NO: 60) | YAQKFQDRVTITR DRSMSTAYMELSS LRAEDTAMYYC | (SEQ ID NO: 41) | NAAYGSS SYPMDY | (SEQ ID NO: 61) | WGQGTL VTVSS | (SEQ ID NO: 19) |
| Ab961 | $X_{H1}$QMQLVQS GAEVKKPGS SVKVSCKAS | (SEQ ID NO: 21) | GFNIKD YYLH | (SEQ ID NO: 59) | WVRQAPG KGLEWMG | (SEQ ID NO: 20) | WIDPDQ GDTE | (SEQ ID NO: 60) | YAQKFQGRVTITR DRSMSTAYMELSS LRAEDTAMYYC | (SEQ ID NO: 42) | NAAYGSS SYPMDY | (SEQ ID NO: 61) | WGQGTL VTVSS | (SEQ ID NO: 19) |
| Ab962 | $X_{H1}$QMQLVQS GAEVKKPGS SVKVSCKAS | (SEQ ID NO: 21) | GFNIKD YYLH | (SEQ ID NO: 59) | WVRQAPG KGLEWMG | (SEQ ID NO: 20) | WIDPDQ GDTE | (SEQ ID NO: 60) | YAQKFQDRVTITR DRSMSTAYMELSS LRAEDTAMYYC | (SEQ ID NO: 43) | NAAYGSS SYPMDY | (SEQ ID NO: 61) | WGQGTL VTVSS | (SEQ ID NO: 19) |
| Ab963 | $X_{H1}$QMQLVQS GAEVKKPGS SVKVSCKAS | (SEQ ID NO: 21) | GFNIKD YYLH | (SEQ ID NO: 59) | WVRQAPG KGLEWMG | (SEQ ID NO: 20) | WIDPDQ GDTE | (SEQ ID NO: 60) | YAQKFQDRVTITR DRSMSTAYMELRS LRAEDTAMYYC | (SEQ ID NO: 44) | NAAYGSS SYPMDY | (SEQ ID NO: 61) | WGQGTL VTVSS | (SEQ ID NO: 19) |
| Ab964 | $X_{H1}$QMQLVQS GAEVKKPGS SVKVSCKAS | (SEQ ID NO: 21) | GFNIKD YYLH | (SEQ ID NO: 59) | WVRQAPG KGLEWMG | (SEQ ID NO: 20) | WIDPDQ GDTE | (SEQ ID NO: 60) | YAQKFQDRVTITR DRSTSTAYMELSS LRAEDTAMYYC | (SEQ ID NO: 45) | NAAYGSS SYPMDY | (SEQ ID NO: 61) | WGQGTL VTVSS | (SEQ ID NO: 19) |
| Ab965 | $X_{H1}$QMQLVQS GAEVKKPGS SVKVSCKAS | (SEQ ID NO: 21) | GFNIKD YYLH | (SEQ ID NO: 59) | WVRQAPG KGLEWMG | (SEQ ID NO: 20) | WIDPDQ GDTE | (SEQ ID NO: 60) | YAQKFQDRVTITR DRSMSTAYMELSS LRAEDTAVYYC | (SEQ ID NO: 46) | NAAYGSS SYPMDY | (SEQ ID NO: 61) | WGQGTL VTVSS | (SEQ ID NO: 19) |
| Ab966 | $X_{H1}$QMQLVQS GAEVKKTGS SVKVSCKAS | (SEQ ID NO: 12) | GFNIKD YYLH | (SEQ ID NO: 59) | WVRQAPG KGLEWMG | (SEQ ID NO: 20) | WIDPDQ GDTE | (SEQ ID NO: 60) | YAQKFQDRVTITR DRSMSTAYMELSS LRAEDTAMYYC | (SEQ ID NO: 47) | NAAYGSS SYPMDY | (SEQ ID NO: 61) | WGQGTL VTVSS | (SEQ ID NO: 19) |

TABLE 3-continued

Exemplary Antibodies with Specific VH FR sequences and specific VH CDR sequences ($X_{H1}$ is M or no amino acid).

| Antibody | VH-FR1 | SEQ ID NO: | VH-CDR 1 | SEQ ID NO: | VH-FR2 | SEQ ID NO: | VH-CDR 2 | SEQ ID NO: | VH-FR3 | SEQ ID NO: | VH-CDR 3 | SEQ ID NO: | VH-FR4 | SEQ ID NO: |
|---|---|---|---|---|---|---|---|---|---|---|---|---|---|---|
| Ab967 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSTSTAYMELSSLRAEDTAVYYC | (SEQ ID NO: 48) | NAAYGSSSYPMDY | (SEQ ID NO: 61) | WGQGTLVTVSS | (SEQ ID NO: 19) |
| Ab968 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRAEDTAVYYC | (SEQ ID NO: 49) | NAAYGSSSYPMDY | (SEQ ID NO: 61) | WGQGTLVTVSS | (SEQ ID NO: 19) |
| Ab969 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQDRVTITRDRSMSTAYMELRSLRAEDTAVYYC | (SEQ ID NO: 50) | NAAYGSSSYPMDY | (SEQ ID NO: 61) | WGQGTLVTVSS | (SEQ ID NO: 19) |
| Ab970 | $X_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSTSTAYMELSSLRAEDTAMYYC | (SEQ ID NO: 47) | NAAYGSSSYPMDY | (SEQ ID NO: 61) | WGQGTLVTVSS | (SEQ ID NO: 19) |
| Ab971 | $X_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSTSTAYMELSSLRAEDTAVYYC | (SEQ ID NO: 48) | NAAYGSSSYPMDY | (SEQ ID NO: 61) | WGQGTLVTVSS | (SEQ ID NO: 19) |
| Ab972 | $X_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRAEDTAVYYC | (SEQ ID NO: 49) | NAAYGSSSYPMDY | (SEQ ID NO: 61) | WGQGTLVTVSS | (SEQ ID NO: 19) |
| Ab973 | $X_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQDRVTITRDRSMSTAYMELRSLRAEDTAVYYC | (SEQ ID NO: 50) | NAAYGSSSYPMDY | (SEQ ID NO: 61) | WGQGTLVTVSS | (SEQ ID NO: 19) |
| Ab974 | $X_{H1}$QMQLVQSGAEVKKTGSSVKVSCKAS | (SEQ ID NO: 12) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRAEDTAVYYC | (SEQ ID NO: 139) | NAAYGSSSYPMDY | (SEQ ID NO: 61) | WGQGTLVTVSS | (SEQ ID NO: 19) |
| Ab975 | $X_{H1}$QMQLVQSGAEVKKPGSSVKVSCKAS | (SEQ ID NO: 21) | GFNIKDYYLH | (SEQ ID NO: 59) | WVRQAPGKGLEWMG | (SEQ ID NO: 20) | WIDPDQGDTE | (SEQ ID NO: 60) | YAQKFQGRVTITRDRSMSTAYMELRSLRAEDTAVYYC | (SEQ ID NO: 139) | NAAYGSSSYPMDY | (SEQ ID NO: 61) | WGQGTLVTVSS | (SEQ ID NO: 19) |

In a specific embodiment, provided herein is an antibody or antigen-binding fragment thereof of any listed in Table 4, which comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence listed in the second column of Table 4 for the antibody or antigen-binding fragment, VL FR2 comprises the amino acid sequence listed in the sixth column of Table 4 for the antibody or antigen-binding fragment, VL FR3 comprises the amino acid sequence listed in the $10^{th}$ column of Table 4 for the antibody or antigen-binding fragment, VL FR4 comprises the amino acid sequence listed in the $14^{th}$ column of Table 4 for the antibody or antigen-binding fragment, VL CDR1 comprises the amino acid sequence listed in the fourth column of Table 4 for the antibody or antigen-binding fragment, VL CDR2 comprises the amino acid sequence listed in the eighth column of Table 4 for the antibody or antigen-binding fragment, and VL CDR3 comprises the amino acid sequence listed in the $12^{nd}$ column of Table 4 for the antibody or antigen-binding fragment.

TABLE 4

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab976 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab977 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab978 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab979 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab980 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab981 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab982 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab983 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab984 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab985 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | RHVFRVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab986 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab987 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab988 | NIQMTQSPSAMSASVG DRVTITC | (SEQ ID NO: 51) | KASQDIHR YLS | (SEQ ID NO: 66) | WFQQKPGK VPKHLIY | (SEQ ID NO: 52) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab989 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab990 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab991 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab992 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab993 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab994 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab995 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab996 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab997 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab998 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | FHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab999 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1000 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1001 | NIQMTQSPSAMSASVG DRVTITC | (SEQ ID NO: 51) | RASQDIHR YLS | (SEQ ID NO: 79) | WFQQKPGK VPKHLIY | (SEQ ID NO: 52) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1002 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1003 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1004 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1005 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1006 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1007 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1008 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1009 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1010 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1011 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1012 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1013 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1014 | NIQMTQSPSSMSASVG DRVTITC | (SEQ ID NO: 53) | KASQDIHR YLS | (SEQ ID NO: 66) | WFQQKPGK VPKHLIY | (SEQ ID NO: 52) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1015 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1016 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1017 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1018 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1019 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1020 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1021 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1022 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1023 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1024 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1025 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1026 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1027 | NIQMTQSPSSMSASVG DRVTITC | (SEQ ID NO: 53) | RASQDIHR YLS | (SEQ ID NO: 79) | WFQQKPGK VPKHLIY | (SEQ ID NO: 52) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1028 | NIQMTQSPSALSASVG DRVTITC | (SEQ ID NO: 54) | KASQDIHR YLS | (SEQ ID NO: 66) | WFQQKPGK VPKHLIY | (SEQ ID NO: 52) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1029 | NIQMTQSPSALSASVG DRVTITC | (SEQ ID NO: 54) | KASQDIHR YLS | (SEQ ID NO: 66) | WFQQKPGK VPKHLIY | (SEQ ID NO: 52) | RVVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1030 | NIQMTQSPSALSASVG DRVTITC | (SEQ ID NO: 54) | KASQDIHR YLS | (SEQ ID NO: 66) | WFQQKPGK VPKHLIY | (SEQ ID NO: 52) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1031 | NIQMTQSPSALSASVG DRVTITC | (SEQ ID NO: 54) | KASQDIHR YLS | (SEQ ID NO: 66) | WFQQKPGK VPKHLIY | (SEQ ID NO: 52) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1032 | NIQMTQSPSALSASVG DRVTITC | (SEQ ID NO: 54) | KASQDIHR YLS | (SEQ ID NO: 66) | WFQQKPGK VPKHLIY | (SEQ ID NO: 52) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1033 | NIQMTQSPSALSASVG DRVTITC | (SEQ ID NO: 54) | KASQDIHR YLS | (SEQ ID NO: 66) | WFQQKPGK VPKHLIY | (SEQ ID NO: 52) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1034 | NIQMTQSPSALSASVG DRVTITC | (SEQ ID NO: 54) | KASQDIHR YLS | (SEQ ID NO: 66) | WFQQKPGK VPKHLIY | (SEQ ID NO: 52) | RIERFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1035 | NIQMTQSPSALSASVG DRVTITC | (SEQ ID NO: 54) | KASQDIHR YLS | (SEQ ID NO: 66) | WFQQKPGK VPKHLIY | (SEQ ID NO: 52) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1036 | NIQMTQSPSALSASVG DRVTITC | (SEQ ID NO: 54) | KASQDIHR YLS | (SEQ ID NO: 66) | WFQQKPGK VPKHLIY | (SEQ ID NO: 52) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1037 | NIQMTQSPSALSASVG DRVTITC | (SEQ ID NO: 54) | KASQDIHR YLS | (SEQ ID NO: 66) | WFQQKPGK VPKHLIY | (SEQ ID NO: 52) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1038 | NIQMTQSPSALSASVG DRVTITC | (SEQ ID NO: 54) | KASQDIHR YLS | (SEQ ID NO: 66) | WFQQKPGK VPKHLIY | (SEQ ID NO: 52) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1039 | NIQMTQSPSALSASVG DRVTITC | (SEQ ID NO: 51) | KASQDIHR YLS | (SEQ ID NO: 54) | WFQQKPGK VPKHLIY | (SEQ ID NO: 52) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1040 | NIQMTQSPSALSASVG DRVTITC | (SEQ ID NO: 51) | KASQDIHR YLS | (SEQ ID NO: 54) | WFQQKPGK VPKHLIY | (SEQ ID NO: 52) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1041 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | RANRLVS | (SEQ ID NO: 61) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1042 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1043 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1044 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1045 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1046 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1047 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1048 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1049 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1050 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1051 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1052 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1053 | NIQMTQSPSALSASVG DRVTITC | (SEQ ID NO: 51) | RASQDIHR YLS | (SEQ ID NO: 79) | WFQQKPGK VPKHLIY | (SEQ ID NO: 52) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1054 | NIQMTQSPSAMSASVG DRVTITC | (SEQ ID NO: 55) | KASQDIHR YLS | (SEQ ID NO: 66) | WYQQKPGK VPKHLIY | (SEQ ID NO: 63) | RANRLVS | (SEQ ID NO: 61) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1055 | NIQMTQSPSAMSASVG DRVTITC | (SEQ ID NO: 51) | KASQDIHR YLS | (SEQ ID NO: 66) | WYQQKPGK VPKHLIY | (SEQ ID NO: 55) | RVVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1056 | NIQMTQSPSAMSASVG DRVTITC | (SEQ ID NO: 51) | KASQDIHR YLS | (SEQ ID NO: 66) | WYQQKPGK VPKHLIY | (SEQ ID NO: 55) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1057 | NIQMTQSPSAMSASVG DRVTITC | (SEQ ID NO: 51) | KASQDIHR YLS | (SEQ ID NO: 66) | WYQQKPGK VPKHLIY | (SEQ ID NO: 55) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1058 | NIQMTQSPSAMSASVG DRVTITC | (SEQ ID NO: 51) | KASQDIHR YLS | (SEQ ID NO: 66) | WYQQKPGK VPKHLIY | (SEQ ID NO: 55) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1059 | NIQMTQSPSAMSASVG DRVTITC | (SEQ ID NO: 51) | KASQDIHR YLS | (SEQ ID NO: 66) | WYQQKPGK VPKHLIY | (SEQ ID NO: 55) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1060 | NIQMTQSPSAMSASVG DRVTITC | (SEQ ID NO: 51) | KASQDIHR YLS | (SEQ ID NO: 66) | WYQQKPGK VPKHLIY | (SEQ ID NO: 55) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1061 | NIQMTQSPSAMSASVG DRVTITC | (SEQ ID NO: 51) | KASQDIHR YLS | (SEQ ID NO: 66) | WYQQKPGK VPKHLIY | (SEQ ID NO: 55) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1062 | NIQMTQSPSAMSASVG DRVTITC | (SEQ ID NO: 51) | KASQDIHR YLS | (SEQ ID NO: 66) | WYQQKPGK VPKHLIY | (SEQ ID NO: 55) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1063 | NIQMTQSPSAMSASVG DRVTITC | (SEQ ID NO: 51) | KASQDIHR YLS | (SEQ ID NO: 66) | WYQQKPGK VPKHLIY | (SEQ ID NO: 55) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1064 | NIQMTQSPSAMSASVG DRVTITC | (SEQ ID NO: 51) | KASQDIHR YLS | (SEQ ID NO: 66) | WYQQKPGK VPKHLIY | (SEQ ID NO: 55) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1065 | NIQMTQSPSAMSASVG DRVTITC | (SEQ ID NO: 51) | KASQDIHR YLS | (SEQ ID NO: 66) | WYQQKPGK VPKHLIY | (SEQ ID NO: 55) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1066 | NIQMTQSPSAMSASVG DRVTITC | (SEQ ID NO: 51) | KASQDIHR YLS | (SEQ ID NO: 66) | WYQQKPGK VPKHLIY | (SEQ ID NO: 55) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1067 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1068 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | RVVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1069 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1070 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1071 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1072 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1073 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1074 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1075 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1076 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1077 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1078 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1079 | NIQMTQSPSAMSASVG DRVTITC | (SEQ ID NO: 51) | RASQDIHR YLS | (SEQ ID NO: 79) | WYQQKPGK VPKHLIY | (SEQ ID NO: 55) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1080 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1081 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1082 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1083 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1084 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1085 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1086 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1087 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1088 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1089 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1090 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1091 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1092 | NIQMTQSPSAMSASVG DRVTITC | (SEQ ID NO: 51) | KASQDIHR YLS | (SEQ ID NO: 66) | WFQQKPGK APKHLIY | (SEQ ID NO: 56) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1093 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1094 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1095 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1096 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1097 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1098 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1099 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1100 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1101 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1102 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1103 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1104 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1105 | NIQMTQSPSAMSASVG DRVTITC | (SEQ ID NO: 51) | RASQDIHR YLS | (SEQ ID NO: 79) | WFQQKPGK APKHLIY | (SEQ ID NO: 56) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1106 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1107 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1108 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1109 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1110 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1111 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1112 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | RIERFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1113 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1114 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1115 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1116 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1117 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1118 | NIQMTQSPSSLSASVG DRVTITC | (SEQ ID NO: 57) | KASQDIHR YLS | (SEQ ID NO: 66) | WFQQKPGK VPKHLIY | (SEQ ID NO: 52) | RHSRDVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1119 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1120 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | RVVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1121 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1122 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1123 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1124 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1125 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1126 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1127 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1128 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1129 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1130 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1131 | NIQMTQSPSSLSASVG DRVTITC | (SEQ ID NO: 53) | RASQDIHR YLS | (SEQ ID NO: 57) | WFQQKPGK VPKHLIY | (SEQ ID NO: 79) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1132 | NIQMTQSPSSMSASVG DRVTITC | (SEQ ID NO: 53) | KASQDIHR YLS | (SEQ ID NO: 66) | WYQQKPGK VPKHLIY | (SEQ ID NO: 55) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1133 | NIQMTQSPSSMSASVG DRVTITC | (SEQ ID NO: 53) | KASQDIHR YLS | (SEQ ID NO: 66) | WYQQKPGK VPKHLIY | (SEQ ID NO: 55) | RVVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1134 | NIQMTQSPSSMSASVG DRVTITC | (SEQ ID NO: 53) | KASQDIHR YLS | (SEQ ID NO: 66) | WYQQKPGK VPKHLIY | (SEQ ID NO: 55) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1135 | NIQMTQSPSSMSASVG DRVTITC | (SEQ ID NO: 53) | KASQDIHR YLS | (SEQ ID NO: 79) | WYQQKPGK VPKHLIY | (SEQ ID NO: 55) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1136 | NIQMTQSPSSMSASVG DRVTITC | (SEQ ID NO: 53) | KASQDIHR YLS | (SEQ ID NO: 79) | WYQQKPGK VPKHLIY | (SEQ ID NO: 55) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1137 | NIQMTQSPSSMSASVG DRVTITC | (SEQ ID NO: 53) | KASQDIHR YLS | (SEQ ID NO: 79) | WYQQKPGK VPKHLIY | (SEQ ID NO: 55) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1138 | NIQMTQSPSSMSASVG DRVTITC | (SEQ ID NO: 53) | KASQDIHR YLS | (SEQ ID NO: 79) | WYQQKPGK VPKHLIY | (SEQ ID NO: 55) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1139 | NIQMTQSPSSMSASVG DRVTITC | (SEQ ID NO: 53) | KASQDIHR YLS | (SEQ ID NO: 79) | WYQQKPGK VPKHLIY | (SEQ ID NO: 55) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1140 | NIQMTQSPSSMSASVG DRVTITC | (SEQ ID NO: 53) | KASQDIHR YLS | (SEQ ID NO: 79) | WYQQKPGK VPKHLIY | (SEQ ID NO: 55) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1141 | NIQMTQSPSSMSASVG DRVTITC | (SEQ ID NO: 53) | KASQDIHR YLS | (SEQ ID NO: 79) | WYQQKPGK VPKHLIY | (SEQ ID NO: 55) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1142 | NIQMTQSPSSMSASVG DRVTITC | (SEQ ID NO: 53) | KASQDIHR YLS | (SEQ ID NO: 79) | WYQQKPGK VPKHLIY | (SEQ ID NO: 55) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1143 | NIQMTQSPSSMSASVG DRVTITC | (SEQ ID NO: 53) | KASQDIHR YLS | (SEQ ID NO: 79) | WYQQKPGK VPKHLIY | (SEQ ID NO: 55) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1144 | NIQMTQSPSSMSASVG DRVTITC | (SEQ ID NO: 53) | KASQDIHR YLS | (SEQ ID NO: 79) | WYQQKPGK VPKHLIY | (SEQ ID NO: 55) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1145 | NIQMTQSPSSMSASVG DRVTITC | (SEQ ID NO: 53) | RASQDIHR YLS | (SEQ ID NO: 53) | WYQQKPGK VPKHLIY | (SEQ ID NO: 55) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1146 | NIQMTQSPSSMSASVG DRVTITC | (SEQ ID NO: 53) | RASQDIHR YLS | (SEQ ID NO: 53) | WYQQKPGK VPKHLIY | (SEQ ID NO: 55) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1147 | NIQMTQSPSSMSASVG DRVTITC | (SEQ ID NO: 53) | RASQDIHR YLS | (SEQ ID NO: 53) | WYQQKPGK VPKHLIY | (SEQ ID NO: 55) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1148 | NIQMTQSPSSMSASVG DRVTITC | (SEQ ID NO: 53) | RASQDIHR YLS | (SEQ ID NO: 53) | WYQQKPGK VPKHLIY | (SEQ ID NO: 55) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1149 | NIQMTQSPSSMSASVG DRVTITC | (SEQ ID NO: 53) | RASQDIHR YLS | (SEQ ID NO: 53) | WYQQKPGK VPKHLIY | (SEQ ID NO: 55) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1150 | NIQMTQSPSSMSASVG DRVTITC | (SEQ ID NO: 53) | RASQDIHR YLS | (SEQ ID NO: 53) | WYQQKPGK VPKHLIY | (SEQ ID NO: 55) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1151 | NIQMTQSPSSMSASVG DRVTITC | (SEQ ID NO: 53) | RASQDIHR YLS | (SEQ ID NO: 79) | WYQQKPGK VPKHLIY | (SEQ ID NO: 55) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1152 | NIQMTQSPSSMSASVG DRVTITC | (SEQ ID NO: 53) | RASQDIHR YLS | (SEQ ID NO: 79) | WYQQKPGK VPKHLIY | (SEQ ID NO: 55) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1153 | NIQMTQSPSSMSASVG DRVTITC | (SEQ ID NO: 53) | RASQDIHR YLS | (SEQ ID NO: 79) | WYQQKPGK VPKHLIY | (SEQ ID NO: 55) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1154 | NIQMTQSPSSMSASVG DRVTITC | (SEQ ID NO: 53) | RASQDIHR YLS | (SEQ ID NO: 79) | WYQQKPGK VPKHLIY | (SEQ ID NO: 55) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1155 | NIQMTQSPSSMSASVG DRVTITC | (SEQ ID NO: 53) | RASQDIHR YLS | (SEQ ID NO: 79) | WYQQKPGK VPKHLIY | (SEQ ID NO: 55) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1156 | NIQMTQSPSSMSASVG DRVTITC | (SEQ ID NO: 53) | RASQDIHR YLS | (SEQ ID NO: 79) | WYQQKPGK VPKHLIY | (SEQ ID NO: 55) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1157 | NIQMTQSPSSMSASVG DRVTITC | (SEQ ID NO: 53) | RASQDIHR YLS | (SEQ ID NO: 79) | WYQQKPGK VPKHLIY | (SEQ ID NO: 55) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1158 | NIQMTQSPSSMSASVG DRVTITC | (SEQ ID NO: 53) | KASQDIHR YLS | (SEQ ID NO: 66) | WFQQKPGK APKHLIY | (SEQ ID NO: 56) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1159 | NIQMTQSPSSMSASVG DRVTITC | (SEQ ID NO: 53) | KASQDIHR YLS | (SEQ ID NO: 66) | WFQQKPGK APKHLIY | (SEQ ID NO: 56) | RVVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1160 | NIQMTQSPSSMSASVG DRVTITC | (SEQ ID NO: 53) | KASQDIHR YLS | (SEQ ID NO: 66) | WFQQKPGK APKHLIY | (SEQ ID NO: 56) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1161 | NIQMTQSPSSMSASVG DRVTITC | (SEQ ID NO: 53) | KASQDIHR YLS | (SEQ ID NO: 66) | WFQQKPGK APKHLIY | (SEQ ID NO: 56) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1162 | NIQMTQSPSSMSASVG DRVTITC | (SEQ ID NO: 53) | KASQDIHR YLS | (SEQ ID NO: 66) | WFQQKPGK APKHLIY | (SEQ ID NO: 56) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1163 | NIQMTQSPSSMSASVG DRVTITC | (SEQ ID NO: 53) | KASQDIHR YLS | (SEQ ID NO: 66) | WFQQKPGK APKHLIY | (SEQ ID NO: 56) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1164 | NIQMTQSPSSMSASVG DRVTITC | (SEQ ID NO: 53) | KASQDIHR YLS | (SEQ ID NO: 66) | WFQQKPGK APKHLIY | (SEQ ID NO: 56) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1165 | NIQMTQSPSSMSASVG DRVTITC | (SEQ ID NO: 53) | KASQDIHR YLS | (SEQ ID NO: 66) | WFQQKPGK APKHLIY | (SEQ ID NO: 56) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1166 | NIQMTQSPSSMSASVG DRVTITC | (SEQ ID NO: 53) | KASQDIHR YLS | (SEQ ID NO: 66) | WFQQKPGK APKHLIY | (SEQ ID NO: 56) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1167 | NIQMTQSPSSMSASVG DRVTITC (SEQ ID NO: 53) | | KASQDIHR YLS (SEQ ID NO: 66) | | WFQQKPGK APKHLIY (SEQ ID NO: 56) | | RHVRFVD (SEQ ID NO: 75) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1168 | NIQMTQSPSSMSASVG DRVTITC (SEQ ID NO: 53) | | KASQDIHR YLS (SEQ ID NO: 66) | | WFQQKPGK APKHLIY (SEQ ID NO: 56) | | RHIRFVD (SEQ ID NO: 76) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1169 | NIQMTQSPSSMSASVG DRVTITC (SEQ ID NO: 53) | | KASQDIHR YLS (SEQ ID NO: 66) | | WFQQKPGK APKHLIY (SEQ ID NO: 56) | | RHERFVD (SEQ ID NO: 77) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1170 | NIQMTQSPSSMSASVG DRVTITC (SEQ ID NO: 53) | | KASQDIHR YLS (SEQ ID NO: 66) | | WFQQKPGK APKHLIY (SEQ ID NO: 56) | | RHSRFVD (SEQ ID NO: 78) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1171 | NIQMTQSPSSMSASVG DRVTITC (SEQ ID NO: 53) | | RASQDIHR YLS (SEQ ID NO: 79) | | WFQQKPGK APKHLIY (SEQ ID NO: 56) | | RANRLVS (SEQ ID NO: 63) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1172 | NIQMTQSPSSMSASVG DRVTITC (SEQ ID NO: 53) | | RASQDIHR YLS (SEQ ID NO: 79) | | WFQQKPGK APKHLIY (SEQ ID NO: 56) | | RYVRFVD (SEQ ID NO: 67) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1173 | NIQMTQSPSSMSASVG DRVTITC (SEQ ID NO: 53) | | RASQDIHR YLS (SEQ ID NO: 79) | | WFQQKPGK APKHLIY (SEQ ID NO: 56) | | RYIRFVD (SEQ ID NO: 68) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1174 | NIQMTQSPSSMSASVG DRVTITC (SEQ ID NO: 53) | | RASQDIHR YLS (SEQ ID NO: 79) | | WFQQKPGK APKHLIY (SEQ ID NO: 56) | | RYERFVD (SEQ ID NO: 69) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1175 | NIQMTQSPSSMSASVG DRVTITC (SEQ ID NO: 53) | | RASQDIHR YLS (SEQ ID NO: 79) | | WFQQKPGK APKHLIY (SEQ ID NO: 56) | | RYSRFVD (SEQ ID NO: 70) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1176 | NIQMTQSPSSMSASVG DRVTITC (SEQ ID NO: 53) | | RASQDIHR YLS (SEQ ID NO: 79) | | WFQQKPGK APKHLIY (SEQ ID NO: 56) | | REVRFVD (SEQ ID NO: 71) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1177 | NIQMTQSPSSMSASVG DRVTITC (SEQ ID NO: 53) | | RASQDIHR YLS (SEQ ID NO: 79) | | WFQQKPGK APKHLIY (SEQ ID NO: 56) | | REIRFVD (SEQ ID NO: 72) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1178 | NIQMTQSPSSMSASVG DRVTITC (SEQ ID NO: 53) | | RASQDIHR YLS (SEQ ID NO: 79) | | WFQQKPGK APKHLIY (SEQ ID NO: 56) | | REERFVD (SEQ ID NO: 73) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1179 | NIQMTQSPSSMSASVG DRVTITC (SEQ ID NO: 53) | | RASQDIHR YLS (SEQ ID NO: 79) | | WFQQKPGK APKHLIY (SEQ ID NO: 56) | | RESRFVD (SEQ ID NO: 74) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1180 | NIQMTQSPSSMSASVG DRVTITC (SEQ ID NO: 53) | | RASQDIHR YLS (SEQ ID NO: 79) | | WFQQKPGK APKHLIY (SEQ ID NO: 56) | | RHVRFVD (SEQ ID NO: 75) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1181 | NIQMTQSPSSMSASVG DRVTITC (SEQ ID NO: 53) | | RASQDIHR YLS (SEQ ID NO: 79) | | WFQQKPGK APKHLIY (SEQ ID NO: 56) | | RHIRFVD (SEQ ID NO: 76) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |
| Ab1182 | NIQMTQSPSSMSASVG DRVTITC (SEQ ID NO: 53) | | RASQDIHR YLS (SEQ ID NO: 79) | | WFQQKPGK APKHLIY (SEQ ID NO: 56) | | RHERFVD (SEQ ID NO: 77) | | GVPSRFSGSGSGTEFTLTISS LQPEDFATYYC (SEQ ID NO: 10) | | LQYDEFPYT (SEQ ID NO: 64) | | FGGGTK VEIK (SEQ ID NO: 11) | |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1183 | NIQMTQSPSMSASVG DRVTITC | (SEQ ID NO: 53) | RASQDIHR YLS | (SEQ ID NO: 79) | WFQQKPGK APKHLIY | (SEQ ID NO: 56) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1184 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1185 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1186 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1187 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1188 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1189 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1190 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1191 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1192 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1193 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1194 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1195 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1196 | NIQMTQSPSALSASVG DRVTITC | (SEQ ID NO: 54) | KASQDIHR YLS | (SEQ ID NO: 66) | WYQQKPGK VPKHLIY | (SEQ ID NO: 55) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1197 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1198 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1199 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | RYIRFVD | | GVPSRFSGSGSGTEFTLTISS LQPEDFATYYC | (SEQ ID NO: 68) | LQYDEFPYT | (SEQ ID NO: 10) | FGGGTK VEIK | (SEQ ID NO: 11) |
| Ab1200 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | RYERFVD | | GVPSRFSGSGSGTEFTLTISS LQPEDFATYYC | (SEQ ID NO: 69) | LQYDEFPYT | (SEQ ID NO: 10) | FGGGTK VEIK | (SEQ ID NO: 11) |
| Ab1201 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | RYSRFVD | | GVPSRFSGSGSGTEFTLTISS LQPEDFATYYC | (SEQ ID NO: 70) | LQYDEFPYT | (SEQ ID NO: 10) | FGGGTK VEIK | (SEQ ID NO: 11) |
| Ab1202 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | REVRFVD | | GVPSRFSGSGSGTEFTLTISS LQPEDFATYYC | (SEQ ID NO: 71) | LQYDEFPYT | (SEQ ID NO: 10) | FGGGTK VEIK | (SEQ ID NO: 11) |
| Ab1203 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | RERIFVD | | GVPSRFSGSGSGTEFTLTISS LQPEDFATYYC | (SEQ ID NO: 72) | LQYDEFPYT | (SEQ ID NO: 10) | FGGGTK VEIK | (SEQ ID NO: 11) |
| Ab1204 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | REERFVD | | GVPSRFSGSGSGTEFTLTISS LQPEDFATYYC | (SEQ ID NO: 73) | LQYDEFPYT | (SEQ ID NO: 10) | FGGGTK VEIK | (SEQ ID NO: 11) |
| Ab1205 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | RESRFVD | | GVPSRFSGSGSGTEFTLTISS LQPEDFATYYC | (SEQ ID NO: 74) | LQYDEFPYT | (SEQ ID NO: 10) | FGGGTK VEIK | (SEQ ID NO: 11) |
| Ab1206 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | RHVRFVD | | GVPSRFSGSGSGTEFTLTISS LQPEDFATYYC | (SEQ ID NO: 75) | LQYDEFPYT | (SEQ ID NO: 10) | FGGGTK VEIK | (SEQ ID NO: 11) |
| Ab1207 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | RHIRFVD | | GVPSRFSGSGSGTEFTLTISS LQPEDFATYYC | (SEQ ID NO: 76) | LQYDEFPYT | (SEQ ID NO: 10) | FGGGTK VEIK | (SEQ ID NO: 11) |
| Ab1208 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | RHERFVD | | GVPSRFSGSGSGTEFTLTISS LQPEDFATYYC | (SEQ ID NO: 77) | LQYDEFPYT | (SEQ ID NO: 10) | FGGGTK VEIK | (SEQ ID NO: 11) |
| Ab1209 | NIQMTQSPSALSASVG DRVTITC | (SEQ ID NO: 54) | RASQDIHR YLS | (SEQ ID NO: 79) | WYQQKPGK VPKHLIY | (SEQ ID NO: 55) | RHSRFVD | | GVPSRFSGSGSGTEFTLTISS LQPEDFATYYC | (SEQ ID NO: 78) | LQYDEFPYT | (SEQ ID NO: 10) | FGGGTK VEIK | (SEQ ID NO: 11) |
| Ab1210 | NIQMTQSPSALSASVG DRVTITC | (SEQ ID NO: 54) | KASQDIHR YLS | (SEQ ID NO: 66) | WFQQKPGK APKHLIY | (SEQ ID NO: 56) | RANRLVS | | GVPSRFSGSGSGTEFTLTISS LQPEDFATYYC | (SEQ ID NO: 63) | LQYDEFPYT | (SEQ ID NO: 10) | FGGGTK VEIK | (SEQ ID NO: 11) |
| Ab1211 | NIQMTQSPSALSASVG DRVTITC | (SEQ ID NO: 54) | KASQDIHR YLS | (SEQ ID NO: 66) | WFQQKPGK APKHLIY | (SEQ ID NO: 56) | RVVRFVD | | GVPSRFSGSGSGTEFTLTISS LQPEDFATYYC | (SEQ ID NO: 67) | LQYDEFPYT | (SEQ ID NO: 10) | FGGGTK VEIK | (SEQ ID NO: 11) |
| Ab1212 | NIQMTQSPSALSASVG DRVTITC | (SEQ ID NO: 54) | KASQDIHR YLS | (SEQ ID NO: 66) | WFQQKPGK APKHLIY | (SEQ ID NO: 56) | RYIRFVD | | GVPSRFSGSGSGTEFTLTISS LQPEDFATYYC | (SEQ ID NO: 68) | LQYDEFPYT | (SEQ ID NO: 10) | FGGGTK VEIK | (SEQ ID NO: 11) |
| Ab1213 | NIQMTQSPSALSASVG DRVTITC | (SEQ ID NO: 54) | KASQDIHR YLS | (SEQ ID NO: 66) | WFQQKPGK APKHLIY | (SEQ ID NO: 56) | RYERFVD | | GVPSRFSGSGSGTEFTLTISS LQPEDFATYYC | (SEQ ID NO: 69) | LQYDEFPYT | (SEQ ID NO: 10) | FGGGTK VEIK | (SEQ ID NO: 11) |
| Ab1214 | NIQMTQSPSALSASVG DRVTITC | (SEQ ID NO: 54) | KASQDIHR YLS | (SEQ ID NO: 66) | WFQQKPGK APKHLIY | (SEQ ID NO: 56) | RYSRFVD | | GVPSRFSGSGSGTEFTLTISS LQPEDFATYYC | (SEQ ID NO: 70) | LQYDEFPYT | (SEQ ID NO: 10) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1215 | NIQMTQSPSALSASVG DRVTITC | (SEQ ID NO: 54) | KASQDIHR YLS | (SEQ ID NO: 79) | WFQQKPGK APKHLIY | (SEQ ID NO: 66) | REVRFVD | (SEQ ID NO: 56) | GVPSRFSGSGSGTEFTLTISS LQPEDFATYYC | (SEQ ID NO: 71) | LQYDEFPYT | (SEQ ID NO: 10) | FGGGTK VEIK | (SEQ ID NO: 11) |
| Ab1216 | NIQMTQSPSALSASVG DRVTITC | (SEQ ID NO: 54) | KASQDIHR YLS | (SEQ ID NO: 79) | WFQQKPGK APKHLIY | (SEQ ID NO: 66) | REIRFVD | (SEQ ID NO: 56) | GVPSRFSGSGSGTEFTLTISS LQPEDFATYYC | (SEQ ID NO: 72) | LQYDEFPYT | (SEQ ID NO: 10) | FGGGTK VEIK | (SEQ ID NO: 11) |
| Ab1217 | NIQMTQSPSALSASVG DRVTITC | (SEQ ID NO: 54) | KASQDIHR YLS | (SEQ ID NO: 79) | WFQQKPGK APKHLIY | (SEQ ID NO: 66) | REERFVD | (SEQ ID NO: 56) | GVPSRFSGSGSGTEFTLTISS LQPEDFATYYC | (SEQ ID NO: 73) | LQYDEFPYT | (SEQ ID NO: 10) | FGGGTK VEIK | (SEQ ID NO: 11) |
| Ab1218 | NIQMTQSPSALSASVG DRVTITC | (SEQ ID NO: 54) | KASQDIHR YLS | (SEQ ID NO: 79) | WFQQKPGK APKHLIY | (SEQ ID NO: 66) | RESRFVD | (SEQ ID NO: 56) | GVPSRFSGSGSGTEFTLTISS LQPEDFATYYC | (SEQ ID NO: 74) | LQYDEFPYT | (SEQ ID NO: 10) | FGGGTK VEIK | (SEQ ID NO: 11) |
| Ab1219 | NIQMTQSPSALSASVG DRVTITC | (SEQ ID NO: 54) | KASQDIHR YLS | (SEQ ID NO: 79) | WFQQKPGK APKHLIY | (SEQ ID NO: 66) | RHVRFVD | (SEQ ID NO: 56) | GVPSRFSGSGSGTEFTLTISS LQPEDFATYYC | (SEQ ID NO: 75) | LQYDEFPYT | (SEQ ID NO: 10) | FGGGTK VEIK | (SEQ ID NO: 11) |
| Ab1220 | NIQMTQSPSALSASVG DRVTITC | (SEQ ID NO: 54) | KASQDIHR YLS | (SEQ ID NO: 79) | WFQQKPGK APKHLIY | (SEQ ID NO: 66) | RHIRFVD | (SEQ ID NO: 56) | GVPSRFSGSGSGTEFTLTISS LQPEDFATYYC | (SEQ ID NO: 76) | LQYDEFPYT | (SEQ ID NO: 10) | FGGGTK VEIK | (SEQ ID NO: 11) |
| Ab1121 | NIQMTQSPSALSASVG DRVTITC | (SEQ ID NO: 54) | KASQDIHR YLS | (SEQ ID NO: 79) | WFQQKPGK APKHLIY | (SEQ ID NO: 66) | RHERFVD | (SEQ ID NO: 56) | GVPSRFSGSGSGTEFTLTISS LQPEDFATYYC | (SEQ ID NO: 77) | LQYDEFPYT | (SEQ ID NO: 10) | FGGGTK VEIK | (SEQ ID NO: 11) |
| Ab1122 | NIQMTQSPSALSASVG DRVTITC | (SEQ ID NO: 54) | KASQDIHR YLS | (SEQ ID NO: 79) | WFQQKPGK APKHLIY | (SEQ ID NO: 66) | RHSRFVD | (SEQ ID NO: 56) | GVPSRFSGSGSGTEFTLTISS LQPEDFATYYC | (SEQ ID NO: 78) | LQYDEFPYT | (SEQ ID NO: 10) | FGGGTK VEIK | (SEQ ID NO: 11) |
| Ab1123 | NIQMTQSPSALSASVG DRVTITC | (SEQ ID NO: 54) | RASQDIHR YLS | (SEQ ID NO: 79) | WFQQKPGK APKHLIY | (SEQ ID NO: 66) | RANRLVS | (SEQ ID NO: 56) | GVPSRFSGSGSGTEFTLTISS LQPEDFATYYC | (SEQ ID NO: 63) | LQYDEFPYT | (SEQ ID NO: 10) | FGGGTK VEIK | (SEQ ID NO: 11) |
| Ab1124 | NIQMTQSPSALSASVG DRVTITC | (SEQ ID NO: 54) | RASQDIHR YLS | (SEQ ID NO: 79) | WFQQKPGK APKHLIY | (SEQ ID NO: 66) | RYVRFVD | (SEQ ID NO: 56) | GVPSRFSGSGSGTEFTLTISS LQPEDFATYYC | (SEQ ID NO: 67) | LQYDEFPYT | (SEQ ID NO: 10) | FGGGTK VEIK | (SEQ ID NO: 11) |
| Ab1125 | NIQMTQSPSALSASVG DRVTITC | (SEQ ID NO: 54) | RASQDIHR YLS | (SEQ ID NO: 79) | WFQQKPGK APKHLIY | (SEQ ID NO: 66) | RYIRFVD | (SEQ ID NO: 56) | GVPSRFSGSGSGTEFTLTISS LQPEDFATYYC | (SEQ ID NO: 68) | LQYDEFPYT | (SEQ ID NO: 10) | FGGGTK VEIK | (SEQ ID NO: 11) |
| Ab1126 | NIQMTQSPSALSASVG DRVTITC | (SEQ ID NO: 54) | RASQDIHR YLS | (SEQ ID NO: 79) | WFQQKPGK APKHLIY | (SEQ ID NO: 66) | RYERFVD | (SEQ ID NO: 56) | GVPSRFSGSGSGTEFTLTISS LQPEDFATYYC | (SEQ ID NO: 69) | LQYDEFPYT | (SEQ ID NO: 10) | FGGGTK VEIK | (SEQ ID NO: 11) |
| Ab1127 | NIQMTQSPSALSASVG DRVTITC | (SEQ ID NO: 54) | RASQDIHR YLS | (SEQ ID NO: 79) | WFQQKPGK APKHLIY | (SEQ ID NO: 66) | RYSRFVD | (SEQ ID NO: 56) | GVPSRFSGSGSGTEFTLTISS LQPEDFATYYC | (SEQ ID NO: 70) | LQYDEFPYT | (SEQ ID NO: 10) | FGGGTK VEIK | (SEQ ID NO: 11) |
| Ab1128 | NIQMTQSPSALSASVG DRVTITC | (SEQ ID NO: 54) | RASQDIHR YLS | (SEQ ID NO: 79) | WFQQKPGK APKHLIY | (SEQ ID NO: 66) | REVRFVD | (SEQ ID NO: 56) | GVPSRFSGSGSGTEFTLTISS LQPEDFATYYC | (SEQ ID NO: 71) | LQYDEFPYT | (SEQ ID NO: 10) | FGGGTK VEIK | (SEQ ID NO: 11) |
| Ab1129 | NIQMTQSPSALSASVG DRVTITC | (SEQ ID NO: 54) | RASQDIHR YLS | (SEQ ID NO: 79) | WFQQKPGK APKHLIY | (SEQ ID NO: 66) | REIRFVD | (SEQ ID NO: 56) | GVPSRFSGSGSGTEFTLTISS LQPEDFATYYC | (SEQ ID NO: 72) | LQYDEFPYT | (SEQ ID NO: 10) | FGGGTK VEIK | (SEQ ID NO: 11) |
| Ab1230 | NIQMTQSPSALSASVG DRVTITC | (SEQ ID NO: 54) | RASQDIHR YLS | (SEQ ID NO: 79) | WFQQKPGK APKHLIY | (SEQ ID NO: 66) | REERFVD | (SEQ ID NO: 56) | GVPSRFSGSGSGTEFTLTISS LQPEDFATYYC | (SEQ ID NO: 73) | LQYDEFPYT | (SEQ ID NO: 10) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1231 | NIQMTQSPSALSASVG DRVTITC | (SEQ ID NO: 51) | RASQDIHR YLS | (SEQ ID NO: 79) | WFQQKPGK APKHLIY | (SEQ ID NO: 56) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1232 | NIQMTQSPSALSASVG DRVTITC | (SEQ ID NO: 51) | RASQDIHR YLS | (SEQ ID NO: 79) | WFQQKPGK APKHLIY | (SEQ ID NO: 56) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1233 | NIQMTQSPSALSASVG DRVTITC | (SEQ ID NO: 51) | RASQDIHR YLS | (SEQ ID NO: 79) | WFQQKPGK APKHLIY | (SEQ ID NO: 56) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1234 | NIQMTQSPSALSASVG DRVTITC | (SEQ ID NO: 51) | RASQDIHR YLS | (SEQ ID NO: 79) | WFQQKPGK APKHLIY | (SEQ ID NO: 56) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1235 | NIQMTQSPSALSASVG DRVTITC | (SEQ ID NO: 51) | RASQDIHR YLS | (SEQ ID NO: 79) | WFQQKPGK APKHLIY | (SEQ ID NO: 56) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1236 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1237 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1238 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1239 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1240 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1241 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1242 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1243 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1244 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1245 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1246 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1247 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1248 | NIQMTQSPSAMSASVG DRVTITC | (SEQ ID NO: 51) | KASQSIHR YLS | (SEQ ID NO: 66) | WYQQKPGK APKHLIY | (SEQ ID NO: 58) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1249 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1250 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1251 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1252 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1253 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1254 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1255 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1256 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1257 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1258 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1259 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1260 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1261 | NIQMTQSPSAMSASVG DRVTITC | (SEQ ID NO: 51) | RASQDIHR YLS | (SEQ ID NO: 79) | WYQQKPGK APKHLIY | (SEQ ID NO: 58) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1262 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1263 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | RVVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1264 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1265 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1266 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1267 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1268 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1269 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1270 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1271 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1272 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1273 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1274 | NIQMTQSPSSLSASVG DRVTITC | (SEQ ID NO: 57) | KASQDIHR YLS | (SEQ ID NO: 66) | WYQQKPGK VPKHLIY | (SEQ ID NO: 55) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1275 | NIQMTQSPSSLSASVG DRVTITC | (SEQ ID NO: 57) | KASQDIHR YLS | (SEQ ID NO: 79) | WYQQKPGK VPKHLIY | (SEQ ID NO: 55) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1276 | NIQMTQSPSSLSASVG DRVTITC | (SEQ ID NO: 57) | KASQDIHR YLS | (SEQ ID NO: 79) | WYQQKPGK VPKHLIY | (SEQ ID NO: 55) | RVVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1277 | NIQMTQSPSSLSASVG DRVTITC | (SEQ ID NO: 57) | KASQDIHR YLS | (SEQ ID NO: 79) | WYQQKPGK VPKHLIY | (SEQ ID NO: 55) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1278 | NIQMTQSPSSLSASVG DRVTITC | (SEQ ID NO: 57) | KASQDIHR YLS | (SEQ ID NO: 79) | WYQQKPGK VPKHLIY | (SEQ ID NO: 55) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1279 | NIQMTQSPSSLSASVG DRVTITC | (SEQ ID NO: 57) | RASQDIHR YLS | (SEQ ID NO: 79) | WYQQKPGK VPKHLIY | (SEQ ID NO: 55) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1280 | NIQMTQSPSSLSASVG DRVTITC | (SEQ ID NO: 57) | RASQDIHR YLS | (SEQ ID NO: 79) | WYQQKPGK VPKHLIY | (SEQ ID NO: 55) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1281 | NIQMTQSPSSLSASVG DRVTITC | (SEQ ID NO: 57) | RASQDIHR YLS | (SEQ ID NO: 79) | WYQQKPGK VPKHLIY | (SEQ ID NO: 55) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1282 | NIQMTQSPSSLSASVG DRVTITC | (SEQ ID NO: 57) | RASQDIHR YLS | (SEQ ID NO: 79) | WYQQKPGK VPKHLIY | (SEQ ID NO: 55) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1283 | NIQMTQSPSSLSASVG DRVTITC | (SEQ ID NO: 57) | RASQDIHR YLS | (SEQ ID NO: 79) | WYQQKPGK VPKHLIY | (SEQ ID NO: 55) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1284 | NIQMTQSPSSLSASVG DRVTITC | (SEQ ID NO: 57) | RASQDIHR YLS | (SEQ ID NO: 79) | WYQQKPGK VPKHLIY | (SEQ ID NO: 55) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1285 | NIQMTQSPSSLSASVG DRVTITC | (SEQ ID NO: 57) | RASQDIHR YLS | (SEQ ID NO: 79) | WYQQKPGK VPKHLIY | (SEQ ID NO: 55) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1286 | NIQMTQSPSSLSASVG DRVTITC | (SEQ ID NO: 57) | RASQDIHR YLS | (SEQ ID NO: 79) | WYQQKPGK VPKHLIY | (SEQ ID NO: 55) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1287 | NIQMTQSPSSLSASVG DRVTITC | (SEQ ID NO: 57) | RASQDIHR YLS | (SEQ ID NO: 79) | WYQQKPGK VPKHLIY | (SEQ ID NO: 55) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1288 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1289 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1290 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1291 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1292 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1293 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1294 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1295 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1296 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1297 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1298 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1299 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1300 | NIQMTQSPSSLSASVG DRVTITC | (SEQ ID NO: 57) | KASQDIHR YLS | (SEQ ID NO: 66) | WFQQKPGK APKHLIY | (SEQ ID NO: 56) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1301 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1302 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1303 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1304 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1305 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1306 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1307 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1308 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1309 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1310 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1311 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1312 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1313 | NIQMTQSPSSLSASVG DRVTITC | (SEQ ID NO: 57) | RASQDIHR YLS | (SEQ ID NO: 79) | WFQQKPGK APKHLIY | (SEQ ID NO: 56) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1314 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1315 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1316 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1317 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1318 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1319 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1320 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1321 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1322 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1323 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1324 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1325 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1326 | NIQMTQSPSALSASVG DRVTITC | (SEQ ID NO: 54) | KASQDIHR YLS | (SEQ ID NO: 66) | WYQQKPGK APKHLIY | (SEQ ID NO: 58) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1327 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1328 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | RVVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1329 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1330 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1331 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1332 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1333 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1334 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1335 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1336 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1337 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1338 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1339 | NIQMTQSPSALSASVG DRVTITC | (SEQ ID NO: 54) | RASQDIHR YLS | (SEQ ID NO: 79) | WYQQKPGK APKHLIY | (SEQ ID NO: 58) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1340 | NIQMTQSPSSLSASVG DRVTITC | (SEQ ID NO: 57) | KASQDIHR YLS | (SEQ ID NO: 66) | WYQQKPGK APKHLIY | (SEQ ID NO: 58) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1341 | NIQMTQSPSSLSASVG DRVTITC | (SEQ ID NO: 57) | KASQDIHR YLS | (SEQ ID NO: 66) | WYQQKPGK APKHLIY | (SEQ ID NO: 58) | RUVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1342 | NIQMTQSPSSLSASVG DRVTITC | (SEQ ID NO: 57) | KASQDIHR YLS | (SEQ ID NO: 66) | WYQQKPGK APKHLIY | (SEQ ID NO: 58) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1343 | NIQMTQSPSSLSASVG DRVTITC | (SEQ ID NO: 57) | KASQDIHR YLS | (SEQ ID NO: 79) | WYQQKPGK APKHLIY | (SEQ ID NO: 58) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1344 | NIQMTQSPSSLSASVG DRVTITC | (SEQ ID NO: 57) | KASQDIHR YLS | (SEQ ID NO: 79) | WYQQKPGK APKHLIY | (SEQ ID NO: 58) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1345 | NIQMTQSPSSLSASVG DRVTITC | (SEQ ID NO: 57) | KASQDIHR YLS | (SEQ ID NO: 79) | WYQQKPGK APKHLIY | (SEQ ID NO: 58) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1346 | NIQMTQSPSSLSASVG DRVTITC | (SEQ ID NO: 57) | KASQDIHR YLS | (SEQ ID NO: 79) | WYQQKPGK APKHLIY | (SEQ ID NO: 58) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1347 | NIQMTQSPSSLSASVG DRVTITC | (SEQ ID NO: 57) | KASQDIHR YLS | (SEQ ID NO: 79) | WYQQKPGK APKHLIY | (SEQ ID NO: 58) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1348 | NIQMTQSPSSLSASVG DRVTITC | (SEQ ID NO: 57) | KASQDIHR YLS | (SEQ ID NO: 79) | WYQQKPGK APKHLIY | (SEQ ID NO: 58) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1349 | NIQMTQSPSSLSASVG DRVTITC | (SEQ ID NO: 57) | KASQDIHR YLS | (SEQ ID NO: 79) | WYQQKPGK APKHLIY | (SEQ ID NO: 58) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1350 | NIQMTQSPSSLSASVG DRVTITC | (SEQ ID NO: 57) | KASQDIHR YLS | (SEQ ID NO: 79) | WYQQKPGK APKHLIY | (SEQ ID NO: 58) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1351 | NIQMTQSPSSLSASVG DRVTITC | (SEQ ID NO: 57) | KASQDIHR YLS | (SEQ ID NO: 79) | WYQQKPGK APKHLIY | (SEQ ID NO: 58) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1352 | NIQMTQSPSSLSASVG DRVTITC | (SEQ ID NO: 57) | KASQDIHR YLS | (SEQ ID NO: 79) | WYQQKPGK APKHLIY | (SEQ ID NO: 58) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1353 | NIQMTQSPSSLSASVG DRVTITC | (SEQ ID NO: 57) | RASQDIHR YLS | (SEQ ID NO: 57) | WYQQKPGK APKHLIY | (SEQ ID NO: 58) | RANRLVS | (SEQ ID NO: 63) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1354 | NIQMTQSPSSLSASVG DRVTITC | (SEQ ID NO: 57) | RASQDIHR YLS | (SEQ ID NO: 57) | WYQQKPGK APKHLIY | (SEQ ID NO: 58) | RYVRFVD | (SEQ ID NO: 67) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1355 | NIQMTQSPSSLSASVG DRVTITC | (SEQ ID NO: 57) | RASQDIHR YLS | (SEQ ID NO: 57) | WYQQKPGK APKHLIY | (SEQ ID NO: 58) | RYIRFVD | (SEQ ID NO: 68) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1356 | NIQMTQSPSSLSASVG DRVTITC | (SEQ ID NO: 57) | RASQDIHR YLS | (SEQ ID NO: 57) | WYQQKPGK APKHLIY | (SEQ ID NO: 58) | RYERFVD | (SEQ ID NO: 69) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1357 | NIQMTQSPSSLSASVG DRVTITC | (SEQ ID NO: 57) | RASQDIHR YLS | (SEQ ID NO: 57) | WYQQKPGK APKHLIY | (SEQ ID NO: 58) | RYSRFVD | (SEQ ID NO: 70) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1358 | NIQMTQSPSSLSASVG DRVTITC | (SEQ ID NO: 57) | RASQDIHR YLS | (SEQ ID NO: 57) | WYQQKPGK APKHLIY | (SEQ ID NO: 58) | REVRFVD | (SEQ ID NO: 71) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

TABLE 4-continued

Exemplary Antibodies with Specific VL FR sequences and specific VL CDR sequences.

| Antibody | VL-FR1 | SEQ ID NO: | VL-CDR 1 | SEQ ID NO: | VL-FR2 | SEQ ID NO: | VL-CDR 2 | SEQ ID NO: | VL-FR3 | SEQ ID NO: | VL-CDR 3 | SEQ ID NO: | VL-FR4 | SEQ ID NO: |
|---|---|---|---|---|---|---|---|---|---|---|---|---|---|---|
| Ab1359 | NIQMTQSPSSLSASVG DRVTITC | (SEQ ID NO: 57) | RASQDIHR YLS | (SEQ ID NO: 79) | WYQQKPGK APKHLIY | (SEQ ID NO: 58) | REIRFVD | (SEQ ID NO: 72) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1360 | NIQMTQSPSSLSASVG DRVTITC | (SEQ ID NO: 57) | RASQDIHR YLS | (SEQ ID NO: 79) | WYQQKPGK APKHLIY | (SEQ ID NO: 58) | REERFVD | (SEQ ID NO: 73) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1361 | NIQMTQSPSSLSASVG DRVTITC | (SEQ ID NO: 57) | RASQDIHR YLS | (SEQ ID NO: 79) | WYQQKPGK APKHLIY | (SEQ ID NO: 58) | RESRFVD | (SEQ ID NO: 74) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1362 | NIQMTQSPSSLSASVG DRVTITC | (SEQ ID NO: 57) | RASQDIHR YLS | (SEQ ID NO: 79) | WYQQKPGK APKHLIY | (SEQ ID NO: 58) | RHVRFVD | (SEQ ID NO: 75) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1363 | NIQMTQSPSSLSASVG DRVTITC | (SEQ ID NO: 57) | RASQDIHR YLS | (SEQ ID NO: 79) | WYQQKPGK APKHLIY | (SEQ ID NO: 58) | RHIRFVD | (SEQ ID NO: 76) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1364 | NIQMTQSPSSLSASVG DRVTITC | (SEQ ID NO: 57) | RASQDIHR YLS | (SEQ ID NO: 79) | WYQQKPGK APKHLIY | (SEQ ID NO: 58) | RHERFVD | (SEQ ID NO: 77) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |
| Ab1365 | NIQMTQSPSSLSASVG DRVTITC | (SEQ ID NO: 57) | RASQDIHR YLS | (SEQ ID NO: 79) | WYQQKPGK APKHLIY | (SEQ ID NO: 58) | RHSRFVD | (SEQ ID NO: 78) | GVPSRFSGSGSGTEFTLTISS LQPEDFATYYC | (SEQ ID NO: 10) | LQYDEFPYT | (SEQ ID NO: 64) | FGGGTK VEIK | (SEQ ID NO: 11) |

In another specific embodiment, provided herein is an antibody or antigen-binding fragment, which comprises (I) four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1 comprises the amino acid sequence listed in the second column of Table 3 for the antibody or antigen-binding fragment, VH FR2 comprises the amino acid sequence listed in the sixth column of Table 3 for the antibody or antigen-binding fragment, VH FR3 comprises the amino acid sequence listed in the $10^{th}$ column of Table 3 for the antibody or antigen-binding fragment, VH FR4 comprises the amino acid sequence listed in the $14^{th}$ column of Table 3 for the antibody or antigen-binding fragment, VH CDR1 comprises the amino acid sequence listed in the fourth column of Table 3 for the antibody or antigen-binding fragment, VH CDR2 comprises the amino acid sequence listed in the eighth column of Table 3 for the antibody or antigen-binding fragment, and VH CDR3 comprises the amino acid sequence listed in the $12^{nd}$ column of Table 3 for the antibody or antigen-binding fragment; and (II) four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1 comprises the amino acid sequence listed in the second column of Table 4 for the antibody or antigen-binding fragment, VL FR2 comprises the amino acid sequence listed in the sixth column of Table 4 for the antibody or antigen-binding fragment, VL FR3 comprises the amino acid sequence listed in the $10^{th}$ column of Table 4 for the antibody or antigen-binding fragment, VL FR4 comprises the amino acid sequence listed in the $14^{th}$ column of Table 4 for the antibody or antigen-binding fragment, VL CDR1 comprises the amino acid sequence listed in the fourth column of Table 4 for the antibody or antigen-binding fragment, VL CDR2 comprises the amino acid sequence listed in the eighth column of Table 4 for the antibody or antigen-binding fragment, and VL CDR3 comprises the amino acid sequence listed in the $12^{nd}$ column of Table 4 for the antibody or antigen-binding fragment.

In another aspect, provided herein is an antibody or antigen-binding fragment thereof which specifically binds to CD47 and comprises VH CDRs described in this Section and VL CDRs described in this Section.

In another aspect, provided herein is an antibody or antigen-binding fragment thereof which specifically binds to CD47 and comprises a VH described in Section 5.1.1, VH CDRs described in this Section, and VL CDRs described in this Section.

In another aspect, provided herein is an antibody or antigen-binding fragment thereof which specifically binds to CD47 and comprises a VL described in Section 5.1.2, VH CDRs described in this Section, and VL CDRs described in this Section.

In another aspect, provided herein is an antibody or antigen-binding fragment thereof which specifically binds to CD47 and comprises a VL described in Section 5.1.1, VL described in Section 5.1.2, VH CDRs described in this Section, and VL CDRs described in this Section.

In any of the aspects and embodiments described above, the VH CDR3 can also comprise the amino acid sequence of AYGSSSYPMDY (SEQ ID NO: 125) instead of NAAYGSSSYPMDY (SEQ ID NO: 61). Thus, the amino acid sequence of the corresponding VH FR3 comprises the additional residues of NA at the C-terminus of the VH FR3 sequence described above.

In any of the aspects and embodiments described above, the VH CDR2 can also comprise the amino acid sequence of WIDPDQGDTEYAQKFQX$_{H75}$ (SEQ ID NO: 126), wherein X$_{H75}$ is D or G, instead of WIDPDQGDTE (SEQ ID NO: 60). Thus, the amino acid sequence of the corresponding VH FR3 is shorter by seven residues at the N-terminus relative to the VH FR3 sequence described above.

In certain embodiments, the boundaries of the CDR sequences described herein are determined according to the Kabat numbering system. In certain embodiments, the boundaries of the CDR sequences described herein are determined according to the Chothia numbering system. In certain embodiments, the boundaries of the CDR sequences described herein are determined according to the IMGT numbering system. In certain embodiments, the boundaries of the CDR sequences described herein are determined according to the ABM numbering system. However, variants of these CDR sequences that are determined according to the Kabat numbering system, the Chothia numbering scheme, the IMGT numbering system, or the ABM numbering system for determining CDRs are also contemplated. Thus, provided herein are also antibodies or antigen-binding fragments that comprise one or more variants of the CDR sequences described above that are determined according to the Kabat numbering system, the Chothia numbering scheme, the IMGT numbering system, or the ABM numbering system. Also provided herein are antibodies or antigen-binding fragments that comprise one or more variants of the CDR sequences described above that are determined according to the Kabat numbering system, the Chothia numbering scheme, the IMGT numbering system, or the ABM numbering system, and further comprise one or more variants of the VH FR sequences described in Section 5.1.1 that are determined in accordance with the Kabat numbering system, the Chothia numbering scheme, the IMGT numbering system, or the ABM numbering system (as the case may be), and/or one or more variants of the VL FR sequences described in Section 5.1.2 that are determined in accordance with the Kabat numbering system, the Chothia numbering scheme, the IMGT numbering system, or the ABM numbering system (as the case may be).

5.2 Antibody Production

Antibodies or antigen-binding fragments thereof described herein can be produced by any method known in the art, for example, by chemical synthesis or by recombinant expression techniques.

Such methods can employ conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates);

*Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

Monoclonal antibodies can, for example, be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981). The term "monoclonal antibody" as used herein is not limited to antibodies produced through hybridoma technology. For example, monoclonal antibodies can be produced recombinantly from host cells (e.g., mammalian host cells such as CHO cells) engineered to express an antibody described herein or an antigen-binding fragment thereof, for example, a light chain and/or heavy chain of such an antibody.

Further, the antibodies described herein or antigen-binding fragments thereof can also be generated using various phage display methods known in the art. In phage display methods, functional antibody domains are displayed on the surface of phage particles which carry the polynucleotide sequences encoding them. Examples of phage display methods that can be used to make the antibodies described herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

In specific aspects, an antibody or antigen-binding fragment thereof as provided herein can be produced using a cell-free (CF) expression system, for example, a CF expression system as known in the art, and, for example, as described in the Examples below. For example, CF expression systems can include cell-free extracts, such as S30 cell-free extracts, with DsbC, and 20 amino acids (e.g., natural or non-natural), and optionally, one or more of iodoacetamide, magnesium glutamate, ammonium glutamate, mM potassium glutamate, sodium pyruvate, AMP, GMP, UMP, and CMP, sodium oxalate, putrescine, spermidine, potassium phosphate, T7 RNAP, and oxidized (GSSG) glutathione. Heavy chain plasmids and light chain plasmids are added accordingly to the CF extract composition for polypeptide production and purification.

In some aspects, the CF expression system is an in vitro transcription and translation system as described in Yin et al., *mAbs*, 2012, 4:217-225, incorporated by reference in its entirety. In some aspects, the cell-free system utilizes a cell-free extract from a eukaryoctic cell or from a prokaryotic cell. In some aspects, the prokaryotic cell is *E. coli*.

In particular embodiments, the CF expression system can utilize a system as described in US Application Publication No. US 2014/0315245, which is hereby incorporated by reference in its entirety. For example, the CF expression system can comprise a bacterial extract having an oxidative phosphorylation system and components necessary for cell free protein synthesis and, in certain embodiments, can further comprise an exogenous protein chaperone, e.g., a protein disulfide isomerase (PDI), or a peptide-prolyl cistrans isomerase. In specific embodiments, the PDI is a member of the Dsb (disulfide bond formation) family of *E. coli*, for example, DsbA or DsbC. In certain embodiments, the CF expression system comprises a cell extract of *E. coli* strain SBDG028, SBDG031, or SBDG044, as described in US Application Publication No. US 2014/0315245, which can, for example, be prepared according to Zawada et al., Biotechnology and Bioengineering (2011) vol. 108, No. 7.

Antibodies or antigen-binding fragments thereof described herein can, for example, include chimeric antibodies. A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816, 567, 4,816,397, and 6,331,415.

Antibodies or antigen-binding fragments produced using techniques such as those described herein can be isolated using standard, well known techniques. For example, antibodies or antigen-binding fragments can be suitably separated from, e.g., culture medium, ascites fluid, serum, cell lysate, synthesis reaction material or the like by conventional immunoglobulin purification procedures such as, for example, protein A-Sepharose, hydroxylapatite chromatography, gel electrophoresis, dialysis, or affinity chromatography. As used herein, an "isolated" or "purified" antibody is substantially free of cellular material or other proteins from the cell or tissue source from which the antibody is derived, or substantially free of chemical precursors or other chemicals when chemically synthesized, or from the components of the CF expression system used to produce the antibodies.

Antibodies or antigen-binding fragments thereof described herein include antibody fragments can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region. Alternatively, antibody fragments described herein can routinely be produced via well known recombinant expression techniques. See, e.g., PCT publication No. WO 92/22324; Mullinax et al., 1992, BioTechniques 12(6):864-869; Sawai et a., 1995, AJRI 34:26-34; and Better et a., 1988, Science 240:1041-1043.

Antibodies or antigen-binding fragments thereof described herein can, for example, include humanized antibodies, e.g., deimmunized or composite human antibodies. A humanized antibody can comprise human constant region sequences. In certain embodiments, a humanized antibody can be selected from any class of immunoglobulins, including IgM, IgG, IgD, IgA and IgE, and any isotype, including IgG$_1$, IgG$_2$, IgG$_3$ and IgG$_4$. In certain embodiments, a humanized antibody can comprise kappa or lambda light chain constant sequences.

Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16): 10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), each of which is incorporated by reference herein in its entirety.

A composite human antibody can be generated using, for example, Composite Human Antibody™ technology (Antitope Ltd., Cambridge, United Kingdom). To generate composite human antibodies, variable region sequences are designed from fragments of multiple human antibody variable region sequences in a manner that avoids T cell epitopes, thereby minimizing the immunogenicity of the resulting antibody. Such antibodies can comprise human constant region sequences, e.g., human light chain and/or heavy chain constant regions.

Antibodies or antigen-binding fragments thereof described herein can, for example, be multispecific, e.g., bispecific, antibodies. Methods for making multispecific (e.g, bispecific antibodies) have been described, see, for example, U.S. Pat. Nos. 7,951,917, 7,183,076, 8,227,577, 5,837,242, 5,989,830, 5,869,620, 6,132,992, and 8,586,713.

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301.

Human antibodies can be produced using any method known in the art. For example, well known transgenic mice which are incapable of expressing functional endogenous murine immunoglobulins, but which can express human immunoglobulin genes, can be used. Alternatively, for example, phage display techniques, described above, can be utilized. Moreover, in some embodiments, human antibodies can, for example, be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen. Such methods are known and are described in the art, see, e.g., Shinmoto et al., Cytotechnology, 2004, 46:19-23; Naganawa et al., Human Antibodies, 2005, 14:27-31.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in International Application Publication No. WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

5.2.1 Polynucleotides, Cells and Vectors

In certain aspects, provided herein are polynucleotides comprising a nucleotide sequence encoding an antibody or an antigen-binding fragment thereof described herein (e.g., a variable light chain region and/or variable heavy chain region), and vectors, e.g., vectors comprising such polynucleotides for recombinant expression in host cells (e.g., *E. coli* and mammalian cells). In certain aspects, provided herein are cells (e.g., host cells) that express such antibodies or antigen-binding fragments. Also provided herein are methods of making the antibodies or antigen-binding fragments thereof described herein.

In certain aspects, provided herein are polynucleotides comprising a nucleotide sequence encoding the light chain or heavy chain of an antibody described herein. In certain embodiments, provided herein are polynucleotides comprising a nucleotide sequence encoding the light chain and heavy chain of an antibody described herein. The polynucleotides can comprise nucleotide sequences encoding a light chain comprising the VL FRs and CDRs of antibodies described herein. The polynucleotides can comprise nucleotide sequences encoding a heavy chain comprising the VH FRs and CDRs of antibodies described herein.

In certain embodiments, a polynucleotide provided herein is linked to a promoter and/or other polynucleotide regulatory element for expression of such polynucleotide sequence in a host cell. In certain embodiments, the promoter is derived from the genome of mammalian cells (e.g., metallothionein promoter) or from mammalian viruses (e.g., the adenovirus late promoter, the vaccinia virus 7.5K promoter). In a specific embodiment, the expression of nucleotide sequences encoding antibodies described herein is regulated by a constitutive promoter, inducible promoter or tissue specific promoter.

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. For example, human constant region sequences can be those described in U.S. Pat. No. 5,693,780.

In a particular embodiment, a polynucleotide provided herein comprises a nucleotide sequence encoding an antibody or antigen-binding fragment thereof described herein, wherein the antibody or antigen-binding fragment thereof comprises a heavy chain, wherein the constant region of the heavy chain comprises the amino acid sequence of a human gamma (γ) heavy chain constant region, for example, human gamma (γ) 1 heavy chain constant region, human gamma (γ) 2 heavy chain constant region, human gamma (γ) 3 heavy chain constant region, or human gamma (γ) 4 heavy chain constant region.

The polynucleotides described herein can be produced and the nucleotide sequences of the polynucleotides determined, by any method known in the art. Nucleotide sequences encoding antibodies described herein can be determined using methods well known in the art, e.g., nucleotide codons known to encode particular amino acids can be identified and assembled in such a way to generate a nucleic acid that encodes the antibody or antigen-binding fragment thereof. Such a polynucleotide encoding the antibody or antigen-binding fragment thereof can be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibod or antigen-binding fragment thereof, annealing and ligating of those oligonucleotides, and then amplification of the ligated oligonucleotides by PCR. Alternatively, a polynucleotide encoding an antibody or antigen-binding fragment thereof described herein can be generated from nucleic acid or nucleic acids using methods well known in the art (e.g., PCR and other molecular cloning methods).

In certain aspects, provided herein are vectors (e.g., expression vectors) comprising a polynucleotide comprising a nucleotide sequence encoding an antibody or an antigen-binding fragment thereof described herein, e.g., for recombinant expression in host cells (e.g., in mammalian cells such as CHO cells) or a CF system.

Also provided herein are isolated cells (e.g., host cells) comprising a polynucleotide described herein. Also provided herein are isolated cells (e.g., host cells) comprising a vector described herein. Also provided herein are isolated cells (e.g., host cells) comprising an antibody or an antigen-binding fragment thereof described herein.

In a particular aspect, provided herein are methods for producing an antibody or antigen-binding fragment thereof described herein, comprising expressing such an antibody or antigen-binding fragment thereof using isolated cells (e.g., host cells). In a specific embodiment, provided herein is a method of making an antibody or antigen-binding fragment thereof, comprising (a) culturing an isolated cell comprising the polynucleictide described herein; and (b) isolating the antibody or antigen-binding fragment thereof. In another specific embodiment, provided herein is a method of making an antibody or antigen-binding fragment thereof, comprising (a) culturing an isolated cell described herein; and (b) isolating the antibody or antigen-binding fragment thereof.

Recombinant expression of an antibody or antigen-binding fragment thereof described herein (e.g., a full-length antibody, heavy and/or light chain of an antibody, or a single chain antibody described herein) involves construction of an expression vector containing a polynucleotide that encodes the antibody or antigen-binding fragment thereof. Once a polynucleotide encoding an antibody molecule, heavy and/or light chain of an antibody, or a fragment thereof (e.g., heavy and/or light chain variable domains) described herein has been obtained, the vector for the production of the antibody molecule, heavy and/or light chain, or a fragment thereof, can be produced by recombinant DNA technology using techniques well-known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antigen-biding fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Application Publication Nos. WO 86/05807 and WO 89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or an antigen-binding fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an antibody described herein or an antigen-binding fragment thereof. In certain embodiments, provided herein is a population of host cells comprising such first host cell and such second host cell.

In a particular embodiment, provided herein is a population of vectors comprising a first vector comprising a polynucleotide encoding a light chain/light chain variable region of an antibody described herein, and a second vector comprising a polynucleotide encoding a heavy chain/heavy chain variable region of an antibody described herein.

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., E. coli and B. subtilis) transformed with recombinant bacteriophage DNA, plasmid DNA or cosmid DNA expression vectors containing antibody coding sequences; yeast (e.g., Saccharomyces Pichia) transformed with recombinant yeast expression vectors containing antibody coding sequences; insect cell systems infected with recombinant virus expression vectors (e.g., baculovirus) containing antibody coding sequences; plant cell systems (e.g., green algae such as Chlamydomonas reinhardtii) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, MDCK, HEK 293, NS0, PER.C6, VERO, CRL7O3O, HsS78Bst, HeLa, and NIH 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein or an antigen-binding fragment thereof are CHO cells, for example CHO cells from the CHO GS System™ (Lonza). In a specific embodiment, a mammalian expression vector is pOptiVEC™ or pcDNA3.3. In a particular embodiment, bacterial cells such as Escherichia coli, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In certain embodiments, antibodies described herein are produced by CHO cells or NS0 cells. In a specific embodiment, the expression of nucleotide sequences encoding antibodies or antigen-binding fragments thereof described herein is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the E. coli expression vector pUR278 (Ruther et al., 1983, EMBO 12:1791), in which the antibody coding sequence can be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV), for example, can be used as a vector to express foreign genes. The virus grows in Spodoptera frugiperda cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, Methods in Enzymol. 153:51-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, COS, MDCK, HEK 293, NIH 3T3, W138, BT483, Hs578T, HTB2, BT20 and T47D, NS0 (a murine myeloma cell line that does not endogenously produce any immunoglobulin chains), CRL7O3O and HsS78Bst cells. In certain embodiments, antibodies or antigen-binding fragments thereof described herein are produced in mammalian cells, such as CHO cells.

For long-term, high-yield production of recombinant proteins, stable expression cells can be generated. For example, cell lines which stably express an antibody described herein or an antigen-binding fragment thereof can be engineered. In specific embodiments, a cell provided herein stably expresses a light chain/light chain variable domain and a heavy chain/heavy chain variable domain which associate to form an antibody described herein or an antigen-binding fragment thereof.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an antibody or antigen-binding fragment thereof described herein. Such engineered cell lines can be particularly useful in screening and evaluation of compositions that interact directly or indirectly with the antibody molecule.

A number of selection systems can be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et a., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et a., 1984, Gene 30:147). Methods commonly known in the art of recombinant DNA technology can be routinely applied to select the desired recombinant clone, and such methods are described, for example, in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds.), *Current Protocols in Human Genetics*, John Wiley & Sons, N Y (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody or antigen-binding fragment thereof described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or antigen-binding fragments thereof described herein can be fused to heterologous polypeptide sequences described herein or otherwise known in the art to facilitate purification.

In specific embodiments, an antibody or antigen-binding fragment described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

5.3 Pharmaceutical Compositions and Kits

Provided herein are compositions, pharmaceutical compositions, and kits comprising one or more antibodies described herein, or antigen-binding fragments thereof, or conjugates thereof. In particular aspects, compositions (e.g., pharmaceutical compositions) described herein can be for in vitro, in vivo, or ex vivo uses. Non-limiting examples of uses include uses to modulate (e.g., inhibit or induce/enhance) antigen activity and uses to manage or treat a disorder, for example, cancer. In specific embodiments, provided herein is a pharmaceutical composition comprising a therapeutically effective amount of an antibody (e.g., a humanized antibody) or antigen-binding fragment thereof described and a pharmaceutically acceptable carrier or excipient.

As used herein, the term "pharmaceutically acceptable" means being approved by a regulatory agency of the Federal or a state government, or listed in the U.S. Pharmacopeia, European Pharmacopeia or other generally recognized Pharmacopeia for use in animals, and more particularly in humans.

Formulations containing one or more antibodies provided herein or an antigen-binding fragment thereof can be prepared for storage by mixing the antibody having the desired degree of purity with optional physiologically acceptable carriers, excipients or stabilizers (*Remington's Pharmaceutical Sciences* (1990) Mack Publishing Co., Easton, Pa.; *Remington: The Science and Practice of Pharmacy*, 21st ed. (2006) Lippincott Williams & Wilkins, Baltimore, Md.). Such formulations can, for example, be in the form of, e.g., lyophilized formulations or aqueous solutions. Pharmaceutical carriers suitable for administration of the antibodies provided herein include any such carriers known to those skilled in the art to be suitable for the particular mode of administration. Acceptable carriers, excipients, or stabilizers are nontoxic to recipients at the dosages and concentrations employed, and include buffers such as phosphate, citrate, and other organic acids; and/or non-ionic surfactants such as TWEEN™, PLURONICS™ or polyethylene glycol (PEG).

Formulations to be used for in vivo administration can be sterile. This can be readily accomplished, for example, by filtration through, e.g., sterile filtration membranes.

In specific aspects, the pharmaceutical compositions provided herein contain therapeutically effective amounts of one or more of the antibodies or antigen-binding fragments provided herein in a pharmaceutically acceptable carrier. Such pharmaceutical compositions are useful in the prevention, treatment, management or amelioration of a condition or disorder described herein or one or more symptoms thereof.

Compositions provided herein can contain one or more antibodies provided herein or an antigen-binding fragment thereof. In one embodiment, compositions are provided wherein antibodies or antigen-binding fragments described herein are formulated into suitable pharmaceutical preparations, such as solutions, suspensions, powders, sustained release formulations or elixirs in sterile solutions or suspensions for parenteral administration, or as transdermal patch preparation and dry powder inhalers.

In one embodiment, compositions provided herein are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

In certain aspects, an antibody provided herein is included in the pharmaceutically acceptable carrier in an effective amount sufficient to exert a therapeutically useful effect in the absence of, or with minimal or negligible, undesirable side effects on the patient treated.

Concentrations of the antibody in a pharmaceutical composition provided herein will depend on, e.g., the physicochemical characteristics of the antibody, the dosage schedule, and amount administered as well as other factors.

Pharmaceutical compositions described herein are provided for administration to humans or animals (e.g., mammals) in unit dosage forms, such as sterile parenteral (e.g., intravenous) solutions or suspensions containing suitable quantities of the compounds or pharmaceutically acceptable derivatives thereof. Pharmaceutical compositions are also provided for administration to humans and animals in unit dosage form, such as tablets, capsules, pills, powders, granules, and oral or nasal solutions or suspensions, and oil-water emulsions containing suitable quantities of an antibody or antigen-binding fragment thereof described herein or pharmaceutically acceptable derivatives thereof. The antibody or antigen-binding fragment thereof described herein is, in one embodiment, formulated and administered in unit-dosage forms or multiple-dosage forms. Unit-dose forms as used herein refers to physically discrete units suitable for human or animal (e.g., mammal) subjects and packaged individually. Each unit-dose contains a predetermined quantity of an antibody or antigen-binding fragment thereof described herein sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles. Hence, in specific aspects, multiple dose form is a multiple of unit-doses which are not segregated in packaging.

In certain embodiments, one or more antibodies described herein or antigen-binding fragments thereof are in a liquid pharmaceutical formulation. Liquid pharmaceutically administrable compositions can, for example, be prepared by dissolving, dispersing, or otherwise mixing an antibody and optional pharmaceutical adjuvants in a carrier, such as, for example, water, saline, aqueous dextrose, glycerol, glycols, and the like, to thereby form a solution or suspension. In certain embodiments, a pharmaceutical composition provided herein to be administered can also contain minor amounts of nontoxic auxiliary substances such as wetting agents, emulsifying agents, solubilizing agents, and pH buffering agents and the like.

Actual methods of preparing such dosage forms are known, or will be apparent, to those skilled in this art; for example, see, e.g., *Remington's Pharmaceutical Sciences* (1990) Mack Publishing Co., Easton, Pa.; *Remington: The Science and Practice of Pharmacy,* 21st ed. (2006) Lippincott Williams & Wilkins, Baltimore, Md.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. Other routes of administration may include, enteric administration, intracerebral administration, nasal administration, intraarterial administration, intracardiac administration, intraosseous infusion, intrathecal administration, and intraperitoneal administration.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as sucrose, glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Pharmaceutical carriers also include ethyl alcohol, polyethylene glycol and propylene glycol for water miscible vehicles; and sodium hydroxide, hydrochloric acid, citric acid or lactic acid for pH adjustment.

In certain embodiments, intravenous or intraarterial infusion of a sterile aqueous solution containing an antibody or antigen-binding fragment thereof described herein is an effective mode of administration. Another embodiment is a sterile aqueous or oily solution or suspension containing an antibody or antigen-binding fragment thereof described herein injected as necessary to produce the desired pharmacological effect.

In specific embodiments, an antibody or antigen-binding fragment thereof described herein can be suspended in micronized or other suitable form. The form of the resulting mixture depends upon a number of factors, including the intended mode of administration and the solubility of the compound in the selected carrier or vehicle.

In other embodiments, the pharmaceutical formulations are lyophilized powders, which can be reconstituted for administration as solutions, emulsions and other mixtures. They can also be reconstituted and formulated as solids or gels.

Lyophilized powder can, for example, be prepared by dissolving an antibody or antigen-binding fragment thereof provided herein, in a suitable solvent. In some embodiments, the lyophilized powder is sterile. Suitable solvents can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. A suitable solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides an example of a formulation. In one embodiment, the resulting solution will be apportioned into vials for lyophilization. Lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier.

In certain aspects, antibodies or antigen-binding fragments thereof provided herein can be formulated for local administration or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

Antibodies or antigen-binding fragments thereof and other compositions provided herein can also be formulated to be targeted to a particular tissue, organ, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, antibodies described herein are targeted (or otherwise administered) to the visual organs, bone marrow, gastrointestinal tract, lungs, brain, or joints. In specific embodiments, an antibody described herein is capable of crossing the blood-brain barrier.

Provided herein is a pharmaceutical pack or kit comprising one or more containers filled with one or more of the ingredients of the pharmaceutical compositions described herein, such as one or more antibodies or antigen-binding fragments thereof provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits comprising one or more of the antibodies or antigen-binding fragments thereof described herein. In one embodiment, a kit comprises an antibody or or antigen-binding fragment thereof described herein, in one or more containers. In a specific embodiment, kits described herein contain a substantially purified antigen as a control. In another specific embodiment, the kits described herein further comprise a control antibody which does not react with an antigen. In another specific embodiment, kits described herein contain one or more elements for detecting the binding of a modified antibody to an antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized antigen. The antigen provided in the kit can also be attached to a solid support. In a more specific embodiment, the detecting means of the above described kit includes a solid support to which an antigen is attached. Such a kit can also include a non-attached reporter-labeled anti-human antibody or anti-mouse/rat antibody. In this embodiment, binding of the antibody to the antigen can be detected by binding of the said reporter-labeled antibody.

5.4 Uses and Methods

In particular aspects, provided herein are methods of modulating an antigen (e.g., CD47) activity with an antibody (e.g., anti-CD47 antibody) or an antigen-binding fragment thereof described herein that specifically binds to the antigen.

In specific embodiments, provided herein are methods of inhibiting (e.g., partially inhibiting) an antigen (e.g., CD47) activity with an antibody (e.g., anti-CD47 antibody) or an antigen-binding fragment thereof described herein that specifically binds to and antagonizes the antigen (e.g., CD47) activity. In specific embodiments, provided herein are methods of activating an antigen activity with an antibody or an antigen-binding fragment thereof described herein that specifically binds to and agonizes the antigen activity.

In certain embodiments, provided herein are methods of managing or treating a condition or disorder, such as cancer, autoimmune disorder, immunological disorder or infectious disease, using an antibody (e.g., anti-CD47 antibody) or an antigen-binding fragment thereof described herein. In certain embodiments, provided herein are methods of protecting against a condition or disorder, such as cancer, autoimmune disorder, immunological disorder or infectious disease, using an antibody (e.g., anti-CD47 antibody) or an antigen-binding fragment thereof described herein. In certain embodiments, provided herein is a method of alleviating, inhibiting or reducing the progression or severity of one or more symptoms associated with the condition or disorder, such as cancer, autoimmune disorder, immunological disorder or infectious disease, using an antibody (e.g., anti-CD47 antibody) or an antigen-binding fragment thereof described herein.

In a specific embodiment, provided herein is a method of treating a condition or disorder, such as cancer, autoimmune disorder, immunological disorder or infectious disease, in a subject comprising administering (e.g., administering concurrently or sequentially) to a subject in need thereof (i) an antibody (e.g., anti-CD47 antibody) or an antigen-binding fragment thereof described herein, and (ii) another agent for treating the condition or disorder.

In a specific embodiment, provided herein is a method of treating a condition or disorder, such as cancer, autoimmune disorder, immunological disorder or infectious disease, in a subject in need thereof, the method comprising administering to the subject an antibody or antigen-binding fragment thereof described herein or the pharmaceutical composition described herein.

In a specific embodiment, provided herein is a method of alleviating a symptom of a condition or disorder, such as cancer, autoimmune disorder, immunological disorder or infectious disease, in a subject in need thereof, the method comprising administering to the subject an antibody or antigen-binding fragment thereof described herein or the pharmaceutical composition described herein.

In various embodiments of the methods described in this Section, the subject being treated or managed with an antibody or an antigen-binding fragment thereof described herein experiences no, minimal or negligible side effects caused by the antibody or antigen-binding fragment thereof during and/or after the treatment or management.

As used herein, "administer" or "administration" refers to the act of injecting or otherwise physically delivering a substance (e.g., a humanized antibody provided herein or an antigen-binding fragment thereof) to a subject or a patient (e.g., human), such as by mucosal, topical, intradermal, parenteral, intravenous, subcutaneous, intramuscular delivery and/or any other method of physical delivery described herein or known in the art.

As used herein, the terms "effective amount" or "therapeutically effective amount" refer to an amount of a therapy (e.g., an antibody or antigen-binding fragment thereof or pharmaceutical composition provided herein) which is sufficient to reduce and/or ameliorate the severity and/or duration of a given condition, disorder or disease (e.g., cancer, metastasis, or angiogenesis) and/or a symptom related thereto. These terms also encompass an amount necessary for the reduction, slowing, or amelioration of the advancement or progression of a given disease, reduction, slowing, or amelioration of the recurrence, development or onset of a given disease, and/or to improve or enhance the prophylactic or therapeutic effect(s) of another therapy (e.g., a therapy other than an antibody or antigen-binding fragment thereof provided herein). In some embodiments, "effective amount" as used herein also refers to the amount of an antibody described herein to achieve a specified result.

As used herein, the term "in combination" in the context of the administration of other therapies refers to the use of more than one therapy. The use of the term "in combination" does not restrict the order in which therapies are administered. The therapies may be administered, e.g., serially, sequentially, concurrently, or concomitantly.

As used herein, the terms "manage," "managing," and "management" refer to the beneficial effects that a subject derives from a therapy (e.g., a prophylactic or therapeutic agent), which does not result in a cure of a condition or disorder. In certain embodiments, a subject is administered one or more therapies (e.g., prophylactic or therapeutic agents, such as an antibody or antigen-binding fragment thereof described herein) to "manage" a condition or disorder described herein, one or more symptoms thereof, so as to prevent the progression or worsening of the condition or disorder.

As used herein, the terms "impede" or "impeding" in the context of a condition or disorder provided herein (e.g., autoimmune disorder, immunological disorder, cancer, infectious disease, or inflammation) refer to the total or partial inhibition (e.g., less than 100%, 95%, 90%, 80%, 70%, 60%, 50%, 40%, 30%, 20%, 10%, or 5%) or blockage of the development, recurrence, onset or spread of a condition or disorder provided herein (e.g., cancer, metastasis, or angiogenesis) and/or symptom related thereto, resulting from the administration of a therapy or combination of therapies provided herein (e.g., a combination of prophylactic or therapeutic agents, such as an antibody or antigen-binding fragment thereof described herein).

As used herein, the terms "subject" and "patient" are used interchangeably. As used herein, a subject is a mammal such as a non-primate (e.g., cows, pigs, horses, cats, dogs, goats, rabbits, rats, mice, etc.) or a primate (e.g., monkey and human), for example a human. In one embodiment, the subject is a mammal, e.g., a human, diagnosed with a condition or disorder provided herein (e.g., cancer, metastasis, or angiogenesis). In another embodiment, the subject is a mammal, e.g., a human, at risk of developing a condition or disorder provided herein (e.g., cancer, metastasis, or angiogenesis). In a preferred embodiment, the subject is a human.

As used herein, the term "side effects" encompasses unwanted and adverse effects of a therapy, and can be caused by immunogenicity of a therapeutic antibody. Unwanted effects are not necessarily adverse. An adverse effect from a therapy can be harmful or uncomfortable or risky. Examples of side effects can include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* ($63^{rd}$ ed., 2009).

In certain embodiments, the antigen to which the antibody or antigen-binding fragment thereof described herein specifically binds (e.g., CD47) is amplified in cells of a subject, e.g., the human subject. Identification of antigen amplification in a sample from a subject can be performed by assays known to one of ordinary skill in the art, such as, e.g., quantitative reverse transcription PCR, immunoblot assays, DNA fingerprinting, karyotyping (for example, by multi-color fluorescence in situ hybridization (mFISH)), comparative genome hybridization, and gene expression profiling. As a non-limiting example, protein expression of tumor samples can be characterized using immunohistochemical assays to measure the amount of the antigen protein present in a sample.

In certain embodiments, the antigen to which the antibody or antigen-binding fragment thereof described herein specifically binds is mutated in cells of a subject, e.g., the human subject. Identification of mutations in a sample from a subject can be performed by assays known to one of ordinary skill in the art, such as, e.g., DNA extraction, generation of complementary DNA, and cDNA sequencing. The cDNA sequence, for example, can be utilized to obtain the translation product by methods known to one of ordinary skill in the art. Genetic mutations and amino acid substitutions can be identified by, for example, comparing the sequence from the sample from the subject to a wild type and/or consensus sequence.

As used herein, the terms "therapies" and "therapy" can refer to any protocol(s), method(s), compositions, formulations, and/or agent(s) that can be used in the prevention, treatment, management, or amelioration of a condition or disorder or symptom thereof (e.g., a condition or disorder provided herein (e.g., cancer) or one or more symptoms or condition associated therewith). In certain embodiments, the terms "therapies" and "therapy" refer to drug therapy, adjuvant therapy, radiation, surgery, biological therapy, supportive therapy, and/or other therapies useful in treatment, management, prevention, or amelioration of a condition or disorder or one or more symptoms thereof (e.g., cancer or one or more symptoms or condition associated therewith). In certain embodiments, the term "therapy" refers to a therapy other than an antibody described herein or pharmaceutical composition thereof. In specific embodiments, an "additional therapy" and "additional therapies" refer to a therapy other than a treatment using an antibody or antigen-binding fragment thereof described herein or pharmaceutical composition thereof. In a specific embodiment, a therapy includes the use of an antibody or antigen-binding fragment thereof described herein as an adjuvant therapy. For example, using an antibody or antigen-binding fragment thereof described herein in conjunction with a drug therapy, biological therapy, surgery, and/or supportive therapy.

Non-limiting examples of a condition which can be treated or managed with an antibody (e.g., anti-CD47 antibody) or an antigen-binding fragment thereof described herein include hematological caner and/or solid tumors, autoimmune disorders, immunological disorders and infectious diseases.

In particular embodiments, provided herein are methods for managing, treating, preventing or protecting against cancer, comprising administering to a subject in need thereof a therapeutically effective amount of an antibody (e.g., anti-CD47 antibody) or an antigen-binding fragment described herein. In certain embodiments, provided herein is a method of alleviating, inhibiting or reducing the progression or severity of one or more symptoms associated with cancer, comprising administering to a subject in need thereof a therapeutically effective amount of an antibody (e.g., anti-CD47 antibody) or an antigen-binding fragment described herein. Then cancer can be a hematological cancer or a solid cancer (i.e., solid tumor).

As used herein, "hematological cancer" refers to a cancer of the blood, and includes leukemia, lymphoma and myeloma among others. "Leukemia" refers to a cancer of the blood in which too many white blood cells that are ineffective in fighting infection are made, thus crowding out the other parts that make up the blood, such as platelets and red blood cells. It is understood that cases of leukemia are classified as acute or chronic. Certain forms of leukemia include, by way of non-limiting example, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. "Lymphoma" may refer to a Hodgkin's lymphoma, both indolent and aggressive non-Hodgkin's lymphoma, Burkitt's lymphoma, and follicular lymphoma (small cell and large cell), among others. Myeloma may refer to multiple myeloma (MM), giant cell myeloma, heavy-chain myeloma, and light chain or Bence-Jones myeloma. In a specific embodiment, the hematological cancer is multiple myeloma, non-Hodgkin's lymphoma, acute myeloid leukemia (AML), breast cancer, bladder cancer, non-small cell lung cancer/carcinoma, hepatocellular carcinoma (HCC), sarcoma, or head and neck cancer.

Solid tumors include, but are not limited to, e.g., breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

Symptoms associated with cancers and other neoplastic disorders include, for example, inflammation, fever, general malaise, fever, pain, often localized to the inflamed area, loss of appetite, weight loss, edema, headache, fatigue, rash, anemia, muscle weakness, muscle fatigue and abdominal symptoms such as, for example, abdominal pain, diarrhea or constipation.

In specific aspects, provided herein is an antibody (e.g., anti-CD47 antibody) or an antigen-binding fragment thereof useful in treating, delaying the progression of, impeding, preventing relapse of or alleviating a symptom of a cancer (e.g., MM, NHL, AML, breast cancer, bladder cancer, non-small cell lung cancer/carcinoma, hepatocellular carcinoma (HCC), sarcoma, and head and neck cancer). For example, in certain embodiments, an antibody (e.g., anti-CD47 antibody) or an antigen-binding fragment thereof described herein is useful in treating hematological malignancies and/or tumors, e.g., hematological malignancies and/or tumors. For example, the anti-CD47 antibodies or antigen-binding fragments thereof described herein are useful in treating CD47+ tumors. By way of non-limiting example, an antibody (e.g., anti-CD47 antibody) or an antigen-binding fragment thereof described herein is useful in treating non-Hodgkin's lymphoma (NHL), acute lymphocytic leukemia (ALL), acute myeloid leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, glioblastoma, breast tumors, ovarian tumors, lung tumors (e.g., NSCLC), pancreatic tumors, prostate tumors, melanoma tumors, colorectal tumors, lung tumors, head and neck tumors, bladder tumors, esophageal tumors, liver tumors (e.g., hepatocellular carcinoma), sarcoma, and/or kidney tumors.

In a specific embodiment, provided herein is a method of treating cancer in a subject in need thereof, the method comprising administering to the subject an antibody or antigen-binding fragment described herein or the pharmaceutical composition described herein. In a further specific embodiment, the method further comprises administering to the subject radiotherapy or chemotherapy. In another further specific embodiment, the method further comprises administering to the subject another anti-cancer agent.

In a specific embodiment, provided herein is a method of alleviating a symptom of a cancer in a subject in need thereof, the method comprising administering to the subject an antibody or antigen-binding fragment described herein or the pharmaceutical composition described herein. In a further specific embodiment, the method further comprises administering to the subject radiotherapy or chemotherapy. In another further specific embodiment, the method further comprises administering to the subject another anti-cancer agent.

In a specific embodiment, provided herein is a method of treating cancer (e.g., a hematological disorder/cancer or solid cancer) in a subject comprising administering (e.g., administering concurrently or sequentially) to a subject in need thereof (i) an antibody (e.g., anti-CD47 antibody) or an antigen-binding fragment thereof described herein, and (ii) another anti-cancer agent. In certain embodiments, the second anti-cancer agent is a chermotherapeutic agent (e.g., microtubule disassembly blocker, antimetabolite, topisomerase inhibitor, and DNA crosslinker or damaging agent). In certain embodiments, the second anti-cancer agent is a tyrosine kinase inhibitor (e.g., GLEEVEC® (imatinib mesylate) or SUTENT® (SU11248 or Sunitinib)). Other non-limiting examples of tyrosine kinse inhibitors include 706 and AMNI07 (nilotinib). RAD00I, PKC412, gefitinib (IRESSA™), erlotinib (TARCEVA®), sorafenib (NEXAVAR®), pazopanib (VOTRIENT™), axitinib, bosutinib, cediranib (RECENTIN®), SPRYCEL® (dasatinib), lapatinib (TYKERB®), lestaurtinib, neratinib, nilotinib (TASIGNA®), semaxanib, toceranib (PALLADIA™), vandetanib (ZACTIMA™), and vatalanib.

In a specific aspect, provided herein is a method of treating cancer (e.g., a hematological disorder/cancer or solid cancer) in a subject comprising administering (e.g., administering concurrently or sequentially) to a subject in need thereof (i) an antibody (e.g., anti-CD47 antibody) or an antigen-binding fragment thereof described herein, and (ii) a radiotherapy.

In a particular aspect, provided herein is a method of promoting (e.g., inducing or increasing) phagocytosis, e.g., macrophage mediated phagocytic killing of tumor cells, comprising contacting an effective amount of an antibody (e.g., anti-CD47 antibody) or an antigen-binding fragment thereof described herein with tumor cells. Also provided herein is a method of promoting (e.g., inducing or increasing) phagocytosis, e.g., macrophage mediated phagocytic killing of tumor cells, in a subject in need thereof (e.g., a subject with tumor cells), comprising administering to the subject an effective amount of an antibody (e.g., anti-CD47 antibody) or an antigen-binding fragment thereof described herein.

In a particular aspect, provided herein is a method of reducing tumor volumn, comprising contacting an effective amount of an antibody (e.g., anti-CD47 antibody) or an antigen-binding fragment thereof described herein. Also provided herein is a method of reducing tumor volumn in a subject in need thereof (e.g., a subject with a tumor), comprising administering to the subject an effective amount of an antibody (e.g., anti-CD47 antibody) or an antigen-binding fragment thereof described herein.

In a particular aspect, provided herein is a method of inhibiting cancer cell growth or proliferation, comprising contacting an effective amount of an antibody (e.g., anti-CD47 antibody) or an antigen-binding fragment thereof described herein with cancer cells. Also provided herein is a method of inhibiting cancer cell growth or proliferation in a subject in need thereof (e.g., a subject with cancer cells), comprising administering to the subject an effective amount of an antibody (e.g., anti-CD47 antibody) or an antigen-binding fragment thereof described herein.

5.4.1 Diagnostic Uses

In one aspect, an antibody (e.g., anti-CD47 antibody) or an antigen-binding fragment thereof described herein can be used for diagnostic purposes to detect, diagnose, or monitor a condition or disorder described herein (e.g., a condition or disorder associated with the antigen, abnormal expression of the antigen, and/or abnormal signaling involving the antigen), such as cancer (e.g., a hematological cancer or solid cancer), autoimmune disorder, immunological disorder or infectious disease. In specific embodiments, an antibody (e.g., anti-CD47 antibody) or an antigen-binding fragment thereof described herein for use in diagnostic purposes is labeled.

Presence of the labeled molecule can be detected in the subject using methods known in the art for in vivo scanning. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

Methods provided herein for diagnostic purposes to detect, diagnose, or monitor a condition described herein can be in vitro methods, in situ methods, or ex vivo methods. Methods provided herein for diagnostic purposes to detect, diagnose, or monitor a condition described herein can be in vivo methods.

In certain embodiments, provided herein are methods for the detection of a condition described herein, such as cancer (e.g., a hematological cancer or solid cancer), autoimmune disorder, immunological disorder or infectious disease, comprising: (a) assaying the expression of an antigen (e.g., CD47) in a sample of a subject using an antibody (e.g., anti-CD47 antibody) or an antigen-binding fragment thereof described herein that specifically binds to the antigen (e.g., CD47); and (b) comparing the expression level of the antigen (e.g., CD47) with a control expression level, e.g., levels in normal tissue samples (e.g., from a patient not having a condition described herein, or from the same patient before onset of the condition), whereby an increase or decrease in the assayed expression level of the antigen (e.g., CD47) compared to the control expression level of the antigen (e.g., CD47) is indicative of a condition described herein.

In certain embodiments, provided herein are methods for the detection of cancer expressing an antigen (e.g., CD47), such as overexpressing the antigen, comprising: (a) assaying the expression of the antigen (e.g., CD47) in a sample of a subject using an antibody (e.g., anti-CD47 antibody) or an antigen-binding fragment thereof that specifically binds to the antigen (e.g., CD47); and (b) comparing the expression level of the antigen (e.g., CD47) with a control expression level, e.g., levels in normal samples (e.g., from a patient not having cancer, a patient having cancer that does not overexpress the antigen (e.g., CD47), or from the same patient before onset of cancer). In specific aspects, an increase or decrease in the assayed expression level of the antigen (e.g., CD47) compared to a control expression level of the antigen (e.g., CD47) is indicative of cancer expressing the antigen (e.g., CD47).

In a specific embodiment, provided herein is a method of diagnosing a cancer expressing an antigen (e.g., CD47) in a patient, wherein the method comprises the steps of:
(a) contacting a biological sample from the patient with an antibody (e.g., anti-CD47 antibody) or an antigen-binding fragment thereof that specifically binds to the antigen (e.g., CD47);
(b) detecting binding of the antibody or antigen-binding fragment to the antigen to determine a protein level of the antigen (e.g., CD47) in the biological sample from the patient; and
(c) comparing the protein level of the antigen (e.g., CD47) with a standard protein level of the antigen (e.g., CD47).

In a specific embodiment, provided herein is a method of monitoring protein level of an antigen (e.g., CD47) during treatment of a cancer expressing the antigen (e.g., CD47) in a patient, wherein the method comprises the steps of:
(a) contacting a biological sample from the patient with an antibody (e.g., anti-CD47 antibody) or an antigen-binding fragment thereof that specifically binds to the antigen (e.g., CD47);
(b) detecting binding of the antibody or antigen-binding fragment to the antigen (e.g., CD47) to determine a protein level of the antigen (e.g., CD47) in the biological sample from the patient; and
(c) comparing the protein level of the antigen (e.g., CD47) with a standard protein level of the antigen (e.g., CD47).

Any sample (e.g., bodily fluid or tissue sample) from a subject can be used in diagnostic methods provided herein. Non-limiting examples of samples which can be used in diagnostic methods provided herein include, serum sample, plasma sample, tissue sample, urine sample, tumor sample, and stool sample.

Antibodies described herein can be used to assay levels of the antigen (e.g., CD47) in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (121In), and technetium (99Tc); luminescent labels, such as luminol; and fluorescent labels, such as fluorescein and rhodamine, and biotin.

In one embodiment, monitoring of a condition or disorder described herein (e.g., a condition or disorder associated with the antigen, abnormal expression of the antigen, and/or abnormal signaling involving the antigen), such as cancer (e.g., a hematological cancer or solid cancer), autoimmune disorder, immunological disorder or infectious disease, is carried out by repeating the method for diagnosing for a period of time after initial diagnosis.

6. EXAMPLES

The examples in this section (i.e., Section 6) are offered by way of illustration, and not by way of limitation.

6.1 Example 1: Antibody Design

Antibodies were designed by engineering variants into a parental anti-CD47 antibody described in International Application Publication No. WO 2013/119714 A1 (i.e. $Ab_{parental}$). Amino acid substitutions were introduced into the frameworks of the light chain and the heavy chain and the CDRs of the light chain.

The in silico immunogenicity analysis tool, Interactive Screening and Protein Reengineering Interface (ISPRI: EpiVax, RI), was applied to obtain EpiMatrix Z-scores. According to EpiVax, the Z-score indicates the potential of a 9-mer peptide to bind to a given HLA allele. All Z-scores in the top 5%, which is a Z-score equal or greater than 1.64, are considered "Hits". Peptides containing four or more alleles scoring above 1.64 are referred to as "effector T cell (Teff) epitopes." Peptides conserved in IgG antibodies and believed to be either passively tolerated or actively regulatory are referred to as "regulatory T cell (Treg) epitopes." Normalized EpiMatrix Z scores adjusted for Treg epitopes along with categorized immunogenicity were taken into account to evaluate potential immunogenicity.

Several framework residues in the parental light and heavy chains that contained high ratios of Teff epitopes or low ratios of Treg epitopes were identified. The light and heavy chain framework residues were aligned with clinically safe antibodies that represent low clinical immunogenicity. Frequently used amino acids from framework regions of the safe antibodies were utilized to site-specifically replace the residues that represent potentially high immunogenicity. The categorized immunogenic potential for the resulting variants was decreased from 7.5% for the parental antibody (EpiMatrix Epx score of approximately −9.95) to 0.5% or less, which is on par with the clinically safe antibodies that contain relatively low ratios of Teff epitopes and high ratios of Treg epitopes. Results of the immunogenicity analysis for certain of the variants are shown in Table 5 and Table 6. A number of the variants were constructed and tested. Several variants demonstrated increased expression, retained affinity, retained in vitro phagocytosis function, no hemagglutination, increased stability and increased solubility, as discussed in detail, below.

The analysis also identified a very high ratio of Teff epitopes in the CDR L2 region of the parental CD47 antibody. Several residues in the CDR L2 interact with CD47. In order to reduce potential immunogenicity by abrogating Teff epitopes while retaining CD47 binding affinity, in silico computational engineering was applied. Briefly, a crystal structure of CD47 co-complexed with 2A1 antibody, which is the original mouse version of the parental antibody described in International Application Publication No. WO 2013/119714 A1, was computationally optimized by filling the structural gaps, adding up hydrogens and energy minimization. A computational protein engineering software, Molecular Operating Environment (MOE; Chemical Computing Group, Montreal, Quebec, Canada) was utilized. Affinity and stability calculation functions in MOE were applied to identify CDR L2 mutants with retained or increased affinity and stability. The engineered CDR L2 sequences that retained or increased affinity and stability were analyzed by EpiVax analysis in order to identify the CDR L2 sequences that decreased the categorized immunogenic potential to 0%. The parental CDR L2 sequence was replaced with the computationally optimized CDR L2 sequences. A number of the variants comprising optimized CDR L2 sequences and framework variants as described above were then constructed and tested. Several of these variants demonstrated increased expression, retained affinity, retained in vitro phagocytosis function, no hemagglutination, and increased stability and increased solubility. Results of the immunogenicity analysis for certain of the variants are shown in Table 5 and Table 6. The results show that the variants have lower immunogenicity potential than the parental antibody in humans.

TABLE 5

Results of the immunogenicity analysis (FR variants).
Immunogenicity Prediction

| Construct: LC/HC | EpiVax Score |
|---|---|
| Ab495/Ab480 | −38.59 |
| Ab495/Ab356 | −37.54 |

TABLE 5-continued

Results of the immunogenicity analysis (FR variants).
Immunogenicity Prediction

| Construct: LC/HC | EpiVax Score |
|---|---|
| Ab1119/Ab480 | −33.11 |
| Ab1119/Ab356 | −32.06 |
| Ab1119/Ab356 | −32.06 |
| Ab1119/Ab387 | −30.74 |
| Ab1119/Ab387 | −30.74 |
| Ab1119/Ab170 | −29.61 |
| Ab482/Ab387 | −26.35 |
| Parental LC-HC | −9.95 |

TABLE 6

Results of the immunogenicity analysis
(FR and CDR L2 variants).
Immunogenicity Prediction

| Construct: LC/HC | EpiVax Score |
|---|---|
| Ab356/Ab1120 | −53.64 |
| Ab480/Ab1120 | −54.68 |
| Ab356/Ab1121 | −52.56 |
| Ab480/Ab1121 | −53.61 |
| Ab356/Ab1122 | −54.77 |
| Ab480/Ab1122 | −55.81 |
| Ab356/Ab1127 | −53.55 |
| Ab480/Ab1127 | −54.6 |
| Ab356/Ab1129 | −38.84 |
| Ab1119/Ab480 | −33.11 |
| Ab1119/Ab356 | −32.06 |
| Parental LC-HC | −9.95 |

6.2 Example 2: Antibody Production

Materials and Methods:

Antibody chains were synthesized by DNA2.0 and subcloned into the pTT5 vector. The antibodies were transiently transfected in all combinations using Expi293 or ExpiCHO-S cells in 24 deep well plates (24-DWP, Axygen, #14222350) according to Thermo Fisher/Life Technologies protocols. For each antibody, a DNA ratio of 3:2 or 1:1 LC:HC was used for expression at 1 μg/mL DNA/expression media, and cultures were shaken at 500 RPM (293) or 350 RPM (CHO) using a 3 mM swing shaking platform. Typically, cultures were incubated at 37° C., but for the purposes of expression optimization, some cultures were incubated at 32° C. (ExpiCHO-S only). Antibody titers for all expressions were assessed using biolayer interferometry (ForteBio Octet), with anti-Fc or Protein A Biosensors. Certain variant antibodies have subtntially higher expression levels than the parental antibody (Table 7 and Table 8). As an initial assessment, antibodies were tested by flow cytometry for binding to the CD47-positive cell line CCRF-CEM. Briefly, for each antibody, $0.5\times10^6$ cells were isolated and stained with 10 μg/mL of antibody in cell supernatant as determined by Octet (FIG. 1). Cells were then stained with 0.1 mL PBS containing 1:100 dilution of Alex fluor 488 anti-human $F(ab')_2$, H+L (Jackson IRR). All cell surface staining was done at 4° C. for 30 minutes and followed with 2× washes with PBS with a final resuspension in PBS prior to running cells on an Attune flow cytometer (Thermo Fisher). In a subsequent flow cytometry experiment using purified mAbs from the same 24-DWP expression, binding of mAbs to CD47 on CCRF-CEM cells was evaluated using a subsaturating concentration of 0.5 μg/mL. These results were compared with in silico immunogenicity and affinity $K_D$'s (FIGS. 2 and 3), and certain antibodies were chosen for additional rounds of expression.

Purifications of samples in 24-DWP were conducted using a Hamilton automated liquid handler using and Protein A affinity capture using Phynexus tips. After elution from the tips with NaOac, pH 3.0, antibodies were resolved using Prepartive SEC (AKTA), and formulated in 10 mm NaOAc, ph 5.5, 9% sucrose. Sample quality was confirmed using analytical SEC (Agilent), LC/MS, SDS-PAGE, and Biacore.

Additional rounds of larger protein expressions were conducted for certain antibodies. Larger scale productions ranged between 150 mL to 25 L in Expi293 or ExpiCHO cells (Thermo Fisher). Protocols were followed according to Thermo Fisher Scientific instructions, but typically $2 \times 10^6$ to $1 \times 10^7$ cells/mL were seeded and LC and HC were transiently transfected at a 1:1 or 3:2 ratio ranging from 0.5-1 µg/mL. For scales from 150 mL to 3 L, Corning unbaffled Erlenmeyer vented cap shake flasks were used. Transfection shake speeds ranged from 70 (ExpiCHO) to 120 RPM (Expi293) with a 25 mM shake platform swing, and post transfection culture temperatures ranged between 32° (ExpiCHO-S) or 37° C. (Expi293 and ExpiCHO-S).

All larger scale protein expressions were purified using Mab SelectSure LX resin (GE Healthcare Life Sciences) on an AKTA Pure (GE Healthcare Life Sciences). After elution from the column with NaOAc, pH 3.0, antibodies were resolved using Prepartive SEC (AKTA), and formulated in 10 mm NaOAc, ph 5.5, 9% sucrose. Sample quality was confirmed using analytical SEC (Agilent), Endotoxin (Endosafe, Charles River), LC/MS, SDS-PAGE, and Biacore.

TABLE 7

Expression of the antibodies (200 mL production, ExpiCHO).

| Construct: LC/HC | mg/L (media) |
|---|---|
| Ab495/Ab480 | 31.5 |
| Ab495/Ab356 | 27.5 |
| Ab1119/Ab480 | 5.32** |
| Ab1119/Ab356 | 93.2 |
| Ab1119/Ab356 | 41.2 |
| Ab1119/Ab387 | 33.4 |
| Ab1119/Ab387 | 10.5 |
| Ab1119/Ab170 | 34.8 |
| Ab482/Ab387 | 26.6 |
| Parental LC-HC | 18.8 |

**In Expi293 24-DPW productivity was ~72 mg/L.

TABLE 8

Expression of the antibodies (200 mL production, ExpiCHO).

| Construct: LC/HC | mg/L (media) |
|---|---|
| Ab356/Ab1120 | ~72 |
| Ab480/Ab1120 | ~72 |
| Ab356/Ab1121 | ~100 |
| Ab480/Ab1121 | ~100 |
| Ab356/Ab1122 | ~72 |
| Ab480/Ab1122 | ~72 |
| Ab356/Ab1127 | ~70 |
| Ab480/Ab1127 | ~70 |
| Ab356/Ab1129 | ~70 |
| Ab1119/Ab480 | 5.32 |

TABLE 8-continued

Expression of the antibodies (200 mL production, ExpiCHO).

| Construct: LC/HC | mg/L (media) |
|---|---|
| Ab1119/Ab356 | 41.2 |
| Parental LC-HC | 18.8 |

6.3 Example 3: Biacore Analysis of CD47 Affinity

Materials and Methods:
The binding kinetics of anti-CD47 antibodies to the recombinant extracellular domain of CD47 were determined by using surface Plasmon resonance (SPR, MASS-1, Sierra Sensors; T200, Biacore, GE Healthcare Life Sciences). Anti-human Fc (P/N: BR-1008-39 (GE Healthcare Life Sciences)) was immobilized on a High Capacity Amine chip (P/N: SPR-AS-HCA, Sierra sensors) or CM5-S Chip (GE Healthcare Life Sciences). CD47 antibodies were captured on Human IgG FC and CD47-ECD was flowed over the surface at various concentrations ranging from zero (for double referencing) to 100 nM. In order to determine $K_D$'s, antibodies were ranked using a 1:1 Langmuir model. The results are shown in Table 9, and show that the variant antibodies have retained substantial binding affinity to CD47.

TABLE 9

Results of Biacore analysis.
Affinity-Biacore

| Construct: LC/HC | ka (1/Ms) | kd (l/s) | KD (M) |
|---|---|---|---|
| Ab495/Ab480 | 3.29E+06 | 4.34E−03 | 1.32E−09 |
| Ab495/Ab356 | 3.13E+06 | 4.26E−03 | 1.36E−09 |
| Ab1119/Ab480 | 1.02E+07 | 5.77E−03 | 5.64E−10 |
| Ab1119/Ab356 | 1.02E+07 | 6.47E−03 | 6.35E−10 |
| Ab1119/Ab356 | 9.85E+06 | 5.90E−03 | 5.99E−10 |
| Ab1119/Ab387 | 1.03E+07 | 5.71E−03 | 5.56E−10 |
| Ab1119/Ab387 | 1.04E+07 | 5.52E−03 | 5.29E−10 |
| Ab1119/Ab170 | 1.04E+07 | 5.83E−03 | 5.62E−10 |
| Ab482/Ab387 | 9.93E+06 | 5.49E−03 | 5.53E−10 |
| Ab356/Ab1120 | 2.69E+06 | 2.74E−03 | 1.02E−09 |
| Ab480/Ab1120 | 2.28E+06 | 2.38E−03 | 1.05E−09 |
| Ab356/Ab1121 | 2.53E+06 | 2.72E−03 | 1.08E−09 |
| Ab480/Ab1121 | 2.67E+06 | 3.03E−03 | 1.14E−09 |
| Ab356/Ab1122 | 2.28E+04 | 4.11E−03 | 7.79E−08 |
| Ab480/Ab1122 | 2.33E+06 | 1.09E−02 | 4.68E−09 |
| Ab356/Ab1127 | 2.22E+06 | 1.06E−02 | 4.76E−09 |
| Ab480/Ab1127 | 2.57E+06 | 6.22E−03 | 2.42E−09 |
| Ab1119/Ab480 | 1.02E+07 | 5.77E−03 | 5.64E−10 |
| Ab1119/Ab356 | 9.85E+06 | 5.90E−03 | 5.99E−10 |
| Parental LC-HC | 7.94E+06 | 1.87E−03 | 2.36E−10 |

6.4 Example 4: Phagocytosis and Flow Cytometry

Materials and Methods:
Phagocytosis screening was conducted by differentiating macrophages from monocytes (Astarte #1009) by plating $3 \times 10^4$ cells in 100 L of complete AIM V media (#12055-091, Thermo Fisher; made complete by adding 50 ng/mL rhuM-CSF (Peprotech, #300-25) and 10% FBS (Hyclone, #SH30088)) in a 96 well black walled plate and incubating in a 5% $CO_2$ atmosphere at 37° C. The culture was replenished with fresh media by removing 50 µL of culture and feeding 100 µL fresh media every 3-4 days for a total of 7 days.

Phagocytosis was assayed by serum starving the macrophages in incomplete AIM V media for two hours. During this incubation period, target cells (CCRF-CEM) from two donors (donor 1 and donor 2) were labeled with CSFE (Invitrogen, #C34554) at 0.3 M for 15 minutes at room temperature. Cells were rinsed twice with PBS (Hyclone, #SH30028.02) and resuspended at $8\times10^5$/mL in AIM V media. Antibody dilutions were prepared at 0.01 ug/ml to 10 ug/ml in half log dilutions and then incubated with the target cell line for 10 minutes at room temperature (a small portion is retained for flow cytometric analysis/cell binding), after which 100 μL of target cell/antibody suspension was added to the macrophage plates. Samples were treated in triplicate and with appropriate isotype controls.

For the phagocytosis assay, the plate was spun at 500 RPM for one minute to establish cell contacts, and then incubated for 3 hours at 37° C., 5% CO2, and in the dark. After the incubation, the plate was washed by hand with PBS and stained with an 1:500 anti-CD14 APC conjugate (Biolegend 325608) for 15 minutes in the dark. Finally, the plate was imaged on a high content imager (Operetta, Perkin Elmer) using the FITC and Alexa 647 channel. For data analysis, cells Alexa 647 and FITC positive cells were identified, with the % of phagocytosed cells=(FITC positive and Alexa 647 positive/Alexa 647 Cells)*100=% Phagocytosis The results for the antibodies listed in Tables 5 and 6, above, are shown in Table 10 and representative data are shown in FIG. 4. The results show that the variant antibodies have retained the desirable ability to promote phagocytosis of target cells.

TABLE 10

Phagocytosis results.
Phagocytosis EC50 (ug/mL)

| Construct: LC/HC | Donor 1 | Donor 2 |
|---|---|---|
| Ab495/Ab480 | 0.59 | 0.94 |
| Ab495/Ab356 | 0.68 | 0.92 |
| Ab1119/Ab480 | 0.19 | 0.24 |
| Ab1119/Ab356 | 0.31 | 0.15 |
| Ab1119/Ab356 | 0.14 | 0.4 |
| Ab1119/Ab387 | 0.14 | 0.52 |
| Ab1119/Ab387 | 0.5 | 0.21 |
| Ab1119/Ab170 | 0.15 | 0.62 |
| Ab482/Ab387 | 0.15 | 0.17 |
| Ab356/Ab1120 | 0.68 | 1.82 |
| Ab480/Ab1120 | 0.73 | 2.01 |
| Ab356/Ab1121 | 0.48 | 1.29 |
| Ab480/Ab1121 | 0.43 | 1.42 |
| Ab356/Ab1122 | 1.07 | 1.83 |
| Ab480/Ab1122 | 1.1 | 1.84 |
| Ab356/Ab1127 | 0.66 | 0.96 |
| Ab480/Ab1127 | 1.88 | 1.95 |
| Ab356/Ab1129 | 12.8 | n.d. |
| Ab1119/Ab480 | 0.44 | 0.71 |
| Ab1119/Ab356 | 0.36 | 0.94 |
| Parental LC-HC | 0.38 | 0.13 |

For flow cytometric staining, excess opsonized cells were transferred to a clean 96-well round bottom plate, rinsed with PBS, and incubated with a 1:1000 dilution of anti-human alexa conjugate 647 (ThermoFisher, A-21445) in FACS buffer (BD Biosciences, 554656). Samples were incubated for 30 minutes at room temperature, rinsed 2× and then resuspended in FACS buffer and analyzed on the Attune. The results are shown in Tables 11 and 12 and representative data are shown in FIG. 4. The EC50 values refer to the concentration that gives half the maximum binding measured as median fluorescent intensity, and was determined by non-linear fit of a sigmoidal dose response within the GraphPad Prism software. The results show that the variant antibodies have retained substantial binding affinity to cell surface-expressed CD47.

TABLE 11

Flow cytometry analysis results.
Cell Binding (a-FACS), EC5O (μg/ml)

| Construct: LC/HC | Cell Binding (a-FACS) |
|---|---|
| Ab495/Ab480 | 0.066 |
| Ab495/Ab356 | 0.035 |
| Ab1119/Ab480 | 0.012 |
| Ab1119/Ab356 | 0.035 |
| Ab1119/Ab356 | 0.014 |
| Ab1119/Ab387 | 0.011 |
| Ab1119/Ab387 | 0.014 |
| Ab1119/Ab170 | 0.015 |
| Ab482/Ab387 | 0.014 |
| Parental LC-HC | 0.014 |

TABLE 12

Flow cytometry analysis results.
Cell Binding (a-FACS), EC5O (μg/ml)

| Construct: LC/HC | Donor 1 | Donor 2 |
|---|---|---|
| Ab356/Ab1120 | 0.17 | 0.16 |
| Ab480/Ab1120 | 0.33 | 0.17 |
| Ab356/Ab1121 | 0.19 | 0.16 |
| Ab480/Ab1121 | 0.17 | 0.17 |
| Ab356/Ab1122 | 0.17 | 0.22 |
| Ab480/Ab1122 | 0.16 | 0.17 |
| Ab356/Ab1127 | 0.11 | 0.15 |
| Ab480/Ab1127 | 0.08 | 0.2 |
| Ab356/Ab1129 | 0.16 | n.d. |
| Ab1119-Ab480 | 0.04 | 0.07 |
| Ab1119-Ab356 | 0.06 | 0.16 |
| Parental LC-HC | n.d. | n.d. |

6.5 Example 5: Hemagglutination

Materials and Methods:

Antibodies were tested for the unwanted ability to hemagglutinate platelets. In this assay, non-hemagglutinated RBCs settle to the bottom of a 96-well plate, whereas hemagglutinated RBCs form a dispersed red haze. Human RBCs (Innovative Research, IPLA-WB3) were washed by dilution of 2 mL of RBCs with 10 mL of 1×dPBS (pH 7.4) in a 15 mL conical tube. After centrifuging RBCs for 10 min. at 500×g, the supernatant was aspirated, 12 mL of dPBS is added and RBCs are mixed by tube inversion. The spin and aspiration steps were repeated and cells were resuspended in 8 mL dPBS and used immediately or stored for 3-5 days at 4° C.

Antibodies were prepared as 2× stocks in PBS and diluted in a 3× dilution series so that the final concentration range tested was between 1000 nM to 51 pM. A control antibody known to cause hemagglutination was included as a positive control, and no antibody was used as a negative control. Using an electronic P1200 multichannel pipette, 50 μL of each antibody titration was added to all wells of a u-bottom 96-well plate, and then followed by 50 μL of washed 20% RBC solution to all wells. No mixing was necessary as the injection force from the pipette is enough to mix the samples. The plate was then incubated at 37° C. for at least 1.5 hours to 12 hours (overnight), and no visual difference in the results was observed within that time frame. The plate was visualized from the top. Negative (non-hemagglutination) results appeared as punctate red dots, while positive (hemagglutination) results appeared as a dispersed red haze. Advantageously, none of the anti-CD47 antibodies listed in Tables 5 and 6, above, resulted in hemagglutination.

6.6 Example 6: Solubility

Materials and Methods:

The colloidal stability, or degree of intermolecular attraction between protein molecules, may be assessed by PEG precipitation. PEG is preferentially excluded from the protein for steric reasons, which in turn causes an increase in the osmotic pressure of the bulk solvent. This increase in osmotic pressure enhances the intrinsic attractive interaction forces (hydrophobic, electrostatic, etc.) between proteins. Depending on the strength of these interactions, aggregation/precipitation will occur at different PEG concentrations. Proteins with strong intermolecular interactions (low colloidal stability) precipitate at low PEG concentrations, while higher PEG concentrations are required to precipitate proteins with greater repulsive intermolecular interactions (high colloidal stability).

PEG solutions (EMD, Cat #PX1286L-4) of 200 µL were prepared containing PEG 6000 MW ranging between 10-20% (or higher or lower if warranted) in 1% increments and antibodies with a final concentration of 1mg/mL. Solutions were mixed using a pipet and incubated overnight at 4° C. Samples were centrifuged in a pre chilled (4° C.) centrifuge for 5 minutes at 25,259×g and supernatants were transferred to a well of a 96-well plate. The protein concentration was measured by absorbance at 280 nm and plotted as protein concentration vs. PEG concentration in a sigmoid data fit model. Data is reported as the PEG % at which 50% of the antibody is soluble. The results for the antibodies tested are shown in FIG. 5 and Table 13, below. The results show that the variant antibodies are highly soluble and, in fact, are substantially more soluble than the parental antibody.

TABLE 13

Solulability analysis results.

| Construct: LC/HC | Solubility Assessment (midpoint) |
|---|---|
| Ab495/Ab480 | 18.26 |
| Ab495/Ab356 | 18.12 |
| Ab1119/Ab480 | 18.93 |
| Ab1119/Ab356 | 18.48 |
| Ab1119/Ab356 | 18.3 |
| Ab1119/Ab387 | 18.52 |
| Ab1119/Ab387 | 18.2 |
| Ab1119/Ab170 | 18.4 |
| Ab482/Ab387 | 18.85 |
| Parental LC-HC | no fit |

6.7 Example 7: Stability

Materials and Methods:

Antibodies were assessed for conformational stability by Differential Scanning Calorimetry (NanoDSC, TA Instruments). An effective means of limiting aggregation for proteins that aggregate through non-native or partially unfolded intermediate states is to increase conformational stability. Conformational stability may be assessed by thermal denaturation studies for those proteins that refold upon cooling. In cases where protein thermal unfolding is not reversible, the midpoint of the thermal unfolding transition or "apparent melting temperature" ($Tm^{app}$) is often reported as a surrogate for conformational stability when comparing formulation or different protein constructs.

Prior to running the Differential Scanning Calorimetry (DSC) assay, reference and sample cells were cleaned with 1% Liquinox and flushed with Milli-Q water. De-gassed formulation buffer was loaded into the reference and sample cells and 3 atm of pressure was applied. Cells were scanned from 20 to 100° C. at 1° C.min$^{-1}$ with a 600 second equilibration at 20° C., and the cell contents were removed. Antibodies were diluted to 0.5-2 mg/mL in formulation buffer, degassed, and loaded into reference or sample cells and scanned using the same parameters. Data analysis was performed using NanoAnalyze software where the buffer run was subtracted, the data was converted to Molar Heat Capacity, and a baseline was established so that each antibody Gaussian curve may be fitted in order to determine $T_m^{app}$. Results for the antibodies tested using this assay are shown in FIG. 6 and Table 14, below. The results show that the variant antibodies have higher stability than the parental antibody.

TABLE 14

Stability analysis results.

| Construct: LC/HC | $Tm^{app}$ (° C.) |
|---|---|
| Ab495/Ab480 | 62.4 |
| Ab495/Ab356 | 76.8 |
| Ab1119/Ab480 | 77.4 |
| Ab1119/Ab356 | 73.4 |
| Ab1119/Ab356 | 76.6 |
| Ab1119/Ab387 | 73.3 |
| Ab1119/Ab387 | 77.4 |
| Ab1119/Ab170 | 70.9 |
| Ab482/Ab387 | 72.3 |
| Parental LC-HC | 59.9 |

All references (e.g., publications or patents or patent applications) cited herein are incorporated herein by reference in their entirety as if each individual reference (e.g., publication or patent or patent application) was specifically and individually indicated to be incorporated by reference in its entirety. In the case of any conflict, this specification will control.

As used herein, the singular forms "a", "and," and "the" include plural referents unless the context clearly indicates otherwise. Thus, for example, reference to "a peptide sequence" includes a plurality of such sequences and so forth.

Other embodiments are within the following claims.

What is claimed:

1. An antibody or an antigen-binding fragment thereof, comprising a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH FR1, VH FR2, VH FR3 and VH FR4 comprise the amino acid sequence of:

$X_{H1}QX_{H3}QLVQSGAEVKKX_{H5}GX_{H6}SVKVSCKAS$ (SEQ ID NO: 5), $WVRQAPGX_{H12}X_{H13}LEWMG$ (SEQ ID NO: 6), $YAQKX_{H16}QX_{H17}RVTX_{H18}TX_{H19}DX_{H21}SX_{H22}STAYMELX_{H25}SLRX_{H31}X_{H27}DTAX_{H28}YYC$ (SEQ ID NO: 7), and $WGX_{H29}GTX_{H30}VTVSS$ (SEQ ID NO: 4) respectively, wherein $X_{H1}$ is M or no amino acid, $X_{H3}$ is M, $X_{H5}$ is P, $X_{H6}$ is S, $X_{H12}$ is K, $X_{H13}$ is G, $X_{H16}$ is F, $X_{H17}$ is G, $X_{H18}$ is I, $X_{H19}$ is R, $X_{H21}$ is R, $X_{H22}$ is T, $X_{H25}$ is R, $X_{H31}$ is A, $X_{H27}$ is E, $X_{H28}$ is V, $X_{H29}$ is Q, and $X_{H30}$ is L.

2. The antibody or antigen-binding fragment of claim 1, further comprising a light chain variable region (VL) that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein VL FR1, VL FR2, VL FR3 and VL FR4 comprise the amino acid sequence of:

$NIQMTQSPSX_{L1}X_{L2}SASVGDRVTITC$ (SEQ ID NO: 8);

$WX_{L3}QQKPGKX_{L4}PKHLIY$ (SEQ ID NO: 9);

GVPSRFSGSGSGTEFTLTISSLQPEDFATYYC (SEQ ID NO: 10); and

FGGGTKVEIK (SEQ ID NO: 11), respectively, wherein $X_{L1}$ is S, $X_{L2}$ is L, $X_{L3}$ is F, and $X_{L4}$ is V.

3. The antibody or antigen-binding fragment of claim 1, wherein the antibody or antigen-binding fragment specifically binds to CD47 and comprises:

(i) a VH that comprises four VH framework regions (VH FR1-4) and three VH complementarity determining regions (VH CDR1-3) in the following N-terminal to C-terminal order: VH FR1-VH CDR1-VH FR2-VH CDR2-VH FR3-VH CDR3-VH FR4, wherein VH CDR1 comprises the amino acid sequence of GFNIKDYYLH (SEQ ID NO: 59); VH CDR2 comprises the amino acid sequence of WIDPDQGDTE (SEQ ID NO: 60); and VH CDR3 comprises the amino acid sequence of NAAYGSSSYPMDY (SEQ ID NO: 61); and (ii) a VL that comprises four VL framework regions (VL FR1-4) and three VL complementarity determining regions (VL CDR1-3) in the following N-terminal to C-terminal order: VL FR1-VL CDR1-VL FR2-VL CDR2-VL FR3-VL CDR3-VL FR4, wherein: (A) VL CDR1 comprises the amino acid sequence of $X_{C1}ASQDIHRYLS$ (SEQ ID NO: 62), wherein $X_{C1}$ is K or R; VL CDR2 comprises the amino acid sequence of RANRLVS (SEQ ID NO: 63); and VL CDR3 comprises the amino acid sequence of LQYDEFPYT (SEQ ID NO: 64); or (B) VL CDR1 comprises the amino acid sequence of $X_{C1}$ASQDIHRYLS (SEQ ID NO: 62), wherein $X_{C1}$ is K or R; VL CDR2 comprises the amino acid sequence of $RX_{C2}X_{C3}$RFVD (SEQ ID NO: 65), wherein $X_{C2}$ is any amino acid with a polar or charged side chain, and $X_{C3}$ is V, I, E, or S; and VL CDR3 comprises the amino acid sequence of LQYDEFPYT (SEQ ID NO: 64).

4. The antibody or antigen-binding fragment of claim 3, wherein $X_{C2}$ is Y, E, or H.

5. The antibody or antigen-binding fragment of claim 1, wherein the antibody or antigen-binding fragment comprises a heavy chain constant region that is a human constant region.

6. The antibody or antigen-binding fragment of claim 1, wherein the antibody or antigen-binding fragment comprises a light chain constant region selected from the group consisting of a human kappa constant region and a human lambda constant region.

7. The antibody or antigen-binding fragment of claim 1, wherein the antibody is a monoclonal antibody or antigen-binding fragment thereof.

8. The antibody or antigen-binding fragment of claim 1, which is conjugated to an agent.

9. A pharmaceutical composition comprising a therapeutically effective amount of the antibody or antigen-binding fragment of claim 1, and a pharmaceutically acceptable carrier.

10. A polynucleotide comprising a nucleotide sequence encoding the antibody or antigen-binding fragment of claim 1.

11. A vector comprising the polynucleotide of claim 10.

12. An isolated cell comprising the polynucleotide of claim 10.

13. A method of making an antibody or antigen-binding fragment thereof, comprising (a) culturing an isolated cell comprising the polynucleotide of claim 10; and (b) isolating the antibody or antigen-binding fragment thereof.

14. A method of treating cancer in a subject in need thereof, the method comprising administering to the subject the antibody or antigen-binding fragment of claim 3.

15. A method of treating cancer in a subject in need thereof, the method comprising administering to the subject a pharmaceutical composition comprising a therapeutically effective amount of the antibody or antigen-binding fragment of claim 3, and a pharmaceutically acceptable carrier.

* * * * *

SEQUENCE LISTING

<160> NUMBER OF SEQ ID NOS: 139

<210> SEQ ID NO 1
<211> LENGTH: 26
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: Q or E
<220> FEATURE:
<221> NAME/KEY: MOD_RES
<222> LOCATION: (3)..(3)
<223> OTHER INFORMATION: V or M
<220> FEATURE:
<221> NAME/KEY: MOD_RES
<222> LOCATION: (10)..(10)
<223> OTHER INFORMATION: A or P
<220> FEATURE:
<221> NAME/KEY: MOD_RES
<222> LOCATION: (15)..(15)
<223> OTHER INFORMATION: P or T
<220> FEATURE:
<221> NAME/KEY: MOD_RES
<222> LOCATION: (17)..(17)
<223> OTHER INFORMATION: A, S or T
<220> FEATURE:
<221> NAME/KEY: MOD_RES
<222> LOCATION: (18)..(18)
<223> OTHER INFORMATION: S or T
<220> FEATURE:
<221> NAME/KEY: MOD_RES
<222> LOCATION: (21)..(21)
<223> OTHER INFORMATION: V or I
<220> FEATURE:
<221> NAME/KEY: MOD_RES
<222> LOCATION: (25)..(25)
<223> OTHER INFORMATION: A or V

<400> SEQUENCE: 1

Met Xaa Xaa Gln Leu Val Gln Ser Gly Xaa Glu Val Lys Lys Xaa Gly
1               5                   10                  15

Xaa Xaa Val Lys Xaa Ser Cys Lys Xaa Ser
            20                  25

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: R or Q
<220> FEATURE:
<221> NAME/KEY: MOD_RES
<222> LOCATION: (6)..(6)
<223> OTHER INFORMATION: P, R or T
<220> FEATURE:
<221> NAME/KEY: MOD_RES
<222> LOCATION: (8)..(8)
<223> OTHER INFORMATION: Q or K
<220> FEATURE:
<221> NAME/KEY: MOD_RES
<222> LOCATION: (9)..(9)
<223> OTHER INFORMATION: G, R or A
<220> FEATURE:
<221> NAME/KEY: MOD_RES
<222> LOCATION: (13)..(13)
<223> OTHER INFORMATION: M or I

<400> SEQUENCE: 2
```

-continued

```
Trp Val Xaa Gln Ala Xaa Gly Xaa Xaa Leu Glu Trp Xaa Gly
1               5                   10
```

<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Q or E
<220> FEATURE:
<221> NAME/KEY: MOD_RES
<222> LOCATION: (5)..(5)
<223> OTHER INFORMATION: F or L
<220> FEATURE:
<221> NAME/KEY: MOD_RES
<222> LOCATION: (7)..(7)
<223> OTHER INFORMATION: G, D or E
<220> FEATURE:
<221> NAME/KEY: MOD_RES
<222> LOCATION: (11)..(11)
<223> OTHER INFORMATION: M or I
<220> FEATURE:
<221> NAME/KEY: MOD_RES
<222> LOCATION: (13)..(13)
<223> OTHER INFORMATION: R, T, E or A
<220> FEATURE:
<221> NAME/KEY: MOD_RES
<222> LOCATION: (14)..(14)
<223> OTHER INFORMATION: D or N
<220> FEATURE:
<221> NAME/KEY: MOD_RES
<222> LOCATION: (15)..(15)
<223> OTHER INFORMATION: T, R, M, E or K
<220> FEATURE:
<221> NAME/KEY: MOD_RES
<222> LOCATION: (17)..(17)
<223> OTHER INFORMATION: I, A T or M
<220> FEATURE:
<221> NAME/KEY: MOD_RES
<222> LOCATION: (18)..(18)
<223> OTHER INFORMATION: S or D
<220> FEATURE:
<221> NAME/KEY: MOD_RES
<222> LOCATION: (20)..(20)
<223> OTHER INFORMATION: A or V
<220> FEATURE:
<221> NAME/KEY: MOD_RES
<222> LOCATION: (25)..(25)
<223> OTHER INFORMATION: S or R
<220> FEATURE:
<221> NAME/KEY: MOD_RES
<222> LOCATION: (26)..(26)
<223> OTHER INFORMATION: S or R
<220> FEATURE:
<221> NAME/KEY: MOD_RES
<222> LOCATION: (30)..(30)
<223> OTHER INFORMATION: D or E
<220> FEATURE:
<221> NAME/KEY: MOD_RES
<222> LOCATION: (34)..(34)
<223> OTHER INFORMATION: V or M

<400> SEQUENCE: 3

```
Tyr Ala Xaa Lys Xaa Gln Xaa Arg Val Thr Xaa Thr Xaa Xaa Xaa Ser
1               5                   10                  15

Xaa Xaa Thr Xaa Tyr Met Glu Leu Xaa Xaa Leu Arg Ala Xaa Asp Thr
            20                  25                  30

Ala Xaa Tyr Tyr Cys
        35
```

```
<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Q or R
<220> FEATURE:
<221> NAME/KEY: MOD_RES
<222> LOCATION: (6)..(6)
<223> OTHER INFORMATION: L, M or T

<400> SEQUENCE: 4

Trp Gly Xaa Gly Thr Xaa Val Thr Val Ser Ser
1               5                   10

<210> SEQ ID NO 5
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (3)..(3)
<223> OTHER INFORMATION: V or M
<220> FEATURE:
<221> NAME/KEY: MOD_RES
<222> LOCATION: (15)..(15)
<223> OTHER INFORMATION: P or T
<220> FEATURE:
<221> NAME/KEY: MOD_RES
<222> LOCATION: (17)..(17)
<223> OTHER INFORMATION: A, S or T

<400> SEQUENCE: 5

Met Gln Xaa Gln Leu Val Gln Ser Gly Ala Glu Val Lys Lys Xaa Gly
1               5                   10                  15

Xaa Ser Val Lys Val Ser Cys Lys Ala Ser
            20                  25

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Q or K
<220> FEATURE:
<221> NAME/KEY: MOD_RES
<222> LOCATION: (9)..(9)
<223> OTHER INFORMATION: G, R or A

<400> SEQUENCE: 6

Trp Val Arg Gln Ala Pro Gly Xaa Xaa Leu Glu Trp Met Gly
1               5                   10

<210> SEQ ID NO 7
```

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: F or L
<220> FEATURE:
<221> NAME/KEY: MOD_RES
<222> LOCATION: (7)..(7)
<223> OTHER INFORMATION: G, D or E
<220> FEATURE:
<221> NAME/KEY: MOD_RES
<222> LOCATION: (11)..(11)
<223> OTHER INFORMATION: M or I
<220> FEATURE:
<221> NAME/KEY: MOD_RES
<222> LOCATION: (13)..(13)
<223> OTHER INFORMATION: R, T, E or A
<220> FEATURE:
<221> NAME/KEY: MOD_RES
<222> LOCATION: (15)..(15)
<223> OTHER INFORMATION: T, R, M, E or K
<220> FEATURE:
<221> NAME/KEY: MOD_RES
<222> LOCATION: (17)..(17)
<223> OTHER INFORMATION: I, A, T or M
<220> FEATURE:
<221> NAME/KEY: MOD_RES
<222> LOCATION: (25)..(25)
<223> OTHER INFORMATION: S or R
<220> FEATURE:
<221> NAME/KEY: MOD_RES
<222> LOCATION: (29)..(29)
<223> OTHER INFORMATION: S or A
<220> FEATURE:
<221> NAME/KEY: MOD_RES
<222> LOCATION: (30)..(30)
<223> OTHER INFORMATION: D or E
<220> FEATURE:
<221> NAME/KEY: MOD_RES
<222> LOCATION: (34)..(34)
<223> OTHER INFORMATION: V or M

<400> SEQUENCE: 7

Tyr Ala Gln Lys Xaa Gln Xaa Arg Val Thr Xaa Thr Xaa Asp Xaa Ser
1               5                   10                  15

Xaa Ser Thr Ala Tyr Met Glu Leu Xaa Ser Leu Arg Xaa Xaa Asp Thr
            20                  25                  30

Ala Xaa Tyr Tyr Cys
        35

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: A or S
<220> FEATURE:
<221> NAME/KEY: MOD_RES
<222> LOCATION: (11)..(11)
<223> OTHER INFORMATION: M or L

<400> SEQUENCE: 8

Asn Ile Gln Met Thr Gln Ser Pro Ser Xaa Xaa Ser Ala Ser Val Gly
1               5                   10                  15
```

```
Asp Arg Val Thr Ile Thr Cys
            20

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: F or Y
<220> FEATURE:
<221> NAME/KEY: MOD_RES
<222> LOCATION: (9)..(9)
<223> OTHER INFORMATION: V or A

<400> SEQUENCE: 9

Trp Xaa Gln Gln Lys Pro Gly Lys Xaa Pro Lys His Leu Ile Tyr
1               5                   10                  15

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Gly Gly Gly Thr Lys Val Glu Ile Lys
1               5                   10

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 12

Met Gln Met Gln Leu Val Gln Ser Gly Ala Glu Val Lys Lys Thr Gly
1               5                   10                  15

Ser Ser Val Lys Val Ser Cys Lys Ala Ser
            20                  25
```

```
<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Val Arg Gln Ala Pro Gly Lys Ala Leu Glu Trp Met Gly
1               5                   10

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Tyr Ala Gln Lys Phe Gln Asp Arg Val Thr Ile Thr Arg Asp Arg Ser
1               5                   10                  15

Met Ser Thr Ala Tyr Met Glu Leu Ser Ser Leu Arg Ser Glu Asp Thr
            20                  25                  30

Ala Met Tyr Tyr Cys
        35

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Gly Gln Gly Thr Thr Val Thr Val Ser Ser
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Val Arg Gln Ala Pro Gly Gln Gly Leu Glu Trp Met Gly
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Val Arg Gln Ala Pro Gly Gln Ala Leu Glu Trp Met Gly
1               5                   10

<210> SEQ ID NO 18
<211> LENGTH: 37
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 18

Tyr Ala Gln Lys Phe Gln Asp Arg Val Thr Ile Thr Arg Asp Arg Ser
1               5                   10                  15

Met Ser Thr Ala Tyr Met Glu Leu Ser Ser Leu Arg Ala Glu Asp Thr
            20                  25                  30

Ala Met Tyr Tyr Cys
        35

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Trp Gly Gln Gly Thr Leu Val Thr Val Ser Ser
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Val Arg Gln Ala Pro Gly Lys Gly Leu Glu Trp Met Gly
1               5                   10

<210> SEQ ID NO 21
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 21

Met Gln Met Gln Leu Val Gln Ser Gly Ala Glu Val Lys Lys Pro Gly
1               5                   10                  15

Ser Ser Val Lys Val Ser Cys Lys Ala Ser
            20                  25

<210> SEQ ID NO 22
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Tyr Ala Gln Lys Phe Gln Gly Arg Val Thr Ile Thr Arg Asp Arg Ser
1               5                   10                  15

Met Ser Thr Ala Tyr Met Glu Leu Ser Ser Leu Arg Ser Glu Asp Thr
            20                  25                  30

Ala Met Tyr Tyr Cys
        35

<210> SEQ ID NO 23
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Tyr Ala Gln Lys Phe Gln Asp Arg Val Thr Ile Thr Arg Asp Arg Ser
1               5                   10                  15

Thr Ser Thr Ala Tyr Met Glu Leu Ser Ser Leu Arg Ser Glu Asp Thr
            20                  25                  30

Ala Met Tyr Tyr Cys
        35

<210> SEQ ID NO 24
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Tyr Ala Gln Lys Phe Gln Asp Arg Val Thr Ile Thr Arg Asp Arg Ser
1               5                   10                  15

Met Ser Thr Ala Tyr Met Glu Leu Arg Ser Leu Arg Ser Glu Asp Thr
            20                  25                  30

Ala Met Tyr Tyr Cys
        35

<210> SEQ ID NO 25
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Tyr Ala Gln Lys Phe Gln Asp Arg Val Thr Ile Thr Arg Asp Arg Ser
1               5                   10                  15

Met Ser Thr Ala Tyr Met Glu Leu Ser Ser Leu Arg Ser Glu Asp Thr
            20                  25                  30

Ala Val Tyr Tyr Cys
        35

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Tyr Ala Gln Lys Phe Gln Gly Arg Val Thr Ile Thr Arg Asp Arg Ser
1               5                   10                  15

```
Thr Ser Thr Ala Tyr Met Glu Leu Ser Ser Leu Arg Ser Glu Asp Thr
            20                  25                  30

Ala Met Tyr Tyr Cys
        35

<210> SEQ ID NO 27
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Tyr Ala Gln Lys Phe Gln Gly Arg Val Thr Ile Thr Arg Asp Arg Ser
1               5                   10                  15

Met Ser Thr Ala Tyr Met Glu Leu Arg Ser Leu Arg Ser Glu Asp Thr
            20                  25                  30

Ala Met Tyr Tyr Cys
        35

<210> SEQ ID NO 28
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Tyr Ala Gln Lys Phe Gln Gly Arg Val Thr Ile Thr Arg Asp Arg Ser
1               5                   10                  15

Met Ser Thr Ala Tyr Met Glu Leu Ser Ser Leu Arg Ser Glu Asp Thr
            20                  25                  30

Ala Val Tyr Tyr Cys
        35

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Tyr Ala Gln Lys Phe Gln Asp Arg Val Thr Ile Thr Arg Asp Arg Ser
1               5                   10                  15

Thr Ser Thr Ala Tyr Met Glu Leu Arg Ser Leu Arg Ser Glu Asp Thr
            20                  25                  30

Ala Met Tyr Tyr Cys
        35

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Tyr Ala Gln Lys Phe Gln Asp Arg Val Thr Ile Thr Arg Asp Arg Ser
```

-continued

```
                 1               5                  10                  15
Thr Ser Thr Ala Tyr Met Glu Leu Ser Ser Leu Arg Ser Glu Asp Thr
                 20                  25                  30
Ala Val Tyr Tyr Cys
         35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Tyr Ala Gln Lys Phe Gln Asp Arg Val Thr Ile Thr Arg Asp Arg Ser
1               5                  10                  15
Met Ser Thr Ala Tyr Met Glu Leu Arg Ser Leu Arg Ser Glu Asp Thr
                 20                  25                  30
Ala Val Tyr Tyr Cys
         35

<210> SEQ ID NO 32
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Tyr Ala Gln Lys Phe Gln Gly Arg Val Thr Ile Thr Arg Asp Arg Ser
1               5                  10                  15
Thr Ser Thr Ala Tyr Met Glu Leu Arg Ser Leu Arg Ser Glu Asp Thr
                 20                  25                  30
Ala Met Tyr Tyr Cys
         35

<210> SEQ ID NO 33
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Tyr Ala Gln Lys Phe Gln Gly Arg Val Thr Ile Thr Arg Asp Arg Ser
1               5                  10                  15
Thr Ser Thr Ala Tyr Met Glu Leu Ser Ser Leu Arg Ser Glu Asp Thr
                 20                  25                  30
Ala Val Tyr Tyr Cys
         35

<210> SEQ ID NO 34
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34
```

Tyr Ala Gln Lys Phe Gln Gly Arg Val Thr Ile Thr Arg Asp Arg Ser
1               5                   10                  15

Met Ser Thr Ala Tyr Met Glu Leu Arg Ser Leu Arg Ser Glu Asp Thr
            20                  25                  30

Ala Val Tyr Tyr Cys
        35

<210> SEQ ID NO 35
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Tyr Ala Gln Lys Phe Gln Asp Arg Val Thr Ile Thr Arg Asp Arg Ser
1               5                   10                  15

Thr Ser Thr Ala Tyr Met Glu Leu Arg Ser Leu Arg Ser Glu Asp Thr
            20                  25                  30

Ala Val Tyr Tyr Cys
        35

<210> SEQ ID NO 36
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Tyr Ala Gln Lys Phe Gln Gly Arg Val Thr Ile Thr Arg Asp Arg Ser
1               5                   10                  15

Thr Ser Thr Ala Tyr Met Glu Leu Arg Ser Leu Arg Ser Glu Asp Thr
            20                  25                  30

Ala Val Tyr Tyr Cys
        35

<210> SEQ ID NO 37
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Tyr Ala Gln Lys Phe Gln Gly Arg Val Thr Ile Thr Arg Asp Arg Ser
1               5                   10                  15

Met Ser Thr Ala Tyr Met Glu Leu Ser Ser Leu Arg Ala Glu Asp Thr
            20                  25                  30

Ala Met Tyr Tyr Cys
        35

<210> SEQ ID NO 38
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Tyr Ala Gln Lys Phe Gln Asp Arg Val Thr Ile Thr Arg Asp Arg Ser
1               5                   10                  15

Thr Ser Thr Ala Tyr Met Glu Leu Ser Ser Leu Arg Ala Glu Asp Thr
            20                  25                  30

Ala Met Tyr Tyr Cys
        35

<210> SEQ ID NO 39
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Tyr Ala Gln Lys Phe Gln Asp Arg Val Thr Ile Thr Arg Asp Arg Ser
1               5                   10                  15

Met Ser Thr Ala Tyr Met Glu Leu Arg Ser Leu Arg Ala Glu Asp Thr
            20                  25                  30

Ala Met Tyr Tyr Cys
        35

<210> SEQ ID NO 40
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Tyr Ala Gln Lys Phe Gln Asp Arg Val Thr Ile Thr Arg Asp Arg Ser
1               5                   10                  15

Met Ser Thr Ala Tyr Met Glu Leu Ser Ser Leu Arg Ala Glu Asp Thr
            20                  25                  30

Ala Val Tyr Tyr Cys
        35

<210> SEQ ID NO 41
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Tyr Ala Gln Lys Phe Gln Gly Arg Val Thr Ile Thr Arg Asp Arg Ser
1               5                   10                  15

Thr Ser Thr Ala Tyr Met Glu Leu Ser Ser Leu Arg Ala Glu Asp Thr
            20                  25                  30

Ala Met Tyr Tyr Cys
        35

<210> SEQ ID NO 42
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 42

Tyr Ala Gln Lys Phe Gln Gly Arg Val Thr Ile Thr Arg Asp Arg Ser
1               5                   10                  15

Met Ser Thr Ala Tyr Met Glu Leu Arg Ser Leu Arg Ala Glu Asp Thr
            20                  25                  30

Ala Met Tyr Tyr Cys
        35

<210> SEQ ID NO 43
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Tyr Ala Gln Lys Phe Gln Gly Arg Val Thr Ile Thr Arg Asp Arg Ser
1               5                   10                  15

Met Ser Thr Ala Tyr Met Glu Leu Ser Ser Leu Arg Ala Glu Asp Thr
            20                  25                  30

Ala Val Tyr Tyr Cys
        35

<210> SEQ ID NO 44
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Tyr Ala Gln Lys Phe Gln Asp Arg Val Thr Ile Thr Arg Asp Arg Ser
1               5                   10                  15

Thr Ser Thr Ala Tyr Met Glu Leu Arg Ser Leu Arg Ala Glu Asp Thr
            20                  25                  30

Ala Met Tyr Tyr Cys
        35

<210> SEQ ID NO 45
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Tyr Ala Gln Lys Phe Gln Asp Arg Val Thr Ile Thr Arg Asp Arg Ser
1               5                   10                  15

Thr Ser Thr Ala Tyr Met Glu Leu Ser Ser Leu Arg Ala Glu Asp Thr
            20                  25                  30

Ala Val Tyr Tyr Cys
        35

<210> SEQ ID NO 46
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 46

Tyr Ala Gln Lys Phe Gln Asp Arg Val Thr Ile Thr Arg Asp Arg Ser
1               5                   10                  15

Met Ser Thr Ala Tyr Met Glu Leu Arg Ser Leu Arg Ala Glu Asp Thr
            20                  25                  30

Ala Val Tyr Tyr Cys
        35

<210> SEQ ID NO 47
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Tyr Ala Gln Lys Phe Gln Gly Arg Val Thr Ile Thr Arg Asp Arg Ser
1               5                   10                  15

Thr Ser Thr Ala Tyr Met Glu Leu Arg Ser Leu Arg Ala Glu Asp Thr
            20                  25                  30

Ala Met Tyr Tyr Cys
        35

<210> SEQ ID NO 48
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Tyr Ala Gln Lys Phe Gln Gly Arg Val Thr Ile Thr Arg Asp Arg Ser
1               5                   10                  15

Thr Ser Thr Ala Tyr Met Glu Leu Ser Ser Leu Arg Ala Glu Asp Thr
            20                  25                  30

Ala Val Tyr Tyr Cys
        35

<210> SEQ ID NO 49
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Tyr Ala Gln Lys Phe Gln Gly Arg Val Thr Ile Thr Arg Asp Arg Ser
1               5                   10                  15

Met Ser Thr Ala Tyr Met Glu Leu Arg Ser Leu Arg Ala Glu Asp Thr
            20                  25                  30

Ala Val Tyr Tyr Cys
        35

<210> SEQ ID NO 50
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

Tyr Ala Gln Lys Phe Gln Asp Arg Val Thr Ile Thr Arg Asp Arg Ser
1               5                   10                  15

Thr Ser Thr Ala Tyr Met Glu Leu Arg Ser Leu Arg Ala Glu Asp Thr
            20                  25                  30

Ala Val Tyr Tyr Cys
        35

<210> SEQ ID NO 51
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn Ile Gln Met Thr Gln Ser Pro Ser Ala Met Ser Ala Ser Val Gly
1               5                   10                  15

Asp Arg Val Thr Ile Thr Cys
            20

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Trp Phe Gln Gln Lys Pro Gly Lys Val Pro Lys His Leu Ile Tyr
1               5                   10                  15

<210> SEQ ID NO 53
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asn Ile Gln Met Thr Gln Ser Pro Ser Ser Met Ser Ala Ser Val Gly
1               5                   10                  15

Asp Arg Val Thr Ile Thr Cys
            20

<210> SEQ ID NO 54
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asn Ile Gln Met Thr Gln Ser Pro Ser Ala Leu Ser Ala Ser Val Gly
1               5                   10                  15

Asp Arg Val Thr Ile Thr Cys
            20

```
<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Trp Tyr Gln Gln Lys Pro Gly Lys Val Pro Lys His Leu Ile Tyr
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Phe Gln Gln Lys Pro Gly Lys Ala Pro Lys His Leu Ile Tyr
1               5                   10                  15

<210> SEQ ID NO 57
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asn Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Tyr Gln Gln Lys Pro Gly Lys Ala Pro Lys His Leu Ile Tyr
1               5                   10                  15

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Phe Asn Ile Lys Asp Tyr Tyr Leu His
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 60

Trp Ile Asp Pro Asp Gln Gly Asp Thr Glu
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Ala Ala Tyr Gly Ser Ser Ser Tyr Pro Met Asp Tyr
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: K or R

<400> SEQUENCE: 62

Xaa Ala Ser Gln Asp Ile His Arg Tyr Leu Ser
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ala Asn Arg Leu Val Ser
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Gln Tyr Asp Glu Phe Pro Tyr Thr
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid with a polar or charged side

```
              chain
<220> FEATURE:
<221> NAME/KEY: MOD_RES
<222> LOCATION: (3)..(3)
<223> OTHER INFORMATION: V, I, E or S

<400> SEQUENCE: 65

Arg Xaa Xaa Arg Phe Val Asp
1               5

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Ala Ser Gln Asp Ile His Arg Tyr Leu Ser
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Tyr Val Arg Phe Val Asp
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Tyr Ile Arg Phe Val Asp
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Tyr Glu Arg Phe Val Asp
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Tyr Ser Arg Phe Val Asp
```

1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Glu Val Arg Phe Val Asp
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Glu Ile Arg Phe Val Asp
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Glu Glu Arg Phe Val Asp
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Glu Ser Arg Phe Val Asp
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg His Val Arg Phe Val Asp
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Arg His Ile Arg Phe Val Asp
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg His Glu Arg Phe Val Asp
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg His Ser Arg Phe Val Asp
1               5

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ala Ser Gln Asp Ile His Arg Tyr Leu Ser
1               5                   10

<210> SEQ ID NO 80
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
                20                  25                  30

Tyr Leu His Trp Val Arg Gln Ala Pro Gly Gln Ala Leu Glu Trp Met
            35                  40                  45

Gly Trp Ile Asp Pro Asp Gln Gly Asp Thr Glu Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln

Gly Thr Thr Val Thr Val Ser Ser
            115                 120

<210> SEQ ID NO 81
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys His Leu Ile
        35                  40                  45

Tyr Arg Ala Asn Arg Leu Val Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 82
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Gln Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val 165                 170                 175
Leu Gln Ser Ser Gly Leu Tyr Ser Leu Ser Ser Val Val Thr Val Pro
                180                 185                 190
Ser Ser Ser Leu Gly Thr Lys Thr Tyr Thr Cys Asn Val Asp His Lys
            195                 200                 205
Pro Ser Asn Thr Lys Val Asp Lys Arg Val Glu Ser Lys Tyr Gly Pro
        210                 215                 220
Pro Cys Pro Pro Cys Pro Ala Pro Glu Phe Glu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
        435                 440                 445

<210> SEQ ID NO 83
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asn Ile Gln Met Thr Gln Ser Pro Ser Ala Met Ser Ala Ser Val Gly
1               5                   10                  15
Asp Arg Val Thr Ile Thr Cys Lys Ala Ser Gln Asp Ile His Arg Tyr
                20                  25                  30
Leu Ser Trp Phe Gln Gln Lys Pro Gly Lys Val Pro Lys His Leu Ile
            35                  40                  45
Tyr Arg Ala Asn Arg Leu Val Ser Gly Val Pro Ser Arg Phe Ser Gly
        50                  55                  60
Ser Gly Ser Gly Thr Glu Phe Thr Leu Thr Ile Ser Ser Leu Gln Pro
65                  70                  75                  80

```
Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 84
<211> LENGTH: 323
<212> TYPE: PRT
<213> ORGANISM: Homo sapiens

<400> SEQUENCE: 84

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
            165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu Leu His
        210                 215                 220

Tyr Tyr Val Phe Ser Thr Ala Ile Gly Leu Thr Ser Phe Val Ile Ala
225                 230                 235                 240
```

```
Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu

<210> SEQ ID NO 85
<211> LENGTH: 305
<212> TYPE: PRT
<213> ORGANISM: Homo sapiens

<400> SEQUENCE: 85

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn Ile Leu Ile Val
        115                 120                 125

Ile Phe Pro Ile Phe Ala Ile Leu Leu Phe Trp Gly Gln Phe Gly Ile
    130                 135                 140

Lys Thr Leu Lys Tyr Arg Ser Gly Gly Met Asp Glu Lys Thr Ile Ala
145                 150                 155                 160

Leu Leu Val Ala Gly Leu Val Ile Thr Val Ile Val Ile Val Gly Ala
                165                 170                 175

Ile Leu Phe Val Pro Gly Glu Tyr Ser Leu Lys Asn Ala Thr Gly Leu
            180                 185                 190

Gly Leu Ile Val Thr Ser Thr Gly Ile Leu Ile Leu Leu His Tyr Tyr
        195                 200                 205

Val Phe Ser Thr Ala Ile Gly Leu Thr Ser Phe Val Ile Ala Ile Leu
    210                 215                 220

Val Ile Gln Val Ile Ala Tyr Ile Leu Ala Val Val Gly Leu Ser Leu
225                 230                 235                 240

Cys Ile Ala Ala Cys Ile Pro Met His Gly Pro Leu Leu Ile Ser Gly
                245                 250                 255

Leu Ser Ile Leu Ala Leu Ala Gln Leu Leu Gly Leu Val Tyr Met Lys
            260                 265                 270

Phe Val Ala Ser Asn Gln Lys Thr Ile Gln Pro Pro Arg Lys Ala Val
        275                 280                 285
```

```
Glu Glu Pro Leu Asn Ala Phe Lys Glu Ser Lys Gly Met Met Asn Asp
    290                 295                 300

Glu
305

<210> SEQ ID NO 86
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (3)..(3)
<223> OTHER INFORMATION: V or I
<220> FEATURE:
<221> NAME/KEY: MOD_RES
<222> LOCATION: (6)..(6)
<223> OTHER INFORMATION: K or R
<220> FEATURE:
<221> NAME/KEY: MOD_RES
<222> LOCATION: (11)..(11)
<223> OTHER INFORMATION: V, T or A
<220> FEATURE:
<221> NAME/KEY: MOD_RES
<222> LOCATION: (17)..(17)
<223> OTHER INFORMATION: E, Q or A
<220> FEATURE:
<221> NAME/KEY: MOD_RES
<222> LOCATION: (25)..(25)
<223> OTHER INFORMATION: V or F

<400> SEQUENCE: 86

Met Gln Xaa Thr Leu Xaa Glu Ser Gly Pro Xaa Leu Val Lys Pro Thr
1               5                   10                  15

Xaa Thr Leu Thr Leu Thr Cys Thr Xaa Ser
            20                  25

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: A or G

<400> SEQUENCE: 87

Trp Ile Arg Gln Pro Pro Gly Lys Xaa Leu Glu Trp Leu Ala
1               5                   10

<210> SEQ ID NO 88
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: T or P
<220> FEATURE:
```

```
<221> NAME/KEY: MOD_RES
<222> LOCATION: (7)..(7)
<223> OTHER INFORMATION: S, T or G
<220> FEATURE:
<221> NAME/KEY: MOD_RES
<222> LOCATION: (11)..(11)
<223> OTHER INFORMATION: I or M
<220> FEATURE:
<221> NAME/KEY: MOD_RES
<222> LOCATION: (12)..(12)
<223> OTHER INFORMATION: S or T
<220> FEATURE:
<221> NAME/KEY: MOD_RES
<222> LOCATION: (13)..(13)
<223> OTHER INFORMATION: K or T
<220> FEATURE:
<221> NAME/KEY: MOD_RES
<222> LOCATION: (17)..(17)
<223> OTHER INFORMATION: K or T
<220> FEATURE:
<221> NAME/KEY: MOD_RES
<222> LOCATION: (18)..(18)
<223> OTHER INFORMATION: N or S
<220> FEATURE:
<221> NAME/KEY: MOD_RES
<222> LOCATION: (25)..(25)
<223> OTHER INFORMATION: T or R
<220> FEATURE:
<221> NAME/KEY: MOD_RES
<222> LOCATION: (29)..(29)
<223> OTHER INFORMATION: P or A
<220> FEATURE:
<221> NAME/KEY: MOD_RES
<222> LOCATION: (30)..(30)
<223> OTHER INFORMATION: V or D
<220> FEATURE:
<221> NAME/KEY: MOD_RES
<222> LOCATION: (34)..(34)
<223> OTHER INFORMATION: T or V

<400> SEQUENCE: 88

Tyr Ser Xaa Ser Leu Lys Xaa Arg Leu Thr Xaa Xaa Xaa Asp Thr Ser
1               5                   10                  15

Xaa Xaa Gln Val Val Leu Thr Met Xaa Asn Met Asp Xaa Xaa Asp Thr
            20                  25                  30

Ala Xaa Tyr Tyr Cys
        35

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Q or R
<220> FEATURE:
<221> NAME/KEY: MOD_RES
<222> LOCATION: (6)..(6)
<223> OTHER INFORMATION: L, M or T

<400> SEQUENCE: 89

Trp Gly Xaa Gly Thr Xaa Val Thr Val Ser Ser
1               5                   10

<210> SEQ ID NO 90
<211> LENGTH: 26
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (17)..(17)
<223> OTHER INFORMATION: Q or A

<400> SEQUENCE: 90

Met Gln Val Gln Leu Gln Gln Ser Gly Pro Gly Leu Val Lys Pro Ser
1               5                   10                  15

Xaa Thr Leu Ser Leu Thr Cys Ala Ile Ser
            20                  25

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: R or K

<400> SEQUENCE: 91

Trp Ile Arg Gln Ser Pro Ser Xaa Gly Leu Glu Trp Leu Gly
1               5                   10

<210> SEQ ID NO 92
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: V or L
<220> FEATURE:
<221> NAME/KEY: MOD_RES
<222> LOCATION: (7)..(7)
<223> OTHER INFORMATION: S or G
<220> FEATURE:
<221> NAME/KEY: MOD_RES
<222> LOCATION: (11)..(11)
<223> OTHER INFORMATION: I or M
<220> FEATURE:
<221> NAME/KEY: MOD_RES
<222> LOCATION: (13)..(13)
<223> OTHER INFORMATION: P or T
<220> FEATURE:
<221> NAME/KEY: MOD_RES
<222> LOCATION: (17)..(17)
<223> OTHER INFORMATION: K or T
<220> FEATURE:
<221> NAME/KEY: MOD_RES
<222> LOCATION: (25)..(25)
<223> OTHER INFORMATION: N or R
<220> FEATURE:
<221> NAME/KEY: MOD_RES
<222> LOCATION: (29)..(29)
<223> OTHER INFORMATION: P or A
<220> FEATURE:
<221> NAME/KEY: MOD_RES
<222> LOCATION: (30)..(30)
<223> OTHER INFORMATION: E or D

<400> SEQUENCE: 92
```

-continued

```
Tyr Ala Val Ser Xaa Lys Xaa Arg Ile Thr Xaa Asn Xaa Asp Thr Ser
1               5                   10                  15

Xaa Asn Gln Phe Ser Leu Gln Leu Xaa Ser Val Thr Xaa Xaa Asp Thr
            20                  25                  30

Ala Val Tyr Tyr Cys
            35

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Q or R
<220> FEATURE:
<221> NAME/KEY: MOD_RES
<222> LOCATION: (6)..(6)
<223> OTHER INFORMATION: L, M or T

<400> SEQUENCE: 93

Trp Gly Xaa Gly Thr Xaa Val Thr Val Ser Ser
1               5                   10

<210> SEQ ID NO 94
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 94

Met Gln Val Gln Leu Val Gln Ser Gly Ser Glu Leu Lys Lys Pro Gly
1               5                   10                  15

Ala Ser Val Lys Val Ser Cys Lys Ala Ser
            20                  25

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Trp Val Arg Gln Ala Pro Gly Lys Gly Leu Glu Trp Met Gly
1               5                   10

<210> SEQ ID NO 96
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: L or F
```

```
<220> FEATURE:
<221> NAME/KEY: MOD_RES
<222> LOCATION: (11)..(11)
<223> OTHER INFORMATION: M or F
<220> FEATURE:
<221> NAME/KEY: MOD_RES
<222> LOCATION: (13)..(13)
<223> OTHER INFORMATION: L or T
<220> FEATURE:
<221> NAME/KEY: MOD_RES
<222> LOCATION: (17)..(17)
<223> OTHER INFORMATION: V or T
<220> FEATURE:
<221> NAME/KEY: MOD_RES
<222> LOCATION: (25)..(25)
<223> OTHER INFORMATION: R or C
<220> FEATURE:
<221> NAME/KEY: MOD_RES
<222> LOCATION: (30)..(30)
<223> OTHER INFORMATION: D or E

<400> SEQUENCE: 96

Tyr Ala Gln Gly Xaa Thr Gly Arg Phe Val Xaa Ser Xaa Asp Thr Ser
1               5                   10                  15

Xaa Ser Thr Ala Tyr Leu Gln Ile Xaa Ser Leu Lys Ala Xaa Asp Thr
            20                  25                  30

Ala Val Tyr Tyr Cys
        35

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Q or R
<220> FEATURE:
<221> NAME/KEY: MOD_RES
<222> LOCATION: (6)..(6)
<223> OTHER INFORMATION: L, M or T

<400> SEQUENCE: 97

Trp Gly Xaa Gly Thr Xaa Val Thr Val Ser Ser
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Phe Asn Ile Lys Asp Tyr Tyr Leu His
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99
```

```
Gly Tyr Thr Phe Thr Tyr Tyr Leu His
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Phe Thr Phe Thr Tyr Tyr Tyr Leu His
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Tyr Asn Phe Thr Tyr Tyr Tyr Leu His
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Tyr Thr Ile Thr Tyr Tyr Tyr Leu His
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Tyr Thr Phe Lys Tyr Tyr Tyr Leu His
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Tyr Thr Phe Thr Asp Tyr Tyr Leu His
1               5                   10

<210> SEQ ID NO 105
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 105

Gly Phe Thr Phe Thr Asp Tyr Tyr Leu His
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Phe Thr Ile Thr Asp Tyr Tyr Leu His
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Tyr Thr Phe Lys Asp Tyr Tyr Leu His
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Phe Thr Phe Lys Asp Tyr Tyr Leu His
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Trp Ile Asp Pro Asp Asn Gly Asp Thr Glu
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Trp Ile Asp Pro Asp Gln Gly Asp Thr Glu
1               5                   10

```
<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Trp Ile Asp Pro Asp Tyr Gly Asp Thr Glu
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Trp Ile Asp Pro Asp Ser Gly Asp Thr Glu
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Trp Ile Asp Pro Asp Asn Ala Asp Thr Glu
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Trp Ile Asp Pro Asp Asn Thr Asp Thr Glu
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asn Ala Ala Tyr Gly Ser Ser Ser Tyr Pro Met Asp Tyr
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116
```

Asn Ala Ala Tyr Gly Ser Ser Pro Tyr Pro Met Asp Tyr
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Lys Ala Ser Gln Asp Ile His Arg Tyr Leu Ser
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Ala Ser Gln Asp Ile His Arg Tyr Leu Ala
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Ala Arg Gln Gly Ile His Arg Tyr Leu Ser
1               5                   10

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Ala Asn Arg Leu Val Asp
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Ala Asn Arg Leu Gln Ser
1               5

<210> SEQ ID NO 122
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 122

Arg Ala Asn Arg Arg Ala Thr
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Ala Asn Arg Leu Val Ser
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Leu Gln Tyr Asp Glu Phe Pro Tyr Thr
1               5

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Tyr Gly Ser Ser Ser Tyr Pro Met Asp Tyr
1               5                   10

<210> SEQ ID NO 126
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: D or G

<400> SEQUENCE: 126

Trp Ile Asp Pro Asp Gln Gly Asp Thr Glu Tyr Ala Gln Lys Phe Gln
1               5                   10                  15

Xaa

<210> SEQ ID NO 127
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 127

Trp Ile Asp Pro Asp Gln Gly Asp Thr Glu Tyr Ala Gln Lys Phe Gln
1               5                   10                  15

Asp

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Tyr Gly Ser Ser Pro Tyr Pro Met Asp Tyr
1               5                   10

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Trp Ile Asp Pro Asp Asn Gly Asp Thr Glu Phe Ala Pro Lys Phe Gln
1               5                   10                  15

Gly

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Trp Ile Asp Pro Asp Asn Gly Asp Thr Glu Tyr Ala Glu Lys Phe Gln
1               5                   10                  15

Gly

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Trp Ile Asp Pro Asp Asn Gly Asp Thr Glu Tyr Ala Gln Lys Phe Gln
1               5                   10                  15

Asp

<210> SEQ ID NO 132
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Trp Ile Asp Pro Asp Asn Gly Asp Thr Glu Tyr Ala Gln Lys Phe Gln
1               5                   10                  15
Gly

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Trp Ile Asp Pro Asp Tyr Gly Asp Thr Glu Tyr Ala Gln Lys Phe Gln
1               5                   10                  15
Asp

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Trp Ile Asp Pro Asp Ser Gly Asp Thr Glu Tyr Ala Gln Lys Phe Gln
1               5                   10                  15
Asp

<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Trp Ile Asp Pro Asp Asn Ala Asp Thr Glu Tyr Ala Gln Lys Phe Gln
1               5                   10                  15
Asp

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Trp Ile Asp Pro Asp Asn Thr Asp Thr Glu Tyr Ala Gln Lys Phe Gln
1               5                   10                  15
Asp

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 137

Trp Ile Asp Pro Asp Asn Gly Thr Glu Tyr Ala Gln Lys Phe Gln Asp
1               5                   10                  15

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Trp Ile Asp Pro Asp Gln Gly Asp Thr Glu Tyr Ala Gln Lys Phe Gln
1               5                   10                  15

Gly

<210> SEQ ID NO 139
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Tyr Ala Gln Lys Phe Gln Gly Arg Val Thr Ile Thr Arg Asp Arg Ser
1               5                   10                  15

Thr Ser Thr Ala Tyr Met Glu Leu Arg Ser Leu Arg Ala Glu Asp Thr
                20                  25                  30

Ala Val Tyr Tyr Cys
                35
```